United States Patent
Zhang et al.

(10) Patent No.: US 11,638,713 B2
(45) Date of Patent: May 2, 2023

(54) PATENTIFLORIN A ANALOGS AS ANTIVIRAL AGENTS

(71) Applicant: Hong Kong Baptist University, Hong Kong (HK)

(72) Inventors: Hongjie Zhang, Hong Kong (HK); Wanfei Li, Hong Kong (HK); Nga Yi Tsang, Hong Kong (HK)

(73) Assignee: Hong Kong Baptist University, Hong Kong (CN)

( * ) Notice: Subject to any disclaimer, the term of this patent is extended or adjusted under 35 U.S.C. 154(b) by 56 days.

(21) Appl. No.: 16/947,935

(22) Filed: Aug. 25, 2020

(65) Prior Publication Data

US 2021/0060042 A1 Mar. 4, 2021

Related U.S. Application Data

(60) Provisional application No. 62/891,441, filed on Aug. 26, 2019.

(51) Int. Cl.
| | | |
|---|---|---|
| *A61K 31/69* | (2006.01) | |
| *A61K 31/365* | (2006.01) | |
| *A61K 31/506* | (2006.01) | |
| *A61K 31/443* | (2006.01) | |
| *A61P 31/16* | (2006.01) | |
| *A61K 31/5377* | (2006.01) | |
| *A61K 31/7048* | (2006.01) | |
| *A61K 31/706* | (2006.01) | |
| *A61P 31/18* | (2006.01) | |
| *A61K 31/381* | (2006.01) | |

(52) U.S. Cl.
CPC ............ *A61K 31/69* (2013.01); *A61K 31/365* (2013.01); *A61K 31/381* (2013.01); *A61K 31/443* (2013.01); *A61K 31/506* (2013.01); *A61K 31/5377* (2013.01); *A61K 31/706* (2013.01); *A61K 31/7048* (2013.01); *A61P 31/16* (2018.01); *A61P 31/18* (2018.01)

(58) Field of Classification Search
CPC .. A61K 31/365; A61K 31/381; A61K 31/443; A61K 31/506; A61K 31/5377; A61K 31/69; A61K 31/7048; A61K 31/706; A61P 31/16; A61P 31/18
See application file for complete search history.

(56) References Cited

U.S. PATENT DOCUMENTS

2014/0357584 A1   12/2014   Zhang et al.

OTHER PUBLICATIONS

International Search Report and Written Opinion of PCT application No. PCT/CN2020/111463 issued from the International Search Authority dated Dec. 2, 2020.

*Primary Examiner* — Savitha M Rao
(74) *Attorney, Agent, or Firm* — S&F/WEHRW

(57) ABSTRACT

The present disclosure relates to patentiflorin A analogs that are useful as antivirals, such as anti-HIV, anti-coronaviral, anti-Ebola viral, and anti-influenza viral agents and methods of use thereof.

11 Claims, 6 Drawing Sheets

PATENTIFLORIN A ANALOGS AS ANTIVIRAL AGENTS

CROSS REFERENCE OF RELATED APPLICATION

This application claims the benefit of priority of U.S. Provisional Patent Application Ser. No. 62/891,441 filed on Aug. 26, 2019, which is hereby incorporated by reference in its entirety for all purposes.

TECHNICAL FIELD

The present disclosure generally relates to the arylnaphthalene glycoside derivatives, the process for their preparation, and their use as antiviral agents. More particularly, the present disclosure relates to patentiflorin A analogs that are useful as antiviral agents, such as anti-HIV, anti-coronaviral, anti-Ebola viral, anti-Marburg viral, and anti-influenza viral agents. The present disclosure also provides methods for treating viral infections, such as HIV, coronaviruses, Ebola virus, Marburg virus and influenza viruses infections.

BACKGROUND

Viruses are important etiologic agents that cause infectious diseases in humans and other mammals. They differ greatly in size, shape, chemical composition, host range, and effects on hosts. After decades of studies, only a limited number of antiviral agents are available for the treatment and/or prevention of diseases caused by viruses such as HIV, coronaviruses, Ebola, Marburg, influenza A and B and hepatitis C viruses. Because of their toxic effects on a host, many antiviral agents are limited in their application. Drug resistance is often very quickly developed against the antiviral agent, and many viral diseases, such as HIV have no vaccines available to treat or prevent them. Accordingly, there is a need for safe and effective antiviral agents against a wide-spectrum of viruses with no or low toxicity to the host.

AIDS (acquired immunodeficiency syndrome) remains one of the most serious threats to public health. In a UNAIDS (Uniting the world against AIDS) report, about 77 million people have been infected with the human immunodeficiency virus (HIV), and 37.9 million people have died from AIDS-related illnesses since the onset of the HIV epidemic in 1981. Since the first anti-HIV drug zidovudine (AZT) was developed and approved in 1987, more than 40 anti-HIV drugs have been formally approved by the U.S. Food and Drug Administration (FDA) for the treatment of HIV infection. These drugs are categorized as nucleoside reverse transcriptase inhibitors (NRTIs), non-nucleoside reverse transcriptase inhibitors (NNRTIs), protease inhibitors (PIs), entry and fusion inhibitors, and HIV integrase strand transfer inhibitors. Although these drugs have significantly extended the lifespan of HIV-positive people, it is worrisome that the prevalence of HIV drug resistance has increased from 11% to 29% since the global rollout of the antiretroviral therapy (ART) in 2001. In addition, the high cost and limited availability of the current ARTs has excluded patients in developing countries from the benefit of combination therapies. Therefore, there is an urgent need to continuously develop novel, more effective, accessible, and affordable anti-HIV therapeutics.

Influenza, a severe viral infection of the respiratory system, remains a major threat to human health. The worldwide outbreak of highly pathogenic H5N1 subtype of avian influenza virus (AIV) and the recent appearance of new type human influenza A/H1N1 have heightened public awareness of potential global influenza pandemics. In addition to domestic poultry, AIV can also infect wild birds, pigs, cats, humans, and other animals. Three drugs, Xofluza, zanamivir and oseltamivir phosphate, have been approved for the treatment of influenza. However, the low oral bioavailability and rapid renal elimination of zanamivir, and the rapid emergence of oseltamivir-resistant influenza viruses, have prompted the further development of more potent, longer duration therapeutic drugs to combat potential human influenza pandemics.

Viruses belonging to Filoviridae contain minus-strand RNA as their genome. There are two genera, namely Marburgvirus and Ebolavirus, under the Filoviridae family. Marburg virus is the only member in Marburgvirus genus. There are five members in Ebolavirus genus, namely Zaire ebolavirus, Sudan ebolavirus, Cote d'Ivoire ebolavirus, Reston ebolavirus and Bundibugyo. Owning to their pathogenic potential, high case mortality rate and the lack of effective therapeutics for infected humans, the members of family Filoviridae have been classified as "biosafety level 4" agents. The infection of filovirus may lead to hemorrhagic fever. In fact, both genera contain species that can cause epidemics of serious hemorrhagic fever in humans as well as non-human primates. The outbreak of Ebola virus (EBOV) disease many occurred in Democratic Republic of the Congo. There were numerous Ebola outbreaks since 1976. The first outbreak was in 1976 at Yambuku, with 318 cases reported and 88% death rate. Later, there were two large outbreaks in 1995 and 2007, in which over 250 Ebola cases were reported in each outbreak. In 2014-2015, West Africa experienced the largest Ebola outbreak. Over 28,000 cases were reported and the fatality rate reached to 40%. Recently, an Ebola outbreak occurred again from Apr. 4, 2018. As of May 30, 2019, a total of 1945 cases have been reported with a death rate of 67%. There is no FDA-approved therapeutic agent specific to treat subjects infected by filovirus. The patients suffered from filovirus infection mainly rely on convalescent whole blood or plasma during Ebola outbreaks. However, this kind of empirical treatment has many limitations, including difficulties in mass-production as well as the compatibility of blood group between donor and recipient. The use of some potential drug candidates, which include Favipiravir, ZMapp and GS-5734, are still under investigation. More clinical data is required to prove the safety and efficacy of these drug candidates in treating filovirus infection.

The emergence of novel coronavirus (SARS-CoV-2) raised international concerns and scientists strive to discover potent inhibitors against novel coronavirus. Coronaviruses (CoVs) are enveloped, single-stranded, positive-sense RNA virus, which include Coronaviridae, Arteriviridae, and Roniviridae families. SARS-CoV-2, that causes the current COVID-19 pandemic, is a β-coronavirus. There have been six CoVs identified as human-susceptible viruses. Two of them, SARS-CoV and MERS-CoV, could lead to severe or even fatal respiratory tract infections. As of Aug. 21, 2020, the COVID-19 epidemic has caused 797,428 deaths among over 15.5 million infected cases. Several EBOV inhibitors, such as remdesivir, toremifene, and favipiravir are repurposed as anti-viral agents active against SARS-CoV-2. However, none of them have been highly effective to curb the COVID-19 epidemic. Highly effective viral inhibitors are thus urgently needed to combat the coronaviruses.

Natural products have been a rich source for the discovery of lead compounds in the modern drug discovery. *Justicia* cf.

*patentiflora* was identified as an anti-HIV plant lead through screening over 3,500 plant extracts. Bioassay-directed fractionation of the methanol extract of the stems and barks of this plant led to the isolation of three ANL (arylnaphthalene) glycoside compounds, which displayed potent inhibitory activity against broad HIV clinical strains with $EC_{50}$ values in the range of 14-37 nM [Zidovudine (AZT): 77-95 nM]. They also showed significant inhibitory effects against drug-resistance HIV strains.

Some arylnaphthalene lignans have been reported to have antiviral activity in the literature. Although some of these compounds showed significant antiviral activities against various virus strains, they were not considered as potential antiviral drug candidates due to their low selectivity indices (SIs).

There thus exists a need to develop improved antiviral agents that address at least some of the aforementioned needs.

SUMMARY

The present disclosure relates to a new class of patentiflorin A analogs, the preparation of these compounds and new intermediates, and their use for treatment of viral infections, such as HIV, CoV, EBOV and AIV.

In a first aspect, provided herein is a method of treating a viral infection in a subject in need thereof, the method comprising administering a therapeutically effective amount of a compound to the subject, wherein the compound has the Formula (I):

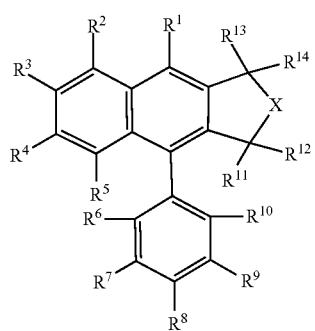

or a pharmaceutically acceptable salt or pro-drug thereof wherein,

X is oxygen or sulfur;

$R^1$ is $R^{15}$, —$OR^{15}$, —$C(O)R^{15}$, or —$C(O)OR^{15}$;

$R^2$, $R^5$, $R^6$, $R^{10}$, $R^{13}$, and $R^{14}$ are each hydrogen;

$R^3$ and $R^4$ are each independently selected from the group consisting of —$OR^{15}$ and —$OC(O)R^{15}$; or $R^3$ and $R^4$ taken together with the carbon atoms to which they are attached form a 5-6 membered heterocyclyl optionally substituted with 1, 2, 3, 4 or 5 group(s) independently selected from $R^{16}$;

$R^7$, $R^8$, and $R^9$ are each independently selected from the group consisting of —$OR^{15}$ and —$OC(O)R^{15}$; or $R^7$ and $R^8$ taken together with the carbon atoms to which they are attached to form a 5-6 membered heterocyclyl optionally substituted with 1, 2, 3, 4 or 5 group(s) independently selected from $R^{16}$; or $R^8$ and $R^9$ taken together with the carbon atoms to which they are attached to form a 5-6 membered heterocyclyl optionally substituted with 1, 2, 3, 4 or 5 group(s) independently selected from $R^{16}$;

$R^{11}$ and $R^{12}$ taken together form oxo; or while one of $R^{11}$ and $R^{12}$ is hydrogen or halogen, the other one of $R^{11}$ and $R^{12}$ is selected from the group consisting of $R^{15}$, —$OR^{15}$, —$C(O)R^{15}$ and —$C(O)OR^{15}$;

$R^{15}$ for each occurrence is independently selected from the group consisting of hydrogen, halogen, trichloromethyl, trifluoromethyl, cyano, nitro, heteroaryl, —$OR^7$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N=C(R^7)R^{18}$, —$N(R^{17})R^{18}$, —$N(R^{17})N(R^{17})R^{18}$, —$N(R^{17})C(O)R^{18}$, —$N(R^{17})S(O)_2R^{18}$, 1,3,2-dioxaborolane optionally substituted with 1, 2, 3, or 4 group(s) independently selected from alkyl, a glycosidic group, alkynyl optionally substituted with a trialkylsilane, hydrocarbyl optionally substituted with 1, 2, 3, 4 or 5 group(s) independently selected from $R^{16}$, heterocyclcyl optionally substituted with 1, 2, 3, 4 or 5 group(s) independently selected from $R^{16}$, and —$(CH_2)_k$-heterocyclyl optionally substituted with 1, 2, 3, 4 or 5 group(s) independently selected from $R^{16}$, wherein k is an integer between 1-6;

$R^{16}$ for each occurrence is independently selected from the group consisting of alkynyl, halogen, trichloromethyl, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{17}$, —$N(R^{17})R^{18}$, —$N(R^{17})N(R^{17})R^{18}$, —$N(R^{17})C(O)R^{18}$ and —$N(R^7)S(O)_2R^{18}$; and $R^{17}$ and $R^{18}$ for each occurrence are independently hydrogen, alkyl, alkynyl, cycloalkyl, aryl, or heteroaryl, or selected from hydrocarbyl and heterocyclyl, either of which is optionally substituted with 1, 2, 3, 4 or 5 group(s) independently selected from the group consisting of halogen, cyano, amino, hydroxy, $C_{1-6}$ alkyl and $C_{1-6}$ alkoxy;

with the proviso that the compound of Formula (I) is not a compound selected from the group consisting of 5, 15a, 15b, 16, 17b, 19d, 25a-25g, and 26a-26g:

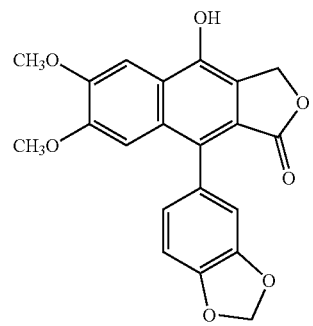

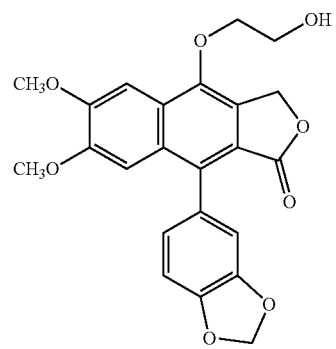

15b
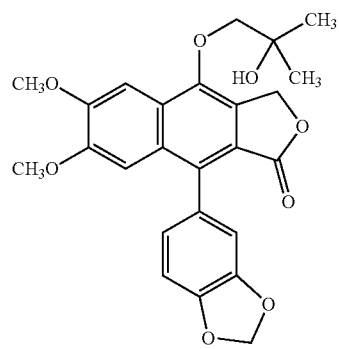
16
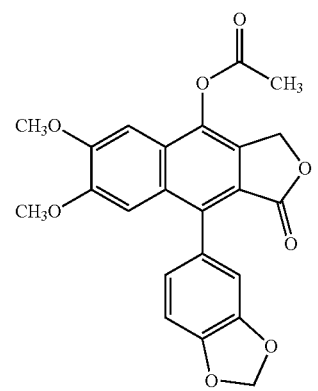
17b
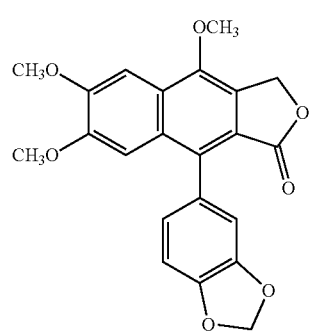
19d
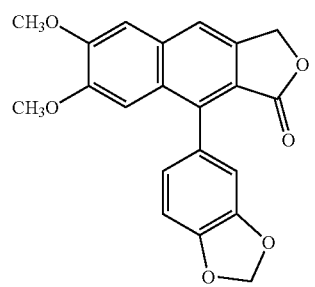
25a
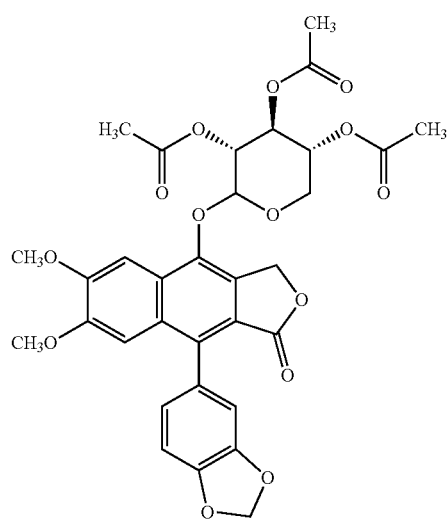
25b
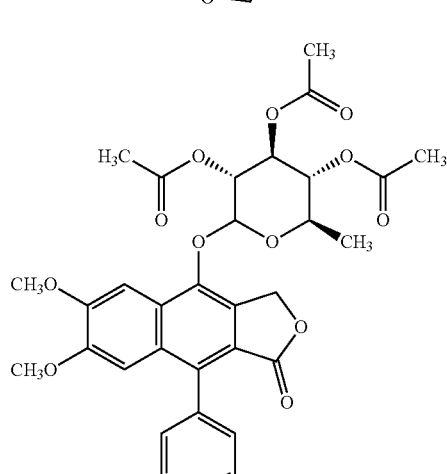
25c
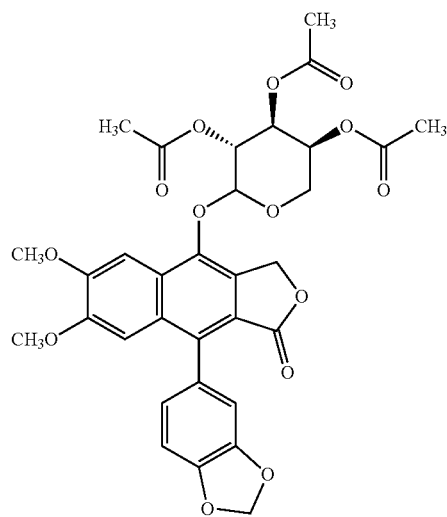

25d
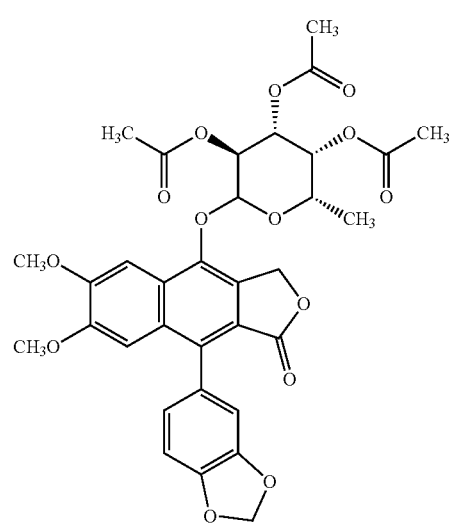
25e
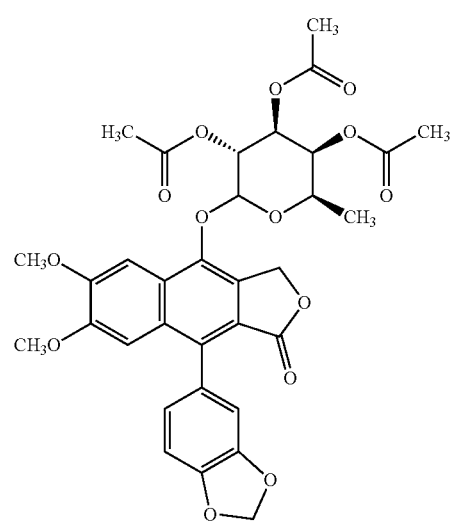
25f
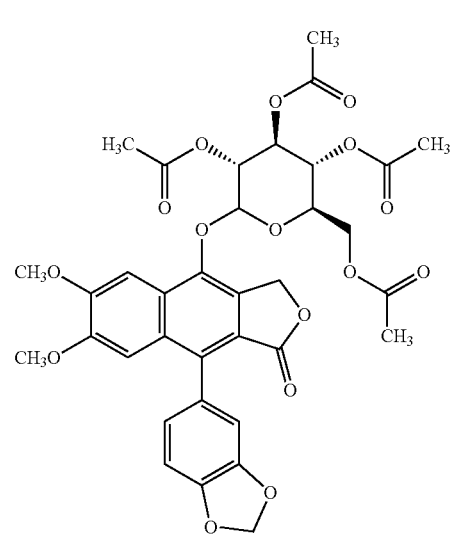
25g
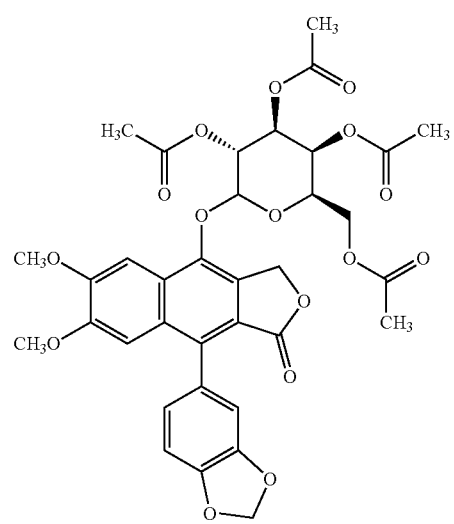
26a
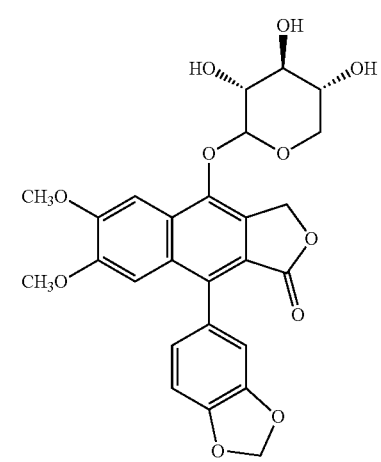
26b
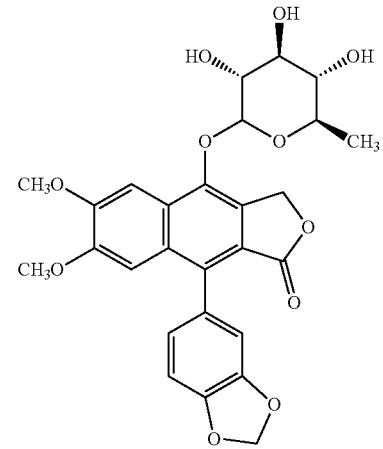

26c 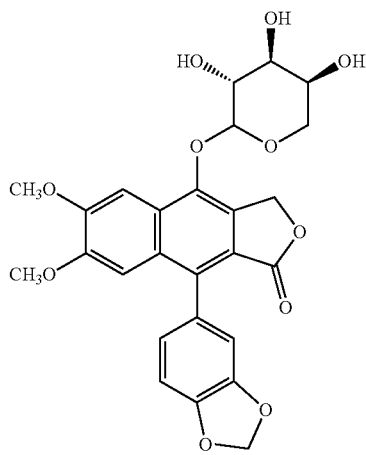

26d 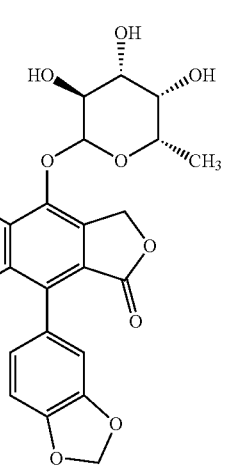

26e 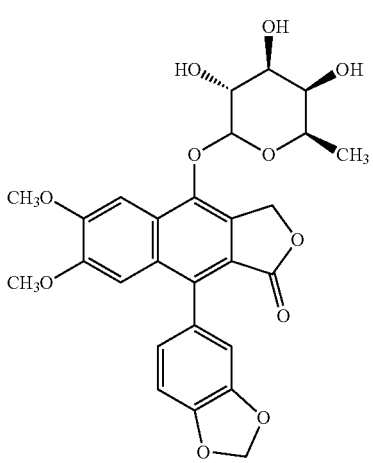

26f 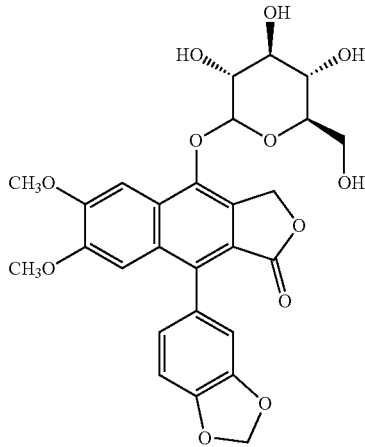

26g 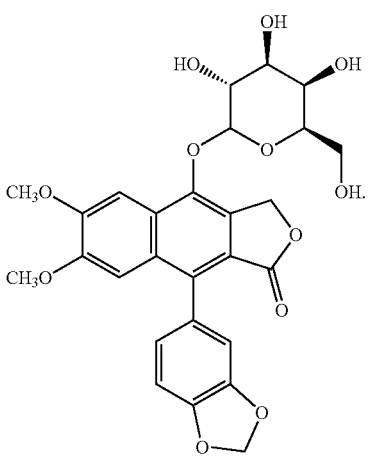

In certain embodiments of the method, each of $R^3$ and $R^4$ is —O-alkyl; $R^8$ and $R^9$ taken together with the carbon atoms to which they are attached form a methylenedioxy ring;

$R^1$ is heteroaryl, —$OR^{15}$, —$C(O)R^{15}$, —$N(R^{17})R^{18}$, —$N(R^{17})C(O)R^{18}$, —$N=C(R^{17})R^{18}$, pinacolboryl, —$OS(O)_2CF_3$, a glycosidic group, heterocyclcyl optionally substituted with 1 or 2 group(s) independently selected from $R^{11}$, or alkynyl optionally substituted with a trialkylsilane; or $R^1$ is —$O(CH_2)_m$-cyano, —$O(CH_2)_m$-alkynyl, —$O(CH_2)_m$—$C(O)N(R^{17})R^{18}$, or —$O(CH_2)_m$—$C(O)OR^{17}$, wherein m is a whole number elected from 1-4; and $R^{11}$ and $R^{12}$ taken together form oxo.

In certain embodiments of the method, the compound is selected from the group consisting of 12a, 12b, 13, 14a, 14b, 17a, 17c, 17d, 17e, 17f, 17g, 17h, 18, 19a, 19b, 19c, 19e, 19f, 19g, 19h, 19i, 19j, 19k, 19l, 19m, 19n, 19o, 19p, 20, 21, 22, 23 and 24:

11
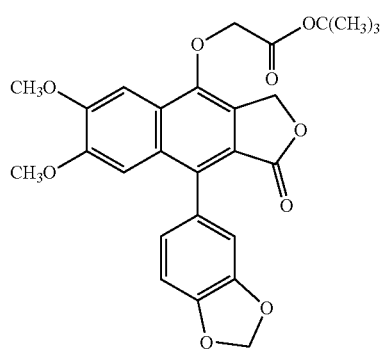
12a
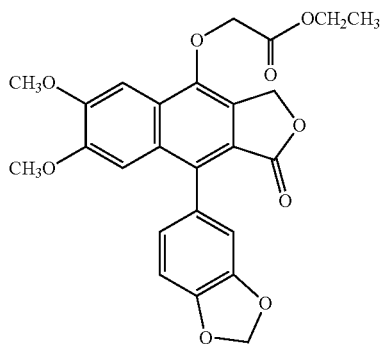
12b
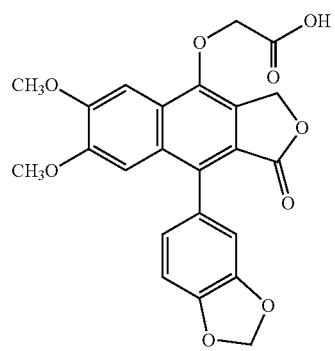
13
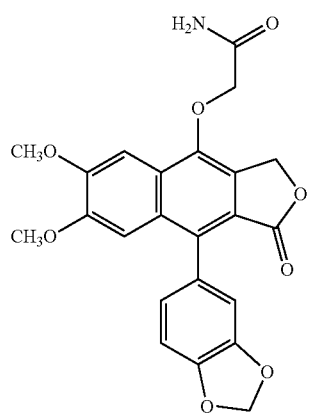
14a
12
-continued
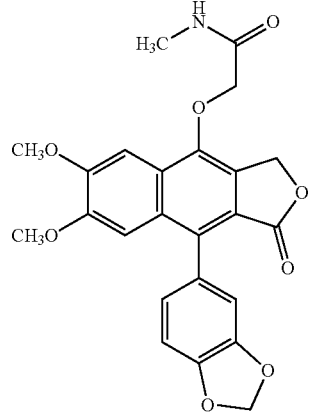
14b
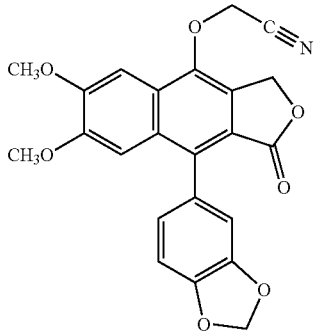
17a
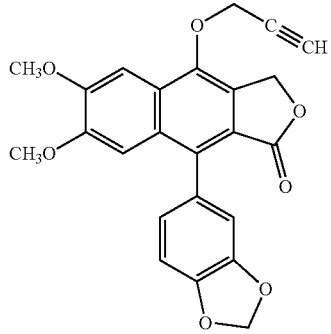
17c
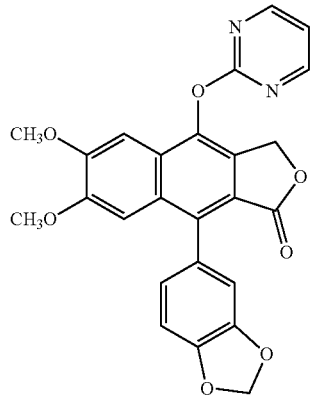
17d 17e
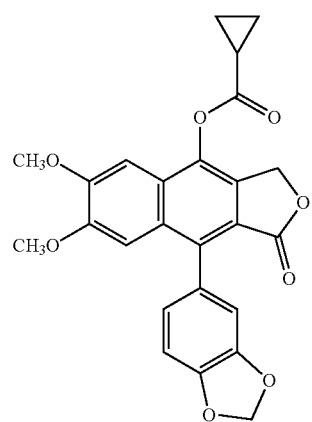
17f
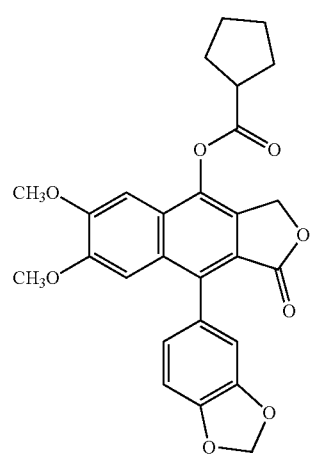
17g
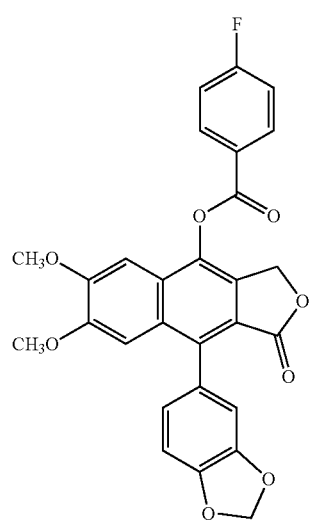
17h
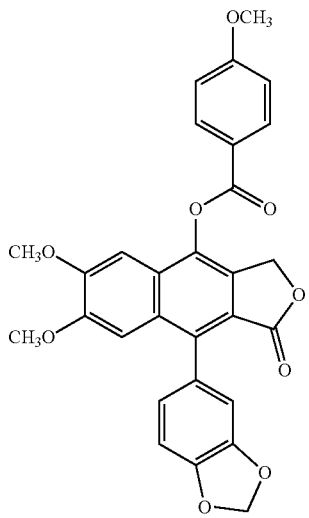
18
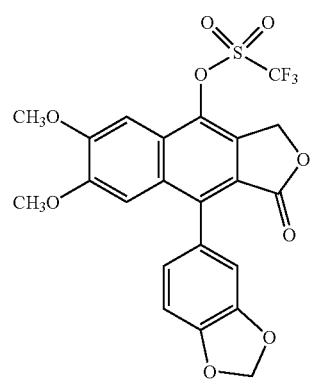
19a
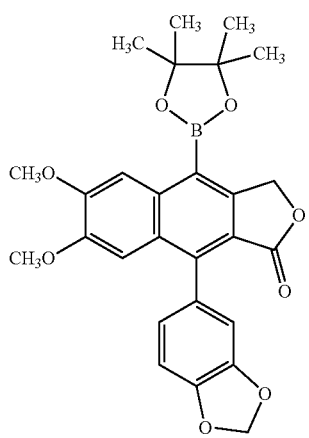
19b
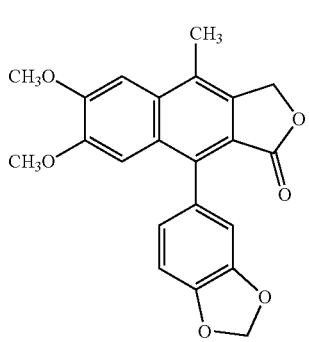

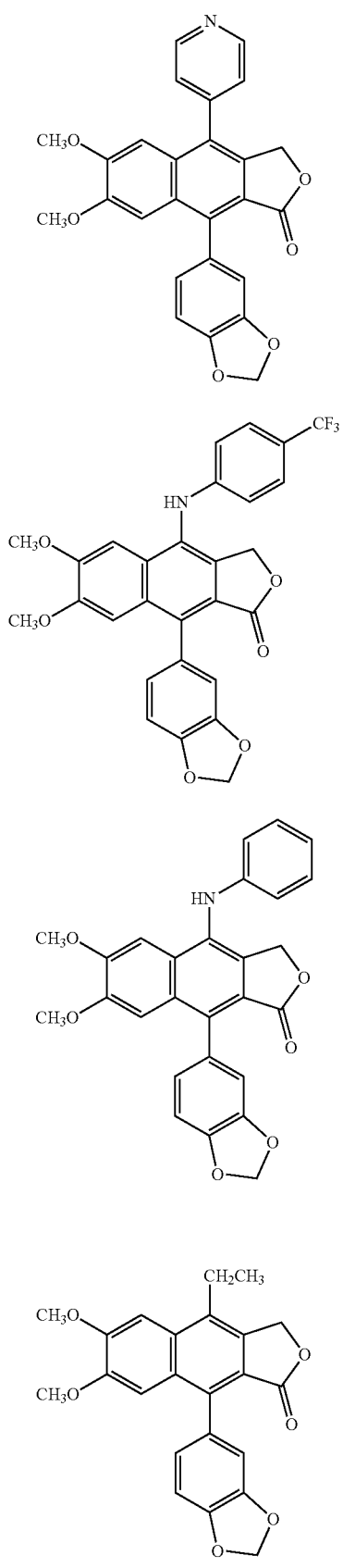
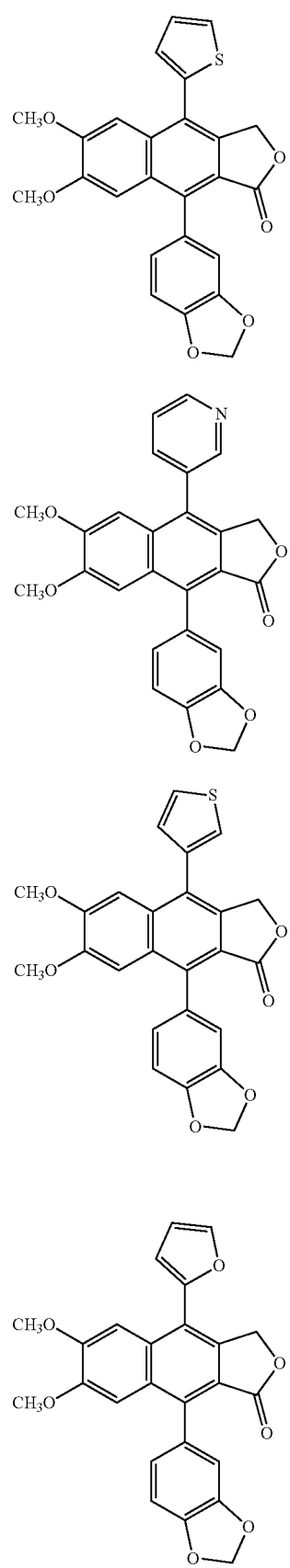

17
-continued
19l
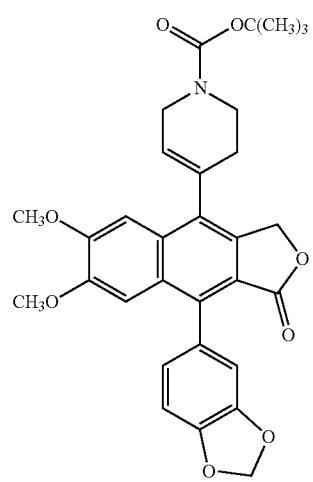
19m
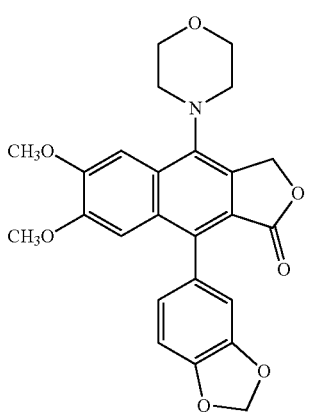
19n
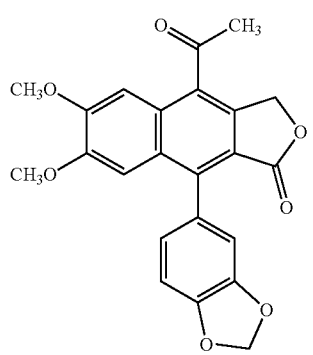
19o
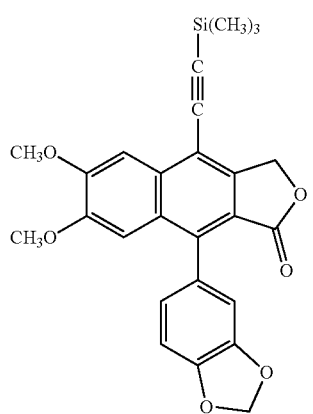
18
-continued
19p
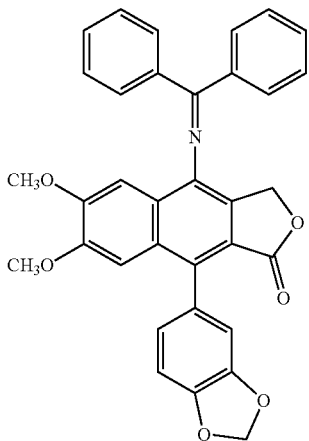
20
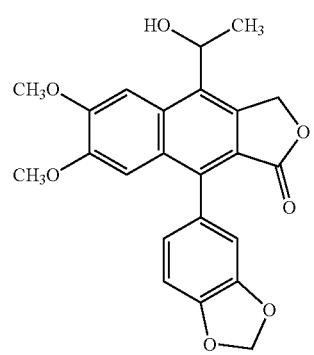
21
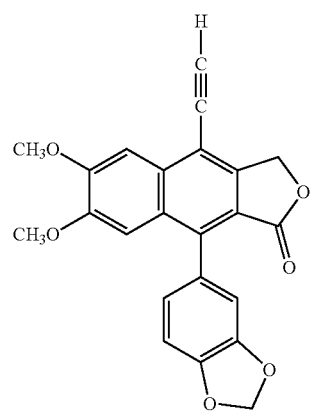
22
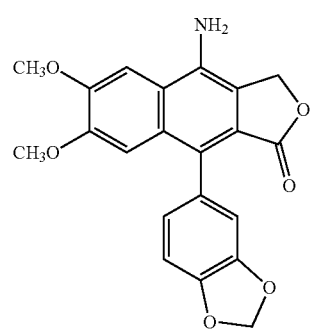

-continued

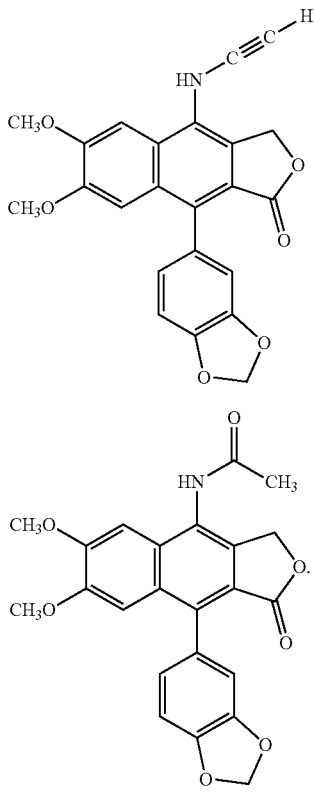

In certain embodiments of the method, the viral infection is selected from the group consisting of HIV, coronaviruses, influenza viruses, Ebola virus, and Marburg virus.

In certain embodiments of the method, $R^1$ is alkynyl, pinacolboryl, —OCH$_2$-cyano, —OCH$_2$—C(O)N(R$^{17}$)R$^{18}$, or —OCH$_2$—C(O)OR$^{17}$; each of $R^3$ and $R^4$ is —OCH$_3$; $R^8$ and $R^9$ taken together with the carbon atoms to which they are attached form a methylenedioxy ring; $R^{11}$ and $R^{12}$ taken together form oxo; and the viral infection is HIV.

In certain embodiments of the method, $R^1$ is a glycosidic group represented by the Formula (V):

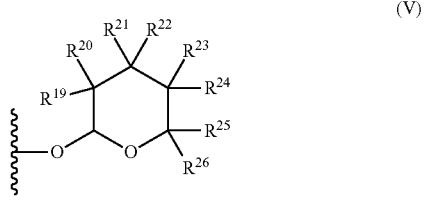

(V)

wherein, $R^{19}$ and $R^{20}$ taken together to form oxo; or while one of $R^{19}$ and $R^{20}$ is hydrogen or halogen, the other one of $R^{19}$ and $R^{20}$ is selected from the group consisting of $R^{27}$, —OR$^{27}$, —OC(O)R$^{27}$, —OC(O)N(R$^{27}$)R$^{27}$, and —OC(O)OR$^{27}$;

$R^{21}$ and $R^{22}$ taken together to form oxo; or while one of $R^{21}$ and $R^{22}$ is hydrogen or halogen, the other one of $R^{21}$ and $R^{22}$ is selected from the group consisting of $R^{27}$, —OR$^{27}$, —OC(O)R$^{27}$, —OC(O)N(R$^{27}$)R$^{27}$, and —OC(O)OR$^{27}$; or $R^{20}$ and $R^{22}$ taken together with the carbon atoms to which they are attached to form a 5-6 membered heterocyclyl optionally substituted with 1, 2, 3, 4 or 5 group(s) independently selected from $R^{16}$;

$R^{23}$ and $R^{24}$ taken together to form oxo; or while one of $R^{23}$ and $R^{24}$ is hydrogen or halogen, the other one of $R^{23}$ and $R^{24}$ is selected from the group consisting of $R^{27}$, —OR$^{27}$, —OC(O)R$^{27}$, —OC(O)N(R$^{27}$)R$^{27}$, and —OC(O)OR$^{27}$; or $R^{22}$ and $R^{24}$ taken together with the carbon atoms to which they are attached to form a 5-6 membered heterocyclyl optionally substituted with 1, 2, 3, 4 or 5 group(s) independently selected from $R^6$;

$R^{25}$ and $R^{26}$ taken together form oxo; or while one of $R^{25}$ and $R^{26}$ is hydrogen or halogen, the other one of $R^{25}$ and $R^{26}$ is selected from the group consisting of $R^{27}$, —OR$^{27}$, —OC(O)R$^{27}$, —OC(O)N(R$^{27}$)R$^{27}$, —OC(O)OR$^{27}$, —CH$_2$R$^{27}$, and —C(O)R$^{27}$; or $R^{24}$ and $R^{26}$ taken together with the carbon atoms to which they are attached to form a 5-6 membered heterocyclyl optionally substituted with 1, 2, 3, 4 or 5 group(s) independently selected from $R^6$;

$R^{27}$ for each occurrence is independently selected from the group consisting of hydrogen, halogen, trichloromethyl, trifluoromethyl, cyano, nitro, —OR$^{29}$, —C(O)R$^{30}$, —C(O)N(R$^{29}$)R$^{30}$, —C(O)OR$^{29}$, —OC(O)R$^{29}$, —S(O)$_2$R$^{29}$, —S(O)$_2$N(R$^{29}$)R$^{30}$, —N(R$^{29}$)R$^{30}$, —N(R$^{29}$)N(R$^{29}$)R$^{30}$, —N(R$^{29}$)C(O)R$^{30}$, —N(R$^{29}$)S(O)$_2$R$^{30}$, hydrocarbyl optionally substituted with 1, 2, 3, 4 or 5 group(s) independently selected from $R^{28}$, heterocyclcyl optionally substituted with 1, 2, 3, 4 or 5 group(s) independently selected from $R^{28}$, and —(CH$_2$)$_k$-heterocyclyl optionally substituted with 1, 2, 3, 4 or 5 group(s) independently selected from $R^{28}$, wherein k is an integer between 1-6;

$R^{28}$ for each occurrence is independently selected from halogen, trichloromethyl, trifluoromethyl, cyano, nitro, oxo, =NR$^{29}$, —OR$^{29}$, —C(O)R$^{30}$, —C(O)N(R$^{29}$)R$^{30}$, —C(O)OR$^{29}$, —OC(O)R$^{29}$, —S(O)$_2$R$^{29}$, —S(O)$_2$N(R$^{29}$)R$^{30}$, —N(R$^{29}$)R$^{30}$, —N(R$^{29}$)N(R$^{29}$)R$^{30}$, —N(R$^{29}$)C(O)R$^{31}$ and —N(R$^{29}$)S(O)$_2$R$^{30}$; and $R^{29}$ and $R^{30}$ for each occurrence are each independently hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

In certain embodiments of the method, $R^{19}$, $R^{21}$, $R^{23}$, and $R^{25}$ are each hydrogen; $R^{20}$, $R^{22}$ and $R^{24}$ are each independently selected from the group consisting of —OR$^{27}$, —OC(O)N(R$^{27}$)R$^{27}$, —OC(O)R$^{27}$ and —OC(O)OR$^{27}$; and $R^{26}$ is hydrogen, methyl, —OR$^{27}$, —OC(O)R$^{27}$ or —CH$_2$—OC(O)R$^{27}$; or $R^{20}$ and $R^{22}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{22}$ and $R^{24}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{24}$ and $R^{26}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; and the glycloside is a monosaccharide.

In certain embodiments of the method, the glycloside is a monosaccharide selected from the group consisting of an α-L isomer and an β-L isomer.

In certain embodiments of the method, the compound is selected from the group consisting of 27aa, 27ab, 27ac, 27ad, 27ae, 27af, 27ba, 27bb, 27bc, 27bd, 27be, 27bf, 28ab1, 28ab2, 28ab3, 28bb1, 28bb2, 28bb3, 29a, 29b, 30a, 30b, 30c, 30d, 30e, 30f, 30g, 30h, 30i, 30j, 30k, 30l, 31a, 31b, 31c, 31d, 31e, 31f, 31g, 31h, 31i, 31j, 31k, 31l, 32a, 32b, 32c and 32d:

27aa
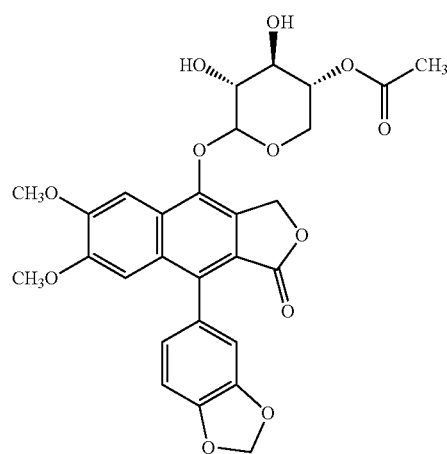
27ab
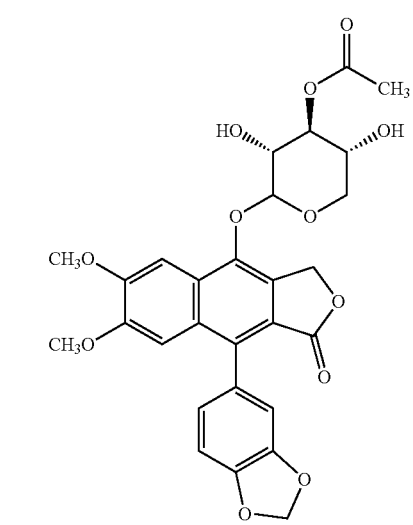
27ac
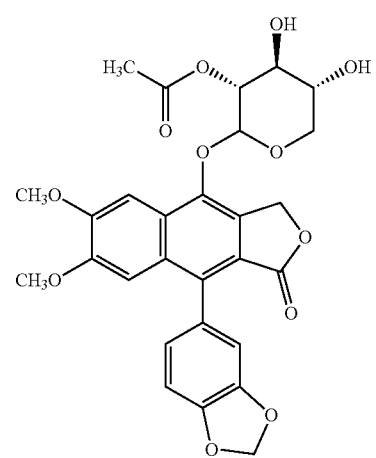
27ad
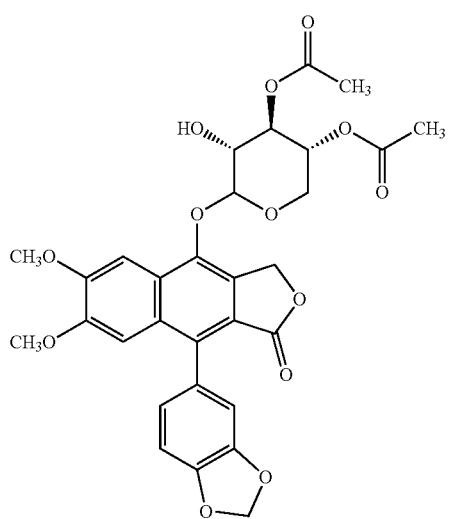
27ae
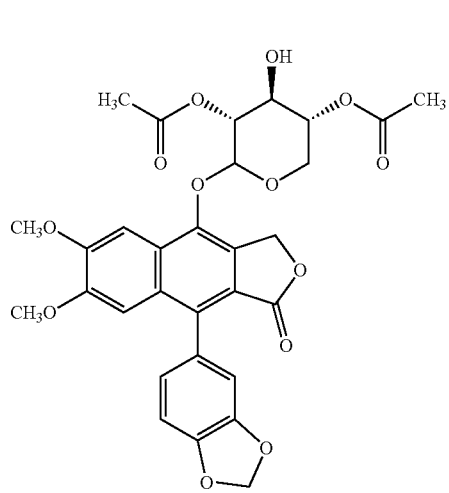
27af
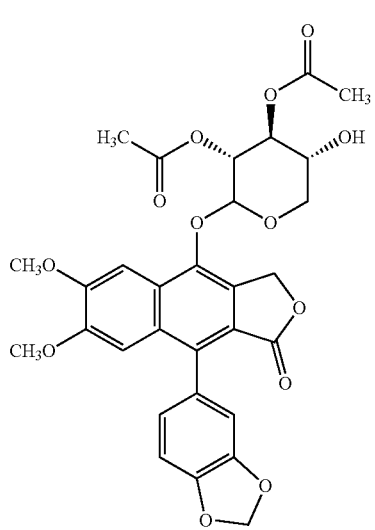

27ba
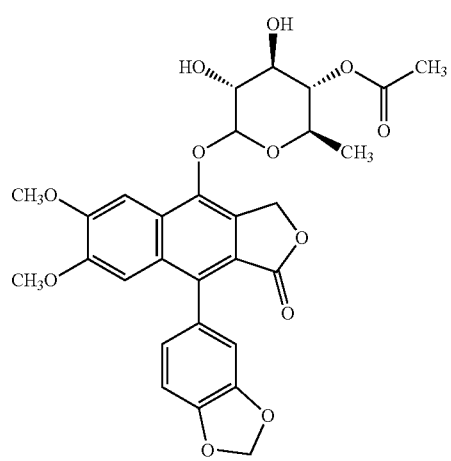
27bb
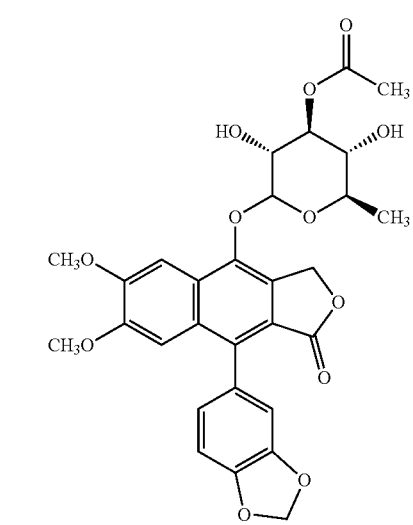
27bc
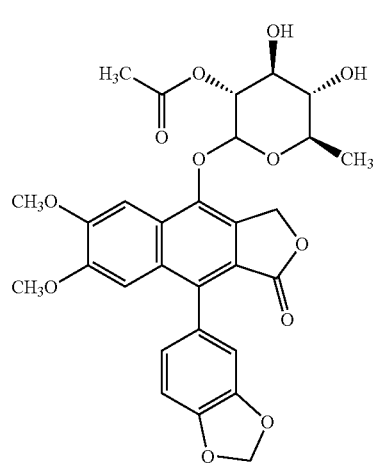
27bd
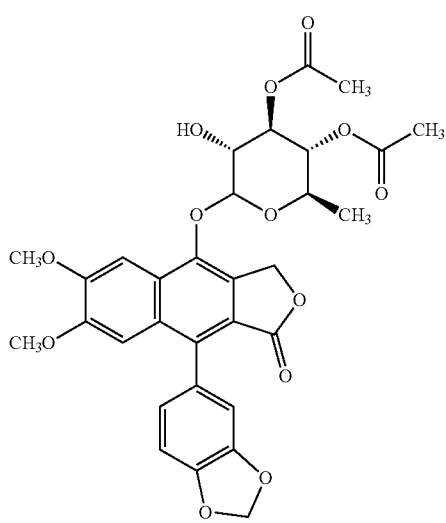
27be
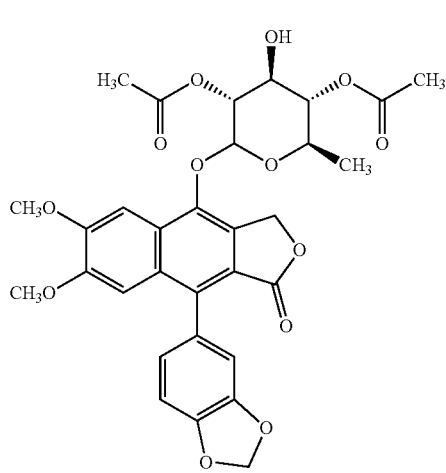
27bf
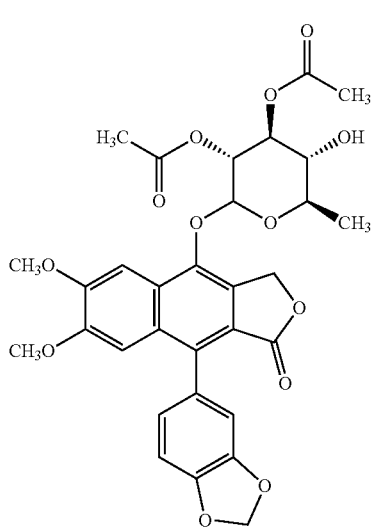

25
-continued
28ab1
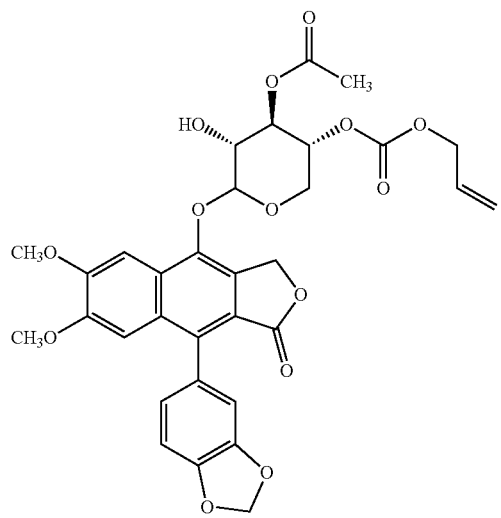
28ab2
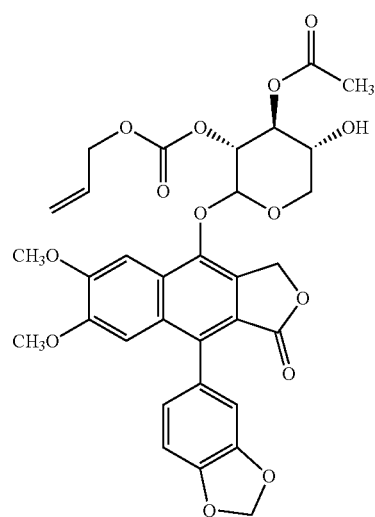
28ab3
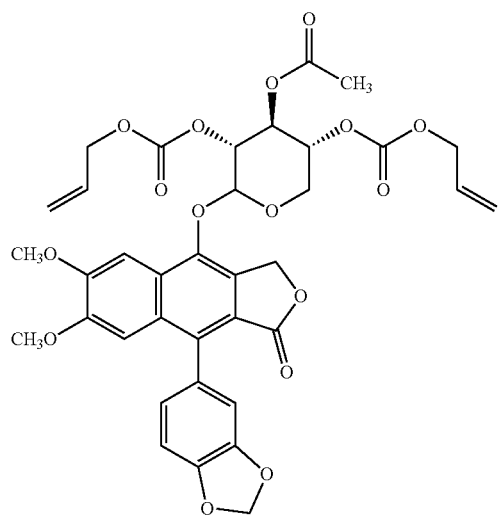
26
-continued
28bb1
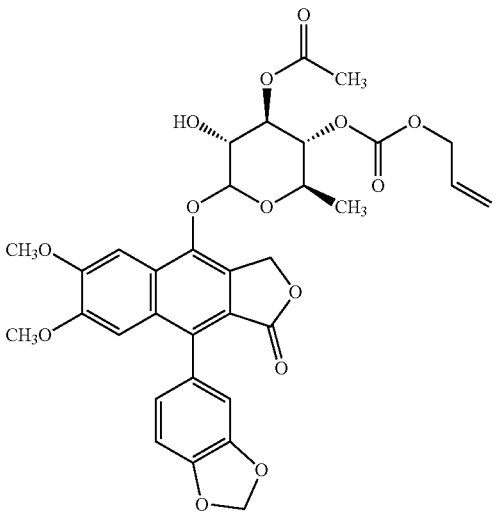
28bb2
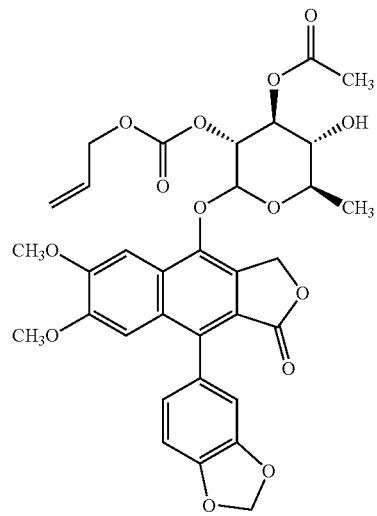
28bb3
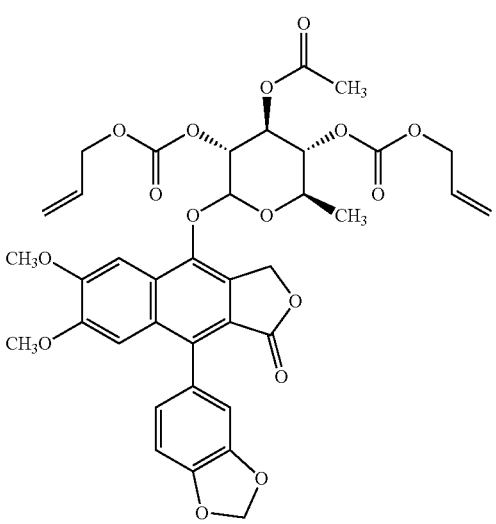

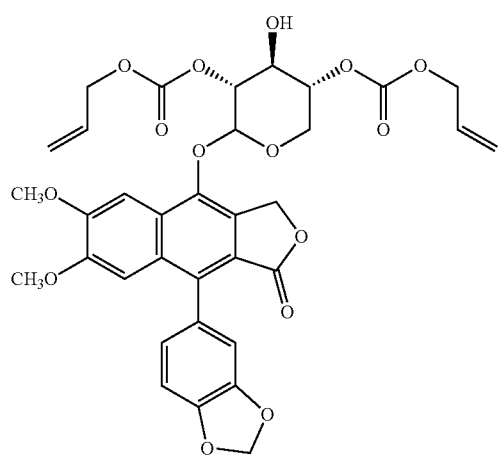
29a
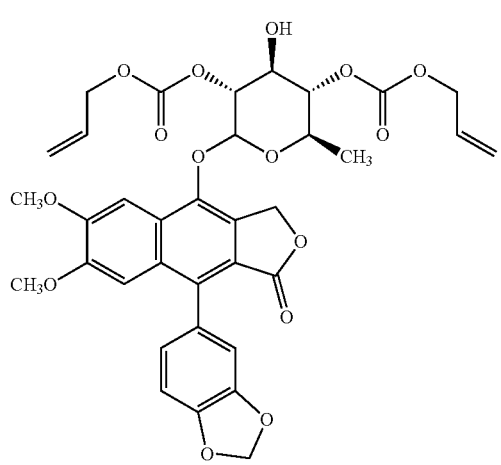
29b
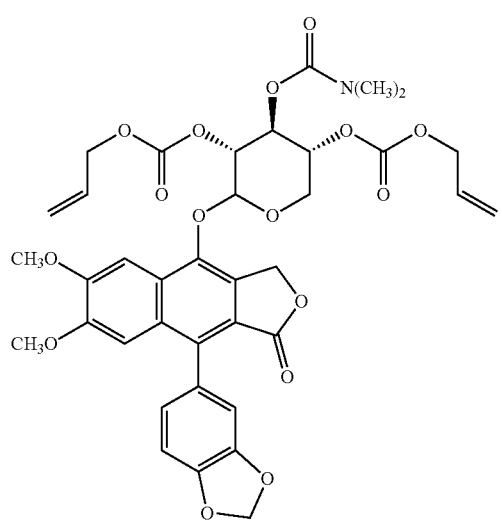
30a
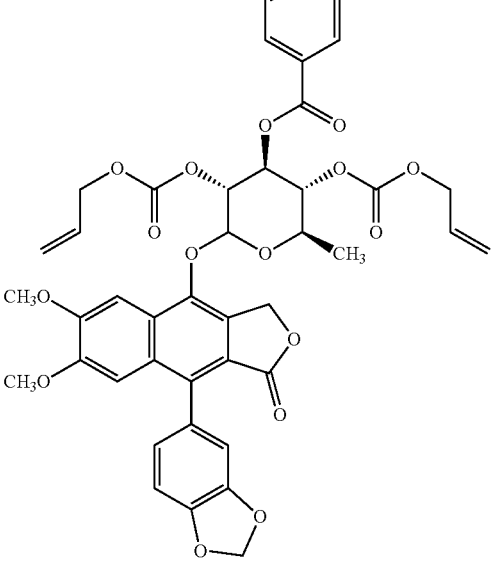
30b
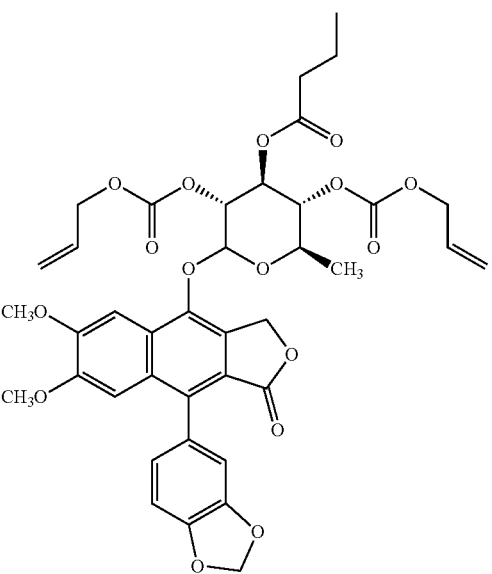
30c

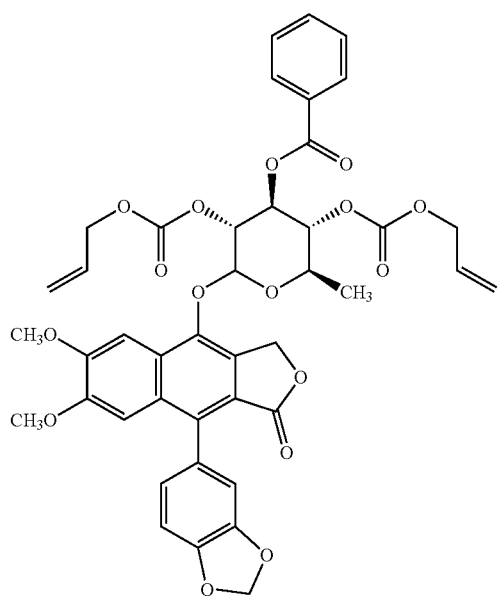
30d
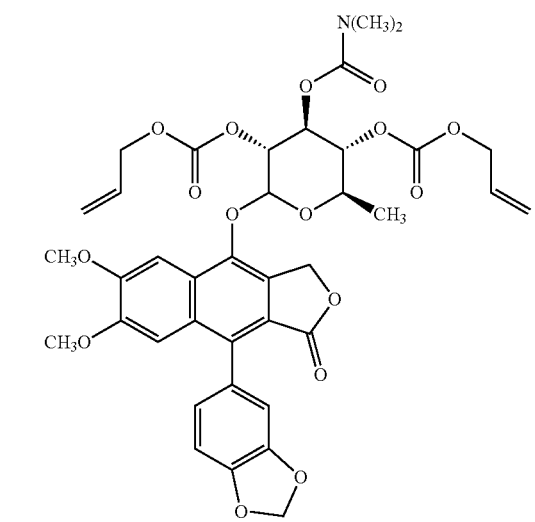
30f
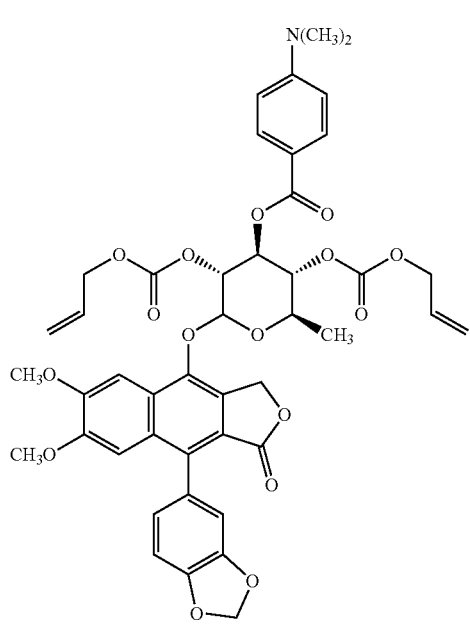
30e
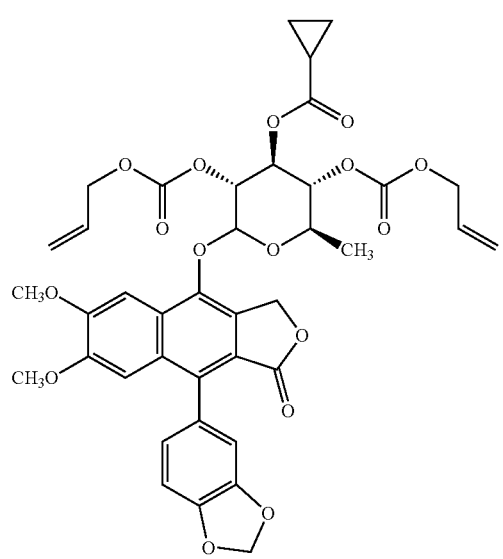
30g

31
-continued
32
-continued
30h
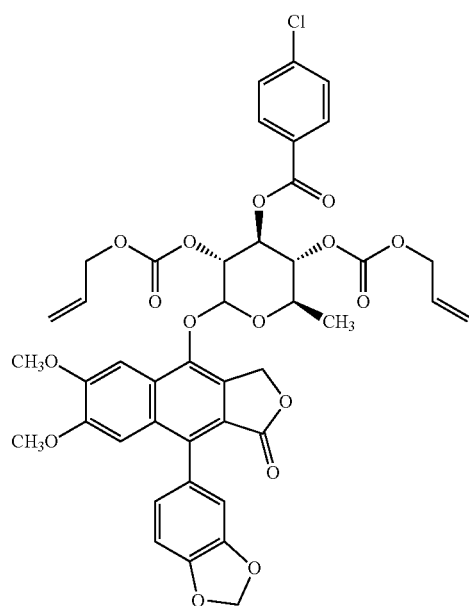
30j
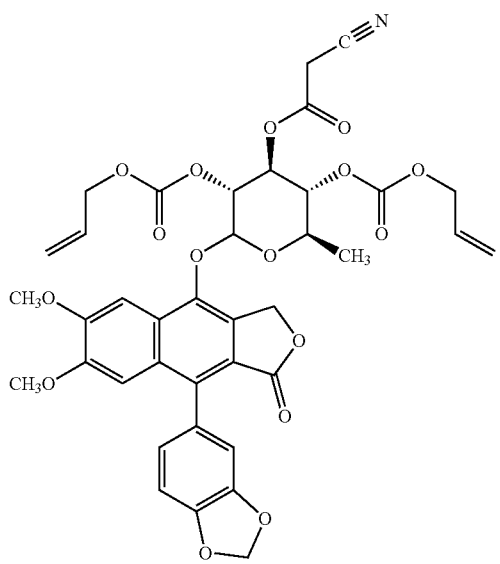
30i
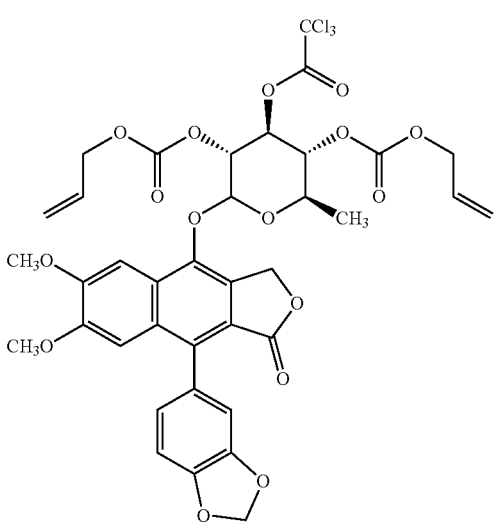
30k

33
-continued
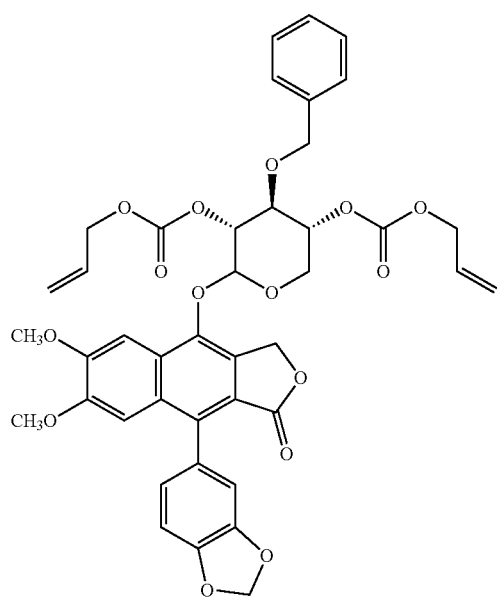
30l
34
-continued
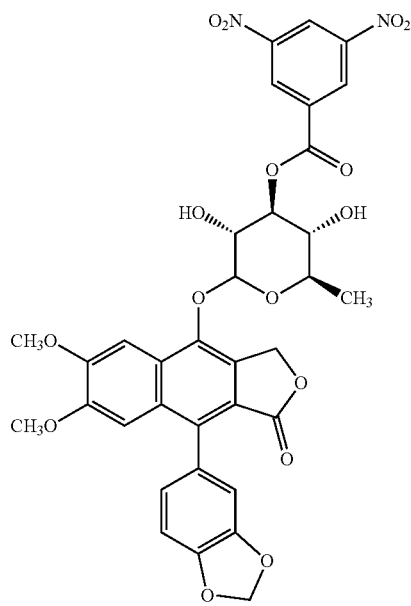
31b
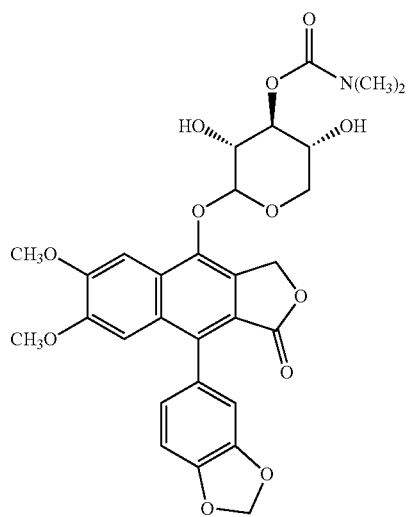
31a
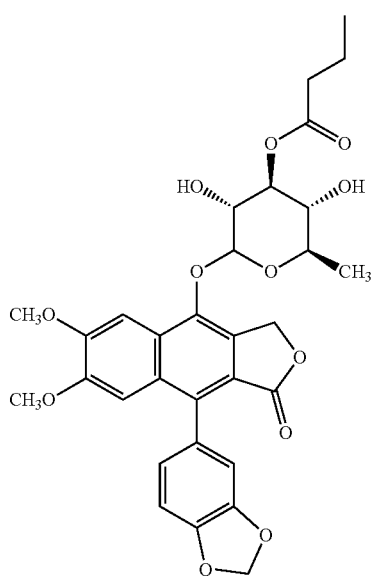
31c -continued
31d
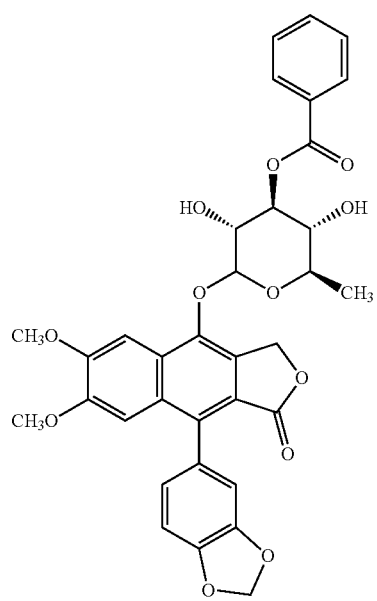
31e
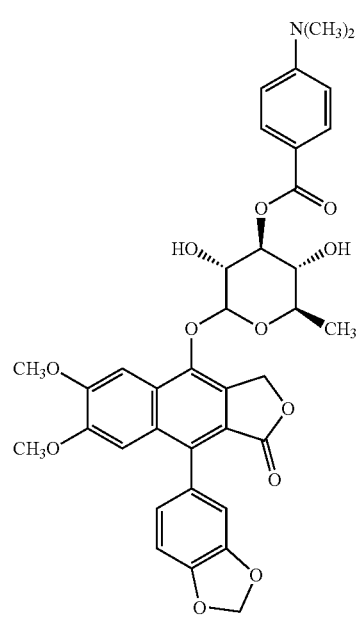
31f
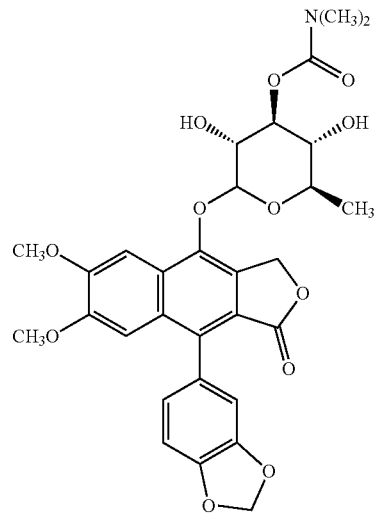
31g
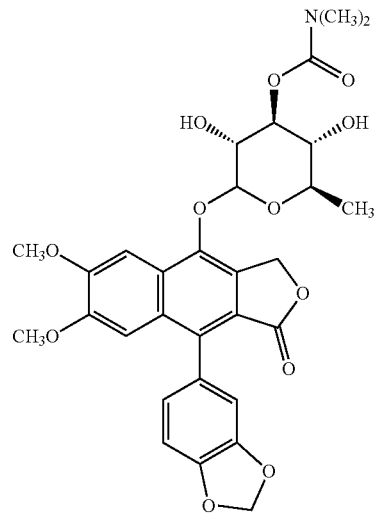
31h
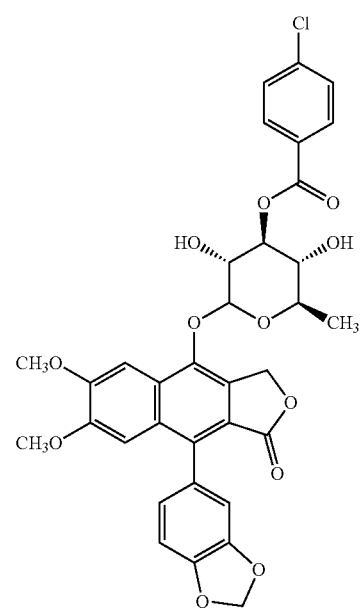

31i
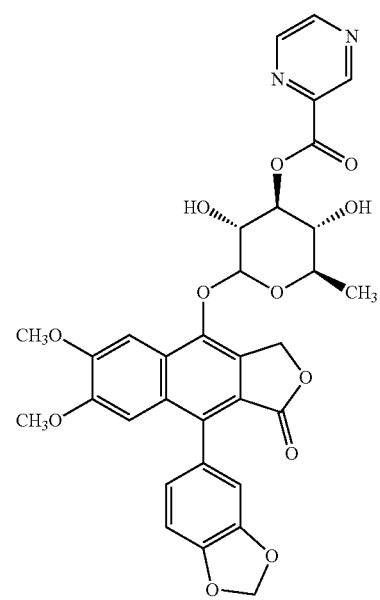
31j
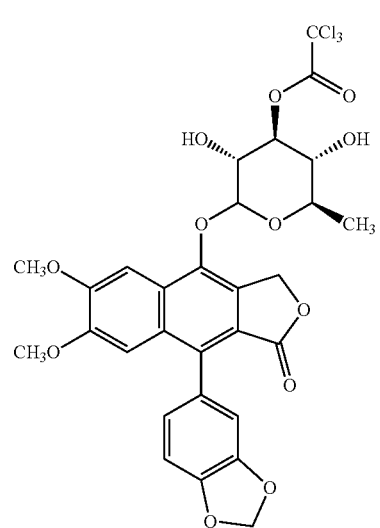
31k
31l
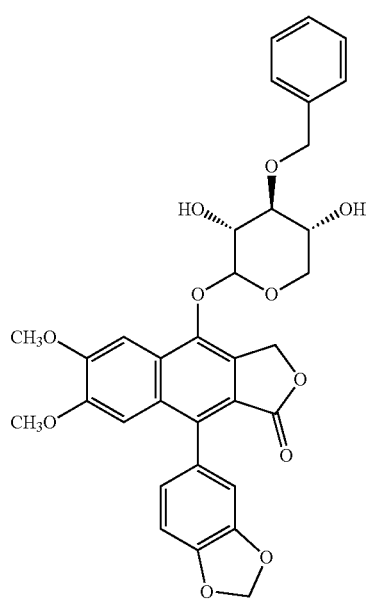
32a
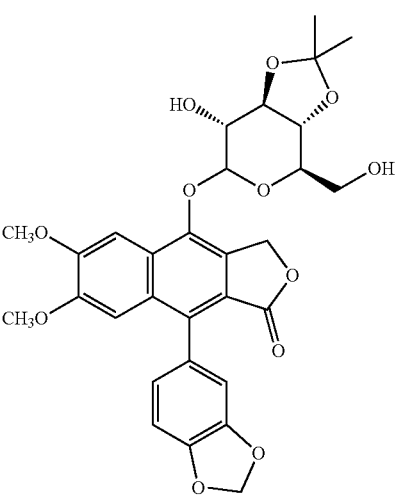
32b
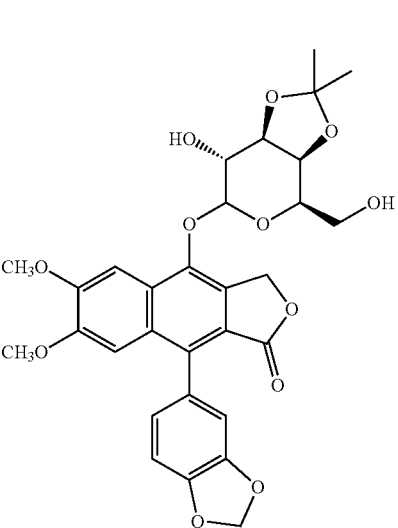

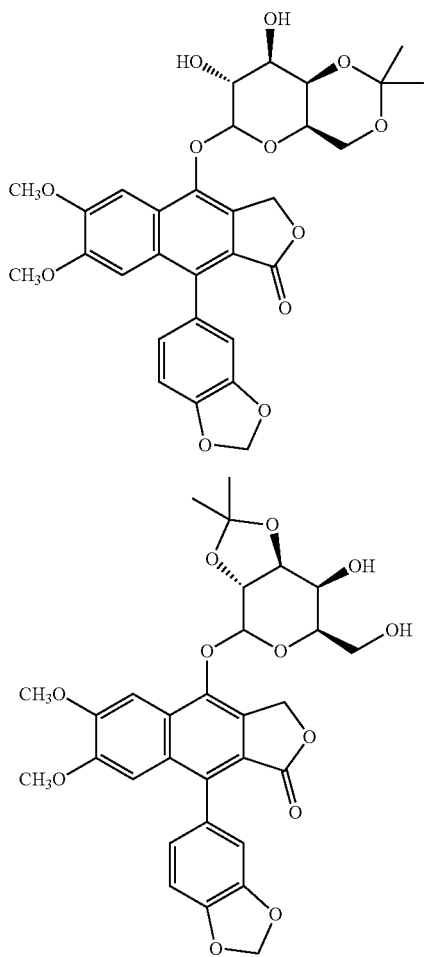

In certain embodiments of the method, the viral infection is selected from the group consisting of HIV, coronaviruses, influenza viruses, Ebola virus, and Marburg virus.

In certain embodiments of the method, each of $R^3$ and $R^4$ is —OCH$_3$; $R^8$ and $R^9$ taken together with the carbon atoms to which they are attached form a methylenedioxy ring; $R^{11}$ and $R^{12}$ taken together form oxo; $R^{19}$, $R^{21}$, $R^{23}$, and $R^{25}$ are each hydrogen; $R^{20}$, $R^{22}$, and $R^{24}$ are each independently selected from the group consisting of —OR$^{27}$, —OC(O)N(R$^{27}$)R$^{27}$, —OC(O)R$^{27}$ and —OC(O)OR$^{27}$; $R^{26}$ is hydrogen, methyl, —OR$^{27}$, —OC(O)R$^{27}$ or —CH$_2$—OC(O)R$^{27}$; or $R^{20}$ and $R^{22}$ taken together with the carbon atoms to which they are attached form a 5-6 membered heterocyclyl, which is optionally substituted with 1 or 2 group(s) independently selected from C$_{1-6}$ alkyl; or $R^{22}$ and $R^{24}$ taken together with the carbon atoms to which they are attached form a 5-6 membered heterocyclyl, which is optionally substituted with 1 or 2 group(s) independently selected from C$_{1-6}$ alkyl; or $R^{24}$ and $R^{26}$ taken together with the carbon atoms to which they are attached form a 5-6 membered heterocyclyl, which is optionally substituted with 1 or 2 group(s) independently selected from C$_{1-6}$ alkyl; and the glycloside is a monosaccaride; and the viral infection is HIV, coronaviruses, influenza viruses, Ebola virus, or Marburg virus.

In a second aspect, provided herein is a compound of Formula (I):

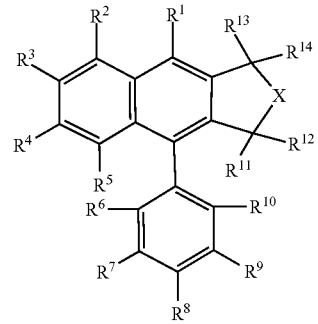

or a pharmaceutically acceptable salt or pro-drug thereof wherein,

X is oxygen or sulfur;

$R^1$ is $R^{15}$, —OR$^{15}$, —C(O)R$^{15}$, or —C(O)OR$^{15}$;

$R^2$, $R^5$, $R^6$, $R^{10}$, $R^{13}$, and $R^{14}$ are each hydrogen;

$R^3$ and $R^4$ are each independently selected from the group consisting of —OR$^5$ and —OC(O)R$^{15}$; or $R^3$ and $R^4$ taken together with the carbon atoms to which they are attached form a 5-6 membered heterocyclyl optionally substituted with 1, 2, 3, 4 or 5 group(s) independently selected from C$_{1-6}$ alkyl and C$_{1-6}$ alkoxy;

$R^7$, $R^8$, and $R^9$ are each independently selected from the group consisting of —OR$^{15}$ and —OC(O)R$^{15}$; or $R^7$ and $R^8$ taken together with the carbon atoms to which they are attached to form a 5-6 membered heterocyclyl optionally substituted with 1, 2, 3, 4 or 5 group(s) independently selected from C$_{1-6}$ alkyl and C$_{1-6}$ alkoxy; or $R^8$ and $R^9$ taken together with the carbon atoms to which they are attached to form a 5-6 membered heterocyclyl optionally substituted with 1, 2, 3, 4 or 5 group(s) independently selected from C$_{1-6}$ alkyl and C$_{1-6}$ alkoxy;

$R^{11}$ and $R^{12}$ taken together form oxo; or while one of $R^{11}$ and $R^{12}$ is hydrogen or halogen, the other one of $R^{11}$ and $R^{12}$ is selected from the group consisting of $R^{15}$, —OR$^{15}$, —C(O)R$^{15}$ and —C(O)OR$^{15}$;

$R^{15}$ for each occurrence is independently selected from the group consisting of hydrogen, halogen, trichloromethyl, trifluoromethyl, cyano, nitro, heteroaryl, —OR$^{17}$, —C(O)R$^{18}$, —C(O)N(R$^{17}$)R$^{18}$, —C(O)OR$^{17}$, —OC(O)R$^{17}$, —S(O)$_2$R$^{17}$, —S(O)$_2$N(R$^{17}$)R$^{18}$, —N=C(R$^{17}$)R$^{18}$, —N(R$^{17}$)R$^{18}$, —N(R$^{17}$)N(R$^{17}$)R$^{18}$, —N(R$^{17}$)C(O)R$^{18}$, —N(R$^{17}$)S(O)$_2$R$^{18}$, 1,3,2-dioxaborolane optionally substituted with 1, 2, 3, or 4 group(s) independently selected from alkyl, a glycosidic group, alkynyl optionally substituted with a trialkylsilane, hydrocarbyl optionally substituted with 1, 2, 3, 4 or 5 group(s) independently selected from R$^{16}$, heterocyclcyl optionally substituted with 1, 2, 3, 4 or 5 group(s) independently selected from R$^{16}$, and —(CH$_2$)$_k$-heterocyclyl optionally substituted with 1, 2, 3, 4 or 5 group(s) independently selected from R$^{16}$, wherein k is an integer between 1-6;

$R^{16}$ for each occurrence is independently selected from the group consisting of alkynyl, halogen, trichloromethyl, trifluoromethyl, cyano, nitro, oxo, =NR$^{17}$, —OR$^{17}$, —C(O)R$^{18}$, —C(O)N(R$^{17}$)R$^{18}$, —C(O)OR$^{17}$, —OC(O)R$^{17}$, —S(O)$_2$R$^{17}$, —S(O)$_2$N(R$^{17}$)R$^{18}$, —N(R$^{17}$)R$^{18}$, —N(R$^{17}$)N(R$^{17}$)R$^{18}$, —N(R$^{17}$)C(O)R$^{18}$ and —N(R$^{17}$)S(O)$_2$R$^{18}$; and $R^{17}$ and $R^{18}$ for each occurrence are independently hydrogen, alkyl, alkynyl, cycloalkyl, aryl, or heteroaryl, or selected from hydrocarbyl and heterocyclyl, either of which is optionally substituted with 1, 2, 3, 4 or 5 group(s)

independently selected from the group consisting of halogen, cyano, amino, hydroxy, $C_{1-6}$ alkyl and $C_{1-6}$ alkoxy,
with the proviso that the compound of Formula (I) is not a compound selected from the group consisting of 5, 15a, 15b, 16, 17b, 19d, 25a-25g, and 26a-26g:
5
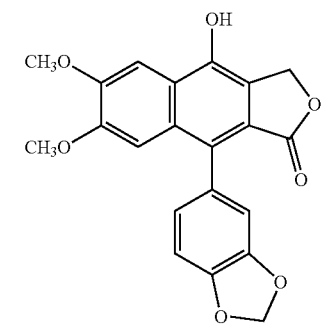
15a
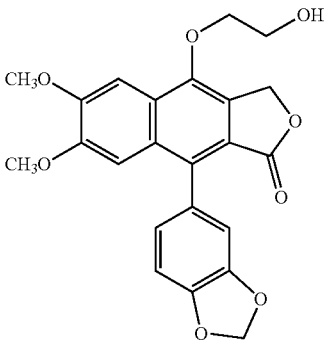
15b
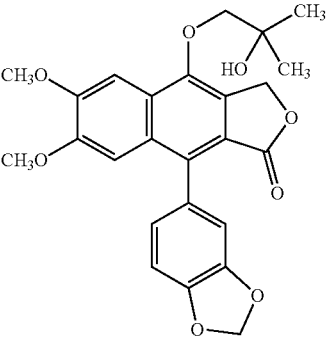
16
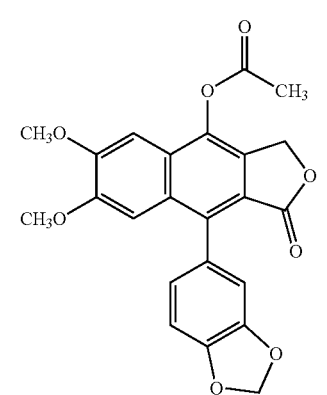
-continued
17b
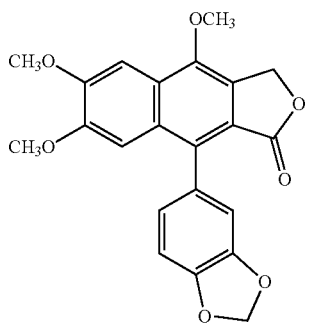
19d
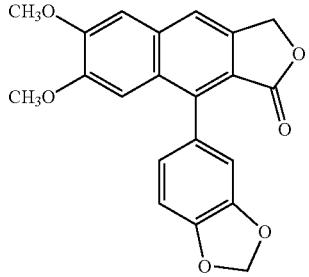
25a
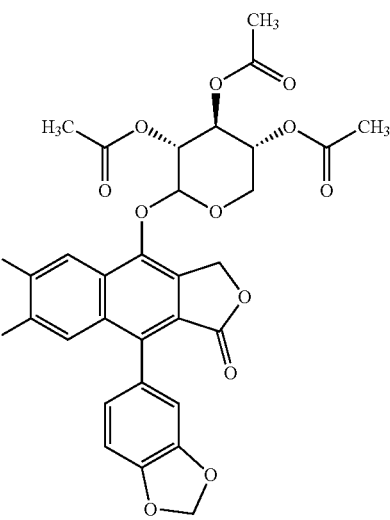
25b
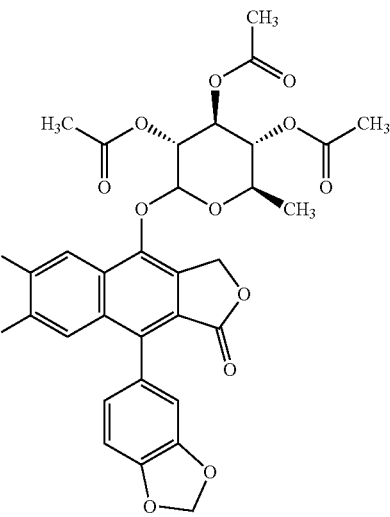

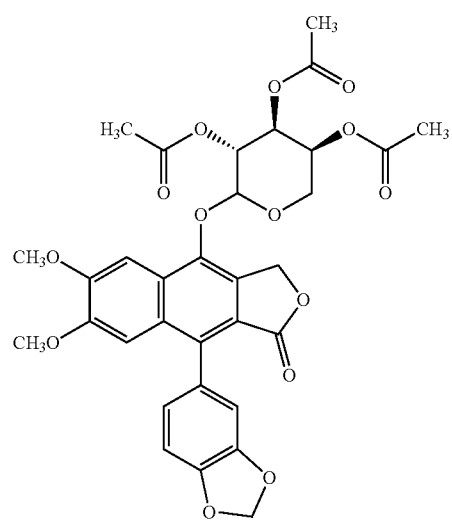
25c
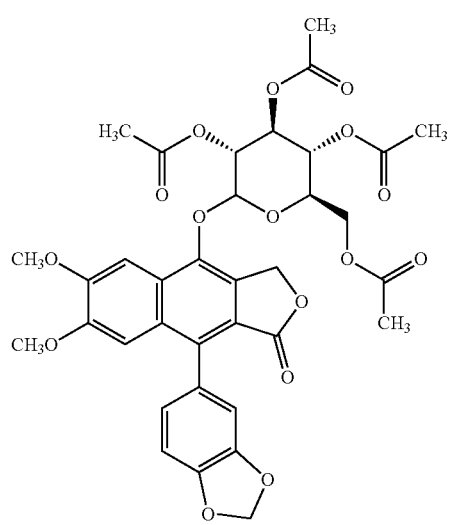
25f
25d
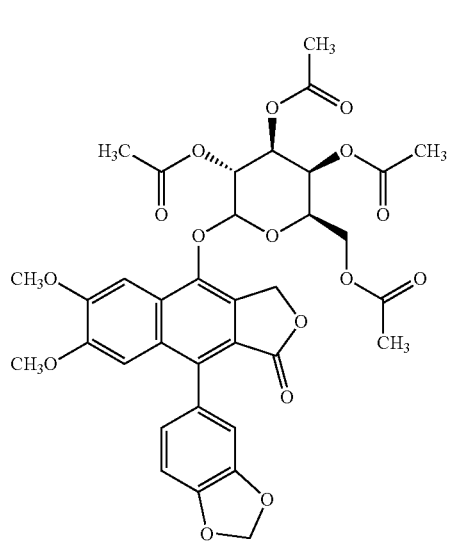
25g
25e
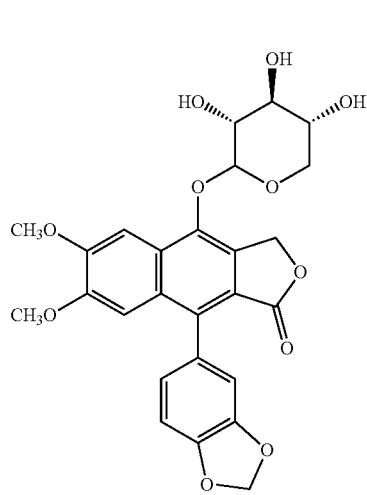
26a

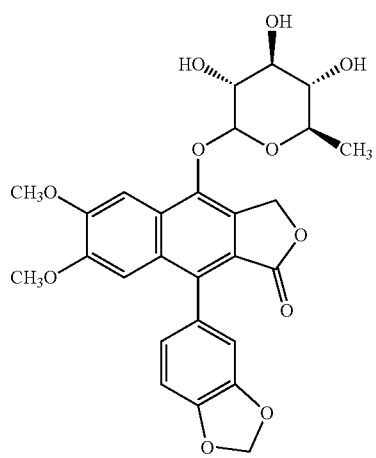

26b

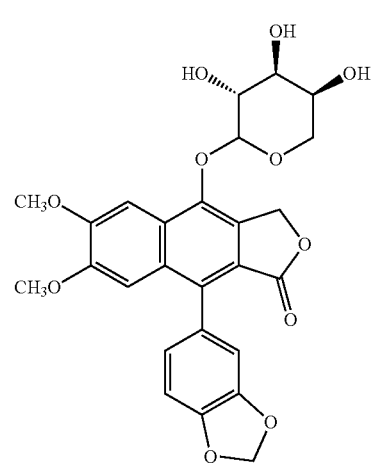

26c

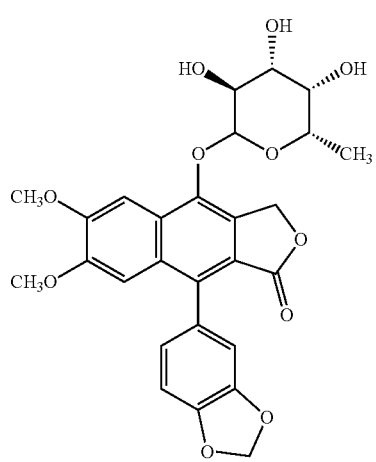

26d

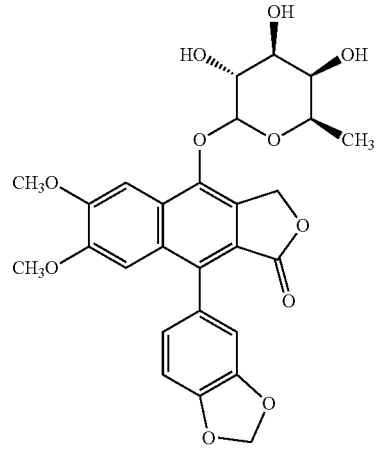

26e

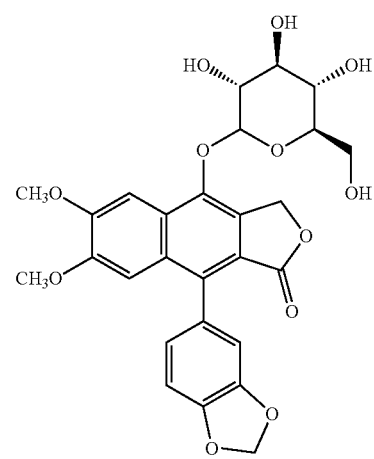

26f

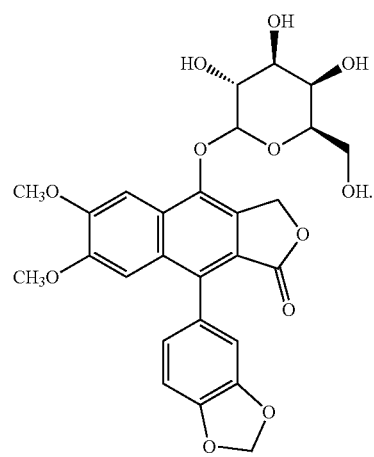

26g

In certain embodiments, each of $R^3$ and $R^4$ is —O-alkyl; $R^8$ and $R^9$ taken together with the carbon atoms to which they are attached form a methylenedioxy ring; and $R^{11}$ and $R^{12}$ taken together form oxo.

In certain embodiments of the compound, $R^1$ is heteroaryl, —$OR^{15}$, —$C(O)R^{15}$, —$N(R^7)R^{18}$, —$N(R^{17})C(O)R^{18}$, —N=$C(R^{17})R^{18}$, pinacolboryl, —$OS(O)_2CF_3$, alkynyl optionally substituted with a trialkylsilane, or heterocyclcyl optionally substituted with 1 or 2 group(s) independently selected from $R^{16}$; or $R^1$ is —$O(CH_2)_m$-cyano, —$O(CH_2)_m$-alkynyl, —$O(CH_2)_m$—$C(O)N(R^{17})R^{18}$, or —$O(CH_2)_m$—$C(O)OR^{17}$, wherein m is a whole number selected from 1-4.

In certain embodiments of the compound, $R^1$ is heteroaryl, —$OR^{15}$, —$C(O)R^{15}$, —$N(R^{17})R^{18}$, —$N(R^{17})C(O)R^{18}$, —$N=C(R^{17})R^{18}$, pinacolboryl, —$OS(O)_2CF_3$, heterocyclcyl optionally substituted with 1 or 2 group(s) independently selected from $R^{16}$, or alkynyl optionally substituted with a trialkylsilane; or $R^1$ is —$O(CH_2)_m$-cyano, —$O(CH_2)_m$-alkynyl, —$O(CH_2)_m$—$C(O)N(R^{17})R^{18}$, or —$O(CH_2)_m$—$C(O)OR^{17}$, wherein m is a whole number selected from 1-4; each of $R^3$ and $R^4$ is —OMe; $R^8$ and $R^9$ taken together with the carbon atoms to which they are attached form a methylenedioxy ring; and $R^{11}$ and $R^{12}$ taken together form oxo.

In certain embodiments of the compound, $R^1$ is alkynyl, pinacolboryl; —$N(R^{17})R^{18}$, —$OCH_2$-cyano, —$OCH_2$-alkynyl, —$OCH_2$—$C(O)N(R^{17})R^{18}$, or —$OCH_2$—$C(O)OR^{17}$.

In certain embodiments of the compound, the compound is selected from the group consisting of 12a, 12b, 13, 14a, 14b, 17a, 17c, 17d, 17e, 17f, 17g, 17h, 18, 19a, 19b, 19c, 19e, 19f, 19g, 19h, 19i, 19j, 19k, 19l, 19m, 19n, 19o, 19p, 20, 21, 22, 23 and 24:

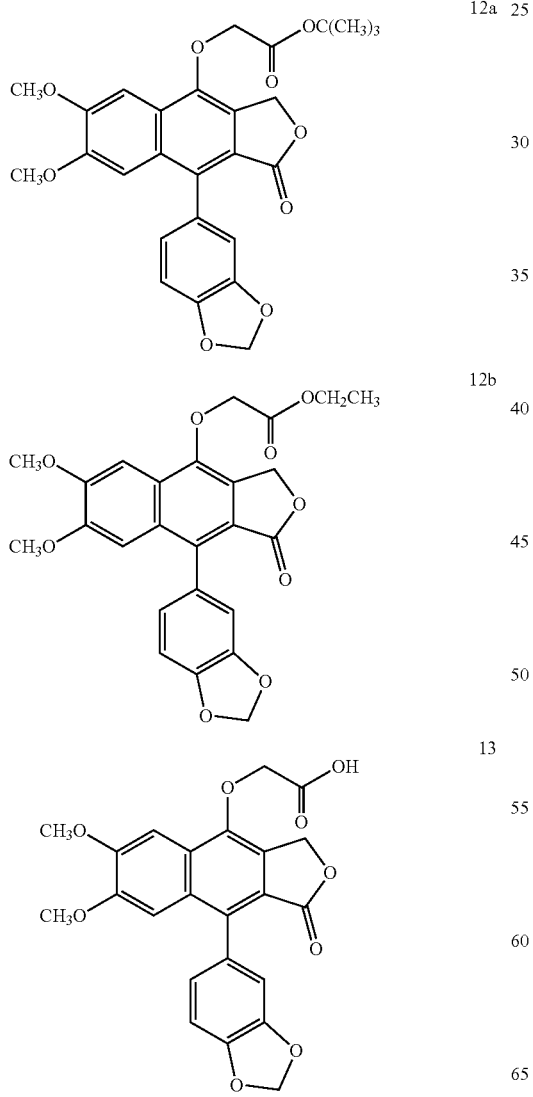

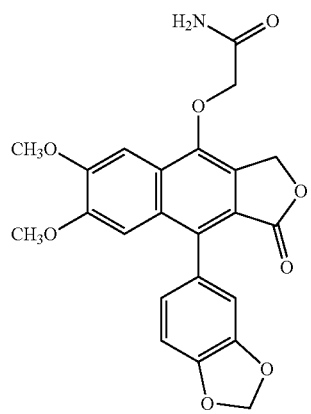

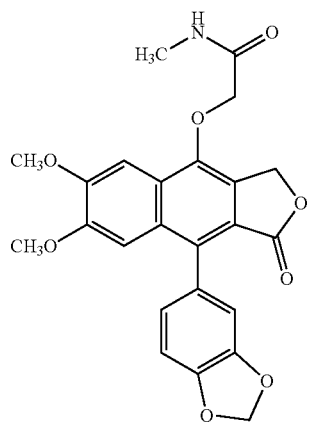

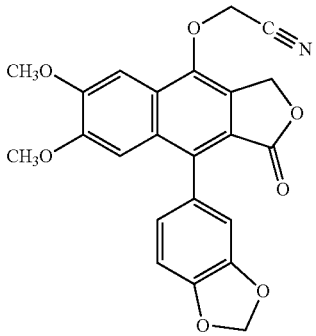

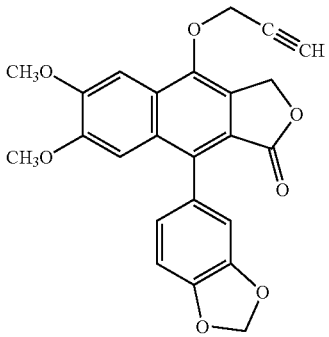

17d
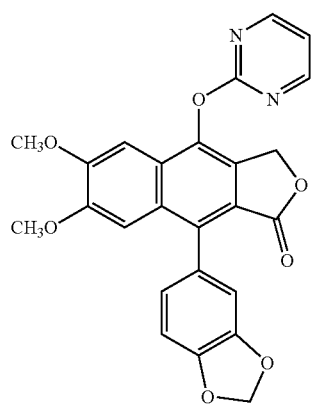
17e
17f
17g
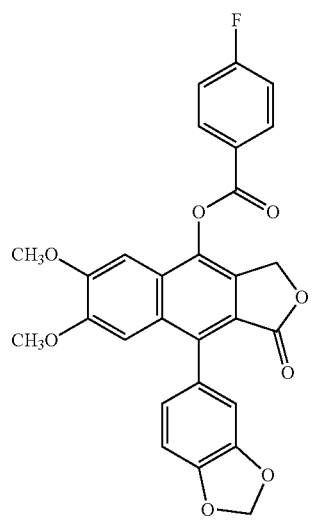
17h
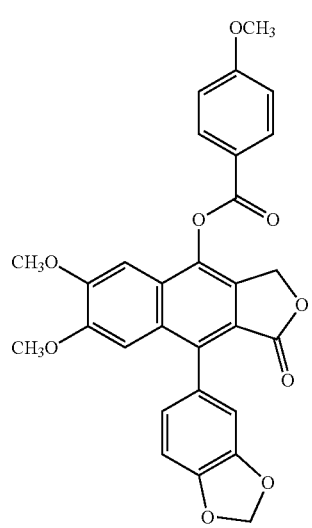
18
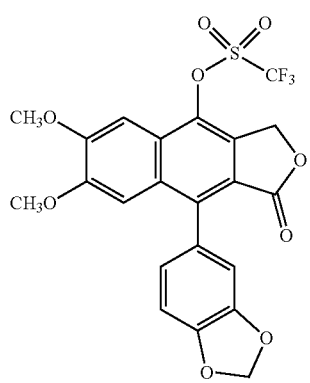

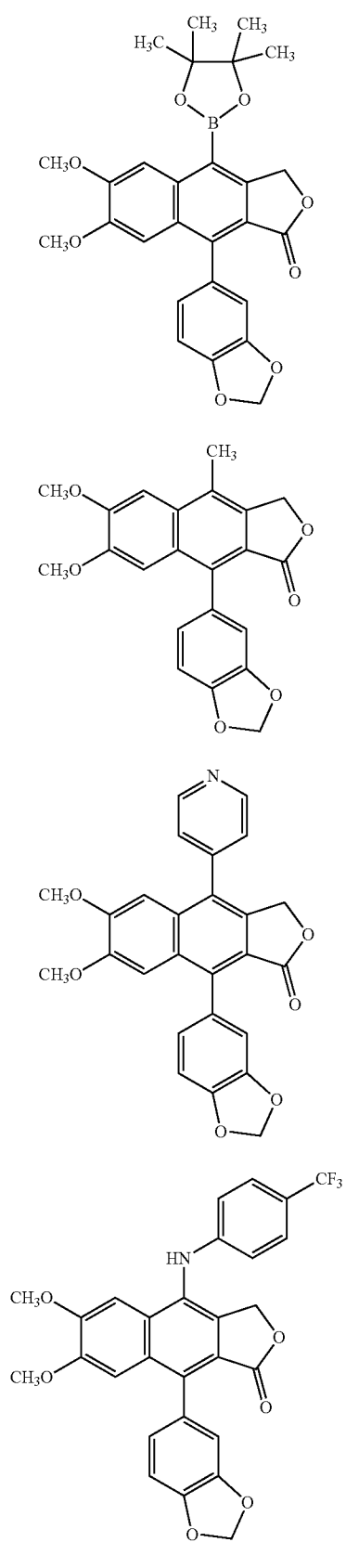
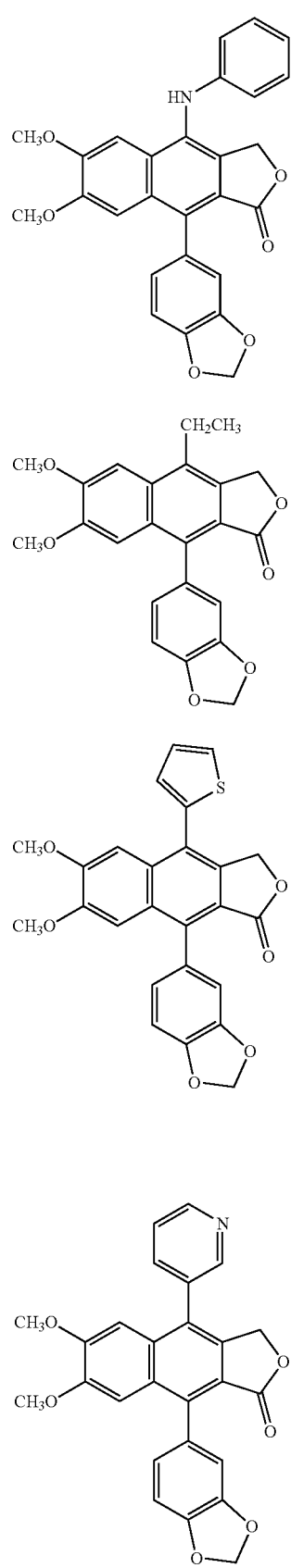

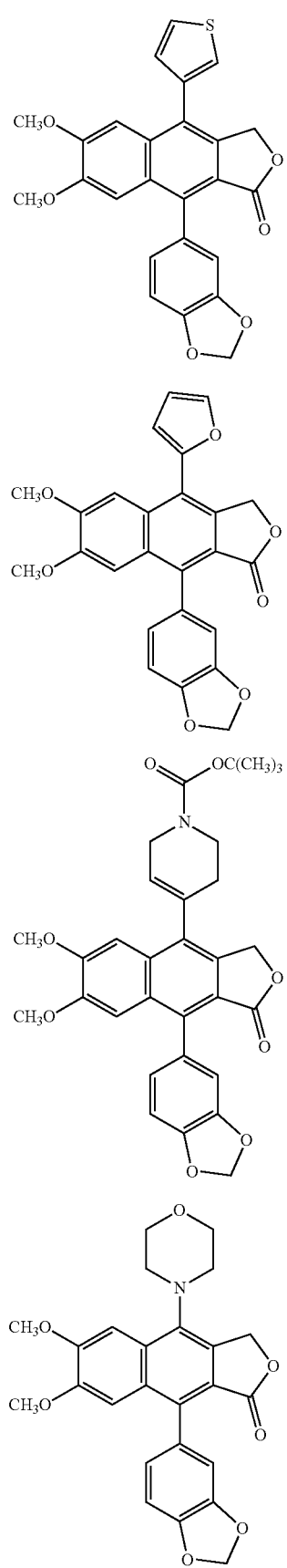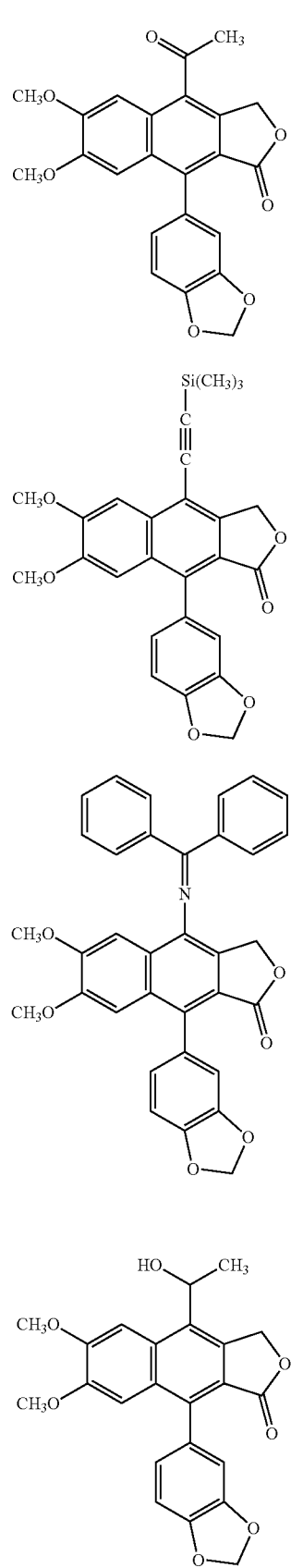

-continued

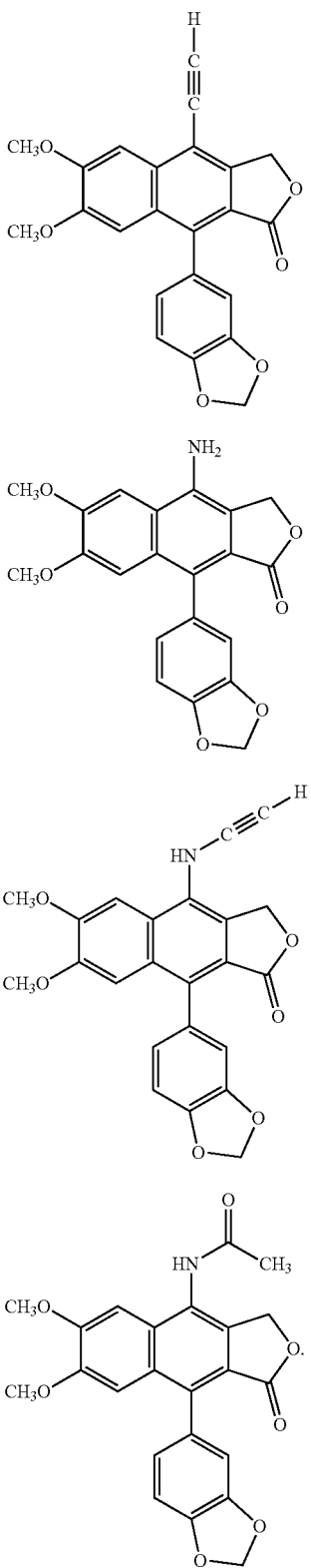

In certain embodiments of the compound, $R^1$ is a glycosidic group selected from the group consisting of a monosaccharide, disaccharide, trisaccharide, tetrasaccharide and polysaccharide group containing less than 30 monosaccharides, wherein the glycosidic group comprises one or more monosaccharides isomers selected from the group consisting of α-D, α-L, β-D, and β-L.

In certain embodiments of the compound, $R^1$ is a glycosidic group represented by the Formula (V):

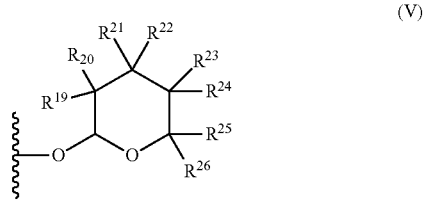

(V)

wherein, $R^{19}$ and $R^{20}$ taken together to form oxo; or while one of $R^{19}$ and $R^{20}$ is hydrogen or halogen, the other one of $R^{19}$ and $R^{20}$ is selected from the group consisting of $R^{27}$, —$OR^{27}$, —$OC(O)R^{27}$, —$OC(O)N(R^{27})R^{27}$, and —$OC(O)OR^{27}$;

$R^{21}$ and $R^{22}$ taken together to form oxo; or while one of $R^{21}$ and $R^{22}$ is hydrogen or halogen, the other one of $R^{21}$ and $R^{22}$ is selected from the group consisting of $R^{27}$, —$OR^{27}$, —$OC(O)R^{27}$, —$OC(O)N(R^{27})R^{27}$, and —$OC(O)OR^{27}$; or $R^{20}$ and $R^{22}$ taken together with the carbon atoms to which they are attached to form a 5-6 membered heterocyclyl, which is optionally substituted with 1, 2, 3, 4 or 5 group(s) independently selected from $C_{1-6}$ alkyl and $C_{1-6}$ alkoxy;

$R^{23}$ and $R^{24}$ taken together to form oxo; or while one of $R^{23}$ and $R^{24}$ is hydrogen or halogen, the other one of $R^{23}$ and $R^{24}$ is selected from the group consisting of $R^{27}$, —$OR^{27}$, —$OC(O)R^{27}$, —$OC(O)N(R^{27})R^{27}$, and —$OC(O)OR^{27}$; or $R^{22}$ and $R^{24}$ taken together with the carbon atoms to which they are attached to form a 5-6 membered heterocyclyl, which is optionally substituted with 1, 2, 3, 4 or 5 group(s) independently selected from $C_{1-6}$ alkyl and $C_{1-6}$ alkoxy;

$R^{25}$ and $R^{26}$ taken together to form oxo; or while one of $R^{24}$ and $R^{25}$ is hydrogen or halogen, the other one of $R^{25}$ and $R^{26}$ is selected from the group consisting of $R^{27}$, —$OR^{27}$, —$OC(O)R^{27}$, —$OC(O)N(R^{27})R^{27}$, —$OC(O)OR^{27}$, —$CH_2R^{27}$, and —$C(O)R^{27}$; or $R^{24}$ and $R^{26}$ taken together with the carbon atoms to which they are attached to form a 5-6 membered heterocyclyl, which is optionally substituted with 1, 2, 3, 4 or 5 group(s) independently selected from $C_{1-6}$ alkyl and $C_{1-6}$ alkoxy;

$R^{27}$ for each occurrence is independently selected from the group consisting of hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, hydrocarbyl optionally substituted with 1, 2, 3, 4 or 5 group(s) independently selected from $R^{28}$, heterocyclcyl optionally substituted with 1, 2, 3, 4 or 5 group(s) independently selected from $R^{28}$, and —$(CH_2)_k$-heterocyclyl optionally substituted with 1, 2, 3, 4 or 5 group(s) independently selected from $R^{28}$, wherein k is an integer between 1-6;

$R^{28}$ for each occurrence is independently selected from halogen, trichloromethyl, trifluoromethyl, cyano, nitro, oxo, =$NR^{29}$, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$ and —$N(R^{29})S(O)_2R^{30}$; and $R^{29}$ and $R^{30}$ for each occurrence are each independently hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

In certain embodiments of the compound, $R^{19}$, $R^{21}$, $R^{23}$, and $R^{25}$ are each hydrogen; $R^{20}$, $R^{22}$, and $R^{24}$ are each independently selected from the group consisting of —$OR^{27}$, —$OC(O)N(R^{27})R^{27}$, —$OC(O)R^{27}$ and —$OC(O)OR^{27}$; and $R^{26}$ is hydrogen, methyl, —$OR^{27}$, —$OC(O)R^{27}$, or —$CH_2$—$OC(O)R^{27}$; or $R^{20}$ and $R^{22}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{22}$ and $R^{24}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{24}$ and $R^{26}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; and the glycloside is a monosaccaride.

In certain embodiments of the compound, the glycloside is a monosaccharide selected from the group consisting of an α-L isomer and an β-L isomer.

In certain embodiments of the compound, the compound is selected from the group consisting of 27aa, 27ab, 27ac, 27ad, 27ae, 27af, 27ba, 27bb, 27bc, 27bd, 27be, 27bf, 28ab1, 28ab2, 28ab3, 28bb1, 28bb2, 28bb3, 29a, 29b, 30a, 30b, 30c, 30d, 30e, 30f, 30g, 30h, 30i, 30j, 30k, 30l, 31a, 31b, 31c, 31d, 31e, 31f, 31g, 31h, 31i, 31j, 31k, 31l, 32a, 32b, 32c and 32d:

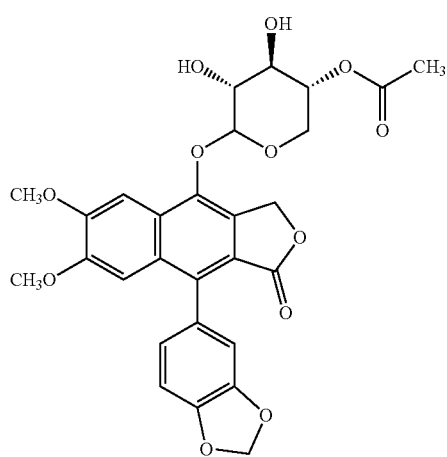

27aa

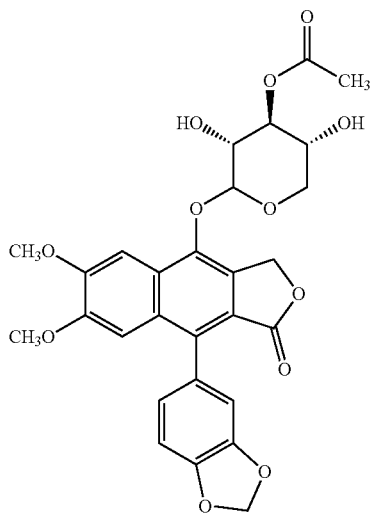

27ab

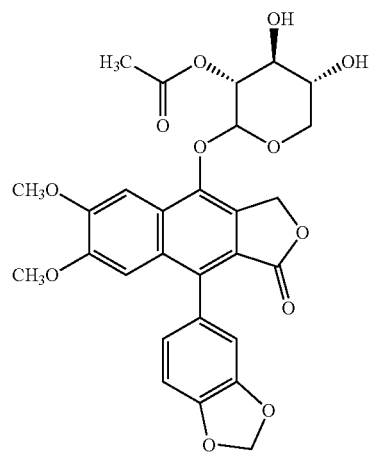

27ac

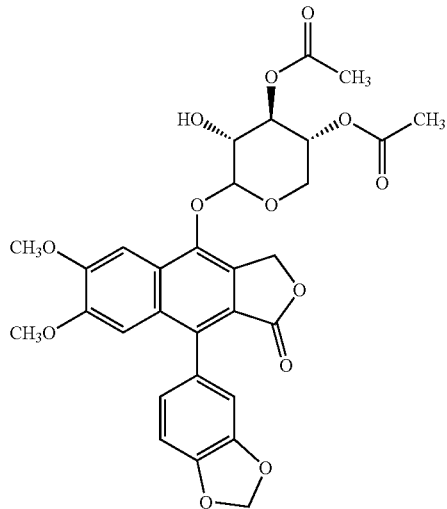

27ad

27ae
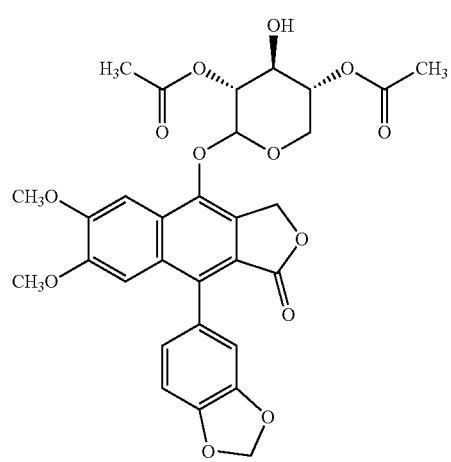
27af
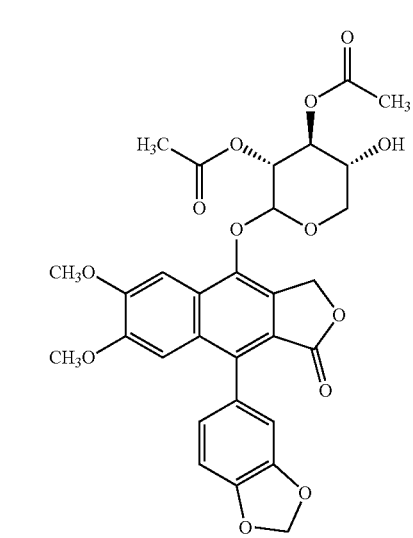
27ba
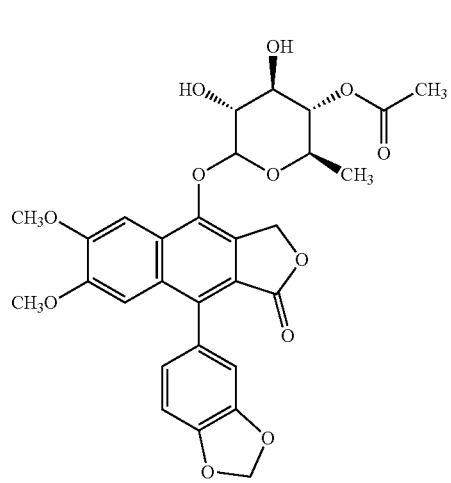
27bb
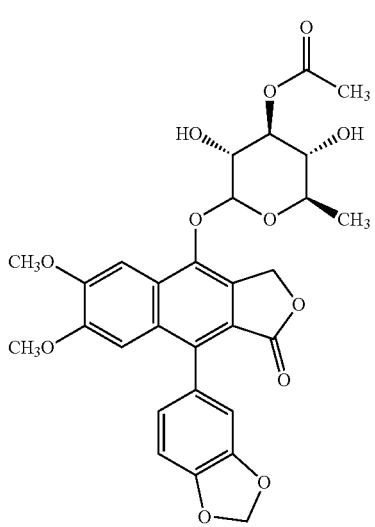
27bc
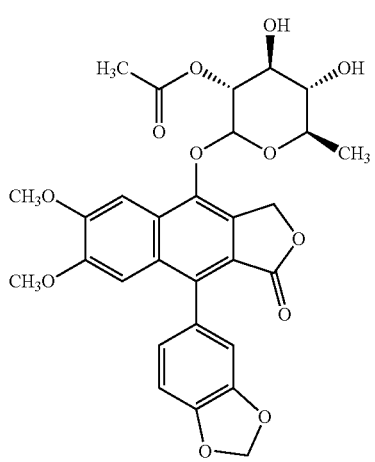
27bd
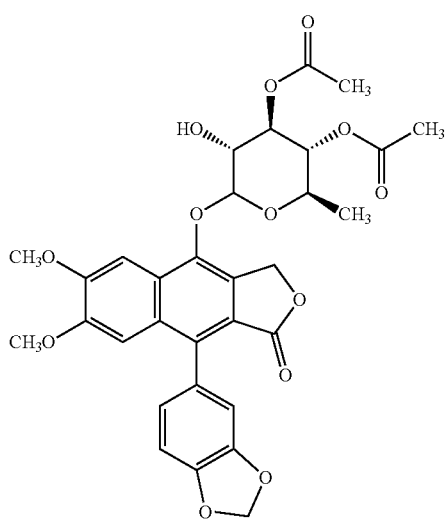

27be
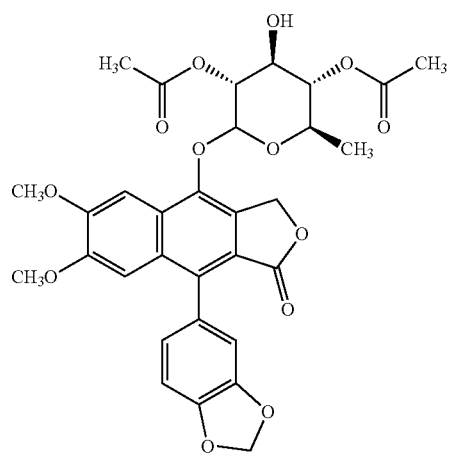
28ab2
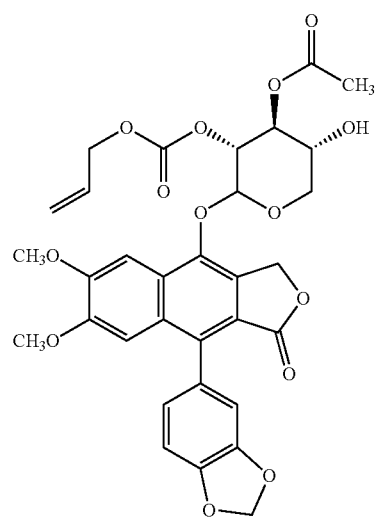
27bf
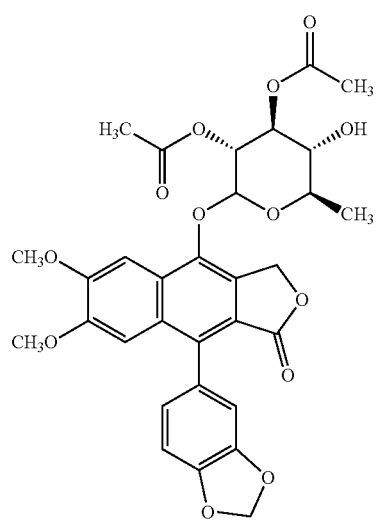
28ab3
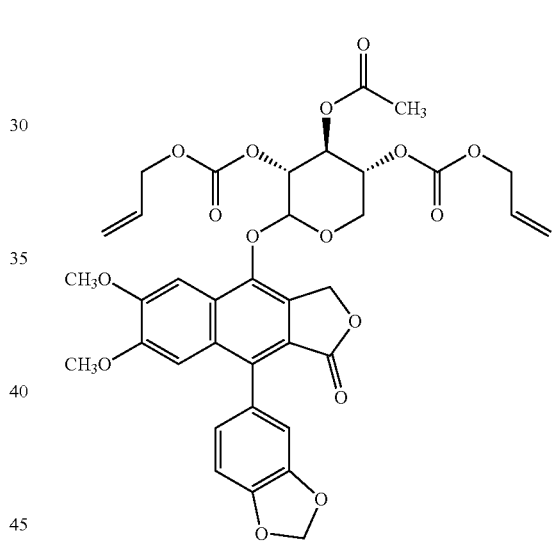
28ab1
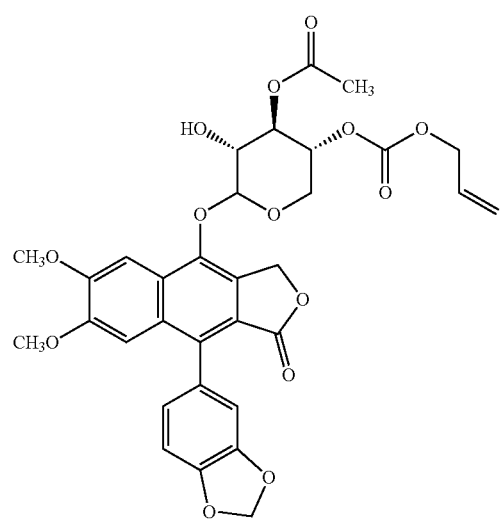
28bb1
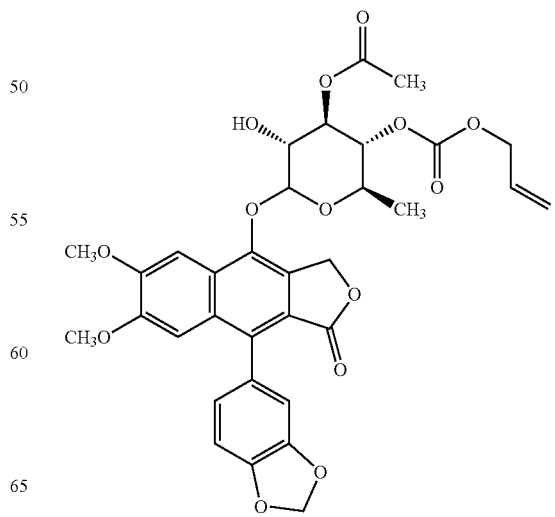

28bb2
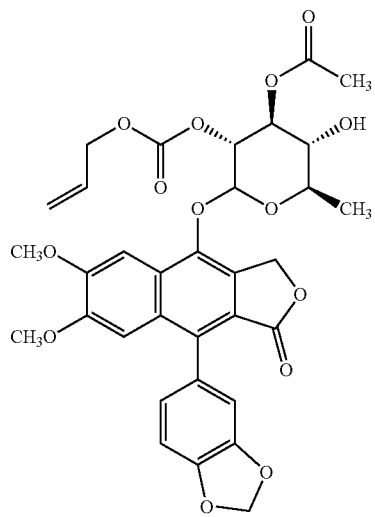
28bb3
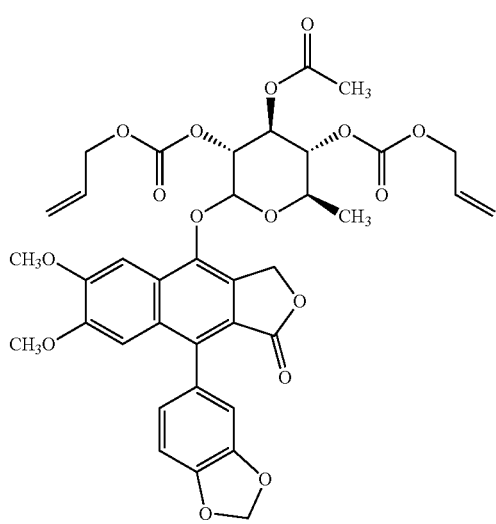
29a
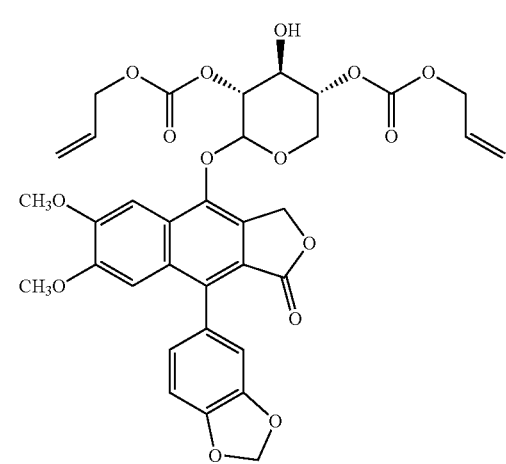
29b
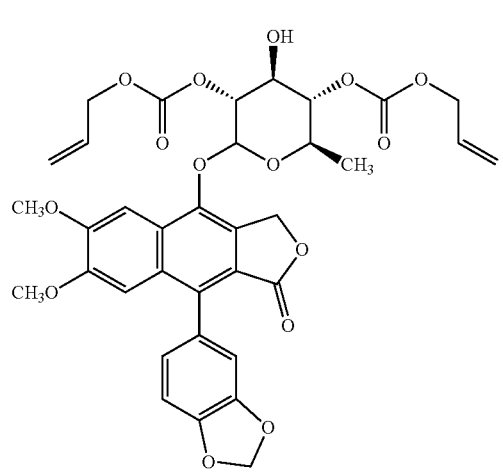
30a
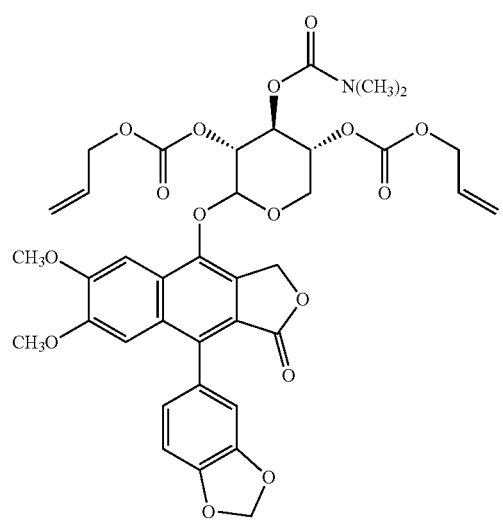
30b
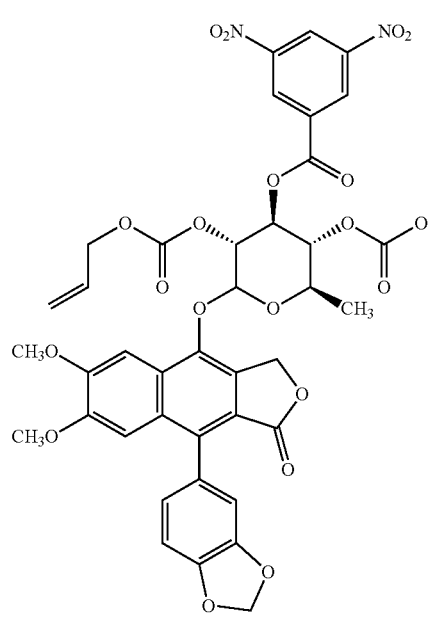

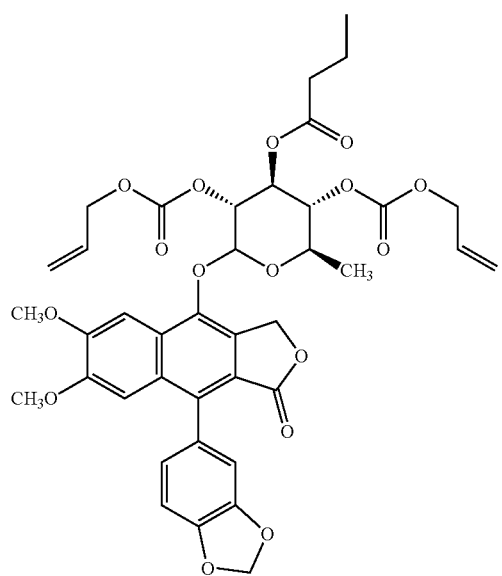
30c
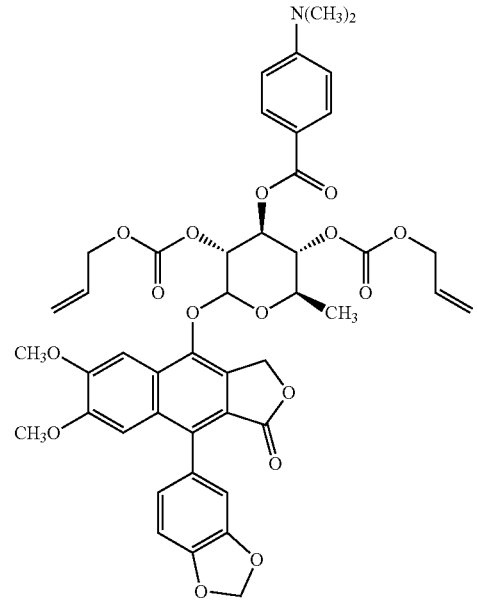
30e
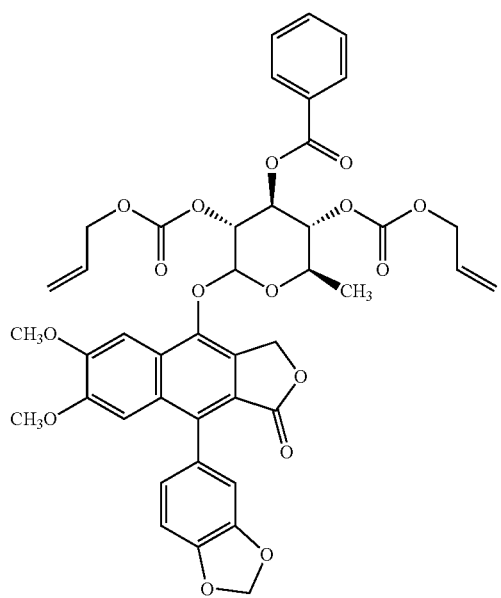
30d
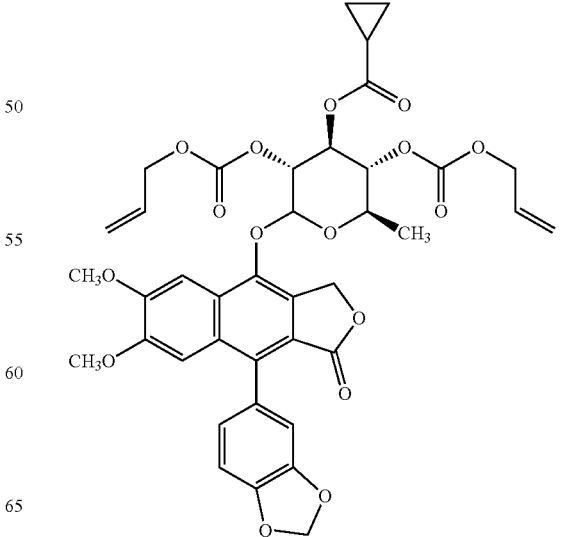
30f
30g

67
-continued
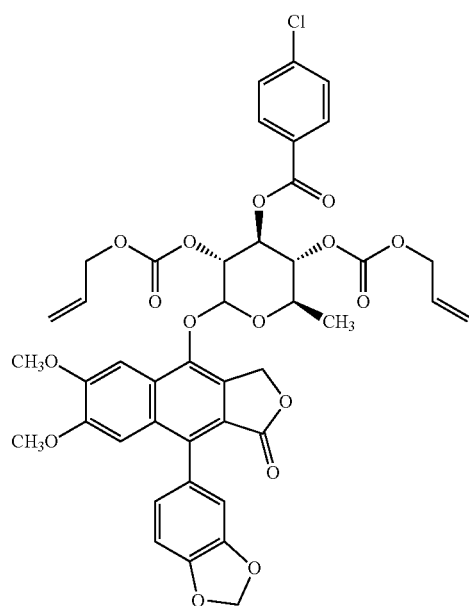
30h
30i
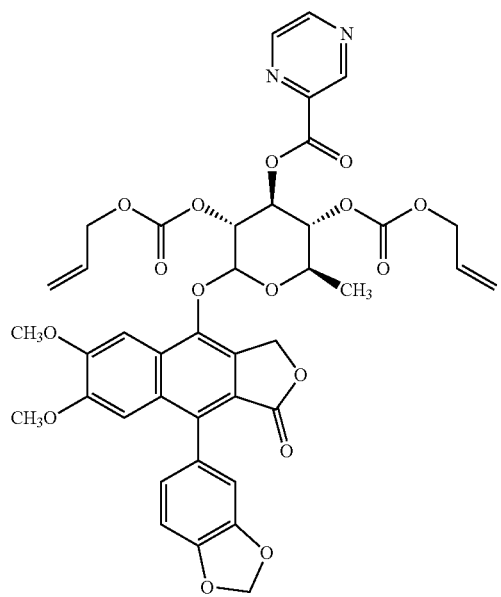
68
-continued
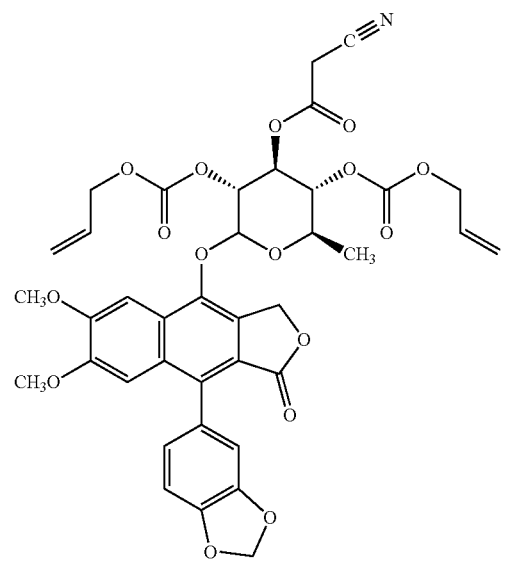
30j
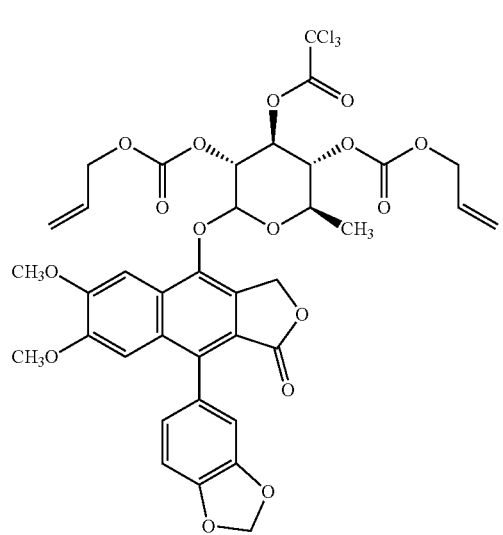
30k
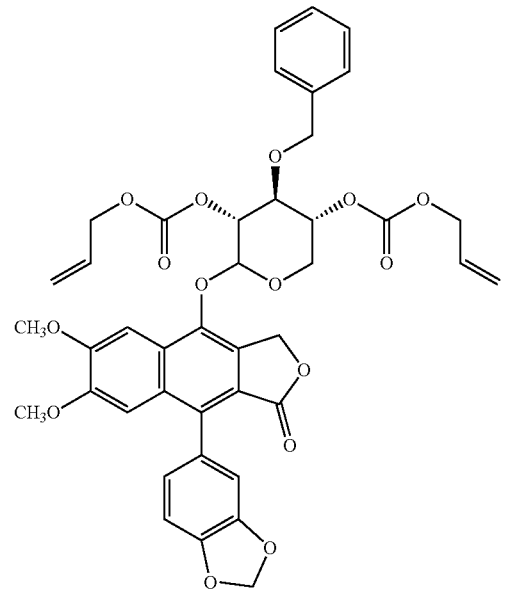
30l -continued

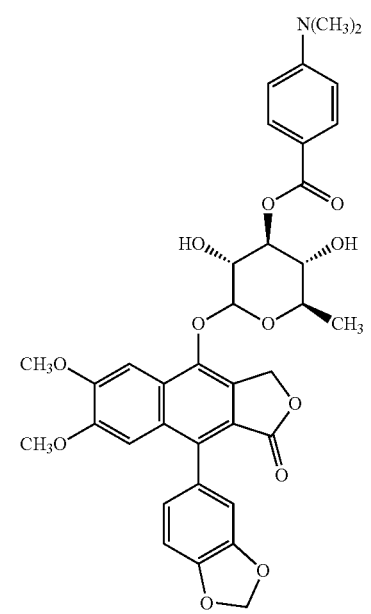
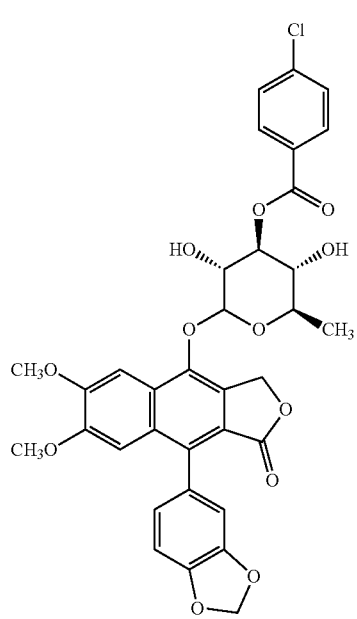

73 74
-continued -continued
31j 32a
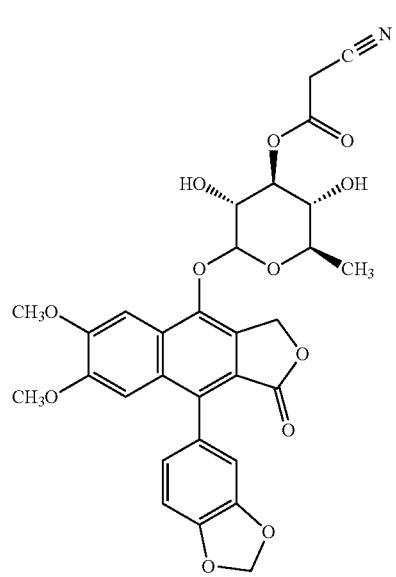 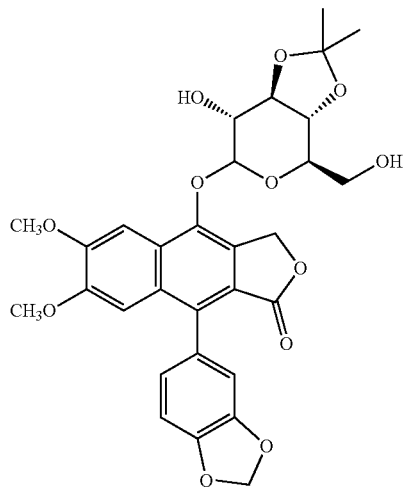
31k 32b
31l 32c
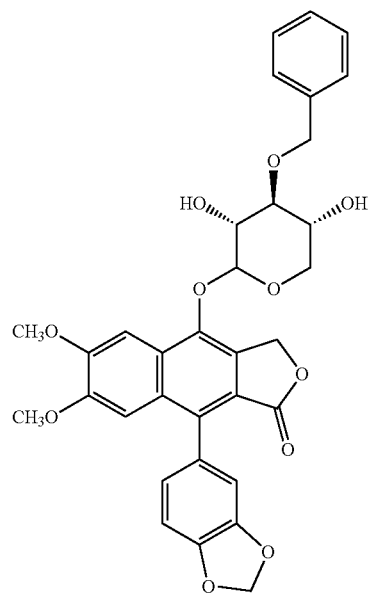 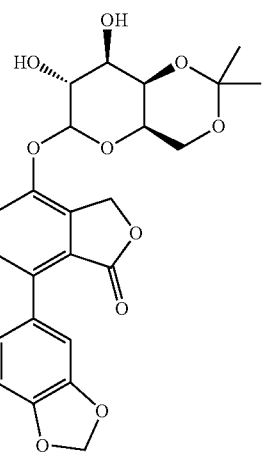

-continued

32d

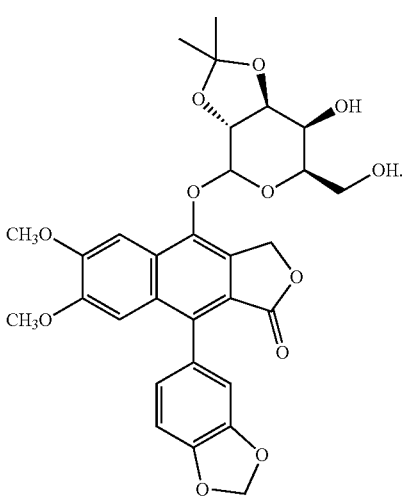

In a third aspect, provided herein is a pharmaceutical composition comprising a compound as described herein and at least one pharmaceutically acceptable excipient.

Also provided herein is an arylnaphthalene lignan compounds having the general Formula (I) or (II) or a pharmaceutically acceptable salt or pro-drug thereof, for use in the treatment, prevention or delay of progression of a virus infection in a patient.

(I)

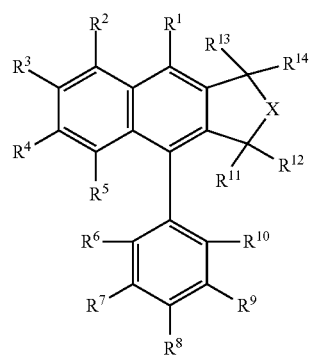

(II)

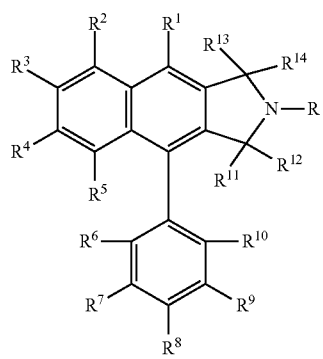

or a stereoisomer thereof, or an enantiomer thereof, or a pharmaceutically acceptable salt or pro-drug thereof, wherein X is oxygen or sulfur;

$R^1$, $R^2$, $R^3$, $R^4$, $R^5$, $R^6$, $R^7$, $R^8$, $R^9$ and $R^{10}$ are each independently hydrogen, halogen or a moiety comprising 1 to 30 plural valence atoms selected from carbon, boron, nitrogen, oxygen, silicon and sulfur; or $R^2$ and $R^3$, $R^3$ and $R^4$, $R^4$ and $R^5$, $R^6$ and $R^7$, $R^7$ and $R^8$, $R^8$ and $R^9$ or $R^9$ and $R^{10}$ may be taken together with the carbon atoms to which they are attached to form a cyclic group which is optionally substituted with 1, 2, 3, 4 or 5 group(s) independently selected from halogen and a moiety comprising 1 to 30 plural valence atoms selected from carbon, boron, nitrogen, oxygen, silicon, and sulfur;

$R^{11}$ and $R^{12}$ taken together form oxo; or while one of $R^{11}$ and $R^{12}$ is hydrogen or halogen, the other one of $R^{11}$ and $R^{12}$ is selected from $R^{15}$, —$OR^{15}$, —$C(O)R^{15}$ and —$C(O)OR^{15}$;

$R^{13}$ and $R^{14}$ taken together form oxo; or while one of $R^{13}$ and $R^{14}$ is hydrogen or halogen, the other one of $R^{13}$ and $R^{14}$ is selected from $R^{15}$, —$OR^{15}$, —$C(O)R^{15}$ and —$C(O)OR^{15}$;

$R^{15}$ is independently selected from hydrogen, halogen, trichloromethyl, trifluoromethyl, cyano, nitro, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$, —$N(R^{17})S(O)_2R^{18}$, hydrocarbyl optionally substituted with 1, 2, 3, 4 or 5 group(s) independently selected from $R^{16}$, heterocyclcyl optionally substituted with 1, 2, 3, 4 or 5 group(s) independently selected from $R^{16}$, and —$(CH_2)_k$-heterocyclyl optionally substituted with 1, 2, 3, 4 or 5 group(s) independently selected from $R^{16}$, wherein k is an integer between 1 and 6 (e.g. 1, 2 or 3);

$R^{16}$ is independently selected from halogen, trichloromethyl, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{17}$ and $R^{18}$ are each independently hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy; and R is hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

The present disclosure also provides an arylnaphthalene lignan compound having the general Formula (III) or (IV) or a pharmaceutically acceptable salt or pro-drug thereof, for use in the treatment, prevention or delay of progression of a virus infection in a patient.

(III)

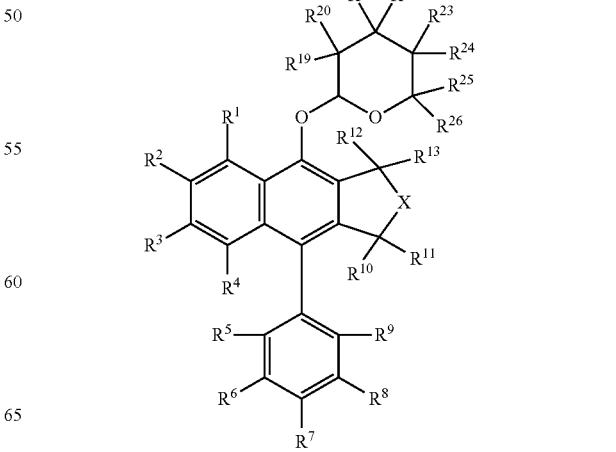

-continued

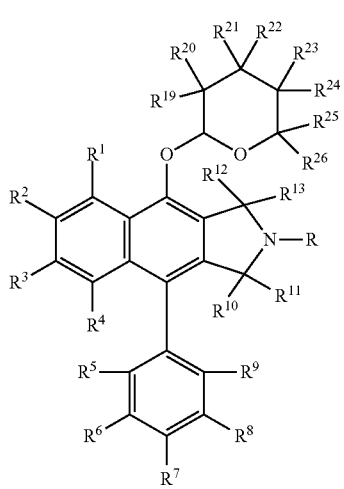

(IV)

or a stereoisomer thereof, or an enantiomer thereof; or a pharmaceutically acceptable salt or pro-drug thereof wherein, X is oxygen or sulfur;

the glycosidic group is generally a carbohydrate group, especially a monosaccharide, disaccharide, trisaccharide, tetrasaccharide or polysaccharide group, and may exist in various isomeric forms, for example α-D, α-L, β-D or β-L forms; the carbohydrate group may be optionally substituted with other type of substituents or even additional glycosidic groups; the total number of monosaccharide and substituted monosaccharide contained in the chemical structure of the compound of Formula (III) and Formula (IV) may not exceed 30;

$R^1$, $R^2$, $R^3$, $R^4$, $R^5$, $R^6$, $R^7$, $R^8$ and $R^9$ are each independently hydrogen, halogen or a moiety comprising 1 to 30 plural valence atoms selected from carbon, nitrogen, oxygen and sulfur; or $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$ may be taken together with the carbon atoms to which they are attached to form a cyclic group which is optionally substituted with halogen or a moiety comprising 1 to 30 plural valence atoms selected from carbon, nitrogen, oxygen and sulfur;

$R^{10}$ and $R^{11}$ may be taken together to form oxo; or while one of $R^{10}$ and $R^{11}$ is hydrogen or halogen, the other one of $R^{10}$ and $R^{11}$ is selected from the group consisting of $R^{27}$, —$OR^{27}$, —$C(O)R^{27}$, and —$C(O)OR^{27}$;

$R^{12}$ and $R^{13}$ may be taken together to form oxo; or while one of $R^{12}$ and $R^{13}$ is hydrogen or halogen, the other one of $R^{12}$ and $R^{13}$ is selected from the group consisting of $R^{27}$, —$OR^{27}$, —$C(O)R^{27}$, and —$C(O)OR^{27}$;

$R^{19}$ and $R^{20}$ taken together to form oxo; or while one of $R^{19}$ and $R^{20}$ is hydrogen or halogen, the other one of $R^{19}$ and $R^{20}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{21}$ and $R^{22}$ taken together to form oxo; or while one of $R^{21}$ and $R^{22}$ is hydrogen or halogen, the other one of $R^{21}$ and $R^{22}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{23}$ and $R^{24}$ taken together form oxo; or while one of $R^{23}$ and $R^{24}$ is hydrogen or halogen, the other one of $R^{23}$ and $R^{24}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{25}$ and $R^{26}$ taken together form oxo; or while one of $R^{25}$ and $R^{26}$ is hydrogen or halogen, the other one of $R^{25}$ and $R^{26}$ is selected from $R^{27}$, —$OR^{27}$, —$C(O)R^{27}$, —$C(O)OR^{27}$, —$CH_2R^{31}$ and —$C(O)R^{31}$;

$R^{27}$ is independently selected from hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, and —$N(R^{29})S(O)_2R^{30}$, hydrocarbyl optionally substituted with 1, 2, 3, 4 or 5 group(s) independently selected from the group consisting of $R^{28}$, heterocyclcyl optionally substituted with 1, 2, 3, 4 or 5 group(s) independently selected from the group consisting of $R^{28}$, and —$(CH_2)_k$-heterocyclyl optionally substituted with 1, 2, 3, 4 or 5 group(s) independently selected from the group consisting of $R^{28}$, wherein k is an integer between 1 and 6 (e.g. 1, 2 or 3);

$R^{28}$ is independently selected from halogen, trichloromethyl, trifluoromethyl, cyano, nitro, oxo, =$NR^{29}$, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, and —$N(R^{29})S(O)_2R^{30}$;

$R^{29}$ and $R^{30}$ are each independently hydrogen or selected from hydrocarbyl and heterocyclyl, either of which is optionally substituted with 1, 2, 3, 4 or 5 group(s) independently selected from the group consisting of halogen, cyano, amino, hydroxy, $C_{1-6}$ alkyl, and $C_{1-6}$ alkoxy;

$R^{31}$ is independently selected from hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, monosaccharide, substituted monosaccharide, disaccharide, substituted disaccharide, trisaccharide, substituted trisaccharide, tetrasaccharide, substituted tetrasaccharide, hydrocarbyl optionally substituted with 1, 2, 3, 4 or 5 group(s) independently selected from the group consisting of $R^{28}$, and heterocyclyl optionally substituted with 1, 2, 3, 4 or 5 group(s) independently selected from the group consisting of $R^{28}$; and R is hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

A fourth aspect of the invention is a pharmaceutical formulation comprising an arylnaphthalene lignan compound, or a pharmaceutically acceptable salt or prodrug thereof, for use in the treatment, prevention or delay of progression of a viral infection in a patient.

A fifth aspect of the invention is a pharmaceutical formulation comprising a glycosidic arylnaphthalene lignan compound, or a pharmaceutically acceptable salt or prodrug thereof, for use in the treatment, prevention or delay of progression of a viral infection in a patient.

A sixth aspect of the invention is a pharmaceutical formulation comprising a diphyllin analog, or a pharmaceutically acceptable salt or prodrug thereof, for use in the treatment, prevention or delay of progression of a viral infection in a patient.

A seventh aspect of the invention is a pharmaceutical formulation comprising a patentiflorin A analog, or a pharmaceutically acceptable salt or prodrug thereof, for use in the treatment, prevention or delay of progression of a viral infection in a patient.

Another aspect of the invention concerns the method to provide synthesis of new arylnaphthalene lignan compounds as well as the intermediate compounds during the synthesis. In addition, the invention is directed to an intermediary compound useful in preparing other compounds of the invention.

Compounds of the invention may exist in different forms, such as free acids, free bases, esters and other prodrugs, salts and tautomers, and the disclosure includes all variant forms of these compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

DETAILED DESCRIPTION

Figure 1:
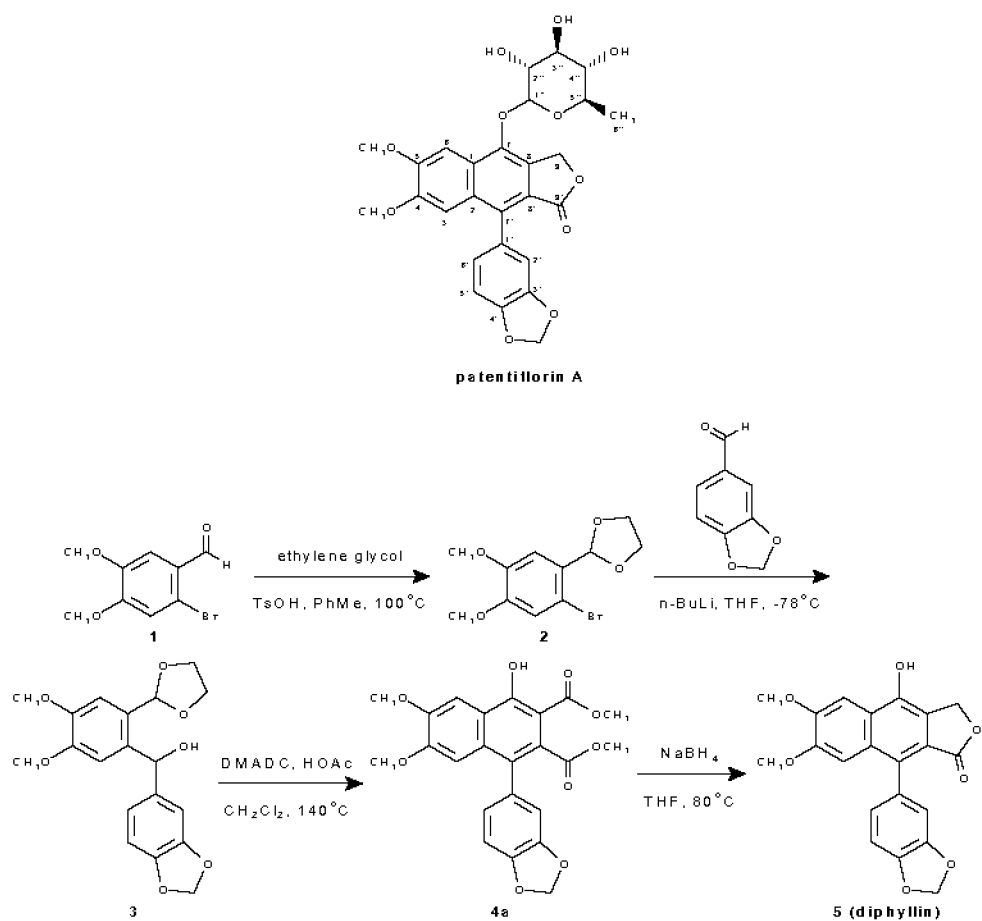
FIG. 1 shows the structure and carbon numbering of patentiflorin A and schematic preparation of diphyllin (5).

The present disclosure is not to be limited in scope by any of the specific embodiments described herein. The following embodiments are presented for exemplification only.

Throughout the description and claims of this specification the word "comprise" and other forms of the word such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "antiviral" refers to the ability to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

The term "therapeutically effective" means the amount of the composition used is of sufficient quantity to ameliorate one or more causes or symptoms of a disease or disorder. Such amelioration only requires a reduction or alteration, not necessarily elimination.

As used herein, the term pharmaceutically acceptable salt refers to any salt of the compound of this invention which retains its biological properties and which is not toxic or otherwise undesirable for pharmaceutical use. Such salts may be derived from a variety of organic and inorganic counterions well known in the art and include them. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion (e.g., an alkali metal ion, an alkaline earth ion or an aluminum ion), or alkali metal or alkaline earth metal hydroxides (e.g., sodium, potassium, calcium, magnesium, aluminum, lithium, zinc, and barium hydroxide), ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. In addition, examples of salts include sodium, potassium, calcium, magnesium, ammonium, tetraalkylammonium and the like, and when the compound contains a basic functionality, salts of non-toxic organic or inorganic acids, such as hydrohalides (e.g., hydrochloride and hydrobromide), sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate; fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "glycoside" or "glycosidic" compound as used herein is interchangeable and includes reference to any of the class of compounds that yield a sugar and an aglycone upon hydrolysis.

The term "ANL" or "aryl naphthalene lignan" or "arylnaphthalene lignan" compound as used herein is interchangeable.

The term "aryl naphthalene lignan" or "arylnaphthalene lignan" or "ANL" as used herein includes reference to a compound comprising the basic structure of 2,3-dimethyl-1-phenyl-naphthalene shown as below:

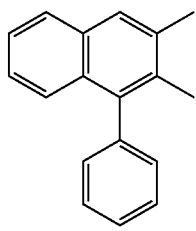 [SMILES: Cc1cc2ccccc2c(-c2ccccc2)c1C]

The carbon numbering of aryl naphthalene lignan molecule as used herein includes reference to a compound comprising numbering system shown as below:

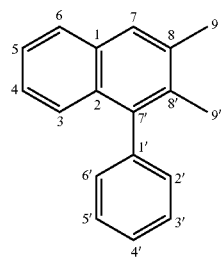

In one class of the core structure of an aryl naphthalene compound, the two methyl groups are forming a γ-lactone ring to become as aryl naphthofuran-2-one lignan or aryl naphthofuran-3-one lignan shown as below:

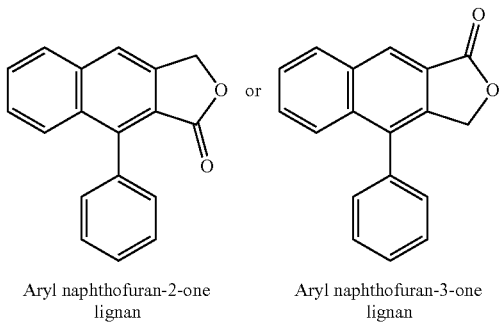 [SMILES: O=C1OCc2cc3ccccc3c(-c3ccccc3)c21 ; O=C1OCc2c1cc1ccccc1c2-c1ccccc1]

Aryl naphthofuran-2-one lignan    Aryl naphthofuran-3-one lignan

The carbon numbering of an aryl naphthalene lignan glycoside molecule as used herein includes reference to a compound comprising numbering system shown as below:

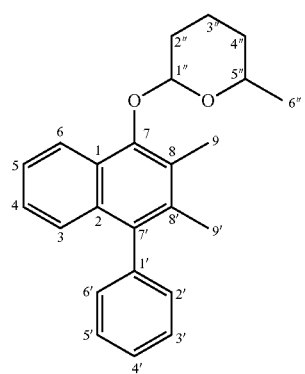 [SMILES: Cc1c(C)c(-c2ccccc2)c2ccccc2c1OC1CCCC(C)O1]

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl); $C_{1-6}$ alkenyl (e.g. ethenyl, 2-propenyl or 3-butenyl); $C_{1-6}$ alkynyl (e.g. ethynyl, 2-propynyl or 3-butynyl) and the like.

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

The terms "alkenyl" as used herein include reference to a straight or branched chain alkyl moiety having 2, 3, 4, 5, 6, 7, 8, 9, 10, 11, 12, 13, 14, 15, 16, 17, 18, 19 or 20 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

The terms "alkynyl" as used herein include reference to a straight or branched chain alkyl moiety having 2, 3, 4, 5, 6, 7, 8, 9, 10, 11, 12, 13, 14, 15, 16, 17, 18, 19 or 20 carbon atoms and having, in addition, at least one triple bond. This term includes reference to groups such as ethynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tertbutoxy, pentoxy, hexoxy and the like.

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

"Cyclic group" means a ring or ring system, which may be unsaturated or partially unsaturated but is usually saturated, typically containing 5 to 13 ring-forming atoms, for example a 5- or 6-membered ring. It includes carbocyclyl and heterocyclyl moeities.

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. A carbocyclic moiety is, for example, selected from cyclopropyl, cyclobutyl, cyclopentyl, cyclohexyl, norbomyl, bicyclo[2.2.2]octyl, phenyl, naphthyl, fluorenyl, azulenyl, indenyl, anthryl and the like.

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from boron, nitrogen, oxygen, phosphorus, silicon and sulfur. In particular, heterocyclyl includes a 3- to 10-membered ring or ring system and more particularly a 5 or 6-membered ring, which may be saturated or unsaturated.

A heterocyclic moiety is, for example, selected from oxiranyl, azirinyl, 1.2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl pyrrolyl pyrrolinyl, pyrrolidinyl, pyrrolizidinyl, imidazolyl, imidazolidinyl, benzimidazolyl, pyrazolyl pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4N-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, B-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, 1,3,2-dioxaborolane, and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulfur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulfur. The group may be a polycyclic ring system, having two or more rings, at least one of which is aromatic, but is more often monocyclic. This term includes reference to groups such as pyrimidinyl, furanyl, benzobthiophenyl, thiophenyl, pyrrolyl, imidazolyl, pyrrolidinyl, pyridinyl, benzobfuranyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolylindazolyl, purinyl, isoquinolinyl, quinazolinyl, pteridinyl and the like.

The term "halogen" as used herein includes reference to F, Cl, Br or I.

The expression "halogen containing moiety" as used herein includes reference to a moiety comprising 1 to 30 plural valence atoms selected from carbon, nitrogen, oxygen and sulfur which moiety includes at least one halogen. The moiety may be hydrocarbyl for example $C_{1-6}$ alkyl or $C_{1-6}$ alkoxy, or carbocyclyl for example aryl.

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted as used herein means substituted or un-substituted. It will, of course, be understood that substituents are only at positions where they are chemically possible, the person skilled in the art being able to decide (either experimentally or theoretically) without inappropriate effort whether a particular substitution is possible.

Where two or more moieties are described as being "each independently" selected from a list of atoms or groups, this means that the moieties may be the same or different. The identity of each moiety is therefore independent of the identities of the one or more other moieties.

The term "enantiomer" as used herein means one of two stereoisomers that have mirror images of one another.

The term "stereoisomer" as used herein means one of class of isomeric molecules that have the same molecular formula and sequence of bonded atoms, but different three-dimensional orientations of their atoms in space.

The term "tautomer" means isomeric molecules that readily interconvert by a chemical reaction. The reaction commonly results in the migration of a hydrogen atom, which results in a switch of a single bond and adjacent double bond.

A prodrug is a medication that is administered as an inactive (or less than fully active) chemical derivative that is subsequently converted to an active pharmacological agent in the body, often through normal metabolic processes.

$CC_{50}$ is a cytotoxicity measure of the concentration for a test drug to inhibit cell growth by 50%.

$EC_{50}$ is an antiviral activity measure of the effective concentration for a test drug to inhibit viral growth by 50%.

The term "selectivity index" or "SI" means a ratio that measures the window between cytotoxicity and antiviral activity by dividing the given $CC_{50}$ value into the $IC_{50}$ value ($CC_{50}/IC_{50}$) of a test drug. The higher SI ratio means more effective and safer a test drug would be for a given viral infection in an in vitro experiment.

The symbol

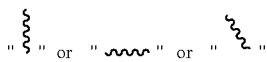

in a chemical structure represents a position from where the specified chemical structure is bonded to another chemical structure.

The symbol "β" in a chemical structure indicates that the bond connection is above (or before) the plane of the paper or screen. The symbol "α" in a chemical structure indicates that the bond connection is below (or behind) the plane of the paper or screen.

A solid wedge in a chemical structure indicates that this bond is above (or before) the plane of the paper or screen toward to the viewer. A hashed (or broken) wedge in a chemical structure indicates that the bond connection is below (or behind) the plane of the paper or screen receding away from the viewer.

Provided herein is a compound and use of the the compound in the manufacture of a medicament for treating a viral infection and a method of using the compound for treating a viral infection in a subject, comprising the step of administering a therapeutically effective amount of the compound to the subject, wherein the compound has the Formula (I):

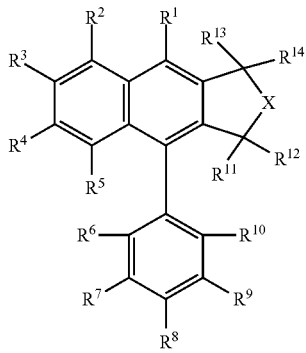

or a pharmaceutically acceptable salt or pro-drug thereof wherein,

X is oxygen or sulfur;

$R^1$ is $R^{15}$, —$OR^{15}$, —$C(O)R^{15}$, or —$C(O)OR^{15}$;

$R^2$, $R^5$, $R^6$, $R^{10}$, $R^{13}$, and $R^{14}$ are each independently hydrogen or halogen;

$R^3$ and $R^4$ are each independently selected from the group consisting of —$OR^D$ and —$OC(O)R^{15}$; or $R^3$ and $R^4$ taken together with the carbon atoms to which they are attached form a 5-6 membered heterocyclyl optionally substituted with 1, 2, 3, 4 or 5 group(s) independently selected from $R^6$;

$R^7$, $R^8$, and $R^9$ are each independently selected from the group consisting of —$OR^{15}$ and —$OC(O)R^{15}$; or $R^7$ and $R^8$ taken together with the carbon atoms to which they are attached to form a 5-6 membered heterocyclyl optionally substituted with 1, 2, 3, 4 or 5 group(s) independently selected from $R^{16}$; or $R^8$ and $R^9$ taken together with the carbon atoms to which they are attached to form a 5-6 membered heterocyclyl optionally substituted with 1, 2, 3, 4 or 5 group(s) independently selected from $R^6$;

$R^{11}$ and $R^{12}$ taken together form oxo; or while one of $R^{11}$ and $R^{12}$ is hydrogen or halogen, the other one of $R^{11}$ and $R^{12}$ is selected from the group consisting of R'S, —$OR^{15}$, —$C(O)R^{15}$ and —$C(O)OR^{15}$;

$R^{15}$ for each occurrence is independently selected from the group consisting of hydrogen, halogen, trichloromethyl, trifluoromethyl, cyano, nitro, heteroaryl, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N=C(R^{17})R^{18}$, —$N(R^{17})R^{18}$, —$N(R^{17})N(R^{17})R^{18}$, —$N(R^{17})C(O)R^{18}$, —$N(R^{17})S(O)_2R^{18}$, 1,3,2-dioxaborolane optionally substituted with 1, 2, 3, or 4 group(s) independently selected from alkyl, a glycosidic group, alkynyl optionally substituted with a trialkylsilane, hydrocarbyl optionally substituted with 1, 2, 3, 4 or 5 group(s) independently selected from $R^{16}$, heterocyclcyl optionally substituted with 1, 2, 3, 4 or 5 group(s) independently selected from $R^{16}$, and —$(CH_2)_k$-heterocyclyl optionally substituted with 1, 2, 3, 4 or 5 group(s) independently selected from $R^{16}$, wherein k is an integer between 1-6;

$R^{16}$ for each occurrence is independently selected from the group consisting of alkynyl, halogen, trichloromethyl, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$; and $R^{17}$ and $R^{18}$ for each occurrence are independently hydrogen, alkyl, alkynyl, cycloalkyl, aryl, or heteroaryl, or selected from hydrocarbyl and heterocyclyl, either of which is optionally substituted with 1, 2, 3, 4 or 5 group(s) independently selected from the group consisting of halogen, trichloromethyl, trifluoromethyl, cyano, amino, hydroxy, $C_{1-6}$ alkyl and $C_{1-6}$ alkoxy.

In certain embodiments, the compound of Formula (I) is not a compound selected from the group consisting of 5, 15a, 15b, 16, 17b, 19d, 25a-25g, and 26a-26g:

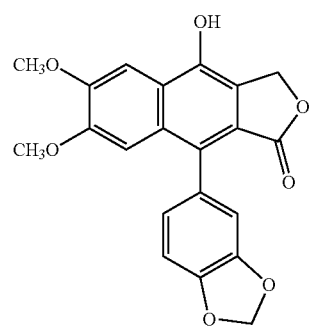

5

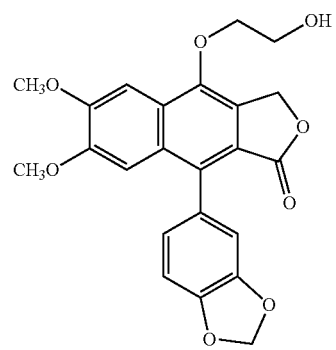

15a

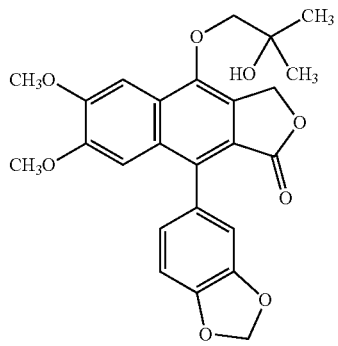

15b

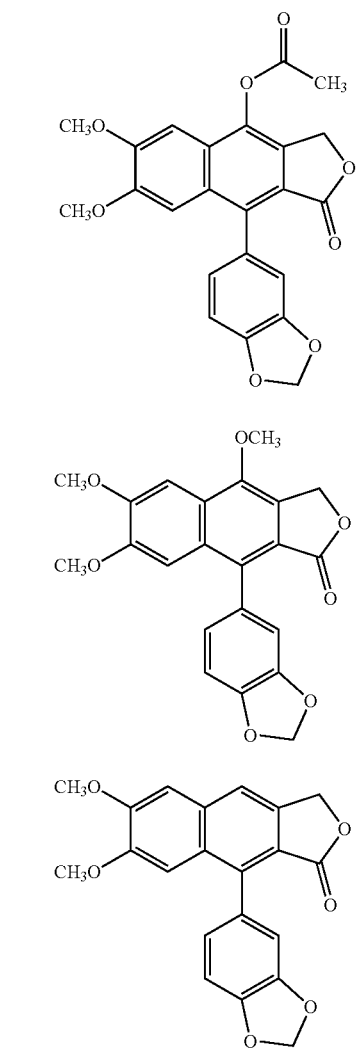
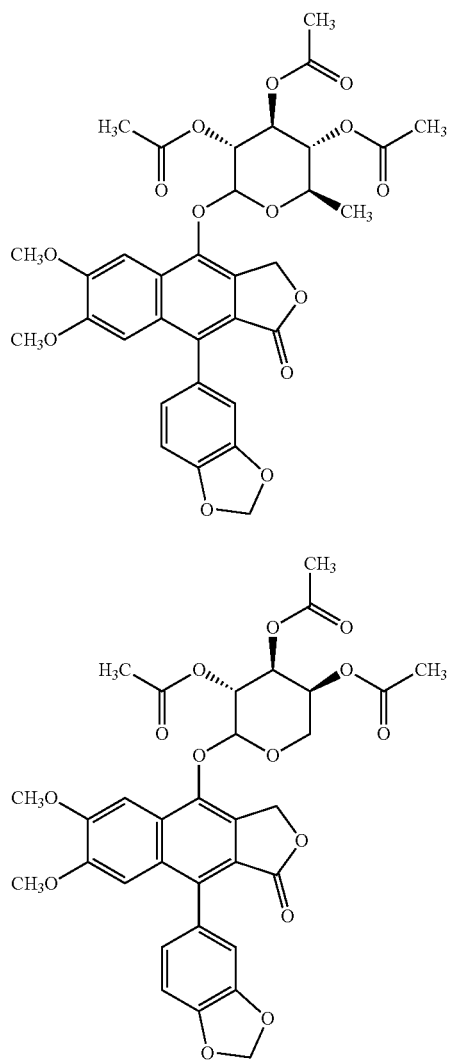
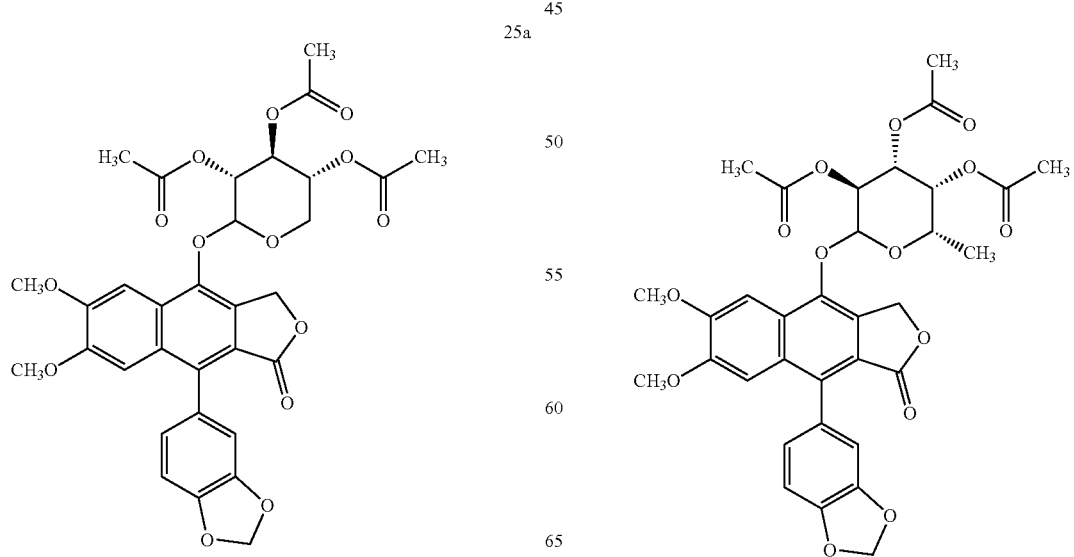

91
-continued
25e
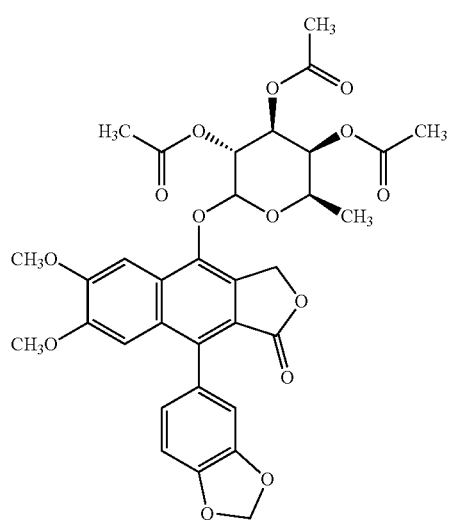
25f
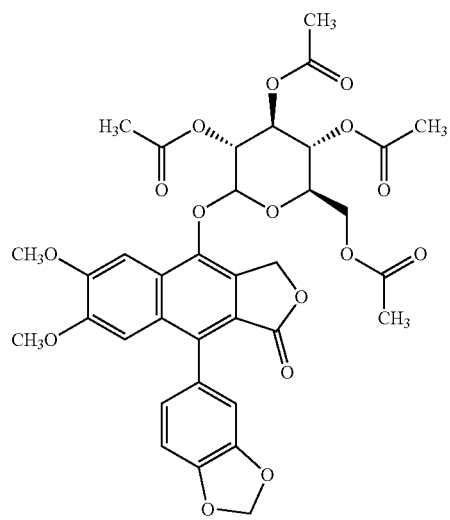
25g
92
-continued
26a
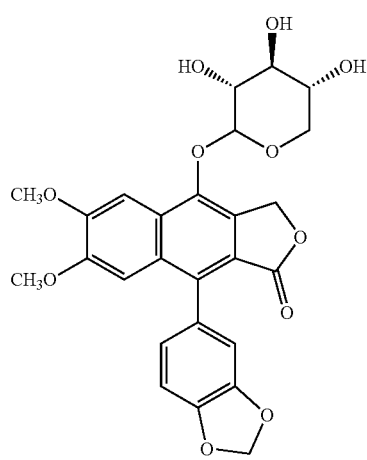
26b
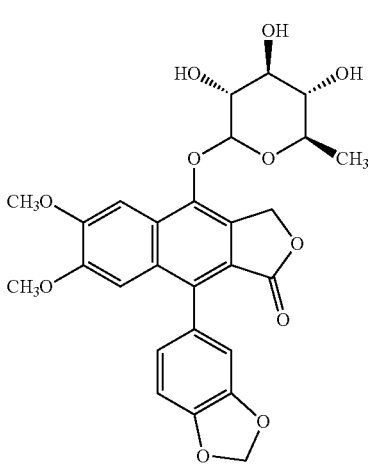
26c
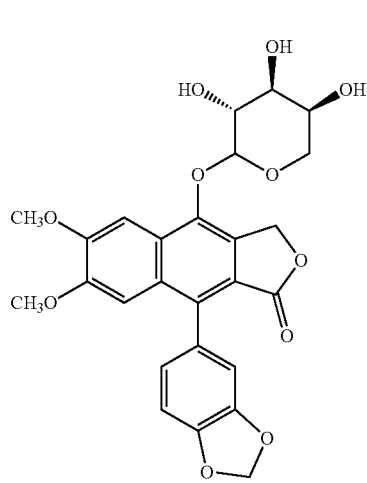

-continued

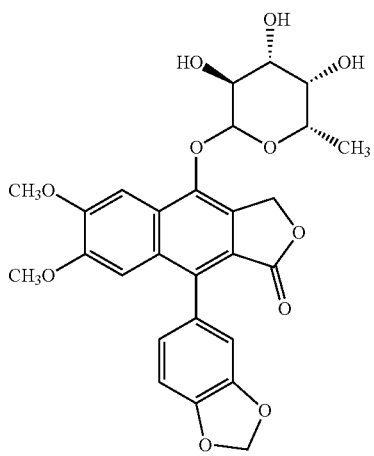

26d

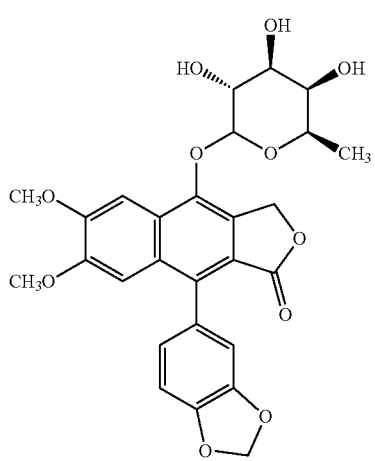

26e

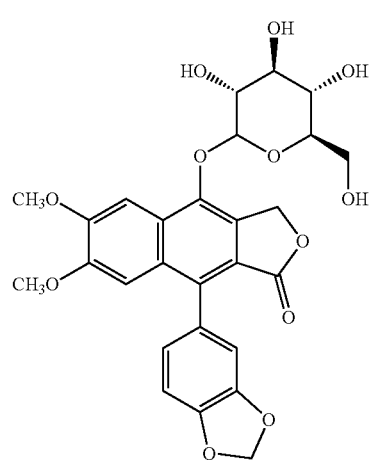

26f

-continued

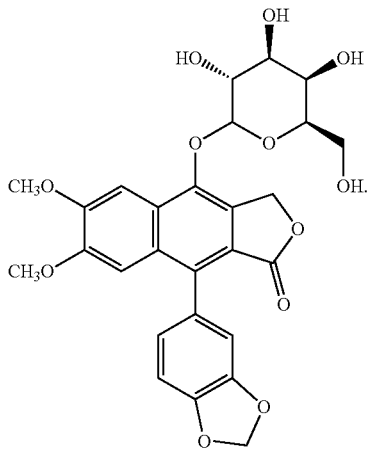

26g

In certain embodiments, R$^1$ is hydrogen, alkyl, aryl, heteroaryl (such as furan, thiophene, pyridine, and the like), —N(R$^{17}$)R$^{18}$, —N=C(R$^{17}$)(R$^{18}$), alkynyl optionally substituted with a trialkylsilane, a glycosidic group, 1,3,2-dioxaborolane optionally substituted with 1, 2, 3, or 4 group(s) independently selected from alkyl, or —O—(CR$_2$)$_m$—R$^{16}$, wherein m is a whole number selected from 1-4, 1-3, or 1-2; R for each occurrence is independently hydrogen, alkyl, cycloalkyl, or aryl; and R$^{16}$ is alkynyl, cyano, —OR$^{17}$, —N(R$^{17}$)R$^{18}$, —C(O)N(R$^{17}$)R$^{18}$, or —C(O)OR$^{17}$.

In certain embodiments, R$^1$ is —O—CH$_2$—R$^{16}$, wherein R$^{16}$ is —C≡CH, cyano, —OR$^{17}$, —N(R$^{17}$)R$^{18}$, —C(O)N(R$^{17}$)R$^{18}$, or —C(O)OR$^{17}$.

In certain embodiments, each of R$^3$ and R$^4$ is independently selected from the group consisting of —OR$^{15}$ and —OC(O)R$^{15}$, wherein R$^{15}$ is hydrogen, alkyl, cycloalkyl, heterocyclcyl, aryl, and heteroaryl; or R$^3$ and R$^4$ taken together with the carbon atoms to which they are attached form a 5-6 membered heterocyclyl. In certain embodiments, R$^3$ and R$^4$ is —OR$^{15}$, wherein R$^{15}$ is C$_1$-C$_6$ alkyl, C$_1$-C$_4$ alkyl, or C$_1$-C$_2$ alkyl.

In certain embodiments, each of R$^8$ and R$^9$ is independently selected from the group consisting of —OR$^{15}$ and —OC(O)R$^{15}$, wherein R$^{15}$ is hydrogen, alkyl, cycloalkyl, heterocyclcyl, aryl, and heteroaryl; or R$^8$ and R$^9$ taken together with the carbon atoms to which they are attached form a 5-6 membered heterocyclyl. In certain embodiments, R$^8$ and R$^9$ taken together with the carbon atoms to which they are attached form a methylenedioxy ring.

In certain embodiments, R$^{11}$ and R$^{12}$ taken together form oxo.

In certain embodiments, each of R$^3$ and R$^4$ is —O-alkyl; R$^8$ and R$^9$ taken together with the carbon atoms to which they are attached form a methylenedioxy ring; R$^1$ is heteroaryl, —OR$^{15}$, —C(O)R$^{15}$, —N(R$^{17}$)R$^{18}$, —N(R$^{17}$)C(O)R$^{18}$, —N=C(R$^{17}$)R$^{18}$, pinacolboryl, —OS(O)$_2$CF$_3$, a glycosidic group, heterocyclcyl optionally substituted with 1 or 2 group(s) independently selected from R$^{16}$ or, alkynyl optionally substituted with a trialkylsilane; or R$^1$ is —OCH$_2$-cyano, —OCH$_2$—C≡CH, —OCH$_2$—C(O)N(R$^{17}$)R$^{18}$, or —C(O)OR$^{17}$; and R$^{11}$ and R$^{12}$ taken together form oxo.

In certain embodiments, the compound is selected compounds 12a, 12b, 13, 14a, 14b, 17a, 17c, 17d, 17e, 17f, 17g, 17h, 18, 19a, 19b, 19c, 19e, 19f, 19g, 19h, 19i, 19j, 19k, 19l, 19m, 19n, 19o, 19p, 20, 21, 22, 23 and 24:

12a
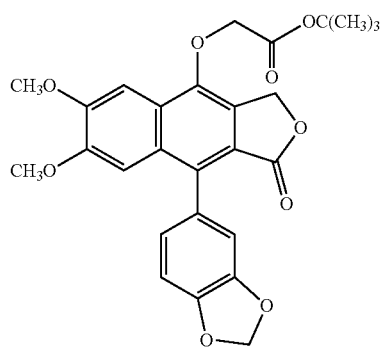
12b
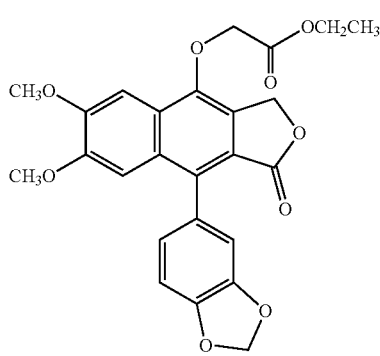
13
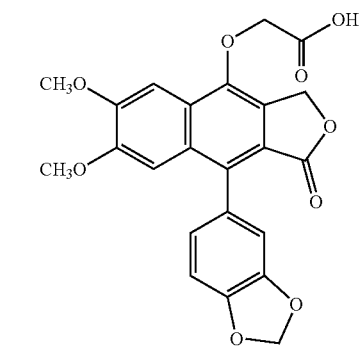
14a
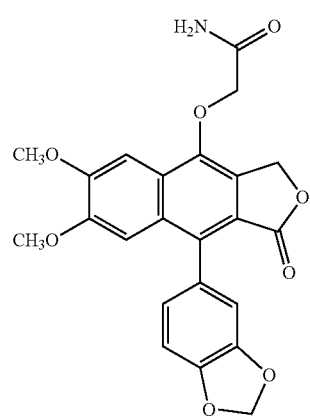
14b
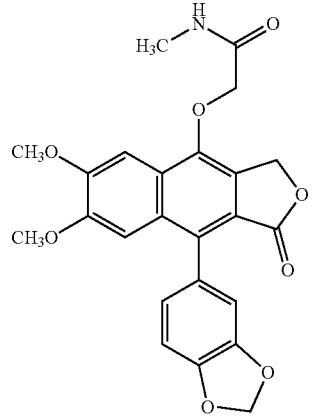
17a
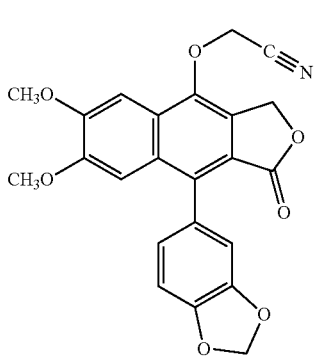
17c
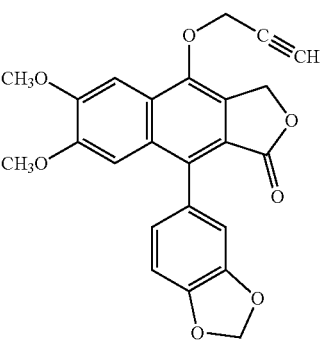
17d
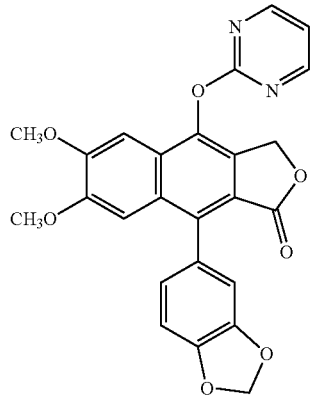

17e 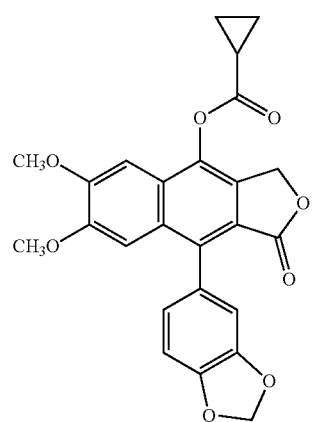
17f 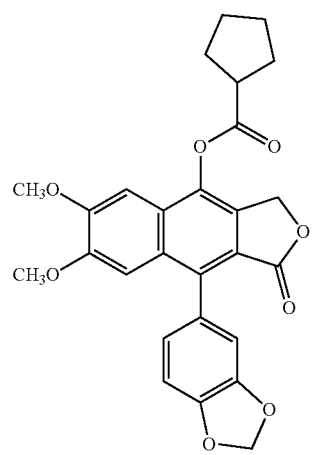
17g 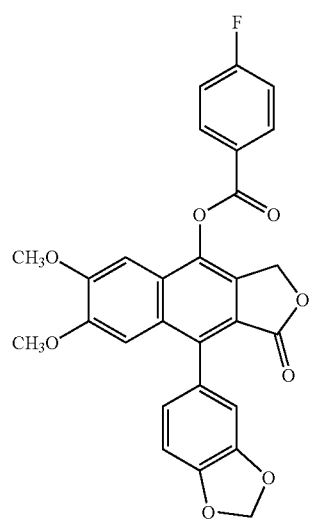
17h 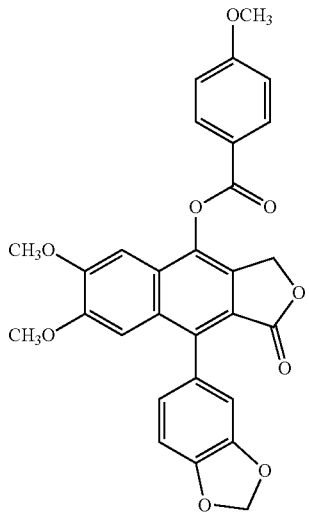
18 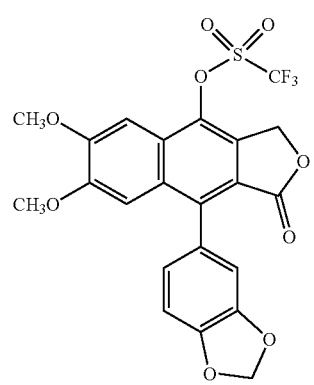
19a 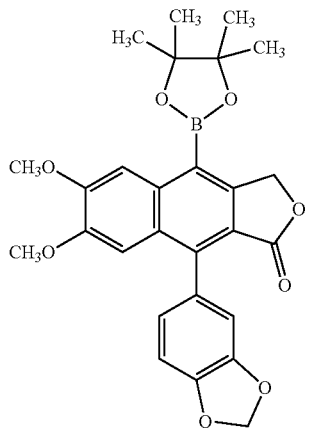
19b 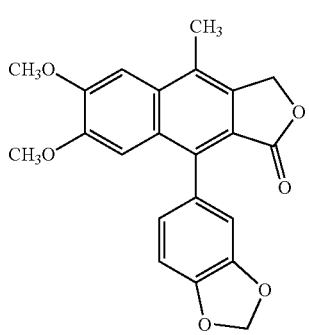

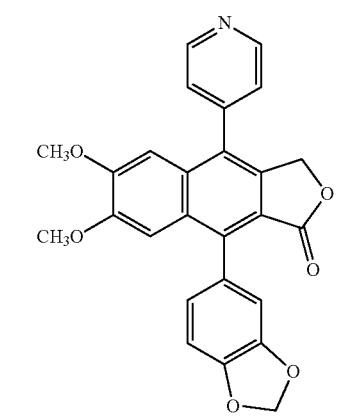
19c
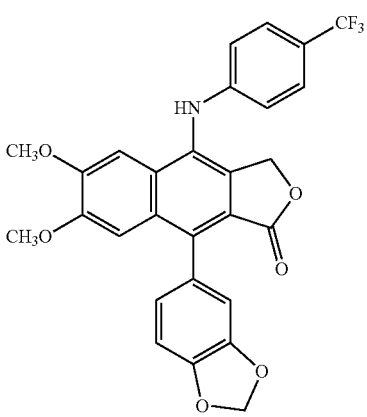
19e
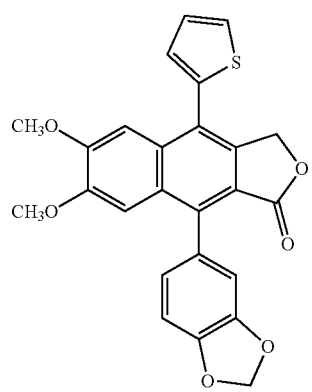
19h
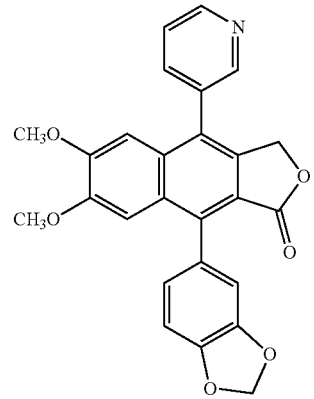
19i
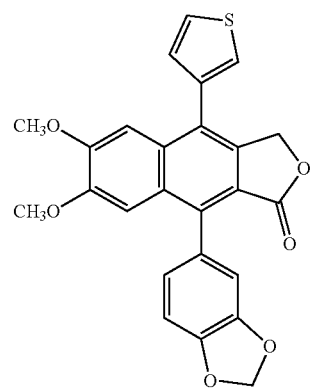
19j
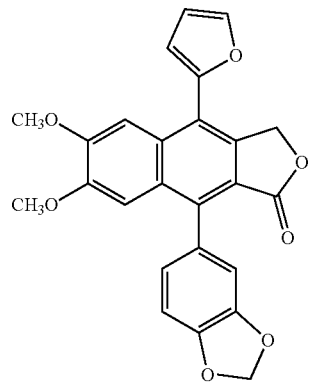
19k

| 19l | 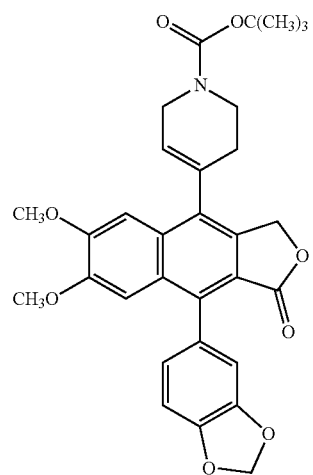 |
| 19m | 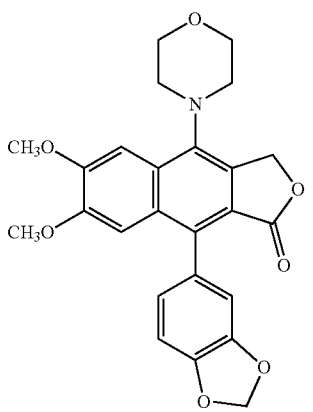 |
| 19n | 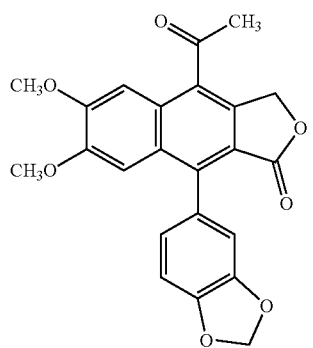 |
| 19o | 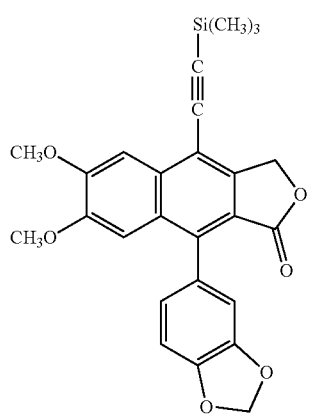 |
| 19p | 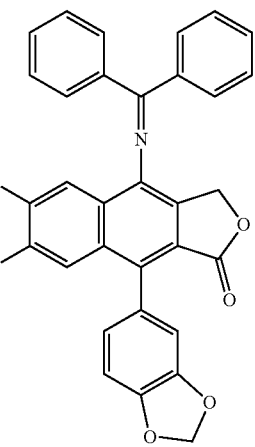 |
| 20 | 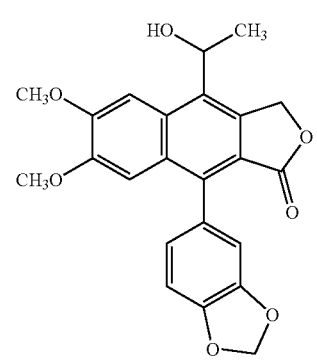 |
| 21 | 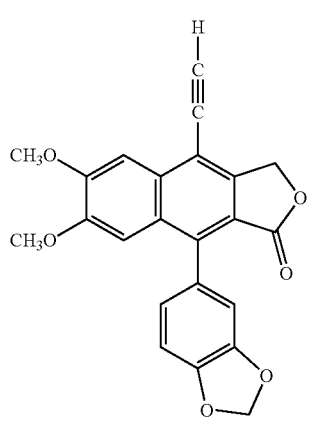 |
| 22 | 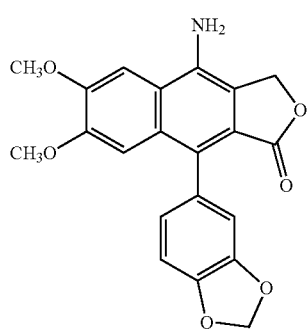 |

23

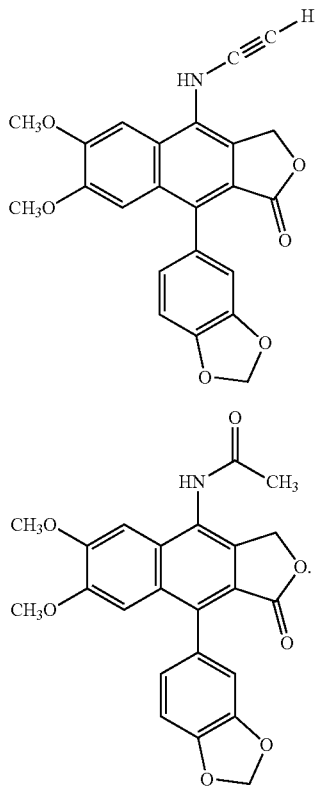

24

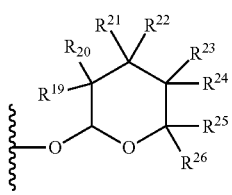

In certain embodiments, $R^1$ is a glycosidic group represented by the Formula (V):

(V)

[structure of formula V with R19, R20, R21, R22, R23, R24, R25, R26]

wherein, $R^{19}$ and $R^{20}$ taken together to form oxo; or while one of $R^{19}$ and $R^{20}$ is hydrogen or halogen, the other one of $R^{19}$ and $R^{20}$ is selected from the group consisting of $R^{27}$, —$OR^{27}$, —$OC(O)R^{27}$, —$OC(O)N(R^{27})R^{27}$, and —$OC(O)OR^{27}$;

$R^{21}$ and $R^{22}$ taken together to form oxo; or while one of $R^{21}$ and $R^{22}$ is hydrogen or halogen, the other one of $R^{21}$ and $R^{22}$ is selected from the group consisting of $R^{27}$, —$OR^{27}$, —$OC(O)R^{27}$, —$OC(O)N(R^{27})R^{27}$, and —$OC(O)OR^{27}$; or $R^{20}$ and $R^{22}$ taken together with the carbon atoms to which they are attached to form a 5-6 membered heterocyclyl, which is optionally substituted with 1, 2, 3, 4 or 5 group(s) independently selected from halogen, cyano, amino, hydroxy, $C_{1-6}$ alkyl and $C_{1-6}$ alkoxy;

$R^{23}$ and $R^{24}$ taken together to form oxo; or while one of $R^{23}$ and $R^{24}$ is hydrogen or halogen, the other one of $R^{23}$ and $R^{24}$ is selected from the group consisting of $R^{27}$, —$OR^{27}$, —$OC(O)R^{27}$, —$OC(O)N(R^{27})R^{27}$, and —$OC(O)OR^{27}$; or $R^{22}$ and $R^{24}$ taken together with the carbon atoms to which they are attached to form a 5-6 membered heterocyclyl, which is optionally substituted with 1, 2, 3, 4 or 5 group(s) independently selected from halogen, cyano, amino, hydroxy, $C_{1-6}$ alkyl and $C_{1-6}$ alkoxy;

$R^{25}$ and $R^{26}$ taken together form oxo; or while one of $R^{25}$ and $R^{26}$ is hydrogen or halogen, the other one of $R^{25}$ and $R^{26}$ is selected from the group consisting of $R^{27}$, —$OR^{27}$, —$OC(O)R^{27}$, —$OC(O)N(R^{27})R^{27}$, —$OC(O)OR^{27}$, —$CH_2R^{27}$, and —$C(O)R^{27}$; or $R^{24}$ and $R^{26}$ taken together with the carbon atoms to which they are attached to form a 5-6 membered heterocyclyl, which is optionally substituted with 1, 2, 3, 4 or 5 group(s) independently selected from halogen, cyano, amino, hydroxy, $C_{1-6}$ alkyl and $C_{1-6}$ alkoxy;

$R^{27}$ for each occurrence is independently selected from the group consisting of hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, hydrocarbyl optionally substituted with 1, 2, 3, 4 or 5 group(s) independently selected from the group consisting of $R^{28}$, heterocyclcyl optionally substituted with 1, 2, 3, 4 or 5 group(s) independently selected from the group consisting of $R^{28}$, and —$(CH_2)_k$-heterocyclyl optionally substituted with 1, 2, 3, 4 or 5 group(s) independently selected from the group consisting of $R^{28}$, wherein k is an integer between 1-6;

$R^{28}$ for each occurrence is independently selected from halogen, trichloromethyl, trifluoromethyl, cyano, nitro, oxo, =$NR^{29}$, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$ and —$N(R^{29})S(O)_2R^{30}$; and $R^{29}$ and $R^{30}$ for each occurrence are each independently hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

In certain embodiments, the glycosidic group is a monosaccharide, disaccharide, trisaccharide, tetrasaccharide or polysaccharide group, and may exist in any isomeric form, for example α-D, α-L, β-D or β-L forms. In certain embodiments, the glycloside is a monosaccharide selected from the group consisting of an α-L isomer and an β-L isomer.

In certain embodiments, $R^{19}$, $R^{21}$, $R^{23}$, and $R^{25}$ are each hydrogen; $R^{20}$, $R^{22}$, and $R^{24}$ are each independently selected from the group consisting of —$OR^{27}$, —$OC(O)N(R^{27})R^{27}$, —$OC(O)R^{27}$ and —$OC(O)OR^{27}$; and $R^{26}$ is hydrogen, methyl, —$OR^{27}$, —$OC(O)R^{27}$, or —$CH_2$—$OC(O)R^{27}$; or $R^{20}$ and $R^{22}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{22}$ and $R^{24}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; or $R^{24}$ and $R^{26}$ taken together with the carbon atoms to which they are attached form a 5-6 membered heterocyclyl, which is optionally substituted with 1, 2, 3, 4 or 5 group(s) independently selected from $C_{1-6}$ alkyl and $C_{1-6}$ alkoxy; and the glycloside is a monosaccaride.

In certain embodiments, $R^{20}$, $R^{22}$, and $R^{24}$ are each independently selected from the group consisting of —$OR^{27}$, —$OC(O)N(R^{27})R^{27}$, —$OC(O)R^{27}$ and —$OC(O)OR^{27}$, wherein $R^{27}$ for each occurrence is independently selected from the group consisting of hydrogen, alkyl, cycloalkyl, alkenyl, aryl, aralkyl, heteroaryl, perhaloalkyl, and —$C(O)CH_2CN$.

In instances in which $R^1$ is a glycosidic group, the compound can be selected from the group consisting of: 27aa, 27ab, 27ac, 27ad, 27ae, 27af, 27ba, 27bb, 27bc, 27bd, 27be, 27bf, 28ab1, 28ab2, 28ab3, 28bb1, 28bb2, 28bb3, 29a, 29b, 30a, 30b, 30c, 30d, 30e, 30f, 30g, 30h, 30i, 30j, 30k, 30l, 31a, 31b, 31c, 31d, 31e, 31f, 31g, 31h, 31i, 31j, 31k, 31l, 32a, 32b, 32c and 32d:
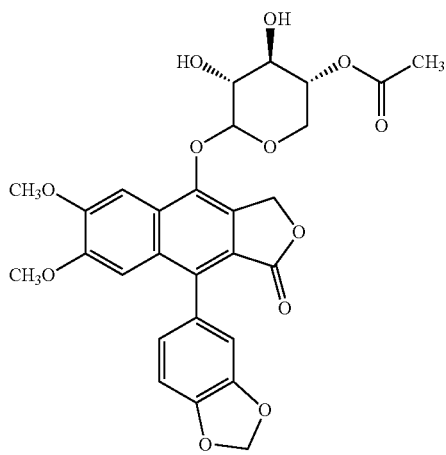
27aa
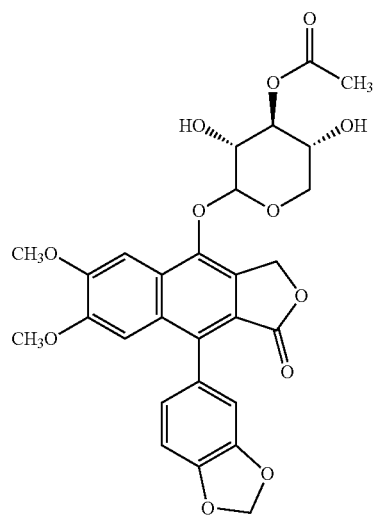
27ab
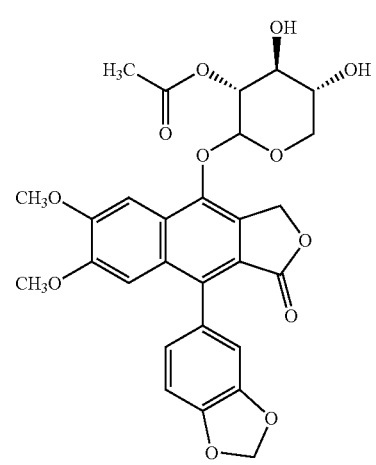
27ac
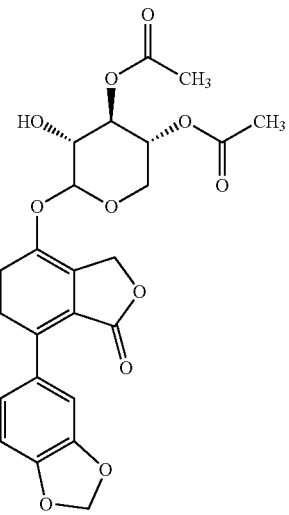
27ad
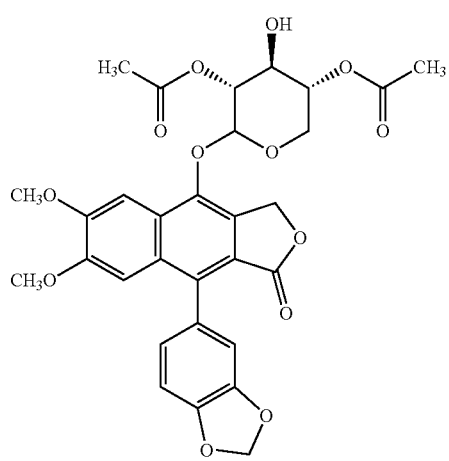
27ae
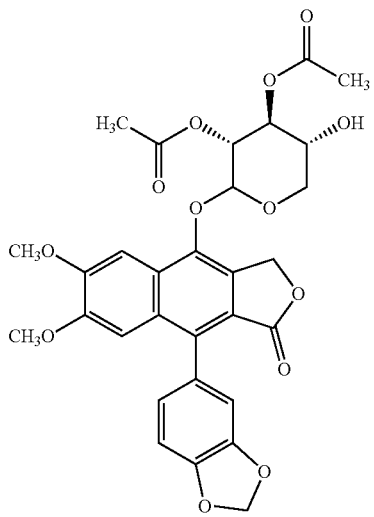
27af

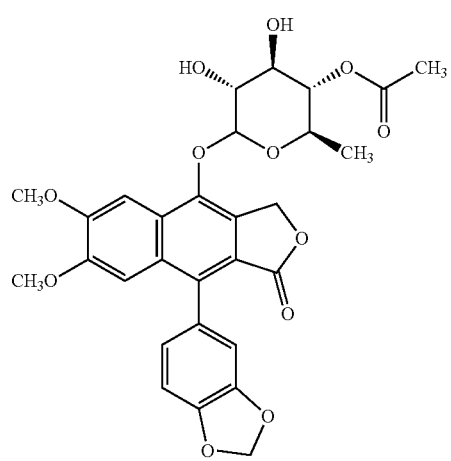
27ba
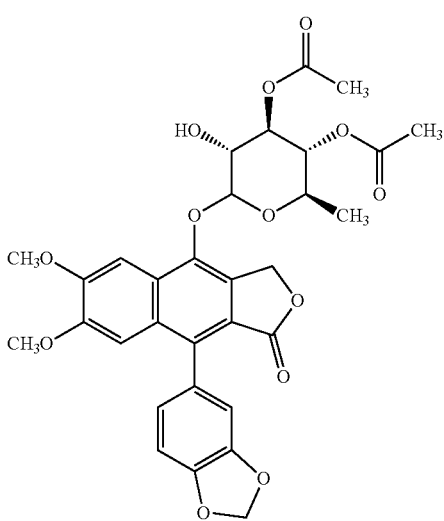
27bd
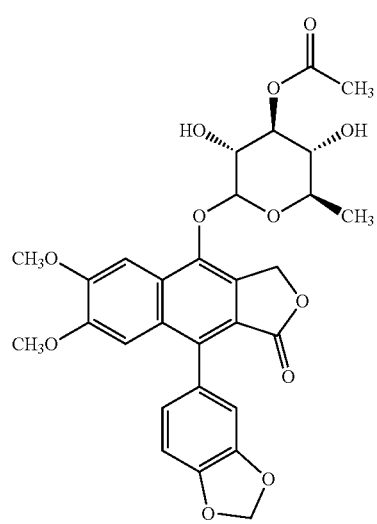
27bb
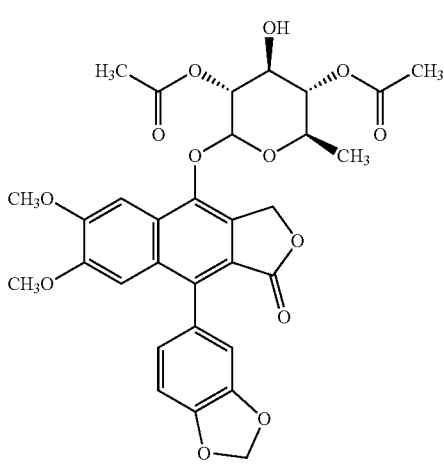
27be
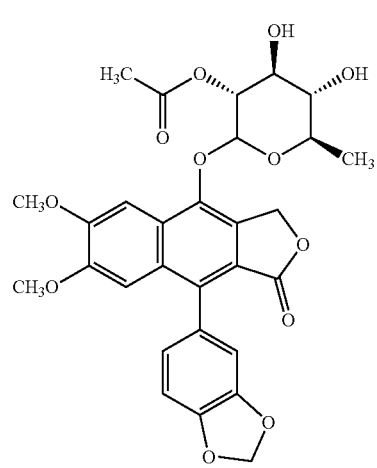
27bc
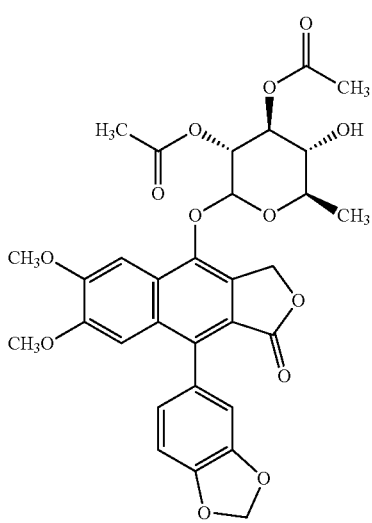
27bf

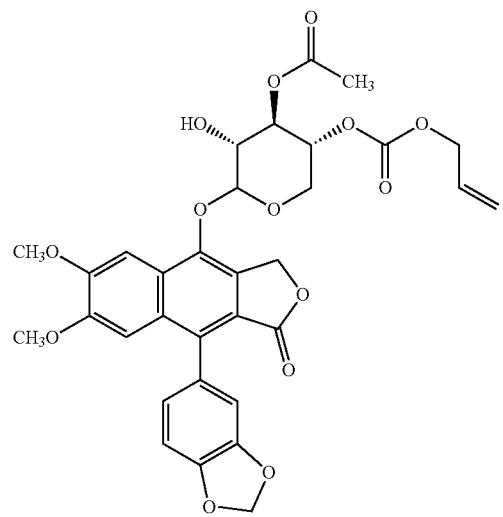
28ab1
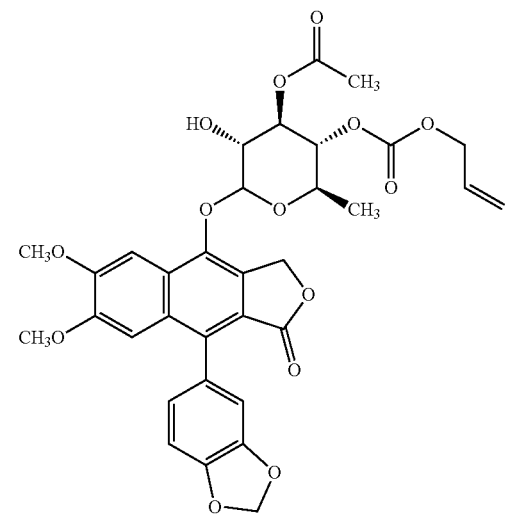
28bb1
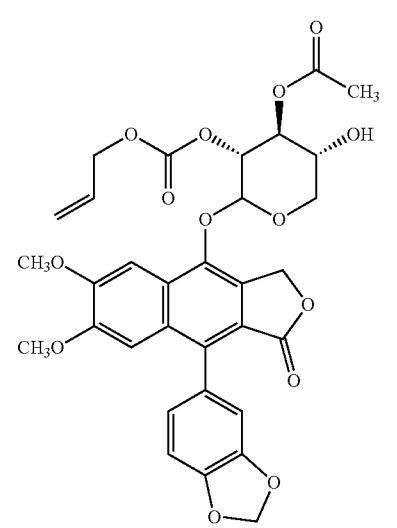
28ab2
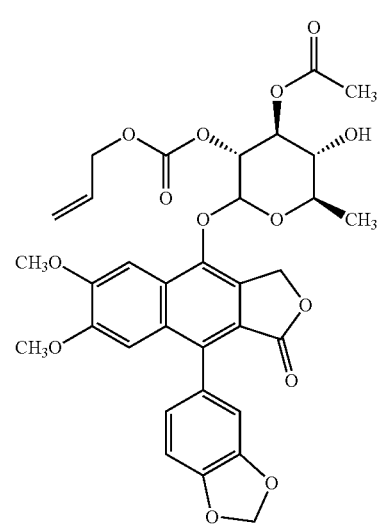
28bb2
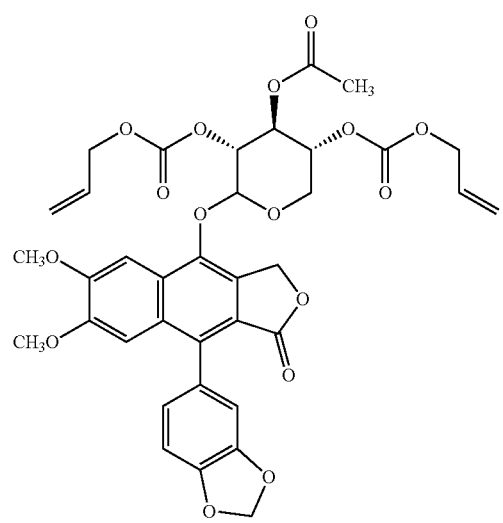
28ab3
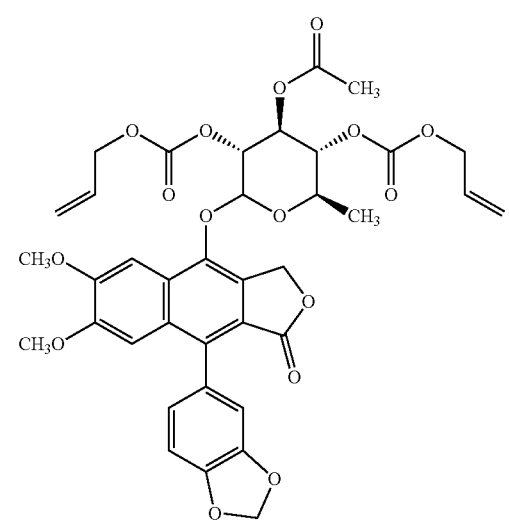
28bb3

111
-continued
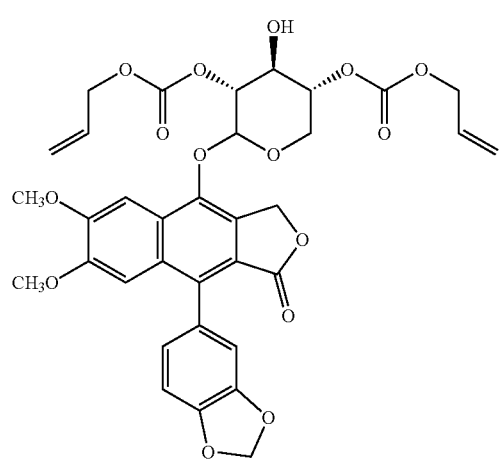
29a
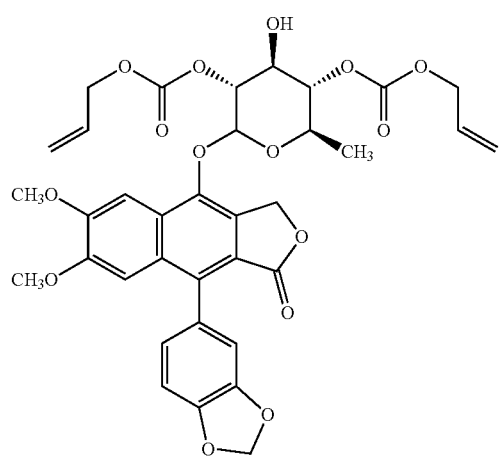
29b
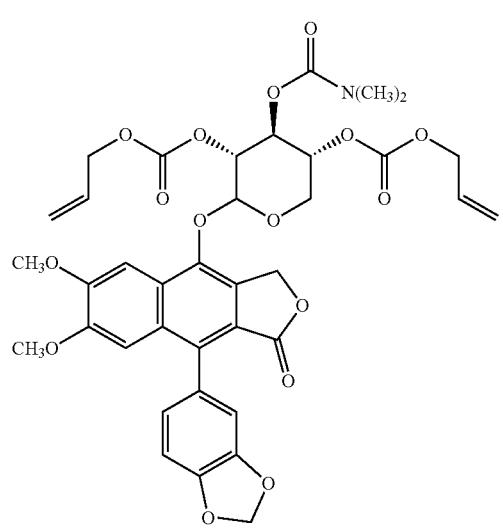
30a
112
-continued
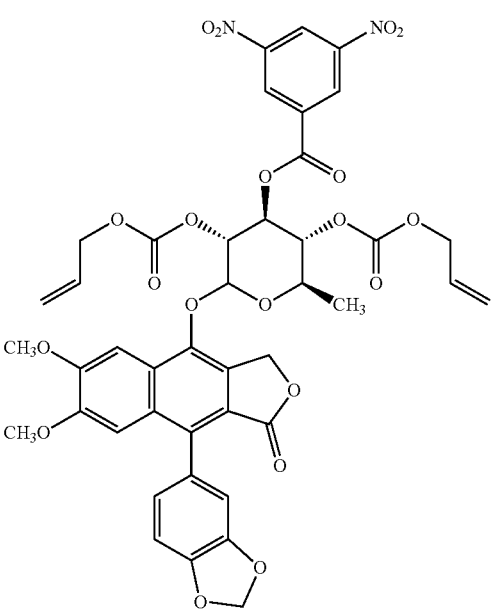
30b
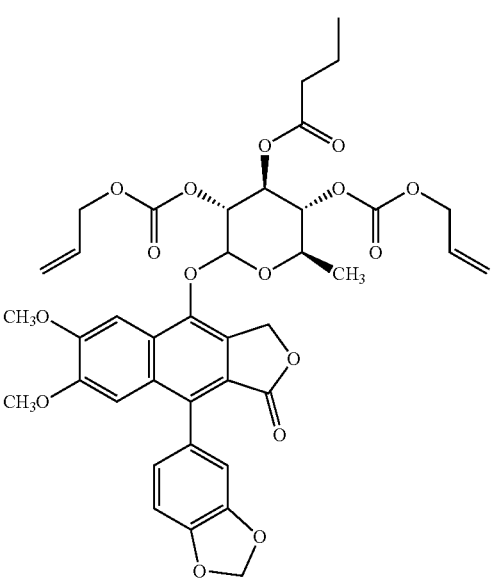
30c 113
-continued
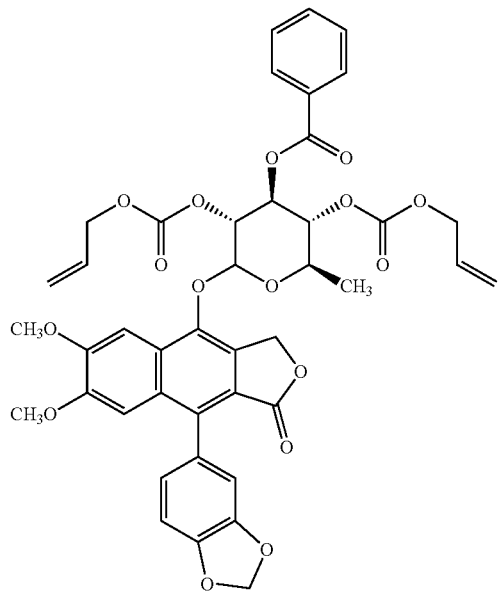
30d
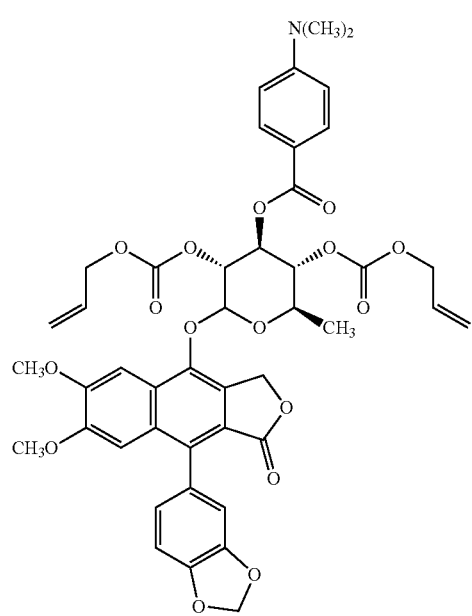
30e
114
-continued
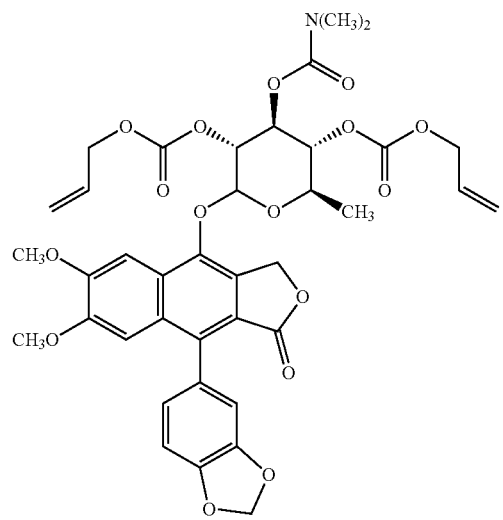
30f
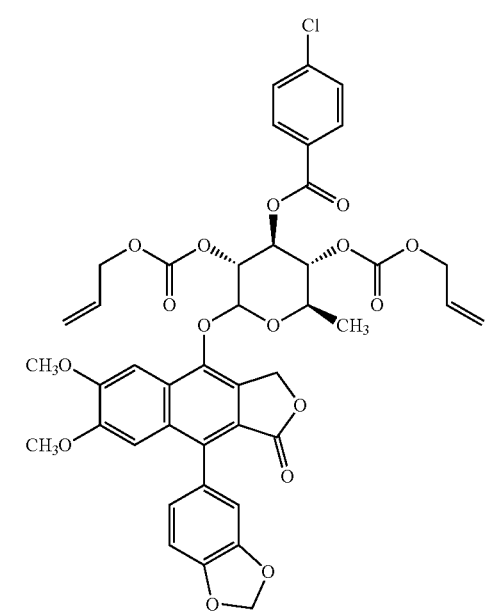
30g
30h -continued
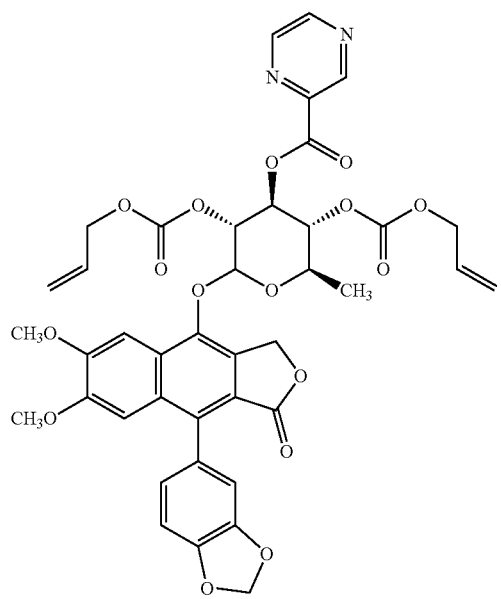
30i
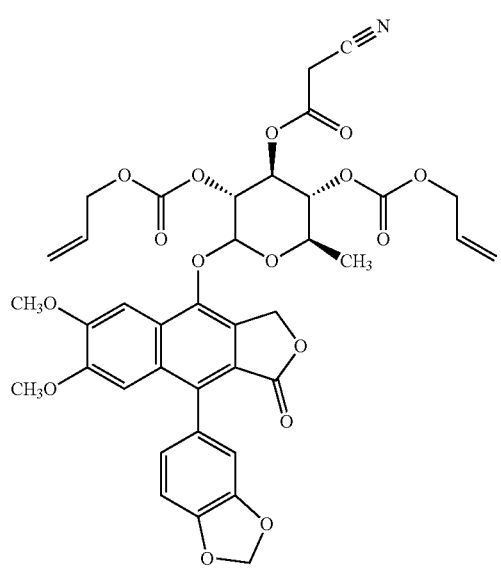
30j
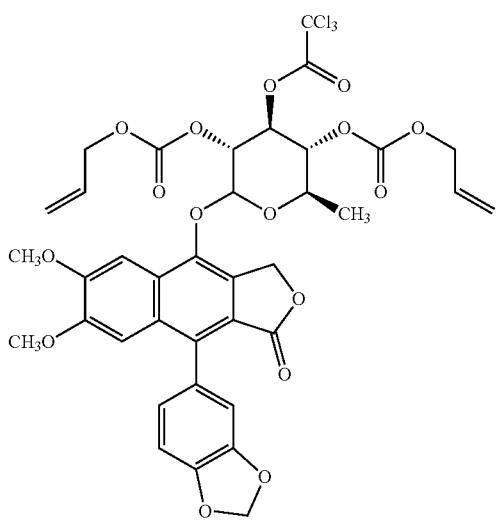
30k
-continued
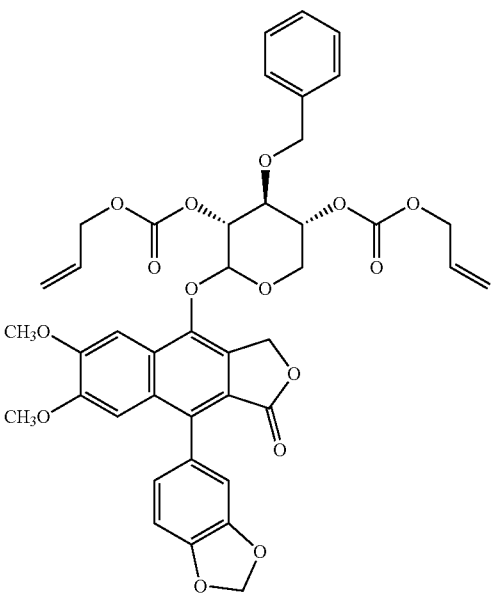
30l
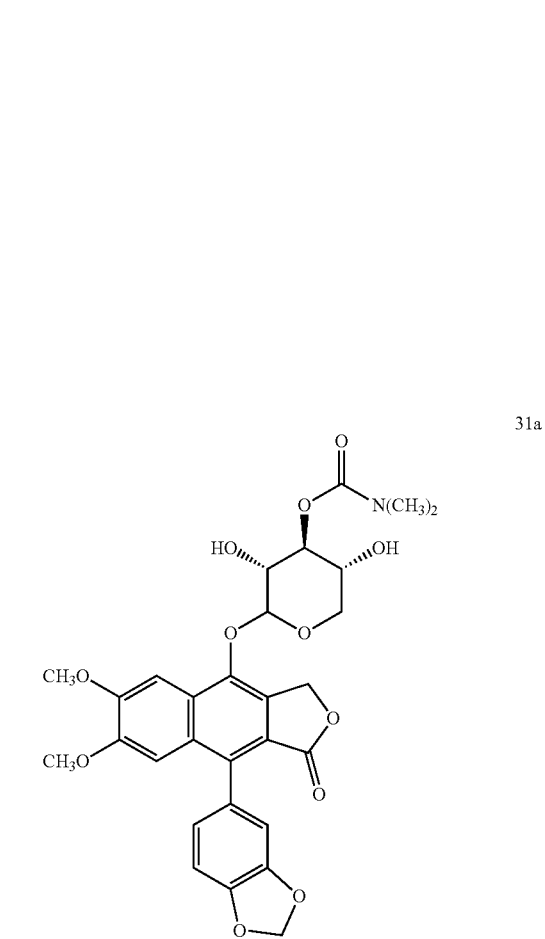
31a

117
-continued
31b
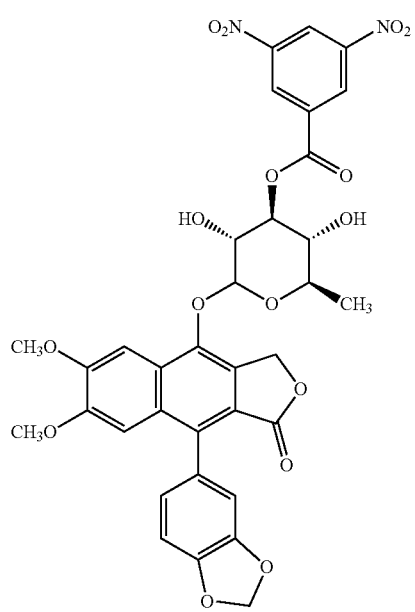
31c
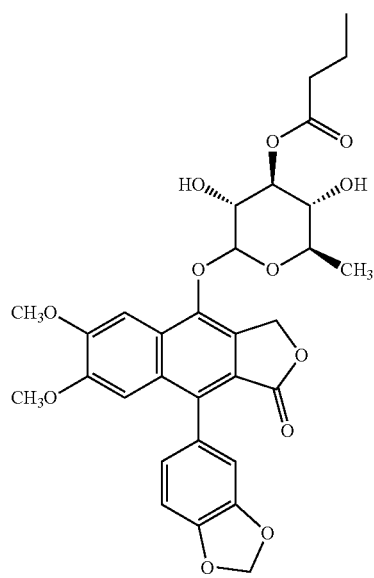
118
-continued
31d
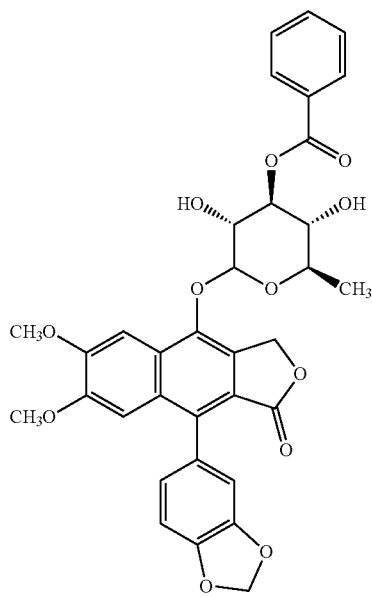
31e
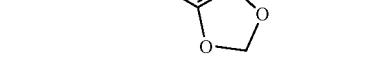

-continued
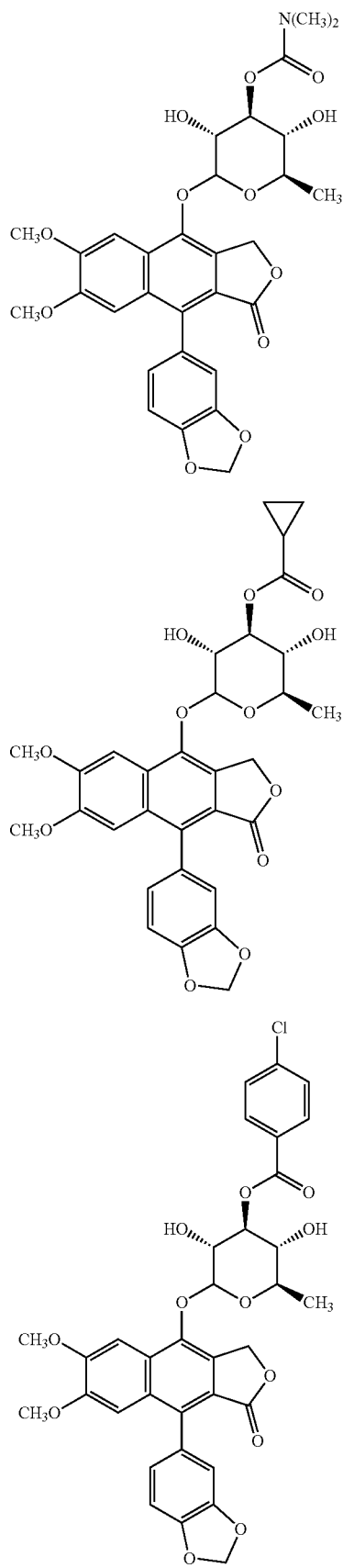
31f
31g
31h
-continued
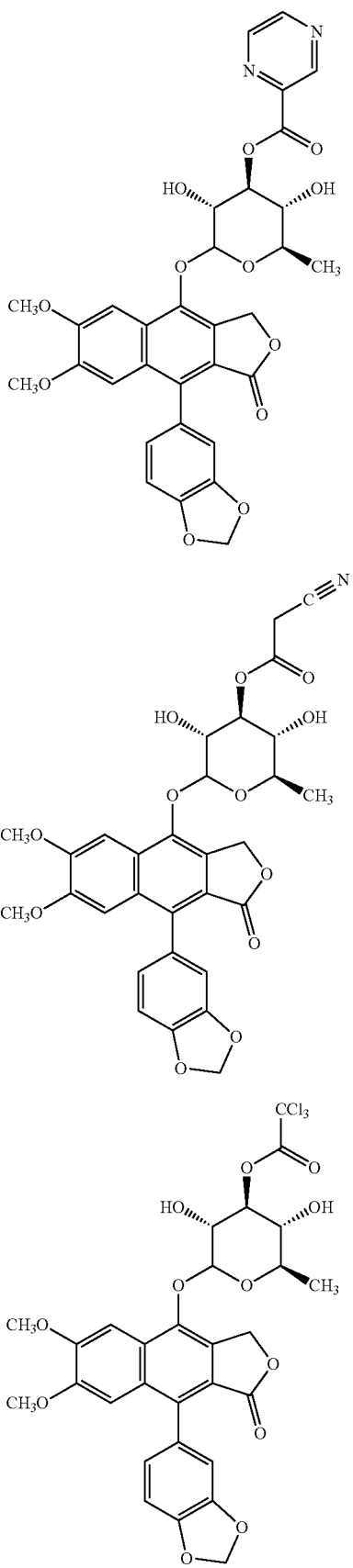
31i
31j
31k

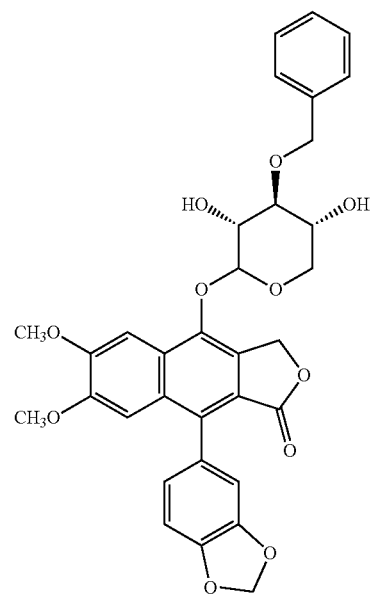
311
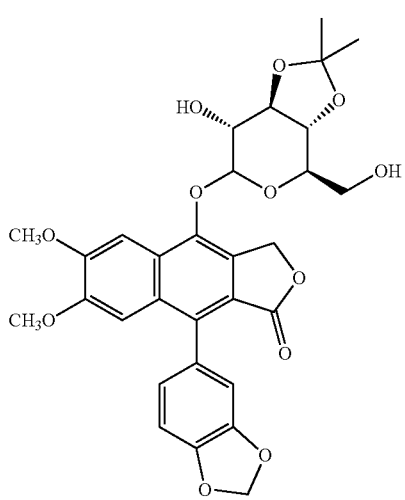
32a
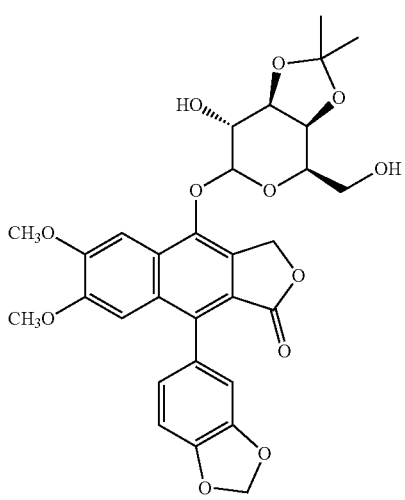
32b
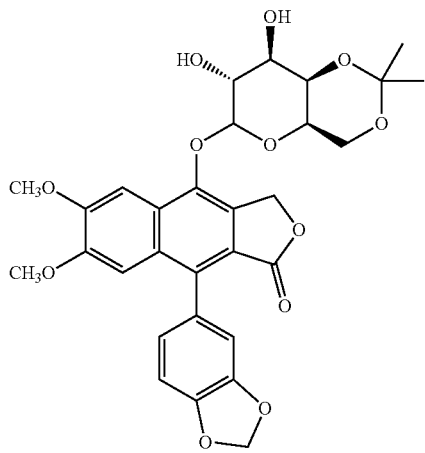
32c
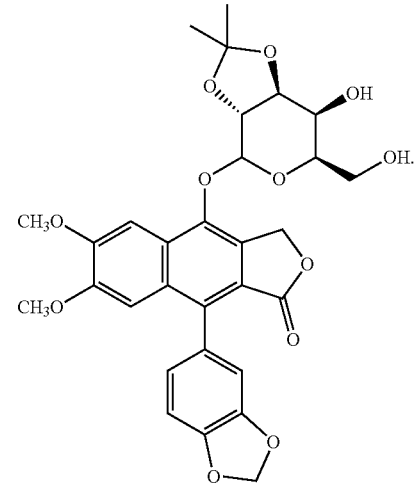
32d
The present disclosure also provides aryl naphthalene glycoside compounds, including derivatives of diphyllin, patentiflorin A, justiprocuminA or justiprocumin B useful in the treatment of viral infections.
In certain embodiments, the compound has the Formula (I) or (II):
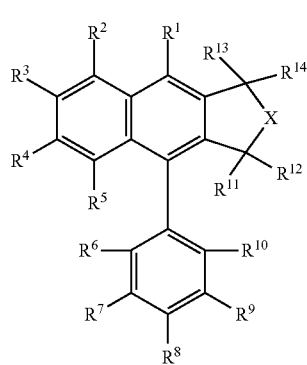
(I)

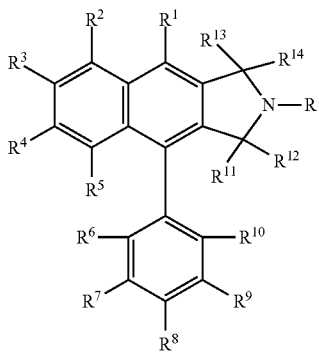

(II)

or a stereoisomer thereof; or an enantiomer thereof; or a pharmaceutically acceptable salt or pro-drug thereof wherein X is oxygen or sulfur;

$R^1$, $R^2$, $R^3$, $R^4$, $R^5$, $R^6$, $R^7$, $R^8$, $R^9$ and $R^{10}$ are each independently hydrogen, halogen or a moiety comprising 1 to 30 plural valence atoms selected from the group consisting of carbon, nitrogen, oxygen and sulfur; or $R^2$ and $R^3$, $R^3$ and $R^4$, $R^4$ and $R^5$, $R^6$ and $R^7$, $R^7$ and $R^8$, $R^8$ and $R^9$ or $R^9$ and $R^{10}$ may be taken together with the carbon atoms to which they are attached to form a cyclic group which is optionally substituted with halogen and a moiety comprising 1 to 30 plural valence atoms selected from the group consisting of carbon, nitrogen, oxygen and sulfur;

$R^{11}$ and $R^{12}$ taken together form oxo; or while one of $R^{11}$ and $R^{12}$ is hydrogen or halogen, the other one of $R^{11}$ and $R^{12}$ is selected from the group consisting of $R^{15}$, —$OR^{15}$, —$C(O)R^{15}$ and —$C(O)OR^{15}$;

$R^{13}$ and $R^{14}$ taken together form oxo; or while one of $R^{13}$ and $R^{14}$ is hydrogen or halogen, the other one of $R^{13}$ and $R^{14}$ is selected from the group consisting of $R^{15}$, —$OR^{15}$, —$C(O)R^{15}$ and —$C(O)OR^{15}$;

$R^{15}$ is independently selected from the group consisting of hydrogen, halogen, trichloromethyl, trifluoromethyl, cyano, nitro, hydrocarbyl optionally substituted with 1, 2, 3, 4 or 5 $R^{16}$, heterocyclcyl optionally substituted with 1, 2, 3, 4 or 5 $R^{16}$, —$(CH_2)_k$-heterocyclyl optionally substituted with 1, 2, 3, 4 or 5 $R^{16}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$, wherein k is an integer between 1 and 6 (e.g. 1, 2 or 3);

$R^{16}$ is independently selected from the group consisting of halogen, trichloromethyl, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$; and $R^{17}$ and $R^{18}$ are each independently hydrogen or selected from the group consisting of hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy.

In certain embodiments, the compounds has the Formula (III) or (IV):

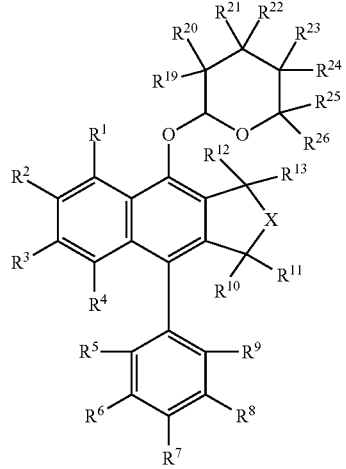

(III)

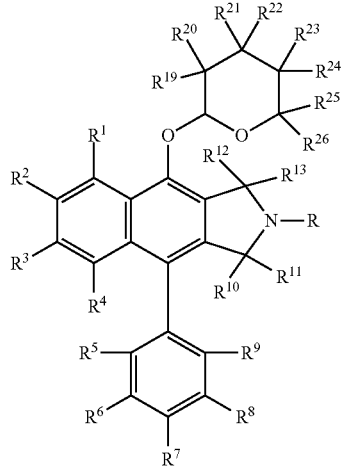

(IV)

or a stereoisomer thereof; or an enantiomer thereof; of a pharmaceutically acceptable salt or pro-drug thereof wherein, X is sulfur or oxygen;

$R^1$, $R^2$, $R^3$, $R^4$, $R^5$, $R^6$, $R^7$, $R^8$ and $R^9$ are each independently hydrogen, halogen or a moiety comprising 1 to 30 plural valence atoms selected from carbon, nitrogen, oxygen and sulfur; or $R^1$ and $R^2$, $R^2$ and $R^3$, $R^3$ and $R^4$, $R^5$ and $R^6$, $R^6$ and $R^7$, $R^7$ and $R^8$, and/or $R^8$ and $R^9$ taken together with the carbon atoms to which they are attached to form a cyclic group which is optionally substituted with 1, 2, 3, 4 or 5 group(s) selected from halogen and a moiety comprising 1 to 30 plural valence atoms selected from the group consisting of carbon, nitrogen, oxygen and sulfur;

$R^{10}$ and $R^{11}$ taken together form oxo; or while one of $R^{10}$ and $R^{11}$ is hydrogen or halogen, the other one of $R^{10}$ and $R^{11}$ is selected from the group consisting of $R^{27}$, —$OR^{27}$, —$C(O)R^{27}$, and —$C(O)OR^{27}$;

$R^{12}$ and $R^{13}$ taken together form oxo; or while one of $R^{12}$ and $R^{13}$ is hydrogen or halogen, the other one of $R^{12}$ and $R^{13}$ is selected from the group consisting of $R^{27}$, —$OR^{27}$, —$C(O)R^{27}$, and —$C(O)OR^{27}$;

$R^{19}$ and $R^{20}$ taken together form oxo; or while one of $R^{19}$ and $R^{20}$ is hydrogen or halogen, the other one of $R^{19}$ and $R^{20}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{21}$ and $R^{22}$ taken together form oxo; or while one of $R^{21}$ and $R^{22}$ is hydrogen or halogen, the other one of $R^{16}$ and $R^{17}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide and substituted tetrasaccharide;

$R^{23}$ and $R^{24}$ taken together form oxo; or while one of $R^{23}$ and $R^{24}$ is hydrogen or halogen, the other one of $R^{23}$ and $R^{24}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{25}$ and $R^{26}$ taken together form oxo; or while one of $R^{25}$ and $R^{26}$ is hydrogen or halogen, the other one of $R^{25}$ and $R^{26}$ is selected from the group consisting of $R^{27}$, —$OR^{27}$, —$C(O)R^{27}$, —$C(O)OR^{27}$, —$CH_2R^{31}$ and —$C(O)R^{31}$;

$R^{27}$ is independently selected from the group consisting of hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, hydrocarbyl optionally substituted with 1, 2, 3, 4 or 5 group(s) selected from the group consisting of $R^{28}$, heterocyclcyl optionally substituted with 1, 2, 3, 4 or 5 group(s) selected from the group consisting of $R^{28}$, and —$(CH_2)_k$-heterocyclyl optionally substituted with 1, 2, 3, 4 or 5 group(s) selected from group(s) independently selected $R^{28}$, wherein k is an integer between 1 and 6 (e.g. 1, 2 or 3);

$R^{28}$ is independently selected from the group consisting of halogen, trichloromethyl, trifluoromethyl, cyano, nitro, oxo, =$NR^{29}$, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$ and —$N(R^{29})S(O)_2R^{30}$;

$R^{29}$ and $R^{30}$ are each independently hydrogen or selected from the group consisting of hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy;

$R^{31}$ is independently selected from the group consisting of hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, monosaccharide, substituted monosaccharide, disaccharide, substituted disaccharide, trisaccharide, substituted trisaccharide, tetrasaccharide, substituted tetrasaccharide, hydrocarbyl optionally substituted with 1, 2, 3, 4 or 5 group(s) selected from the group consisting of $R^{28}$, and heterocyclyl optionally substituted with 1, 2, 3, 4 or 5 group(s) selected from the group consisting of $R^{28}$; and R is hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy.

In certain embodiments, the glycosidic group can be a carbohydrate group, such as a monosaccharide, disaccharide, trisaccharide, tetrasaccharide or polysaccharide group, and may exist in any isomeric form, for example α-D, α-L, β-D or β-L forms. The carbohydrate group may be optionally substituted with other type of substituents or even additional glycosidic groups. However, the total number of monosaccharide and substituted monosaccharide contained in the chemical structure of a compound is generally 30 or less.

In certain embodiments, the glycosidic group may comprise one or more monosaccaride units of Formula (V) or (VI):

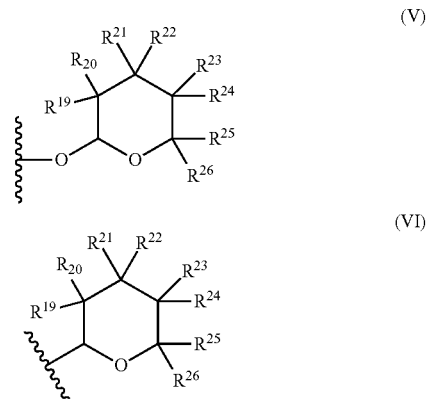

wherein $R^{19}$ and $R^{20}$ taken together form oxo; or while one of $R^{19}$ and $R^{20}$ is hydrogen or halogen, the other one of $R^{19}$ and $R^{20}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{21}$ and $R^{22}$ taken together form oxo; or while one of $R^{21}$ and $R^{22}$ is hydrogen or halogen, the other one of $R^{21}$ and $R^{22}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide, and substituted tetrasaccharide;

$R^{23}$ and $R^{24}$ taken together form oxo; or while one of $R^{23}$ and $R^{24}$ is hydrogen or halogen, the other one of $R^{23}$ and $R^{24}$ is selected from the group consisting of $R^{27}$, —$OR^{27}$, —$C(O)R^{27}$, —$C(O)OR^{27}$, monosaccharide, substituted monosaccharide, disaccharide, substituted disaccharide, trisaccharide, substituted trisaccharide, tetrasaccharide and substituted tetrasaccharide;

$R^{25}$ and $R^{26}$ taken together form oxo; or while one of $R^{25}$ and $R^{26}$ is hydrogen or halogen, the other one of $R^{25}$ and $R^{26}$ is selected from the group consisting of $R^{27}$, —$OR^{27}$, —$C(O)R^{27}$, —$C(O)OR^{27}$, —$CH_2R^{31}$, and —$C(O)R^{31}$;

$R^{27}$ is independently selected from the group consisting of hydrogen, halogen, trichloromethyl, trifluoromethyl, cyano, nitro, —$OR^{29}$, —$C(O)R^{30}$, —$C(O)N(R^{29})R^{30}$, —$C(O)OR^{29}$, —$OC(O)R^{29}$, —$S(O)_2R^{29}$, —$S(O)_2N(R^{29})R^{30}$, —$N(R^{29})R^{30}$, —$N(R^{29})N(R^{29})R^{30}$, —$N(R^{29})C(O)R^{30}$, —$N(R^{29})S(O)_2R^{30}$, hydrocarbyl optionally substituted with 1, 2, 3, 4 or 5 group(s) independently selected from the group consisting of $R^{28}$, heterocyclcyl optionally substituted with 1, 2, 3, 4 or 5 group(s) independently selected from the group consisting of $R^{28}$, and —$(CH_2)_k$-heterocyclyl optionally substituted with 1, 2, 3, 4 or 5 group(s) independently selected from the group consisting of $R^{28}$, wherein k is an integer between 1 and 6 (e.g. 1, 2 or 3);

$R^{28}$ is independently selected from the group consisting of halogen, trichloromethyl, trifluoromethyl, cyano, nitro, oxo, =$NR^{29}$, —$OR^{29}$, —$C(O)R^{30}$, —$C(O)N(R^{29})R^{30}$, —$C(O)$ $OR^{29}$, $-OC(O)R^{29}$, $-S(O)_2R^{29}$, $-S(O)_2N(R^{29})R^{30}$, $-N(R^{29})R^{30}$, $-N(R^{29})N(R^{29})R^{30}$, $-N(R^{29})C(O)R^{30}$ and $-N(R^{29})S(O)_2R^{30}$;

$R^{29}$ and $R^{30}$ are each independently hydrogen or selected from the group consisting of hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy; and $R^{31}$ is independently selected from the group consisting of hydrogen, halogen, trichloromethyl, trifluoromethyl, cyano, nitro, $-OR^{29}$, $-C(O)R^{30}$, $-C(O)N(R^{29})R^{30}$, $-C(O)OR^{29}$, $-OC(O)R^{29}$, $-S(O)_2R^{29}$, $-S(O)_2N(R^{29})R^{30}$, $-N(R^{29})R^{30}$, $-N(R^{29})N(R^{29})R^{30}$, $-N(R^{29})C(O)R^{30}$, $-N(R^{29})S(O)_2R^{30}$, monosaccharide, substituted monosaccharide, disaccharide, substituted disaccharide, trisaccharide, substituted trisaccharide, tetrasaccharide, substituted tetrasaccharide, hydrocarbyl optionally substituted with 1, 2, 3, 4 or 5 group(s) independently selected from the group consisting of $R^{28}$, heterocyclcyl optionally substituted with 1, 2, 3, 4 or 5 group(s) independently selected from the group consisting of $R^{28}$, and $-(CH_2)_k$-heterocyclyl optionally substituted with 1, 2, 3, 4 or 5 group(s) independently selected from the group consisting of $R^{28}$, wherein k is an integer between 1 and 6 (e.g. 1, 2 or 3).

In certain embodiments, the glycosidic group comprises 1, 2, 3, or 4 monosaccharide units, wherein each monosaccharide unit in the glycosidic group is independently for each occurrence a monosaccharide unit of Formula (V) or Formula (VI).

In certain embodiments, $R^1$, $R^4$, $R^5$, $R^8$ and $R^9$ are each independently hydrogen, hydroxy or methoxy; $R^2$ and $R^3$ are each independently hydrogen, hydroxy, methoxy, or taken together with the carbon atoms to which they are attached form a [1,3] dioxole cyclic group; $R^6$ and $R^7$ are each independently hydrogen, hydroxy, methoxy; or $R^6$ and $R^7$ taken together with the carbon atoms to which they are attached form a [1,3] dioxole cyclic group; $R^{10}$ and $R^{11}$ taken together form oxo; $R^{12}$ and $R^{13}$ are each independently hydrogen; and X is oxygen.

Exemplary glycosidic groups include glucopyranoside, galactopyranoside, mannopyranoside, fucopyranoside, arabinopyranoside, glucopyranoside, galactopyranoside, glucuronide, lactopyranoside, xylopyranoside, glucosaminide, galactosaminide, alloside, lyxoside, taloside, threoside, riboside, fructoside, rhamnoside and guloside groups. More particularly, the glycosidic group may be selected from α-D-glucopyranoside, α-D-galactopyranoside, α-D-mannopyranoside, α-L-fucopyranoside, α-L-arabinopyranoside, β-D-glucopyranoside, β-D-galactopyranoside, β-D-glucuronide, β-D-lactopyranoside, β-D-xylopyranoside, β-D-glucosaminide, β-D-galactosaminide, β-D-alloside, β-D-lyxoside, β-D-taloside, β-D-threoside, β-D-riboside, β-D-fructoside, β-D-rhamnoside and β-L-guoside groups.

Examples of compounds of the present disclosure include those shown below. It will of course be appreciated that, where appropriate, each compound may be in the form of the free compound, an acid or base addition salt, or a prodrug.

The present disclosure also provides a pharmaceutical composition comprising at least one of the compounds described herein and at least one pharmaceutically acceptable excipient.

The compounds described herein and their pharmaceutically acceptable salts can be administered to a subject either alone or in combination with pharmaceutically acceptable, excipients, carriers, and/or diluents in a pharmaceutical composition according to standard pharmaceutical practice. The compounds can be administered orally or parenterally.

Parenteral administration includes intravenous, intramuscular, intraperitoneal, subcutaneous and topical, the preferred method being intravenous and topical administrations.

Accordingly, the present disclosure provides pharmaceutically acceptable compositions, which comprise a therapeutically effective amount of one or more of the compounds described herein, formulated together with one or more pharmaceutically, excipients, acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the compounds described herein may contain a basic functional group, such as amino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional non-toxic salts or quaternary ammonium salts of the compounds, e.g., from non-toxic organic or inorganic acids. For example, such conventional non-toxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations or compounds include the step of bringing into association a compound described herein with the carrier or excipient and, optionally, one or more accessory ingredients. In general, the formulations are prepared by uniformly and intimately bringing into association a compound of the present disclosure with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present disclosure suitable for parenteral administration comprise one or more compounds described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

The present disclosure provides diphyllin and patentiflorin A analogs with anti-HIV and anti-influenza virus activity and synthesis thereof. The compounds of the present disclosure were synthesized and evaluated for their anti-HIV and anti-influenza viral activity.

The synthetic or semi-synthetic analogues of diphyllin can be exemplified by 12a, 12b, 13, 14a, 14b, 15a, 15b, 16, 17a, 17b, 17c, 17d, 17e, 17f, 17g, 17h, 18, 19a, 19b, 19c, 19d, 19e, 19f, 19g, 19h, 19i, 19j, 19k, 19l, 19m, 19n, 19o, 19p, 20, 21, 22, 23 and 24.

The synthetic or semi-synthetic analogues of patentiflorin A can be exemplified by 25a, 25b, 25c, 25d, 25e, 25f, 25g, 26a, 26b, 26c, 26d, 26e, 26f, 26g, 27aa, 27ab, 27ac, 27ad, 27ae, 27af, 27ba, 27bb, 27bc, 27bd, 27be, 27bf, 28ab1, 28ab2, 28ab3, 28bb1, 28bb2, 28bb3, 29a, 29b, 30a, 30b, 30c, 30d, 30e, 30f, 30g, 30h, 30i, 30j, 30k, 30l, 31a, 31b, 31c, 31d, 31e, 31f, 31g, 31h, 31i, 31j, 31k, 31l, 32a, 32b, 32c and 32d.

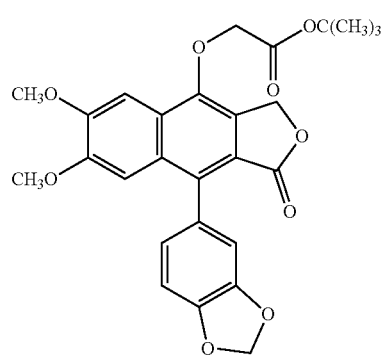

12a

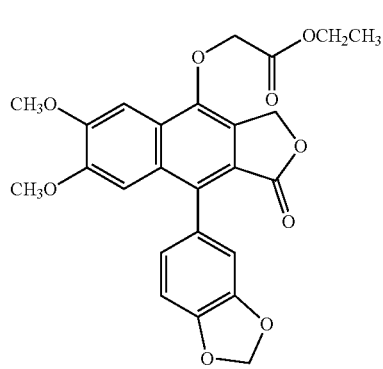

12b

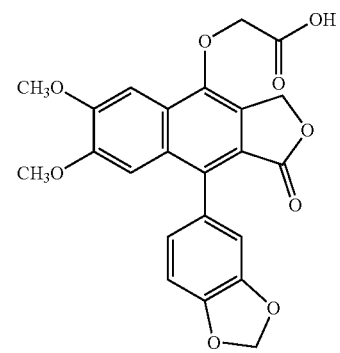

13

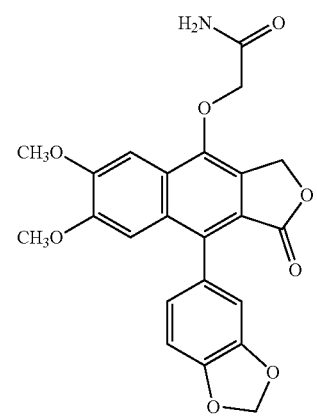

14a

131
-continued
14b
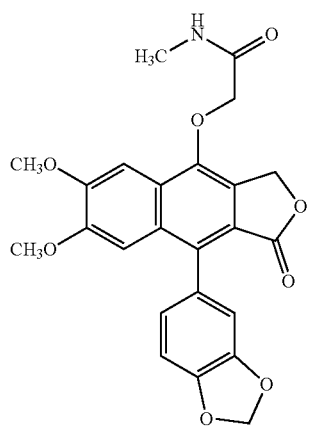
15a
15b
16
132
-continued
17a
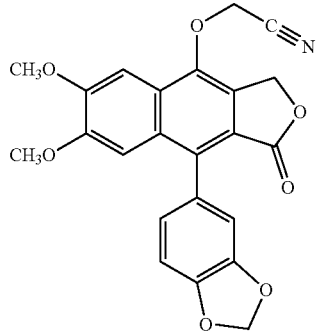
17b
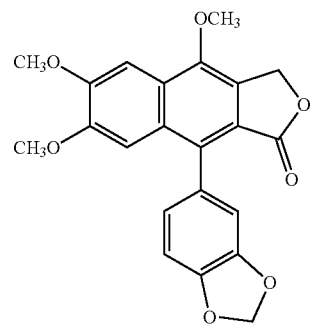
17c
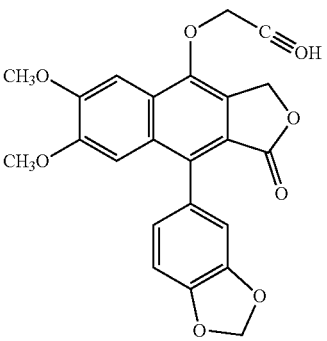
17d
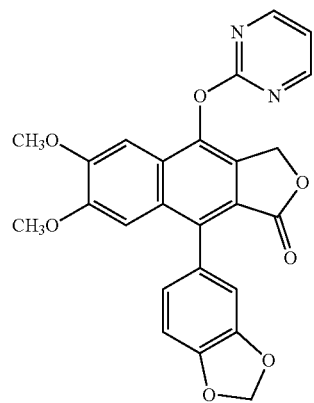

17e
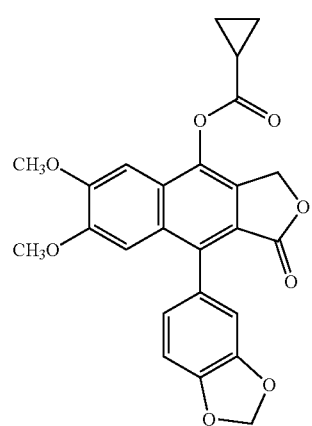
17f
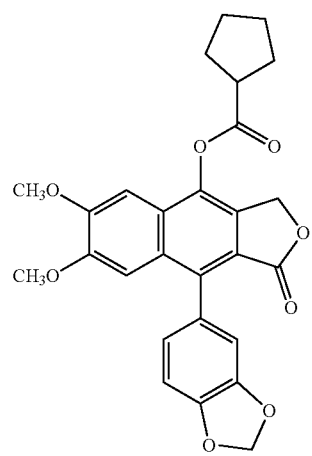
17g
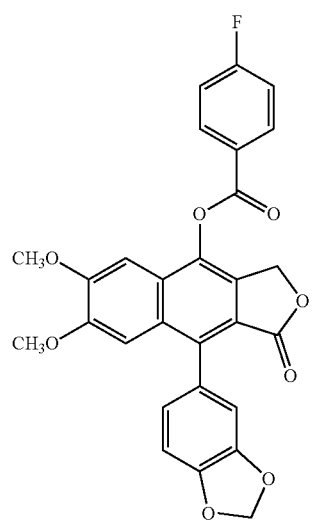
17h
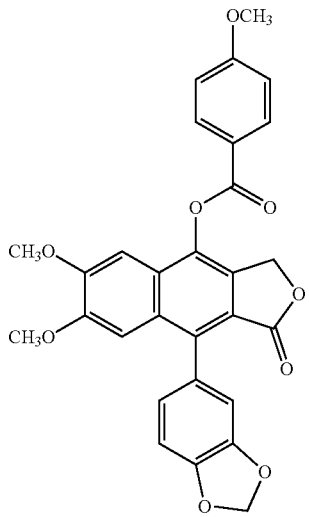
18
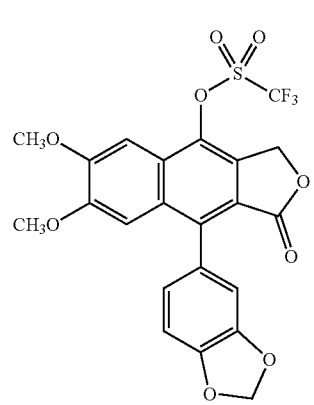
19a
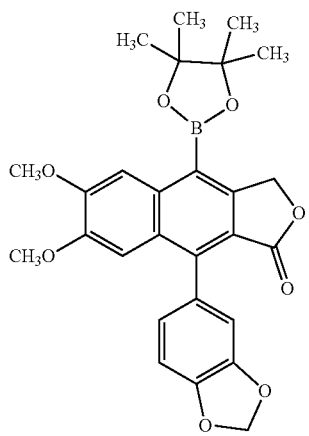
19b
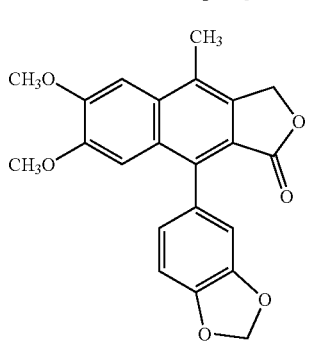

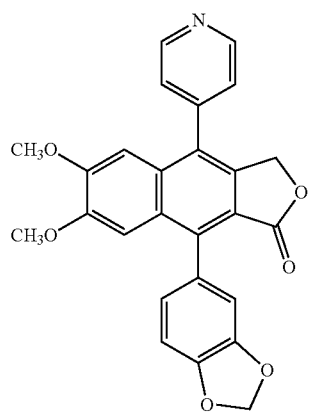
19c
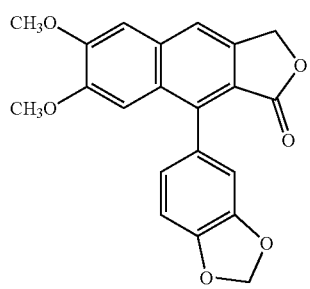
19d
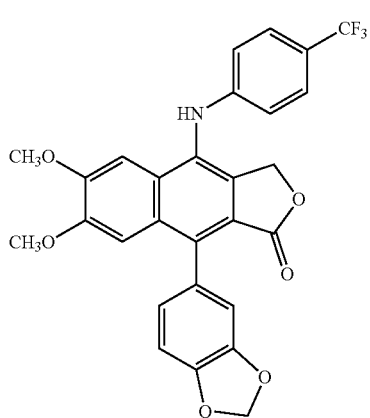
19e
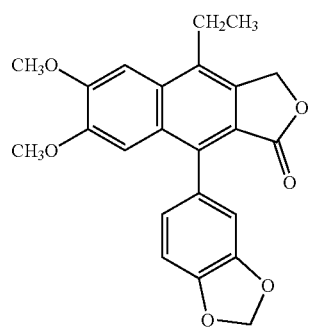
19g
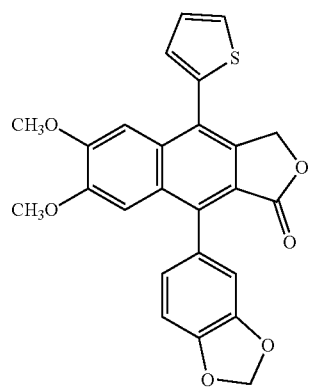
19h
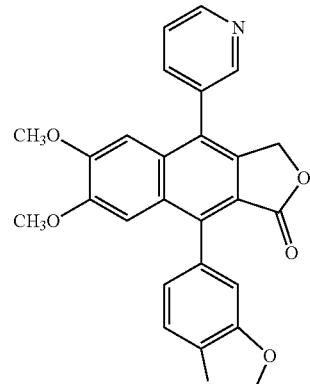
19i
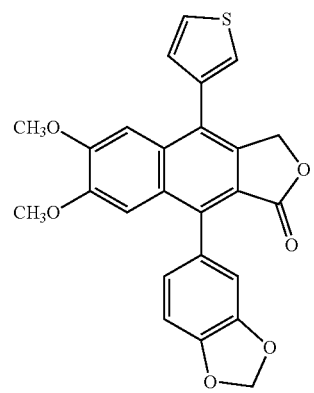
19j

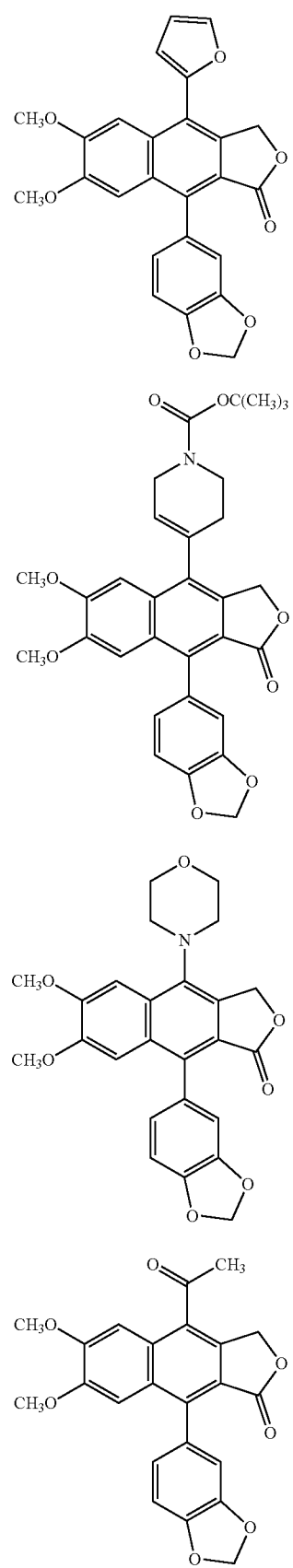
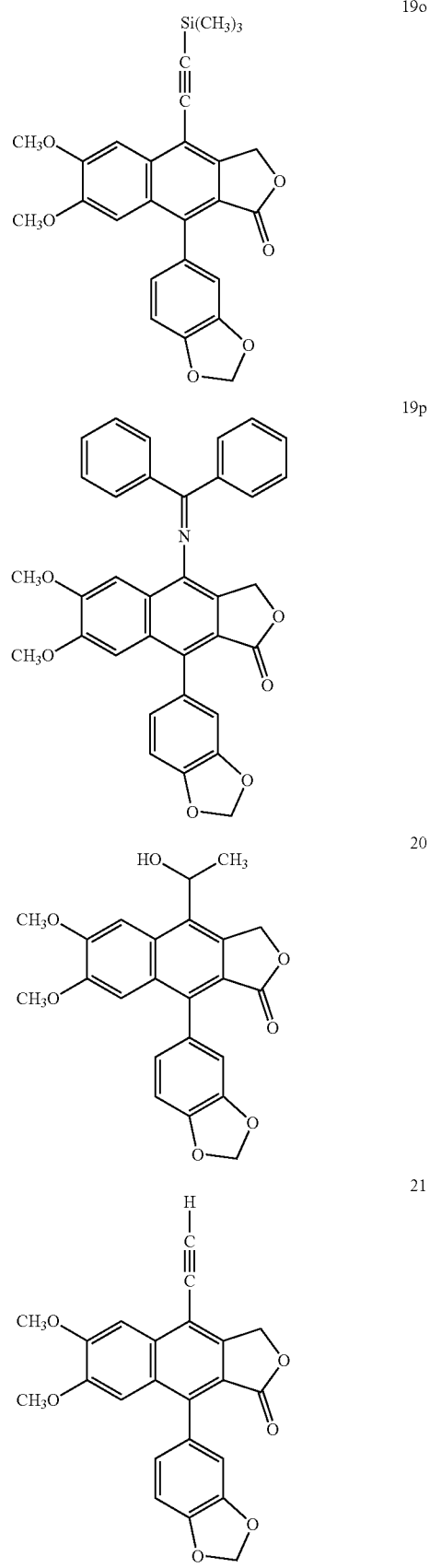

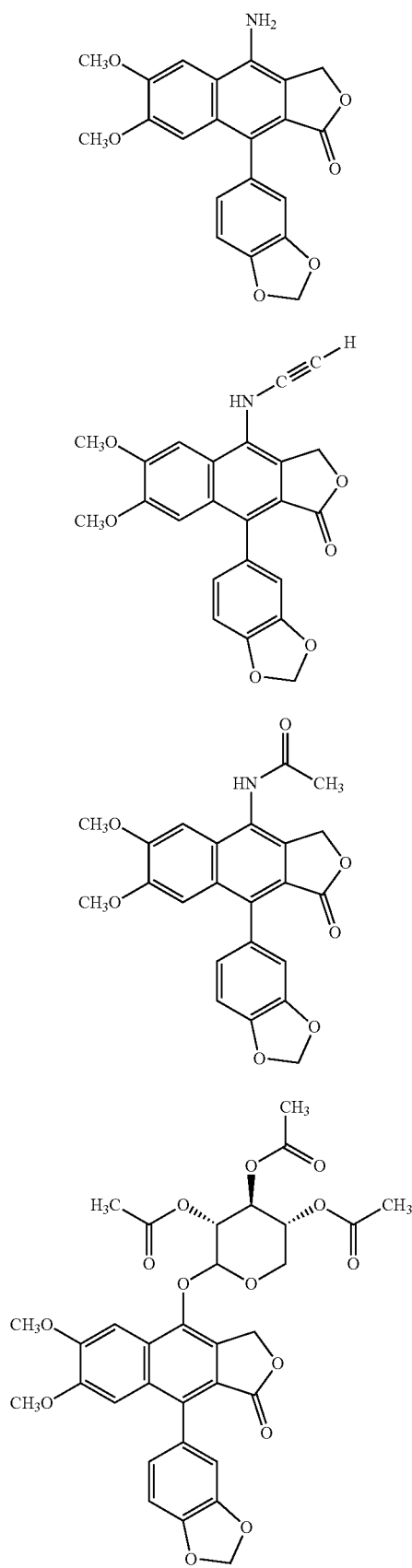

25e
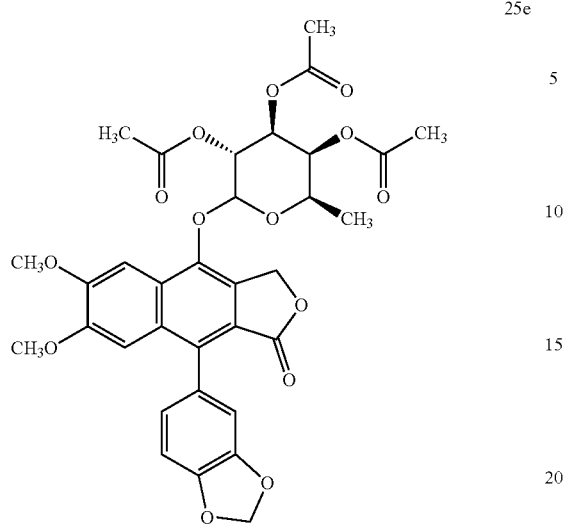
25f
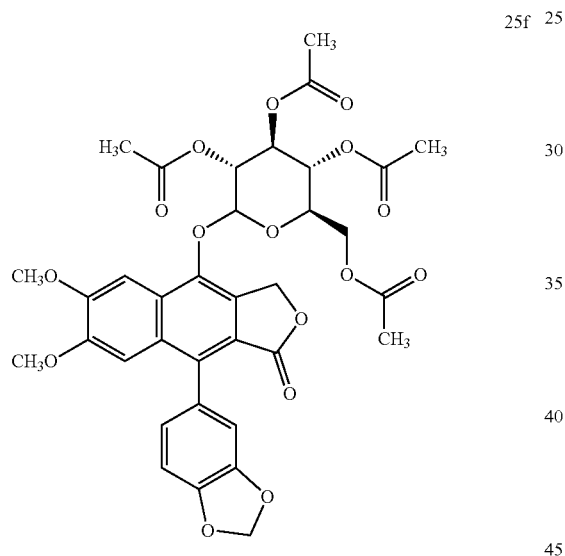
25g
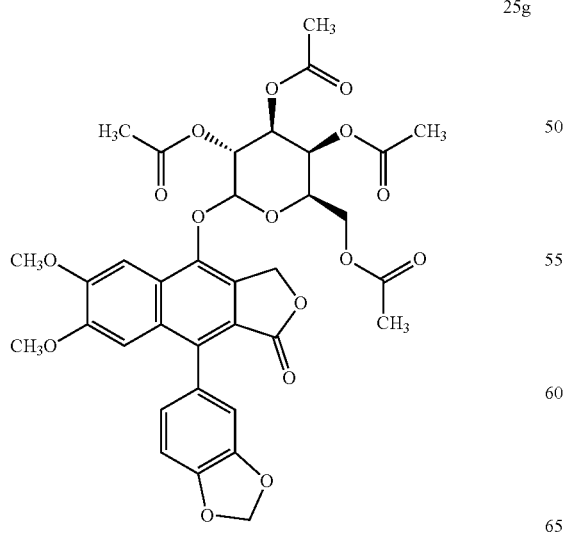
26a
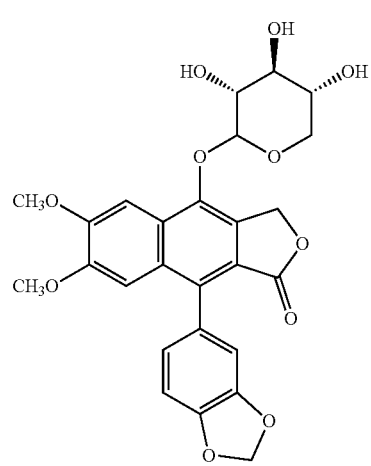
26b
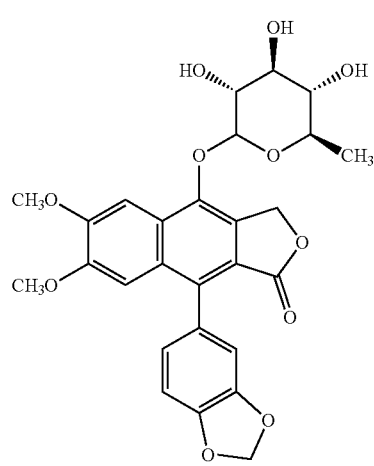
26c
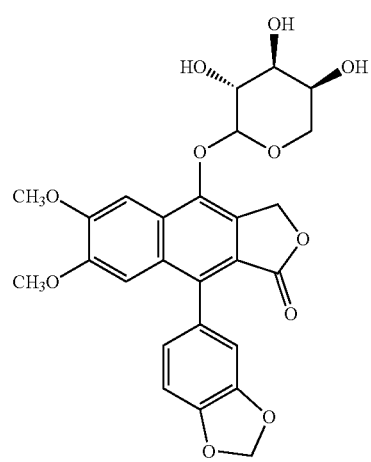

143
26d 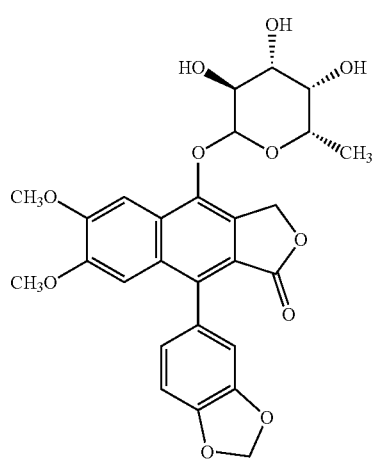
26e 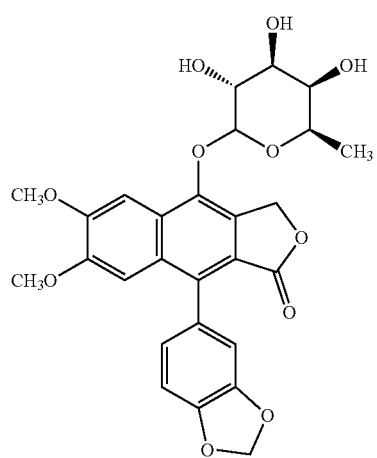
26f 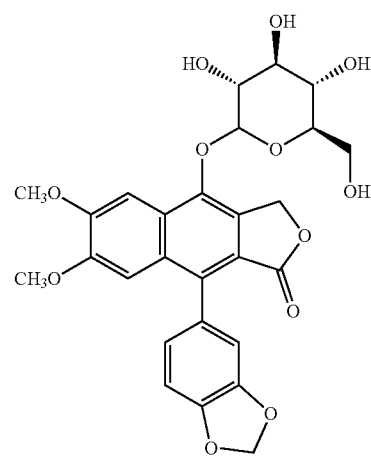
144
26g 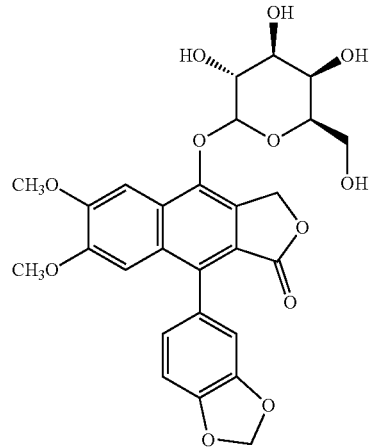
27aa 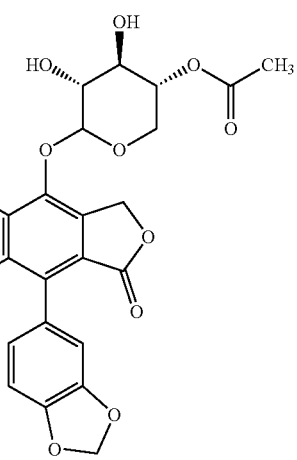
27ab 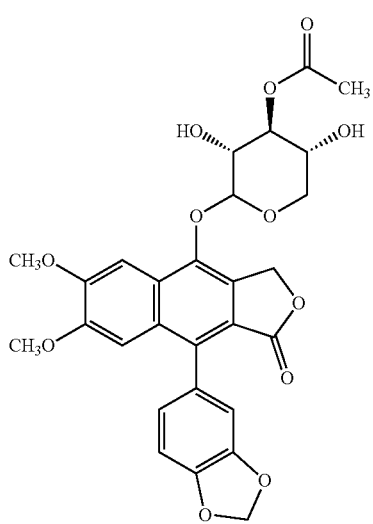

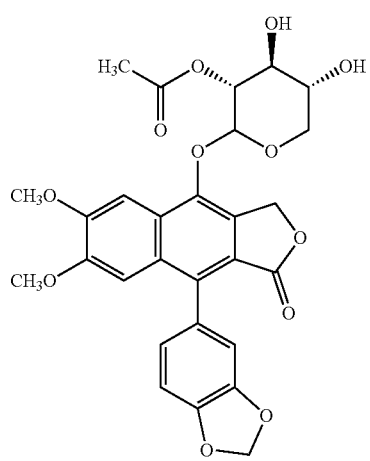
27ac
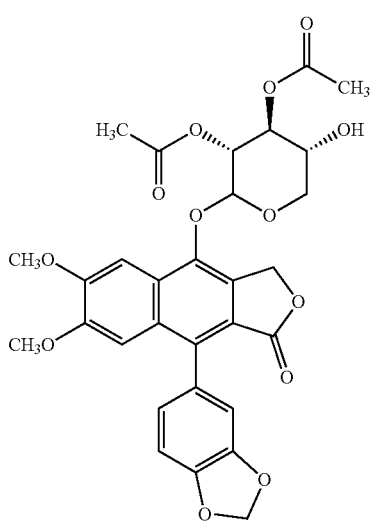
27af
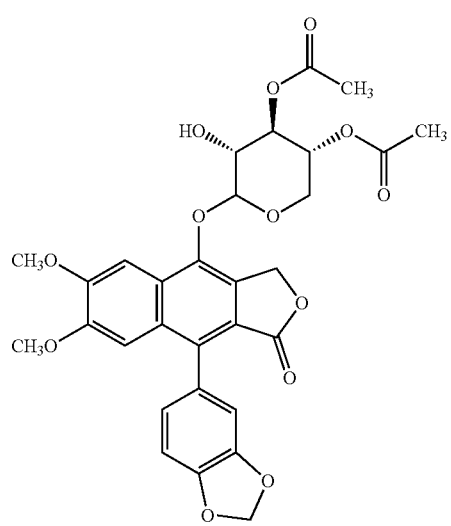
27ad
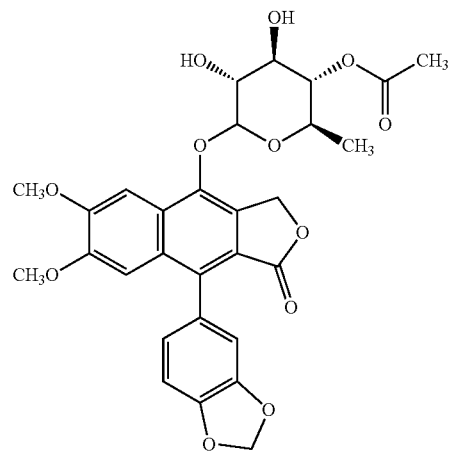
27ba
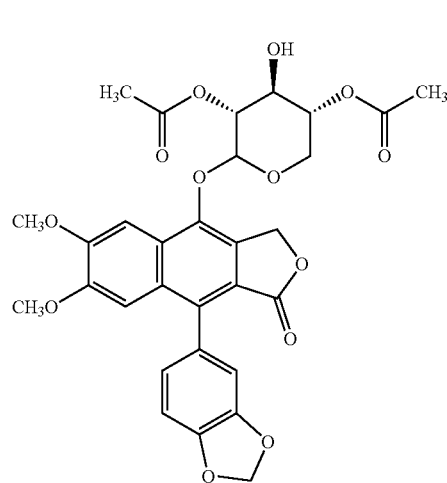
27ae
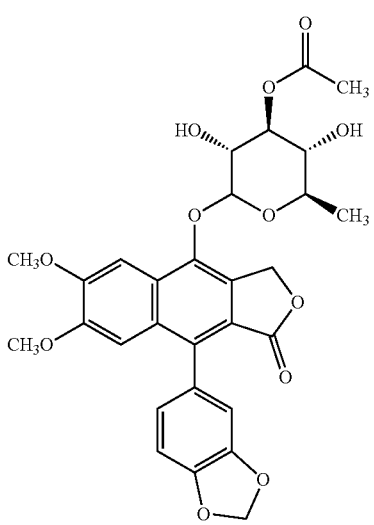
27bb

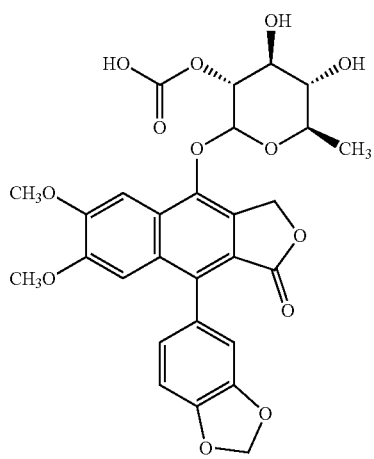
27bc
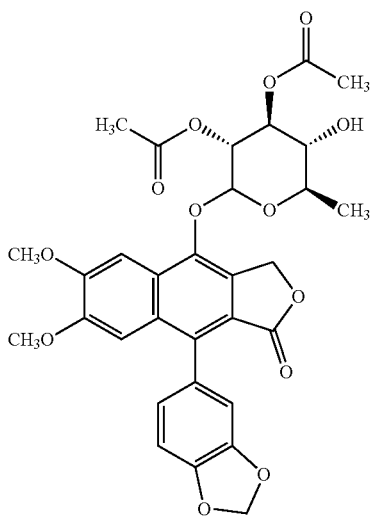
27bf
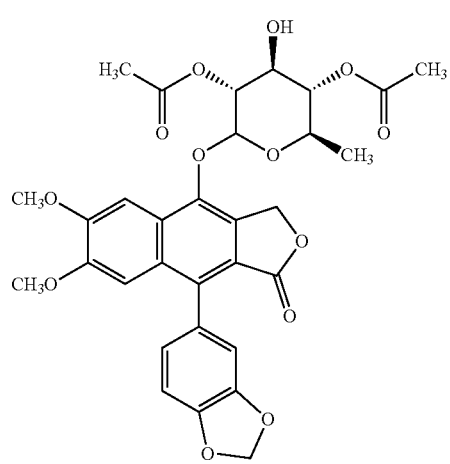
27bd
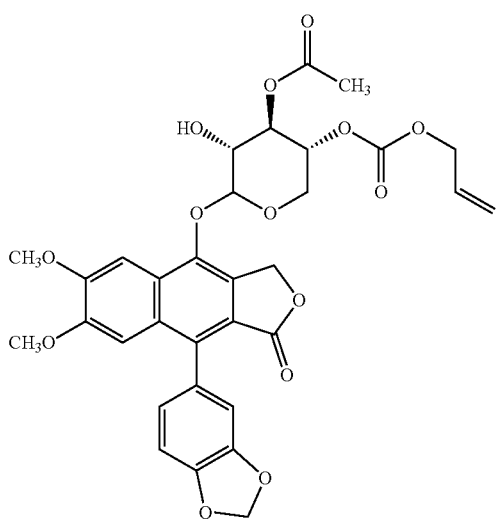
28ab1
28ab2

-continued
28ab3
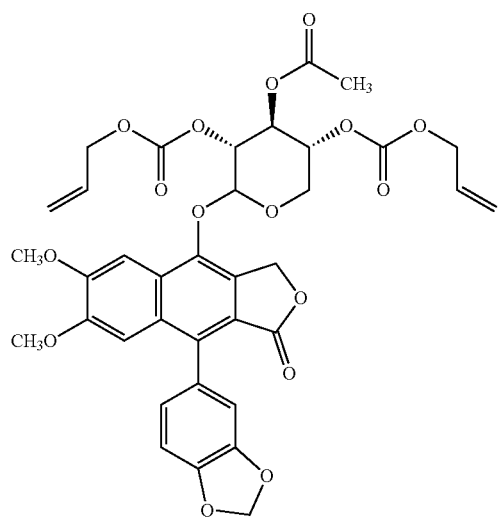
28bb1
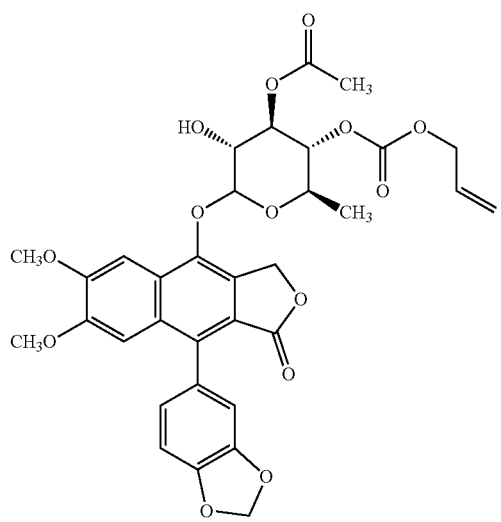
28bb2
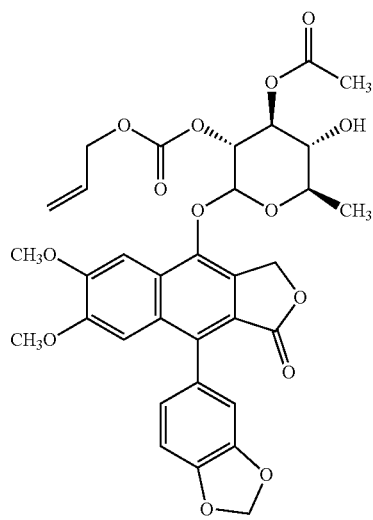
-continued
28bb3
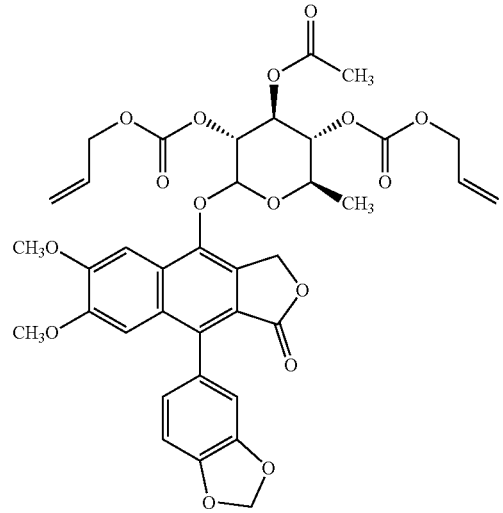
29a
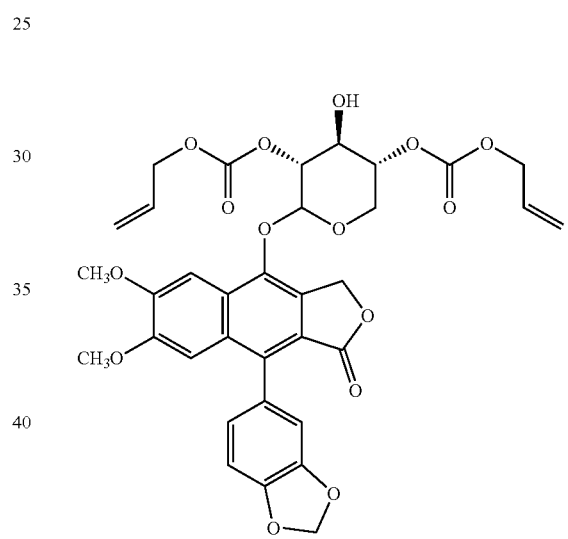
29b
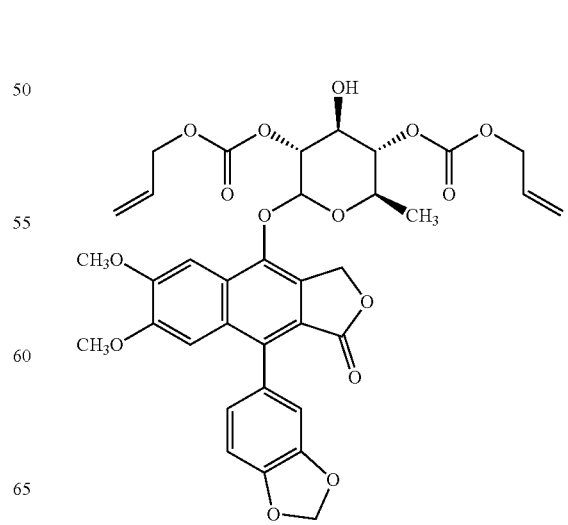

151
-continued
30a
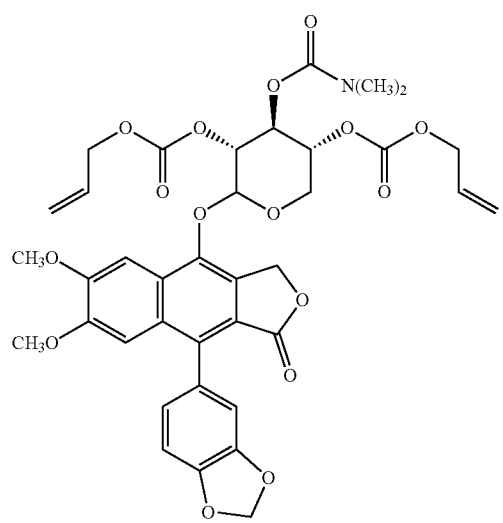
30b
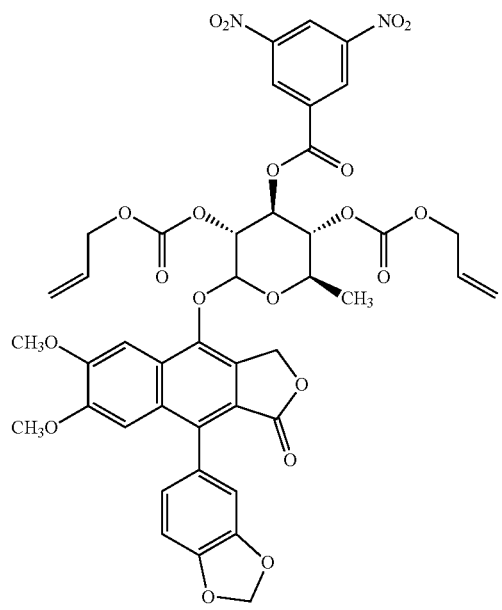
152
-continued
30c
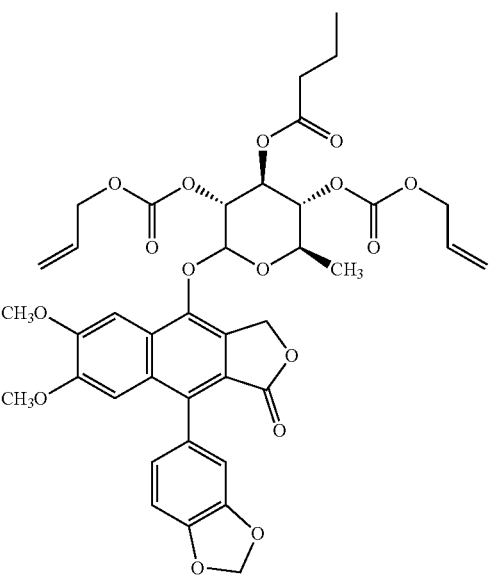
30d
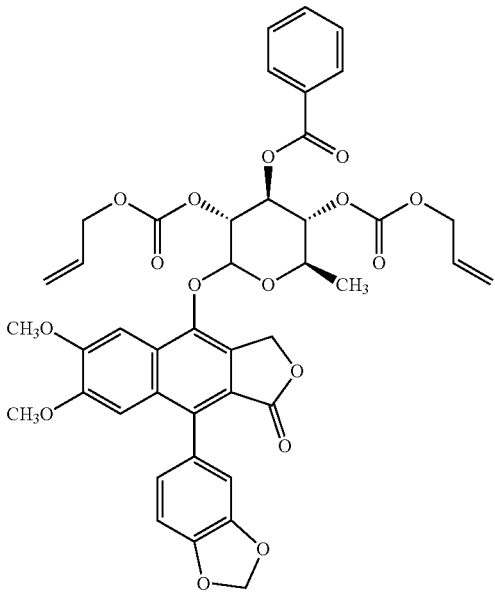

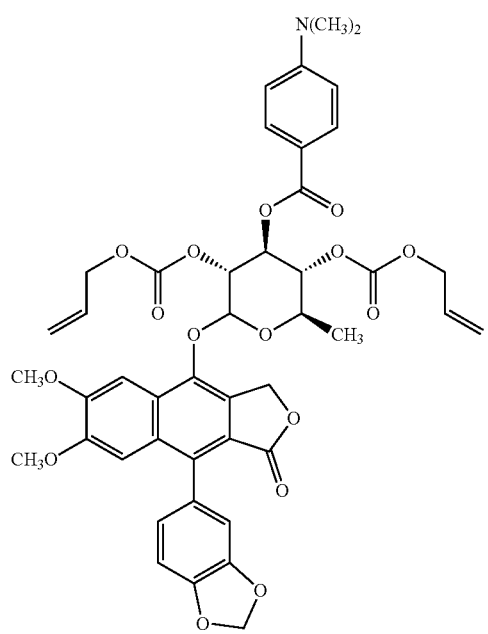
30e
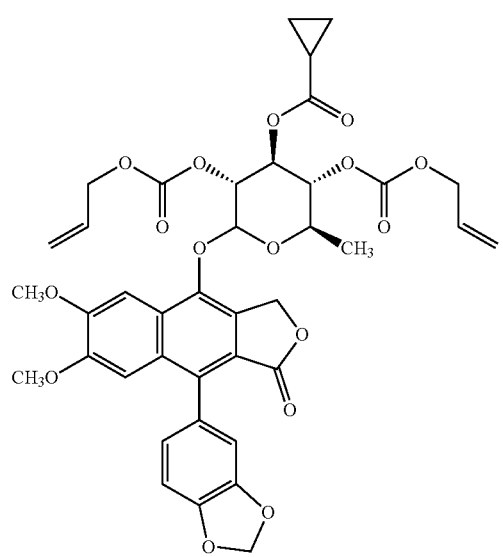
30g
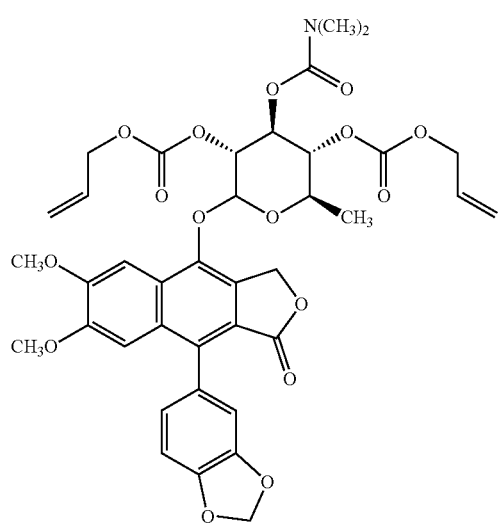
30f
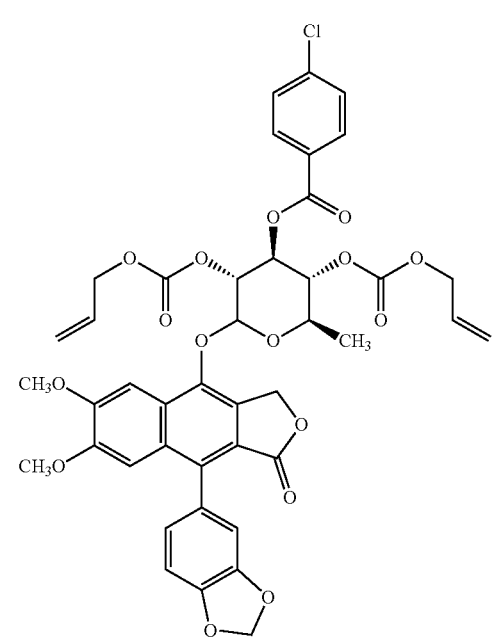
30h

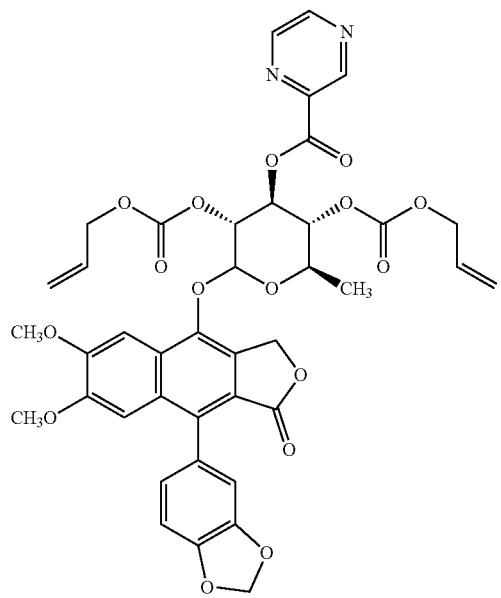
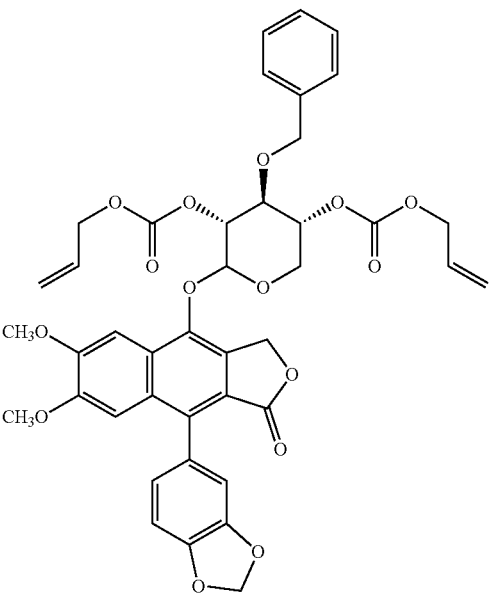

157 -continued
31b
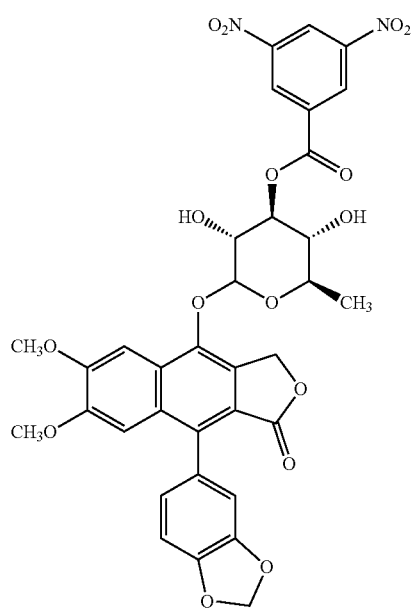
31c
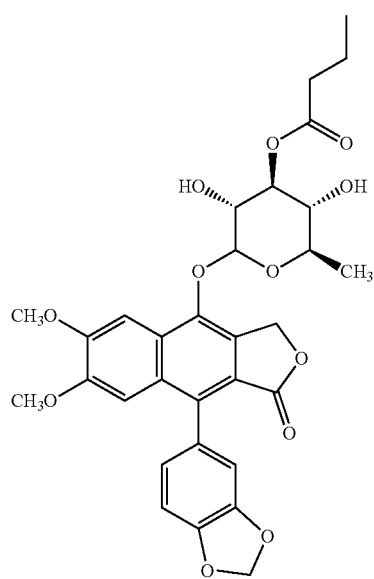
158 -continued
31d
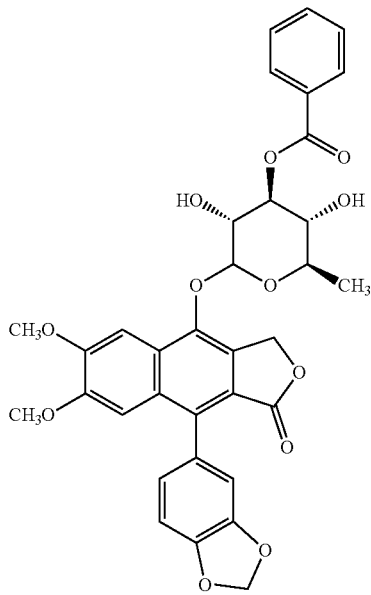
31e
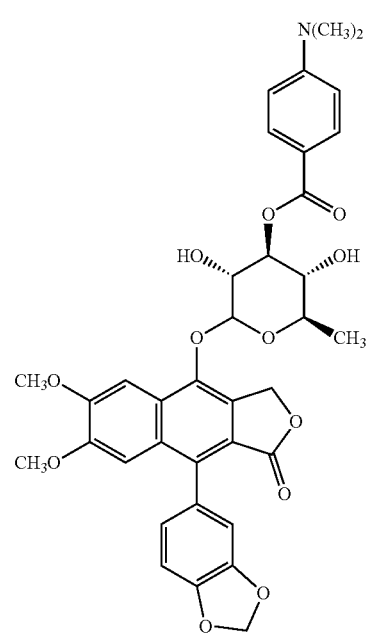

31f
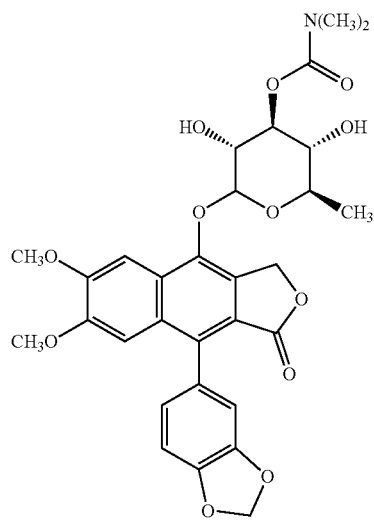
31h
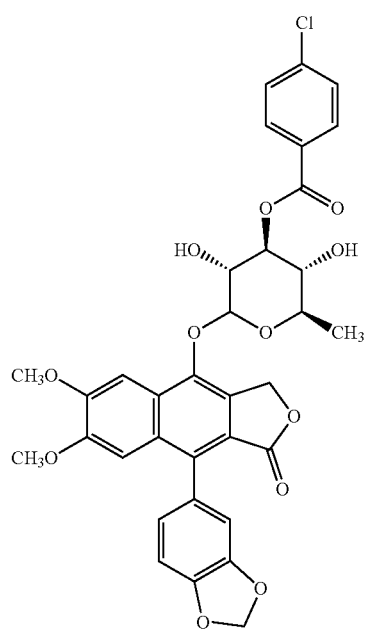
31g
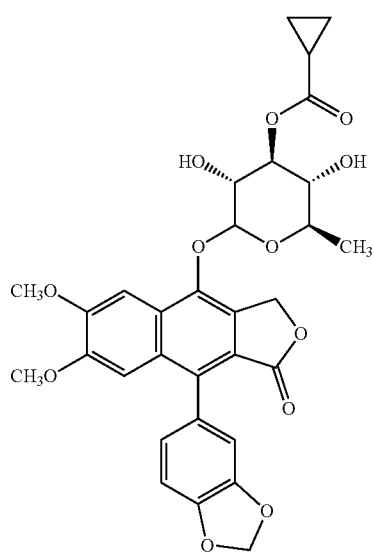
31i
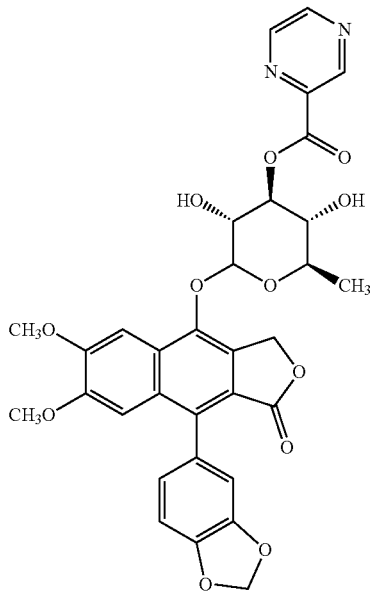

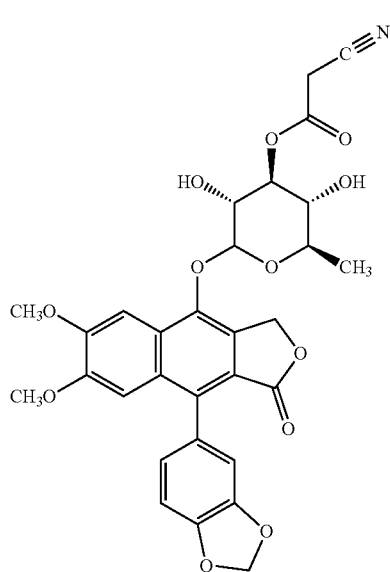
31j
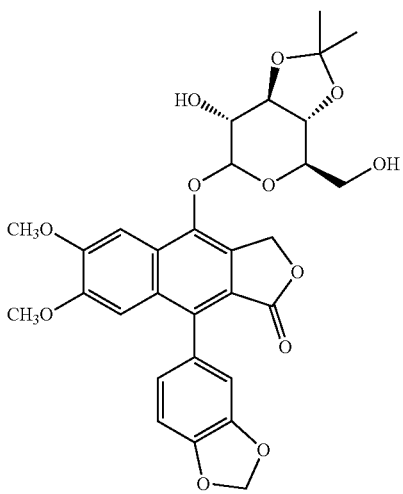
32a
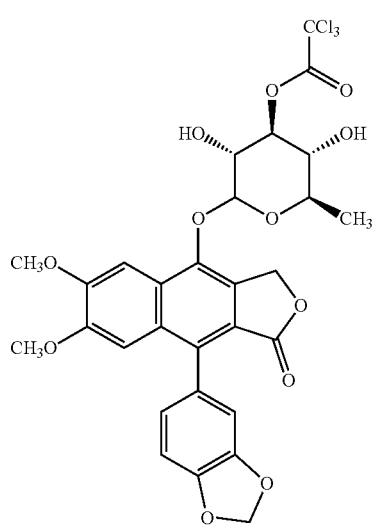
31k
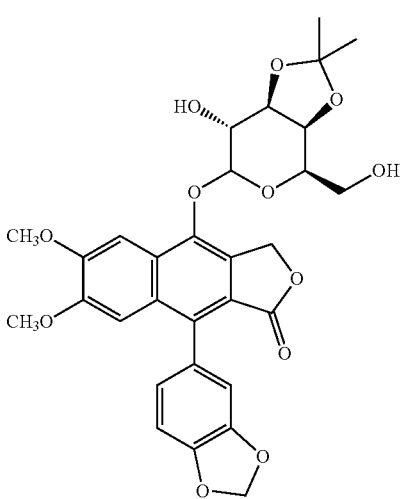
32b
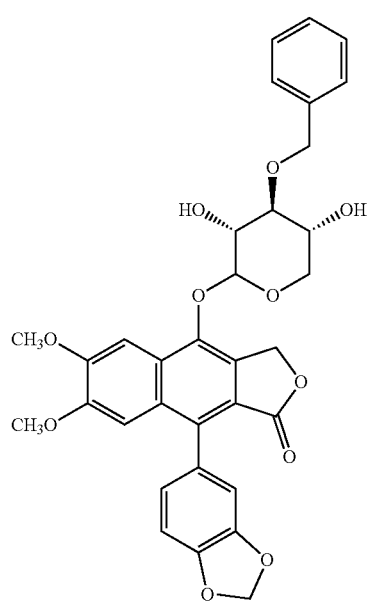
31l
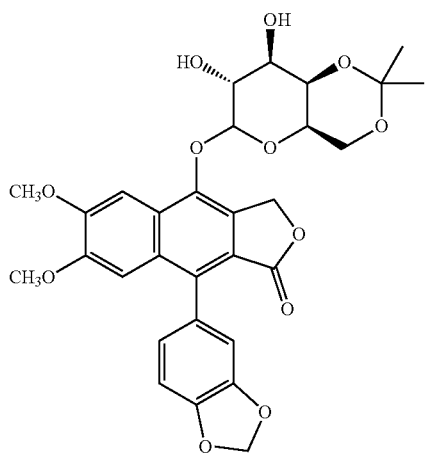
32c -continued 32d

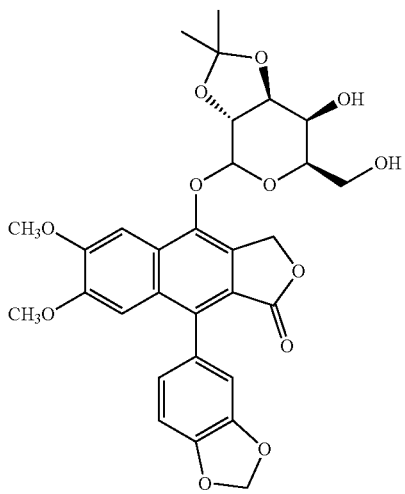

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Unless indicated otherwise, parts are parts by weight, temperature is ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Examples of compounds of the present disclosure include those shown below. It will of course be appreciated that, where appropriate, each compound may be in the form of the free compound, an acid or base addition salt, or a prodrug.

Figure 2:
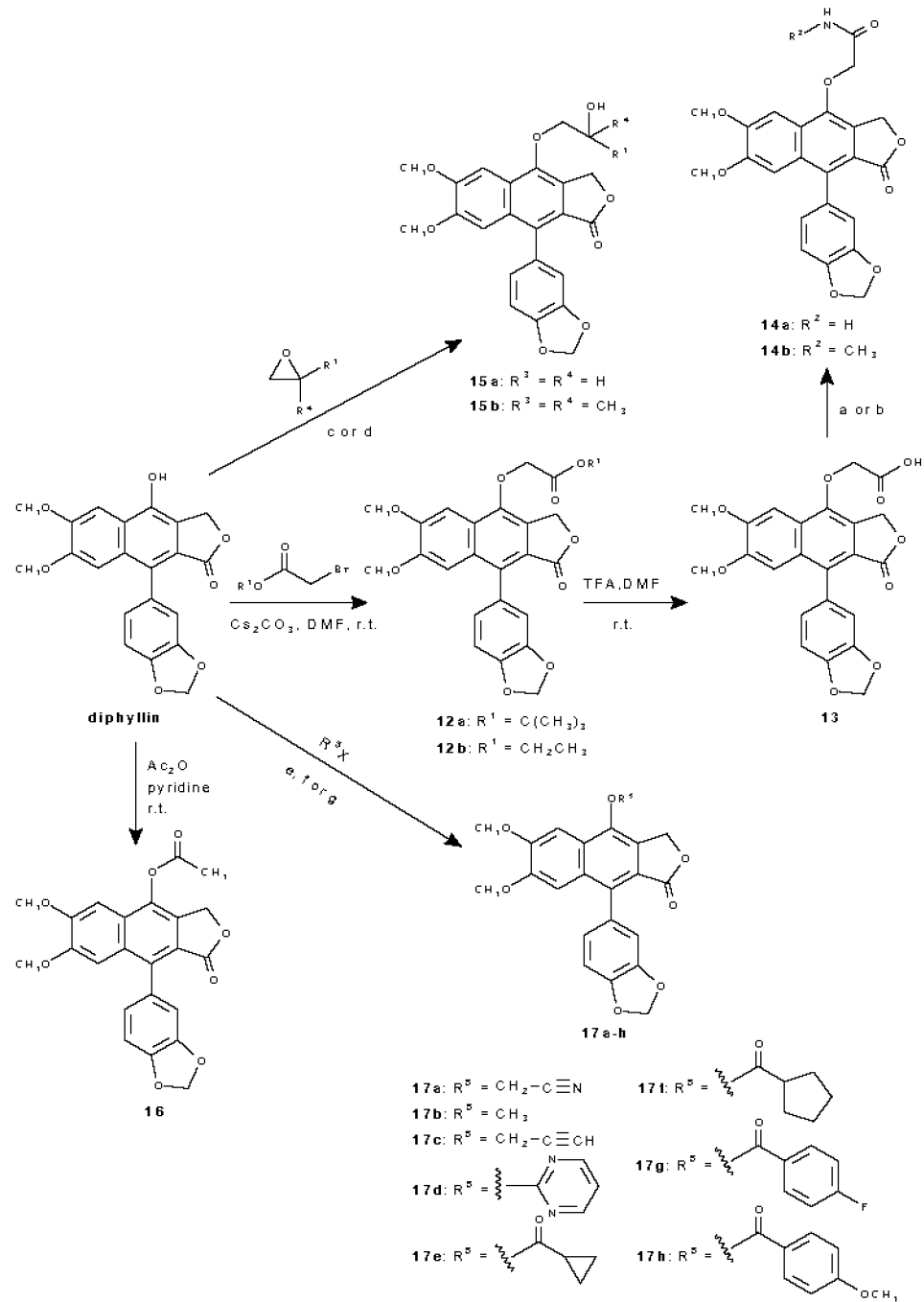
FIG. 2 shows schematic preparation of diphyllin analogs 12-17 (for preparation of compound 14a, the reaction reagents and conditions of a: $NH_4Cl$, HATU, $Et_3N$, $CH_2Cl_2$; for preparation of compound 14b, the reaction reagents and conditions of b: $MeNH_2$, EDCI, HOBt and THF; for preparation of compound 15a, the reaction reagents and conditions of c: $PdCl_2$, $K_2CO_3$, TBAB, $H_2O$, 60° C.; for preparation of compound 15b, the reaction reagents and conditions of d: $Cs_2CO_3$, DMF, 120° C.; for preparation of compounds 17a-17c, the reaction reagents and conditions of e: $Cs_2CO_3$, acetone, r.t.; for preparation of compounds 17d, the reaction reagents and conditions of f: $K_2CO_3$, DMF, 100° C.; for preparation of compounds 17e-17h, the reaction reagents and conditions of g: $Et_3N$, DMAP, $CH_2Cl_2$, 25° C.).
Figure 3:
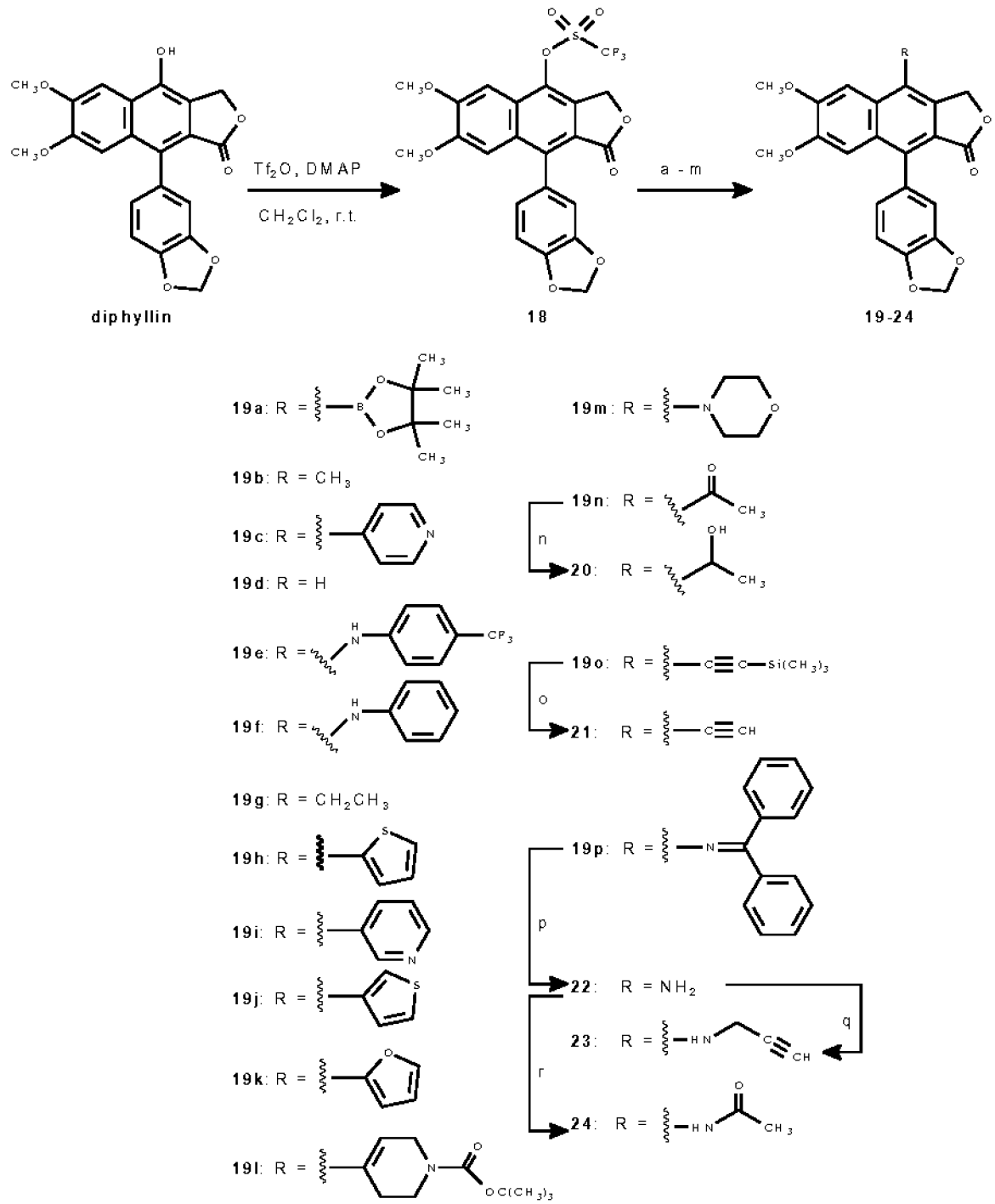
FIG. 3 shows schematic preparation of diphyllin analogs 18-24 (for preparation of compound 19a, the reaction reagents and conditions of a: $[Pd(dppf)Cl_2]CH_2Cl_2$, KOAc, $B_2(Pin)_2$, dioxane, 100° C.; for preparation of compound 19b, the reaction reagents and conditions of b: $[Pd(dppf)Cl_2]CH_2Cl_2$, $AlMe_3$, toluene, 100° C.; for preparation of compound 19c, the reaction reagents and conditions of c: $[Pd(dppf)Cl_2]CH_2Cl_2$, $Na_2CO_3$, pyridine-4-boronic acid, $H_2O$, Dioxane, 100° C.; for preparation of compound 19d, the reaction reagents and conditions of d: $Pd(OAc)_2$, $PPh_3$, $Et_3N$, $HCO_2H$, DMF, 100° C.; for preparation of compounds 19e and 19f, the reaction reagents and conditions of e: $Pd(OAc)_2$, BINAP, $Cs_2CO_3$, RH, toluene, 100° C.; for preparation of compound 19g, the reaction reagents and conditions of f: $Pd(PPh_3)_4$, $Et_2Zn$, THF, 100° C.; for preparation of compounds 19h-19j, the reaction reagents and conditions of g: $Pd(PPh_3)_4$, $K_2CO_3$, $RB(OH)_2$, DMF, 100° C.; for preparation of compound 19k, the reaction reagents and conditions of h: $Pd(PPh_3)_4$, $Na_2CO_3$, furan-2-boronic acid, $H_2O$, Dioxane, 100° C.; for preparation of compound 19l, the reaction reagents and conditions of i: $Pd(PPh_3)_4$, $Na_2CO_3$, 1-Boc-3,6-dihydro-2H-pyridine-4-boronic acid pinacol ester, $H_2O$, Dioxane, 100° C.; for preparation of compound 19m, the reaction reagents and conditions of j: $Pd_2(dba)_3$, XantPhos, $Cs_2CO_3$, morpholine DMF, 100° C.; for preparation of compound 19n, the reaction reagents and conditions of k: $Pd(PPh_3)_2Cl_2$, tributyl(1-ethoxyvinyl)tin, PhMe, 100° C., followed by 50% HCl; for preparation of compound 19o, the reaction reagents and conditions of l: $Pd(PPh_3)_2Cl_2$, CuI, $Et_3N$, DMF, trimethylsilylacetylene, 80° C.; for preparation of compound 19p, the reaction reagents and conditions of m: $Pd(OAc)_2$, $Cs_2CO_3$, Xantphos, $Et_3N$, benzophenone imine, dioxane, 100° C.; for preparation of compound 20, the reaction reagents and conditions of n: $NaBH_4$, MeOH, rt; for preparation of compound 21, the reaction reagents and conditions of o: $K_2CO_3$, MeOH, r.t.; for preparation of compound 22, the reaction reagents and conditions of p: HCl, THF, r.t., followed by KOH, r.t.; for preparation of compound 23, the reaction reagents and conditions of q: $Cs_2CO_3$, propargyl bromide, MeCN, r.t.; for preparation of compound 24, the reaction reagents and conditions of r: $Ac_2O$, pyridine, r.t.).

By using diphyllin (5) as a structural scaffold, the general synthetic route for its C—O derivatization on C-7 is illustrated in FIG. 2. Esters 12a and 12b were prepared from 5 by a substitution reaction. Acidic hydrolysis of ester 12a provided acid 13, which was converted to amides 14a and 14b by coupling with ammonium chloride (NH$_4$Cl) or an amine in the presence of 1-[bis(dimethylamino)methylene]-1H-1,2,3-triazolo[4,5-b]pyridinium 3-oxid hexafluorophosphate (HATU) or 1-hydroxybenzotriazole hydrate (HOBt). O-alkoxyl alcohols 15a and 15b were obtained from the reactions of 5 with the corresponding epoxides ethylene oxide and isobutylene oxide, respectively. Derivatives 17a-17h were prepared from 5, respectively, in one step. Alkylation of 5 with cesium carbonate (Cs$_2$CO$_3$) followed by bromoacetonitrile, iodomethane or propargyl bromide rendered derivatives 17a-17c, respectively. Addition of potassium carbonate (K$_2$CO$_3$) and 2-chloropyrimidinein to 5 in dimethylformamide (DMF) under 100° C. provided compound 17d. Similarly, the addition of trimethylamine (Me$_3$N), 4-dimethylaminopyridine (DMAP) and corresponding acyl chlorides to 5 gave esters 17e-17h, respectively. The synthesis for C-7 alkyl derivatives (FIG. 3) envisioned conversion of 5 to the corresponding trifluoromethanesulfonate 18, which would undergo palladium-catalyzed coupling reactions to afford derivatives 19a-19p and 20-24.

Figure 4:
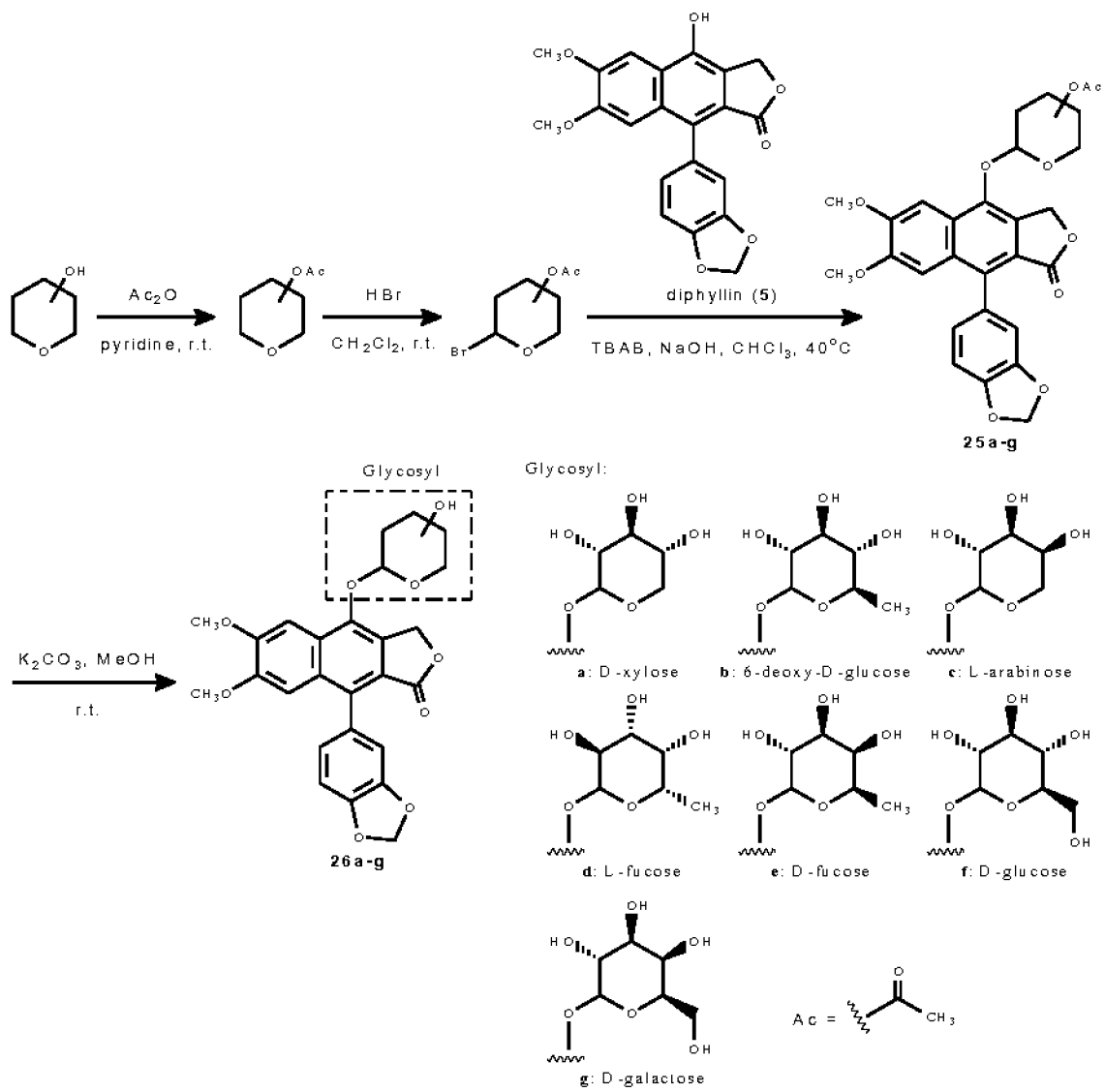
FIG. 4 shows schematic preparation of patentiflorin A analogs 25a-25g and 26a-26g. Compounds 26a, 26b, 26c, 26d, 26e, 26f and 26g are produced from 25a, 25b, 25c, 25d, 25e, 25f and 25g, respectively.
Figure 5:
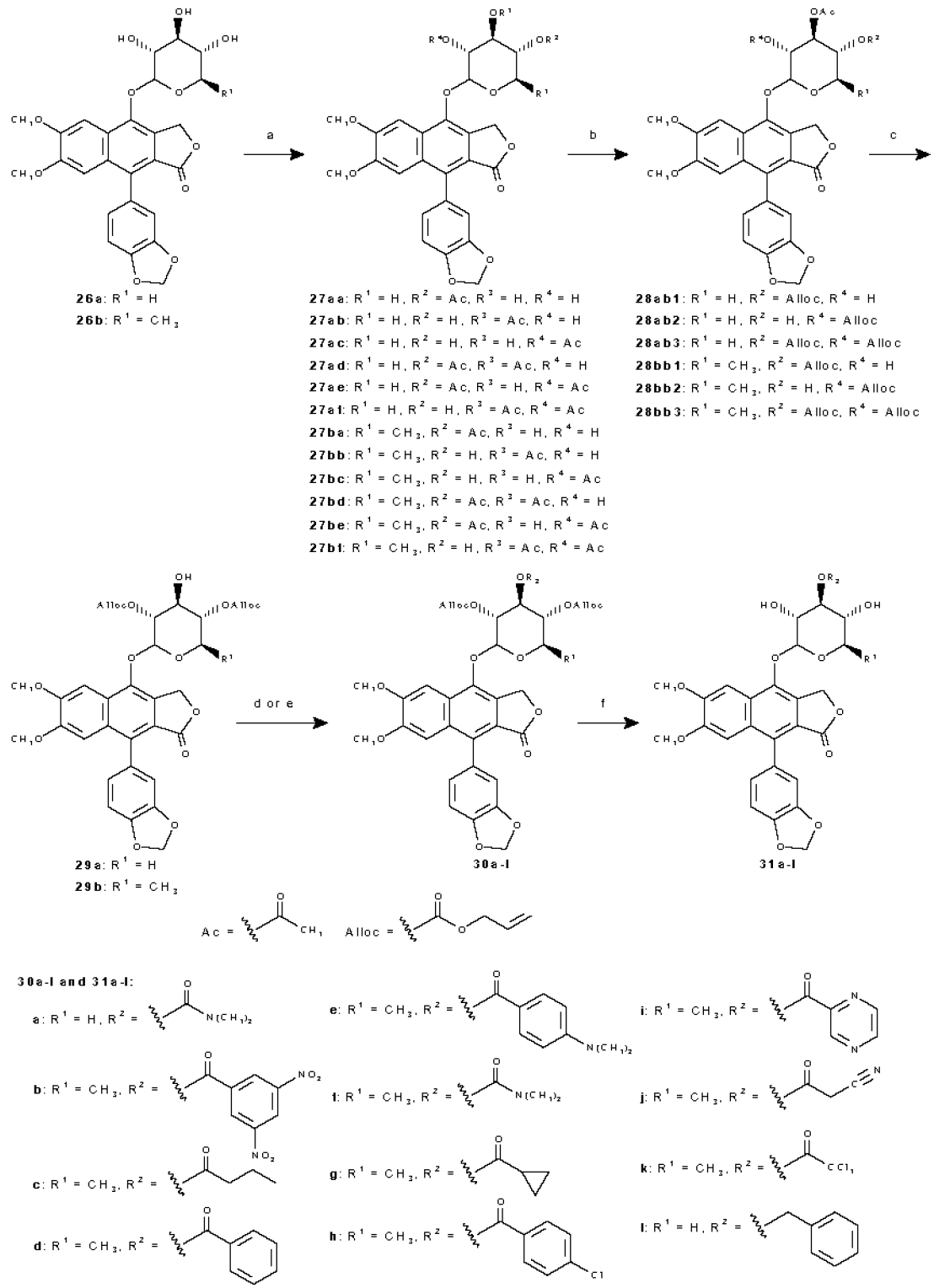
FIG. 5 shows schematic preparation of patentiflorin A analogs 27aa-27af, 27ba-27bf, 28ab1-28ab3, 28bb1-28bb3, 29a, 29b, 30a-30l and 31a-31l (for preparation of compounds 27aa-27af and 27ba-27bf, the reaction reagents and conditions of a: $Ac_2O$, TBAOAc, MeCN, 40° C.; for preparation of compounds 28ab1 to 28ab3 and 28bb1 to 28bb3, the reaction reagents and conditions of b: AllocOCl, $Et_3N$, $CH_2Cl_2$, 0° C. to r.t.; for preparation of compounds 29a and 29b, the reaction reagents and conditions of c: AcCl, $CH_2Cl_2$, MeOH, 0° C. to r.t.; for preparation of compounds 30a-k, the reaction reagents and conditions of d: $Et_3N$, DMAP, dry $CH_2Cl_2$, 0° C. to r.t.; for preparation of compounds 30l, the reaction reagents and conditions of e: KOH, 18-Crown-6, THF, r.t.; for preparation of compounds 31a-1, the reaction reagents and conditions of f: $(PPh_3)_4Pd$, $PPh_3$, $Et_3N$, HCOOH, THF, $N_2$, 55° C.). Compounds 27aa, 27ab, 27ac, 27ad, 27ae and 27af are produced from 26a. Compounds 27ba, 27bb, 27bc, 27bd, 27be and 27bf are produced from 26b. Compounds 28ab1, 28ab2 and 28ab3 are produced from 27ab. Compounds 28bb1, 28bb2 and 28bb3 are produced from 27bb. Compounds 29a and 29b are produced from 28ab3 and 28bb3, respectively. Compounds 30a and 30l are produced from 29a. Compounds 30b, 30c, 30d, 30e, 30f, 30g, 30h, 30i, 30j and 30k are produced from 29b. Compounds 31a, 31b, 31c, 31d, 31e, 31f, 31g, 31h, 31i, 31j, 31k and 31l are produced from 30a, 30b, 30c, 30d, 30e, 30f, 30g, 30h, 30i, 30j, 30k and 30l, respectively.

ANL analogs and compounds 25a-25g and 26a-26g containing different sugar units outlined in FIG. 4 were prepared, and which were further modified to provide additional ANL analogs 27aa-27bf, 28ab1-28bb3, 29a, 29b, 30a-30l and 31a-31l outlined in FIG. 5.

Glycosylation of diphyllin (5) at C-7 with different sugar units (a-g) led to synthesis of a series of diphyllin glycosides (26a-26g), respectively (FIG. 4). The synthesis involved the production of glycosyl bromides through bromination reactions of the per-acetylated glycosides, followed by its phase transfer catalysis (PTC) glycosylation treatment with 0.1 mol/L aqueous sodium hydroxide (NaOH) in the presence of tetrabutylammonium bromide (TBAB) at 40° C. The resulted per-acetyl glycosides 25a-25g were subsequently deacetylated with K$_2$CO$_3$ in methanol (MeOH) to afford the deprotected glycosides 26a-26g, respectively.

To significantly increase the number of the ANL library compounds, further structural modification on the hydroxy groups in the sugar units of ANLs (FIG. 5) were proposed. Firstly, 3"-O-acetyl diphyllin glycosides 27aa-27af and 27ba-27bf were prepared from the reactions of acetic anhydride (Ac$_2$O) and tetrabutylammonium acetate (TBOAc) with the corresponding 26a and 26b. Separation by silica gel column chromatography of the reaction mixture of 26a afforded the six single compounds 27aa-27af (27aa, 27ab, 27ac, 27ad, 27ae and 27af). Separation by silica gel column chromatography of the reaction mixture of 26b afforded the six single compounds 27ba-27bf (27ba, 27bb, 27bc, 27bd, 27be and 27bf).

Compound 27ab or 27bb was treated with allyl chloroformate (AllocOCl) to give the bis-protected ANL glycosides the corresponding 28ab1-28ab3 and 28bb1-28bb3. Separation by silica gel column chromatography of the reaction mixture of 27ab afforded the three single compounds 28ab1-28ab3 (28ab1, 28ab2 and 28ab3). Separation by silica gel column chromatography of the reaction mixture of 27bb afforded the three single compounds 28bb1-28bb3 (28bb1, 28bb2 and 28bb3). The acetyl group in compound 28ab3 or 28bb3 was removed by further treatment with acetyl chloride (AcCl) to give the bis-choloroformate protected ANL glycosides 29a and 29b, respectively. Substitution of 29a or 29b with triethylamine (Et$_3$N) and DMAP, followed by different acyl chlorides yielded derivatives 30a-k, respectively. Addition of potassium hydroxide (KOH), 18-crown-6 and benzyl bromide to 29a in tetrahydrofuran (THF) under r.t. provided compound 30l. The two allyl groups of 30a-l were deprotected by treatment of tetrakis(triphenylphosphine)palladium(0)[Pd(PPh$_3$)$_4$], triphenylphosphine (PPh$_3$), Et$_3$N and HCOOH in THF to produce derivatives 31a-l, respectively.

The compounds described herein can exhibit broad antiviral properties. According to methods of the present disclosure, compounds of Formula (I) are administered to a patient to inhibit replication of or reduce cytopathic effects of viruses, such as IV, coronaviruses, Ebola virus, Marburg virus or influenza viruses. Other viruses that may be inhibited by compounds of Formula (I) include, but are not limited to, cytomegalovirus (CMV), HSV-1 (herpes simplex virus type 1), HSV-2 (herpes simplex virus type 2), HBV (hepatitis B virus), HCV (hepatitis C virus), HPV (human papilloma virus), influenza A, influenza B, RSV (respiratory syncitial virus), RV (rhinovirus), AV (adenovirus), PIV (human parainfluenza viruses), Epstein-Barr virus (EBV), varicella zoster virus (VZV), dengue virus and Zika virus.

The compounds, pharmaceutical compositions, and therapeutic methods described herein are useful for preventing or treating or ameliorating HIV infections.

The compounds, pharmaceutical compositions, and therapeutic methods described herein are useful for preventing, treating, or ameliorating infections caused by influenza viruses, including but not limited to: any of the subtypes of influenza A, influenza B, or influenza C.

In certain embodiments, the compounds, pharmaceutical compositions, and therapeutic methods disclosed herein are useful for preventing, treating, or ameliorating infections caused by influenza A viruses, including but not limited to, any of the strains of H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, H3N5, H3N6, H3N7, H3N8, H3N9, H4N1, H5N1, H5N2, H5N3, H5N4, H5N5, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H8N8, H8N9, H9N1, H9N2, H9N3, H9N4, H9N5, H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N7, H13N8, H13N9, H14N1, H14N2, H14N3, H14N4, H14N5, H14N6, H14N7, H14N8, H14N9, H15N1, H15N2, H15N3, H15N4, H15N5, H15N6, H1N7, H15N8, and H15N9.

In certain embodiments, the compounds, pharmaceutical compositions, and therapeutic methods disclosed herein are useful for preventing, treating, or ameliorating infections caused by influenza A virus strains having a type 5 hemagglutinin protein. In certain embodiments, the influenza A virus strain has a type 5 hemagglutinin protein and neuraminidase protein selected from types 1 to 11. In certain embodiments, the influenza A virus is selected from the group consisting of H5N1 and H5N2.

In certain embodiments, the compounds, pharmaceutical compositions, and therapeutic methods disclosed herein are useful for preventing, treating, or ameliorating infections caused by H5N1.

The term "HIV", as used herein, refers to the human immunodeficiency virus and includes HIV-1, HIV-2 and SIV. In certain embodiments, HIV refers to HIV-1 and/or HIV-2. "HIV-1" means the human immunodeficiency virus type-1. HIV-1 can include but is not limited to extracellular virus particles and the forms of HIV-1 associated with HIV-1 infected cells. The HIV-1 virus can include any of the known major subtypes (classes A, B, C, D, E, F, G and H) or outlying subtype (group O) including laboratory strains and primary isolates. "HIV-2" means the human immunodeficiency virus type-2. HIV-2 can include but is not limited to extracellular virus particles and the forms of HIV-2 associated with HIV-2 infected cells. The term "SIV" refers to simian immunodeficiency virus, which is an HIV-like virus that infects monkeys, chimpanzees, and other nonhuman primates. SIV can include but is not limited to extracellular virus particles and the forms of SIV associated with SIV infected cells.

In certain embodiments, the compounds, pharmaceutical compositions, and therapeutic methods disclosed herein are useful for preventing, treating, or ameliorating infections caused by HIV-1 and/or HIV-2. In certain embodiments, the compounds, pharmaceutical compositions, and therapeutic methods disclosed herein are useful for preventing, treating or ameliorating infections caused by HIV-1 subtype B.

In certain embodiments, the compounds, pharmaceutical compositions, and therapeutic methods disclosed herein are useful for preventing, treating, or ameliorating infections caused by SIV.

The compounds, pharmaceutical compositions, and therapeutic methods described herein are useful for preventing, treating, or ameliorating infections caused by filoviruses, including but not limited to: Marburg virus, Zaire ebolavirus, Sudan ebolavirus, Cote d'Ivoire ebolavirus, Reston ebolavirus and Bundibugyo ebolavirus.

The compounds, pharmaceutical compositions, and therapeutic methods described herein are useful for preventing, treating, or ameliorating infections caused by coronaviruses including, but not limited to, SARS-CoV-2, SARS-CoV and MERS-CoV.

Antiviral Evaluation Using the "One-Stone-Two-Birds" Pseudo-Type Assay.

Production of HIV Pseudovirions. This protocol is designed to identify potential inhibitors for HIV, coronavirus, Ebola, Marburg and influenza replication (post entry steps). HIV/VSVG or HIV/SARSP or HIV/HA or HIV/EBOV or HIV/MARV virions were produced, respectively, by co-transfecting with either 0.5 µg VSVG (vesicular stomatitis virus glycoprotein) envelope expression plasmid 0.5 µg SARSP (SARS-CoV-2 spike protein) expression plasmid or 0.5 µg hemagglutinin (HA) envelope expression plasmid with 0.5 µg neuraminidase (NA) expression plasmid or 0.5 µg EBVG (Ebola virus glycoprotein) envelope expression plasmid or 0.5 µg MAVG (Marburg virus glycoprotein) envelope expression plasmid and 2 µg replication-defective HIV vector (pNL4-3.Luc.RE) into human embryonic kidney 293T cells (90% confluent) in six-well plates via PEI (polyethylenimine) (Invitrogen, Carlsbad, Calif., USA), as previously described with a modified procedure. The HIV vector pNL4-3.Luc.RE was obtained through the AIDS Research and Reference Reagent Program (Division of AIDS, NIAID, NIH). Sixteen hours post-transfection, all media were replaced with fresh, complete DMEM. Eight hours post-transfection, all media were replaced with fresh complete DMEM. Forty-eight hours post-transfection, the supernatants were collected and filtered through a 0.45-µm-pore-size filter (Millipore, Billerica, Mass., USA) and the pseudo virions were directly used for infection.

Anti-HIV and anti-H5N1 Influenza Virus Evaluation Assay. This protocol is to identify potential inhibitors for HIV and influenza virus replication (post-entry steps). In this system, the HIV vector pNL4-3.Luc.RE was co-transfected with the VSVG to generate HIV/VSVG virions (HIV virion with VSV glycoprotein on the viral surface), and the same HIV vector was co-transfected with the H5N1 HA and NA constructs to generate HIV virions with bird flu HA on the viral surface [HIV/HA (HIV virion with HA and NA glycoproteins on the viral surface)]. This pNL4-3 was derived from an infectious molecular clone of a SI (syncytium inducing), T-tropic virus, which is replication deficient since the HIV is Env⁻ and Vpr⁻. In addition, the luciferase gene (luc) carried by this recombinant HIV vector served as the reporter for HIV replication (reverse transcription, integration and HIV gene expression).

The infection level was measured as relative light units (RLUs) in the infected cells. The luciferase activities of the 293T cells infected with the HIV vector pNL4-3.Luc.RE reached the range of $10^5$-$10^6$ RLUs, approximately 100-fold higher than the background levels when measured using the HIV virions without VSVG. The evaluation principle is that the level of the luciferase activity in the cells should be proportional to the level of viral entry and replication. If a sample can interfere with HIV replication/or HA-mediated viral entry, the level of the luciferase activity in the infected cells will be reduced. Thus, using this protocol, a sample capable of inhibiting HIV or influenza virus replication was identified. The test fractions or compounds were evaluated as follows. Target A549 human lung cells were seeded at $0.5 \times 10^5$ cells per well (24-well plate) in complete DMEM. The lung cell line was used since it is susceptible to HA-mediated viral entry. The stock HIV/VSVG or HIV/HA virions (approximately $2 \times 10^6$ relative light units, or RLUs, on the target cells) were mixed with the individual sample first, and the mixture was incubated with the A549 target cells for 24 hours. Ten microliters of serial concentrations (for example, 20, 10, 5, 2.5, 1.25, 0.625 and 0.3125 µg/mL) and 190 µL of the pseudovirus were incubated with target cells. Twenty-four (24) hours post-infection, all media containing sample and virus was removed from target cells and replaced with fresh and complete DMEM. Forty-eight (48) hours post-infection, the target cells were lysed and the luciferase activity was determined. Two different outcomes may occur: 1) It is likely that some samples will "inhibit replication" of both HIV/VSVG and HIV/HA virions (lower Luc for HA and VSVG), since some of these samples can block post-entry steps during viral entry, or some of them are just toxic to the target cells. These samples are classified as anti-HIV. 2) The samples which can specifically inhibit the HIV/HA viral entry (lower Luc for HIV/HA, but not for HIV/VSVG) will be classified as anti-HA inhibitors (influenza virus inhibitors). The concentration of drug inhibiting 50% of virus infectivity ($EC_{50}$ value) was determined.

Anti-HIV, anti-Ebola and anti-Marburg Virus Evaluation Assay. This protocol was modified from the aforementioned anti-H5N1 influenza virus evaluation assay, which was designed to identify potential inhibitors for HIV, Ebola and Marburg viruses replication (post-entry steps). In this system, the HIV vector pNL4-3.Luc. R.E. was co-transfected with the VSVG to generate HIV/VSVG virions, and the same HIV vector was co-transfected with the Ebola or Marburg glycoprotein (GP) constructs to generate HIV virions with Ebola or Marburg GP on the viral surface (HIV/EBVG or HIV/MAVG). The infection level was measured as relative light units (RLUs) in the infected cells. The luciferase activities of the 293T cells infected with the HIV vector pNL4-3.Luc. R.E. reached the range of $10^5$-$10^6$ RLUs, approximately 100-fold higher than the background levels when measured using the HIV virions without VSVG. The evaluation principle is that the level of the luciferase activity in the cells should be proportional to the level of viral entry and replication. If a compound can interfere with HIV replication/or EBVG or MAVG-mediated viral entry, the level of the luciferase activity in the infected cells will be reduced. Thus, using this protocol, compounds capable of inhibiting HIV, EBOV and MARV replication were identified. The test compounds were evaluated as follows. Target A549 human lung cells were seeded at $0.5 \times 10^5$ cells per well (24-well plate) in complete DMEM. The lung cell line was used since it is susceptible to EBVG or MAVG-mediated viral entry. The stock HIV/VSVG or HIV/EBVG or HIV/MAVG virions (approximately $2 \times 10^6$ relative light units, or RLUs, on the target cells) were mixed with the individual sample first, and the mixture was incubated with the A549 target cells for 24 hours. Ten microliter of each sample in varying concentrations and 190 µL of the pseudovirus were incubated with target cells. Twenty-four (24) hours post-infection, all media containing sample and virus was removed from target cells and replaced with fresh and complete DMEM. Forty-eight (48) hours post-infection, the target cells were lysed and the luciferase activity was determined.

Anti-SARS-CoV-2 Evaluation Assay. This protocol was modified from the aforementioned anti-H5N1 influenza virus evaluation assay, which was designed to identify potential inhibitors for SARS-CoV-2. In this assay, the HIV vector pNL4-3.Luc. R.E. was co-transfected with SARS-CoV-2 spike protein (SARSP) expression plasmid to generate SARS-CoV-2 pseudovirions (HIV/SARSP). Target Hep G2 liver cancer cells were seeded at $4 \times 10^3$ cells per well (96-well plate) in complete EMEM. The liver cell line was used because it is susceptible to SARS-CoV-2 mediated viral entry. Ten microliter of each sample in varying concentrations and 190 µL of the HIV/SARSP were incubated with target cells. Forty-eight (48) hours post-infection, the target cells were lysed and the luciferase activity was determined. Arbidol was used as positive control in the experiments. The $IC_{50}$ value of arbidol against SARS-CoV-2 pseudovirion was measured as 5.23 µM, which was in agreement with the literature reported value (4.11 µM).

Anti-HIV Evaluation Using HIV-1 Clinical Strains.

The HIV-1 clinical strains such as BAL and SF162 (macrophage-tropic: M-tropic), BAL (T-cell line tropic: T-tropic), and 89.6 (a dual tropic strain), HIV-1$_{LAV}$ (wild type), NRTI (nucleoside reverse transcriptase inhibitor)-resistant isolate (HIV-1$_{1617.1}$) (AZT resistant strain from AIDS repository) and NNRTI (non-nucleoside reverse transcriptase inhibitor)-resistant isolate (HIV-1$_{N119}$) (nevaripine resistant strain from AIDS repository) were used in the study. A standardized human peripheral blood mononuclear cell culture (PBMC) assay was used to determine the compound susceptibility of these HIV-1 strains. AZT, an anti-HIV drug in clinical use, was used as a positive control. All data were generated from three independent experiments, each performed in triplicate. Prior to HIV-1 infection, fresh human PBMCs were used in each experiment. Briefly, donor PBMCs were suspended in R-3 medium [RPMI 1640 medium supplemented with 15-20% FBS (fetal bovine serum), 5% IL-2 (human interleukin-2), 250 U of penicillin per mL, 250 µg of streptomycin per mL and 2 mM L-glutamine] was stimulated with PHA (phytohaemagglutinin, 2-3 µg/mL) for seven days. The preparations (samples) were added to the cultured cells, and the different HIV-1 strains were used to challenge the cultured cells in 96-well plates [$1 \times 10^5$ cells per well with 1000 $TCID_{50}$ (virus 50% tissue culture infectious doses) of HIV strain]. After seven days of incubation, the supernatants were collected and the HIV p24 levels of the infected cells were determined using a p24 antigen ELISA. To measure $IC_{50}$ values, each drug was tested using a serial of concentrations (for example, 5, 1, 0.2, 0.04, 0.008, 0.016 and 0 µg/mL). The $IC_{50}$s were calculated by comparing p24 antigen values for the samples-containing wells with those for no drug control wells. For the p24 assay, the maximum cutoff should be around 120-150 µg/mL.

Antiviral Evaluation Using Infectious Influenza Viruses.

A panel of influenza viruses such as influenza H1N1 (A/HK/415742/09), H3N2 (A/Hong Kong/I/1968), H5N1 (A/Vietnam/1203/2004H), H7N1 (A/Rhea/North Carolina/39482/93), H7N7 (A/Netherlands/219/2003), H7N9 (A/Anhui/1/2013) and H9N2 (A/Chicken/Y280/97) were used in the studies. Samples were evaluated for their antiviral activities against the influenza viruses in A549 cells. Briefly, the preparations (samples) were added to the cultured cells, and the different influenza strains were used to challenge the cultured cells in 24-well plates ($1\times10^5$ cells per well). After removal of the unbound viruses, the cells were incubated for 48 h. The viral supernatants were collected and viral titers were determined by standard plaque assay in MDCK (Madin-Darby canine kidney) cells.

Cytotoxicity Evaluation Using the SRB Assay.

The cytotoxicity of the sample for A549 cells was measured using the sulforhodamine B (SRB) assay (Vichai V, Kirtikara K. Nature protocols 2006; 1: 1112-1116). Briefly, 190 μL of A549 cells ($2\times10^4$ cells/mL) was seeded in each well of a 96-well cell culture plate. After 24 hours, 10 μL of DMSO alone, 10 μL of zidovudine (AZT) as positive controlin 10% DMSO, and 10 μL of each sample in 10% (v/v) DMSO were respectively added to wells of a 96-well tissueculture plate. 10 μL of 10% (v/v) DMSO was added into each blank well of a 96-well tissueculture plate as a background calculation plate. After incubation at 37° C. for 2 days, 50 μL cold 50% (w/v) trichloroacetic acid (TCA) were added into each well of the plates, and were further incubated at 4° C. for 1 h. The plates were then washed four times with low-running tap water, and they were allowed to dry at room temperature (r.t.). 50 μL of 0.4% (w/v) SRB solution was added to each well. The plate was left at r.t. for 5~10 mins and were quickly rinsed with 1% (v/v) acetic acid to remove unbound dye. The plates were allowed to dry at r.t. 100 mL of 10 mM Tris base solution (pH 10.5) was added to each well and the plates were shake on a gyratory shaker for at least 30 min to solubilize the protein-bound dye. The OD values were measured at 515 nm in a microplate reader. The $CC_{50}$ (the concentration of an agent causing 50% cytotoxicity) values were calculated using the GraphPad Prism version 5.0 (GraphPad Software, San Diego, Calif.).

Toxicity Evaluation in Mice. Repeated-dose toxicity study in mice was applied on the selected samples. The animal study was approved and performed according to Animal Care and Use Guidelines of the Animal Ethics Committee at Hong Kong Baptist University and performed following Animal Care and Use guidelines set by NIH (National Institute of Health, USA). BALB/c nude mice, SPF class, male or female, 6-8 weeks old, were purchased from Charles River Laboratories. Before the experiment, the mice are kept for one week of acclimatization to SPF class laboratory conditions. The mice were then divided into three groups: two dose (25 and 50 mg/kg: 10 mice/each dose group) groups of an ANL compound and one dose of vehicle (negative control: 10 mice). Daily injections at i.p. sites were scheduled for 28 days. Weights of mice were measured twice a week until the end of the experiment. Skin conditions, food intake, water consumption and posture of mice were also inspected. All mice were sacrificed as the end of the experiment to inspect the essential organs such as liver, heart, kidney, lung and spleen.

TABLE 1

Anti-HIV activity of ANLs.[a]

| Compound No. | $CC_{50}$ (nM) | $EC_{50}$ (nM) | SI |
|---|---|---|---|
| 5 (diphyllin) | 3607 | 37.1 | 97.3 |
| 12a | >10111 | 517.7 | >19 |
| 12b | >26800 | 206.7 | >129 |
| 13 | >114000 | 23143.0 | >4.9 |
| 14a | 548.5 | 102.7 | 5.3 |
| 14b | 2124.5 | 277.9 | 7.6 |
| 15a | 918.1 | 33.6 | 27.3 |
| 15b | 1331.1 | 15.5 | 85.7 |
| 16 | 3397.3 | NE | — |
| 17a | 45235.1 | 72.0 | 627.9 |
| 17b | 2143.9 | 2.6 | 815.3 |
| 17c | 889.8 | 4.8 | 186.9 |
| 17d | 61056.9 | 1588.6 | 38.4 |
| 17f | 7073.4 | 772.5 | 9.2 |
| 17g | 1322.0 | 79.9 | 16.6 |
| 17h | 1457.9 | 96.5 | 15.1 |
| 18 | 1360.9 | 487.6 | 2.8 |
| 19a | 10494.5 | 77.2 | 136.0 |
| 19b | 77.3 | 6.1 | 12.7 |
| 19c | 1672.9 | 88.9 | 18.8 |
| 19d | 5426.1 | 22.9 | 237.4 |
| 19e | >9551 | 211.7 | >45 |
| 19f | 4505.2 | 975.9 | 4.6 |
| 19g | 196.2 | 19.3 | 10.2 |
| 19h | 2392.3 | 270.0 | 8.9 |
| 19i | 38358.6 | 877.1 | 43.7 |
| 19k | 1064.9 | 60.1 | 17.7 |
| 19l | 4185.5 | 75.9 | 55.1 |
| 19m | 1496.5 | 88.6 | 16.9 |
| 19n | 1056.3 | 39.5 | 26.8 |
| 19o | 1218.8 | 35.7 | 34.2 |
| 19p | >9198 | 249.3 | >36 |
| 20 | 388.8 | 21.7 | 17.9 |
| 21 | 207.2 | 17.8 | 11.7 |
| 22 | 358.23 | 1.61 | 222.2 |
| 23 | 1581 | 18.8 | 84 |
| 24 | >11864 | 88.9 | >133 |
| 25a | 3083.4 | 7.0 | 438.6 |
| 25b | 259.1 | NE | — |
| 26a | 6220.8 | NE | — |
| 26b (patentiflorin A) | 347.0 | 21.1 | 16.4 |
| 26c | >9756.7 | NE | — |
| 26d | >9496.9 | 42.3 | >426.1 |
| 26e | >9496.9 | NE | — |
| 26f | >9216.8 | NE | — |
| 26g | 7767.9 | 1402.8 | 5.5 |
| 27ab | 2757.4 | NE | — |
| 27ac | 2936.0 | NE | — |
| 27ad | 782.7 | NE | — |
| 27ae | 2593.3 | NE | — |
| 27af | 2251.3 | NE | — |
| 27ba | 1162.3 | 8.47 | 137.3 |
| 27bb | 589.2 | 1.01 | 584.1 |
| 27bc | 1365.1 | 0.93 | 1472.4 |
| 27bd | 420.8 | 6.39 | 65.9 |
| 27be | 1668.9 | 1.96 | 852 |
| 27bf | 308.2 | 1.17 | 263.9 |
| 28ab1 | 512.7 | NE | — |
| 28ab2 | 386.0 | 2.3 | 167.7 |
| 28ab3 | 385.5 | 22.9 | 16.8 |
| 29a | 438.3 | NE | — |
| 29b | 187.2 | 4.7 | 40.2 |
| 30a | 145.3 | NE | — |
| 31a | 55.8 | NE | — |
| 31b | 684.0 | 13.4 | 51.0 |
| 31c | 13.4 | 0.03 | 477.0 |
| 31d | >63 | 1.36 | >74 |
| 31e | 17.7 | 2.41 | 7.3 |
| 31f | 3.74 | NE | — |
| 31g | 26.7 | NE | — |
| 31h | 336.5 | NE | — |
| 31l | 5733.7 | 14.4 | 399.6 |
| 31j | 6.68 | 0.91 | 7.3 |
| 31k | 507.8 | NE | — |
| 32a | 52.7 | NE | — |
| 32b | 52.7 | NE | — |
| 32c | 52.7 | NE | — |

TABLE 1-continued

Anti-HIV activity of ANLs.[a]

| Compound No. | CC$_{50}$ (nM) | EC$_{50}$ (nM) | SI |
|---|---|---|---|
| 32d | 52.7 | NE | — |
| AZT[c] | | 2.6 | |

[a]Results are expressed as CC$_{50}$ (the concentration caused inhibition of cell growth of host A549 cells by 50%) and EC$_{50}$ (effective concentration of compound to inhibit viral growth by 50%) values in nM, and data were obtained from triplicate experiments. SI = CC$_{50}$/EC$_{50}$
b NE: No effect at the CC$_{50}$ tested in the host A549 cells
[c]Positive control compound.

TABLE 2

Anti-H5N1 viral activity of ANLs.[a]

| Compound No. | Concentration (ng/mL) | % Inhibition against H5N1 virus |
|---|---|---|
| 26a | 5000 | 97.8% |
| | 1000 | 93.6% |
| 26e | 5000 | 88.9% |
| | 1000 | 48.5% |
| 27ab | 5000 | 97.8% |
| | 1000 | 96.9% |
| 29a | 250 | 97.3% |
| | 50 | 59.4% |
| 30a | 250 | 97.6% |
| | 50 | 95.7% |
| | 12.5 | 44.1% |
| | 250 | 97.6% |
| 31a | 50 | 94.4% |
| | 12.5 | 87.9% |
| 31e | 250 | 98.4% |
| | 50 | 97.9% |
| | 12.5 | 98.1% |
| 31g | 250 | 98.1% |
| | 50 | 97.9% |
| | 12.5 | 97.9% |
| 31h | 250 | 97.6% |
| | 50 | 94.6% |
| 31j | 250 | 97.9% |
| | 50 | 87.6% |
| 31k | 250 | 95.7% |
| | 50 | 86.0% |
| 31l | 250 | 96.8% |
| | 50 | 96.0% |
| | 12.5 | 82.8% |
| AZT[b] | 20 | 96.5% |

[a]Results are from three triplicate experiments.
[b]Positive control compound.

TABLE 3

Inhibitory effects of selected ANLs against H5N1 virus, EBOV, VSV and A549 cells.[a]

| Compound No. | Concentration (ng/mL) | % Inhibition against H5N1 virus | % Inhibition against EBOV | % Inhibition against VSV | % Inhibition against A549 cells |
|---|---|---|---|---|---|
| 19p | 5000 | 96.5 | 89.4 | — | 17.2 |
| | 1000 | 82.1 | 58.1 | — | -13.0 |
| 26f | 500 | 87.2 | 89.1 | 70.8 | 18.2 |
| | 100 | 62.4 | 82.7 | 47.18 | -3.84 |
| 28ab1 | 50 | 86.0 | 82.4 | 83.5 | 40.9 |
| | 12.5 | 91.8 | 81.0 | 85.9 | 35.5 |
| 31a | 5000 | 98.4 | 95.2 | 99.6 | 99.8 |
| | 1000 | 94.7 | 81.8 | 80.4 | 47.5 |
| 31e | 50 | 96.5 | 86.5 | 86.3 | 66.8 |
| | 12.5 | 95.4 | 77.5 | 77.4 | 53.1 |
| 31g | 50 | 89.0 | 90.9 | 95.7 | 54.6 |
| | 10 | 78.9 | 79.1 | 63.3 | 11.0 |
| 31j | 50 | 98.2 | 96.6 | 99.9 | 93.8 |
| | 12.5 | 97.5 | 93.9 | 98.4 | 77.0 |
| 31l | 50 | 95.6 | 94.2 | 98.4 | 82.1 |
| | 12.5 | 95.1 | 86.4 | 88.7 | 52.0 |
| 32b | 50 | 88.1 | 92.7 | 99.6 | 76.0 |
| | 10 | 91.7 | 86.4 | 90.9 | 40.5 |
| 32c | 500 | 88.1 | 88.2 | 88.1 | 39.7 |
| | 100 | 65.1 | 85.5 | 48.87 | 2.9 |
| 32d | 500 | 83.5 | 82.7 | 71.7 | 24.3 |
| | 100 | 19.3 | 65.5 | 100.2 | -2.0 |
| AZT[b] | 20 | 92.7 | 93.6 | 99.4 | 1.1 |
| Toremifene[b] | 500 | 28.4 | 93.6 | 6.58 | -15.1 |

[a]Results are from three triplicate experiments.
[b]Positive control compounds.

Figure 6:
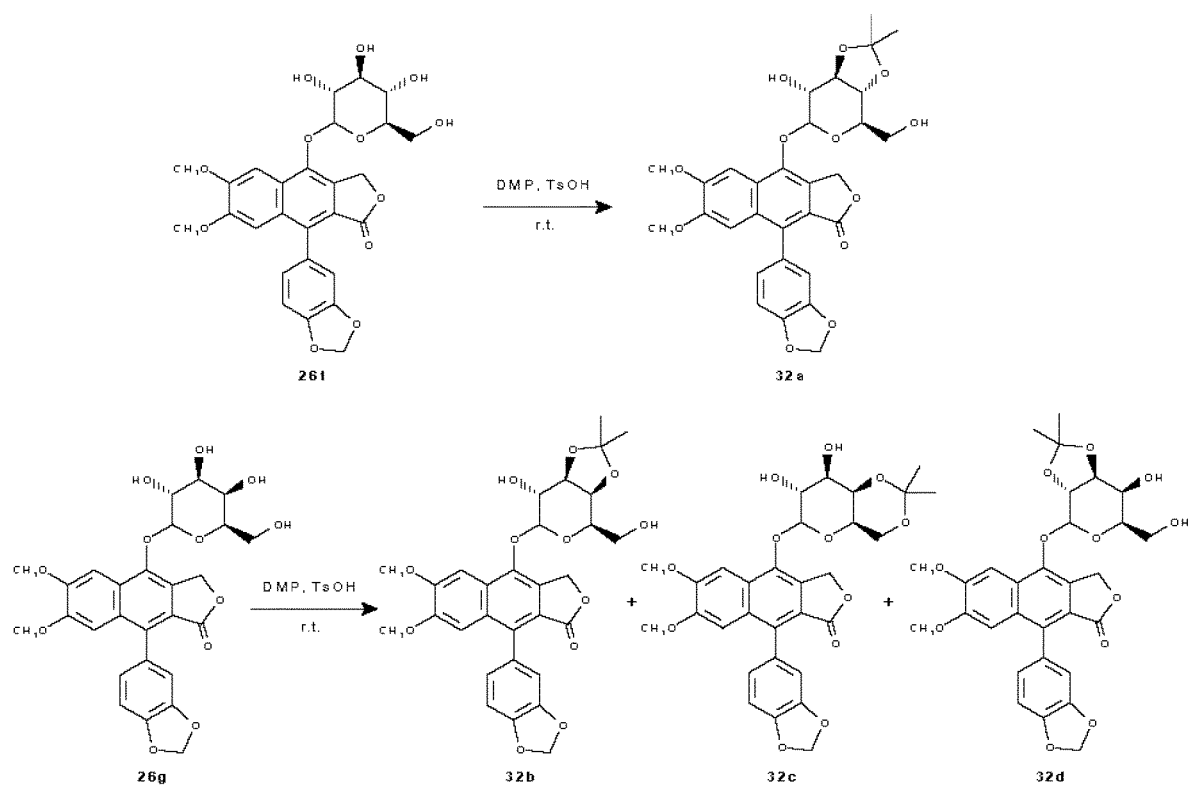
FIG. 6 shows schematic preparation of patentiflorin A analogs 32a-32d. Compounds 32a is produced from 26f. Compounds 32b-32d are produced from 26g.

Compound 26b (patentiflorin A) was identified as an anti-HIV lead compound from both methanol extracts of *J. cf. patentiflora* (the roots and stems of) and *J. procumbens* (aerial parts), and compound 5 (diphyllin) was isolated as a pure compound from the methanol extract of *J. procumbens* (aerial parts). Compound 5 was also obtained as an intermediate through the total synthesis of 26b in our previous studies. Compounds 26b and 5 showed anti-HIV activities with EC$_{50}$ values of 21.1 and 37.1 nM and SIs of 16.4 and 97.3, respectively, in our present "One-Stone-Two-Birds" evaluation system. In order to improve their antiviral activities and reduce their cytotoxicities, we synthesized numerous analogues of the two compounds. We designed synthetic route to replace the hydroxyl group of 5 with different functional groups, which led to the preparation of compounds 12-24 (FIG. 2). We further designed synthetic route to replace the 6-deoxymethyl glucose sugar unit of 26b with different sugar units or to selectively substitute one or two or three or four hydroxyl groups on the sugar moieties of 26a-g, which resulted in the preparation of compounds 25-32 (FIGS. 4-6). These compounds were evaluated for their antiviral activities in the "One-Stone-Two-Birds" system. As shown in the results of Table 1, compounds 17a, 17b, 17c, 19a, 19d, 22, 25a, 26d, 27bb, 31c and 31i, displayed much more improved anti-HIV activity than patentiflorin A (26b) and diphyllin (5) in terms of SI values. It was observed that in certain instances the stereochemistry of the sugar units is essential for the biological activities among these synthesized diphyllin glycosides. Compared with 26e, the anti-HIV activity of 26d was much higher (26d, EC$_{50}$=42.3 nM, and SI>426.1; 26e, no inhibition at 9496.9 nM). The high anti-HIV activity and selectivity of 26d were achieved by replacing the D-(+)-fucose in 26e with L-(−)-fucose in 26d. Compounds 12b, 17a, 19a and 21 were selected to be further evaluated against a broad spectrum of HIV-1 clinical and resistant strains. Compound 12b showed inhibitory effects against SF162, 89.6, Bal, Lav.04, 1617-1 and N119 with IC$_{50}$ values of 340, 376, 458, 312, 537 and 638 nM, respectively (the CC$_{50}$ value against PBMC at >100 µM). Compound 17a showed inhibitory effects against SF162, 89.6, Bal, Lav.04, 1617-1 and N119 with IC$_{50}$ values of 122, 134, 168, 151, 174 and 203 nM, respectively (the CC$_{50}$ value against PBMC at >100 µM). Compound 19a showed inhibitory effects against SF162, 89.6, Bal, Lav.04, 1617-1 and N119 with $IC_{50}$ values of 154, 143, 188, 138, 152 and 185 nM, respectively (the $CC_{50}$ value against PBMC at >100 µM). Compound 21 showed inhibitory effects against SF162, 89.6, Bal, Lav.04, 1617-1 and N119 with $IC_{50}$ values of 23.9, 28.7, 26.5, 30.1, 39.3 and 42.1 nM, respectively (the $CC_{50}$ value against PBMC at 25.6 µM). Compounds 19p, 26f, 28ab1, 31a, 31e, 31g, 31j, 31l, 32b, 32c and 32d were selected to be tested for their inhibitory effects in several concentrations against H5N1 virus, EBOV (Ebola virus) and VSV (vesicular stomatitis virus) in comparison with their inhibitory effects against the A549 host cells (Table 3). Compounds 28ab1, 31e, 31g, 31l, 31j and 32b showed more than 77% inhibitory effects against the three viruses (H5N1 virus, EBOV and VSV) in a concentration of below 12.5 ng/mL. The compound series of 26-32 were repeatedly tested for their antiviral activities against H5N1 virus, EBOV and VSV. Compounds 26b, 26f, 26g, 28ab1, 28ab2, 28ab3, 29a, 30a, 31e, 31j, 31l, 32a, 32b, 32c, 32d and AZT (the positive control) were measured to show inhibitory effects against H5N1 virus with $EC_{50}$ values of 4.48, 371.3, 63.6, 5.05, 0.23, 1.16, 5.57, 3.88, 0.74, 0.84, 0.013, 0.63, 0.77, 5.20, 199.8 and 3.48 nM, respectively. Compounds 26b, 26f, 26g, 28ab1, 28ab2, 28ab3, 29a, 30a, 31e, 31j, 31l, 32a, 32b, 32c, 32d, AZT (the positive control) and toremifene (the positive control) were measured to show inhibitory effects against EBOV with $EC_{50}$ values of 54.8, 515.6, 123.0, 18.9, 16.3, 0.98, 10.6, 1.84, 1.13, 0.84, 0.19, 1.20, 0.85, 20.3, 395.7, 3.80 and 212.1 nM, respectively. Compounds 26b, 26f, 26g, 28ab1, 28ab2, 28ab3, 29a, 30a, 31e, 31j, 31l, 32a, 32b, 32c, 32d and AZT (the positive control) were measured to show inhibitory effects against VSV with $EC_{50}$ values of 42.5, 1035, 210.1, 3.78, 4.98, 0.85, 10.6, 8.60, 2.41, 0.91, 0.37, 18.1, 3.15, 123.9, 286.1 and 7.06 nM, respectively. Compounds 5, 26b, 26e, 28ab1, 31j, 32a, 32b, 32c, 32d and arbidol (the positive control) were measured to show inhibitory effects against SARS-CoV-2 with $EC_{50}$ values of 150.1, 67.2, 30.4, 26.3, 10.3, 2.95, 3.01, 50.8, 80.4, and 4,110 nM, respectively. Compounds 26b, 26f, 26g, 28ab1, 28ab2, 28ab3, 29a, 30a, 31e, 31j, 31l, 32a, 32b, 32c and 32d and taxol (the positive control) were measured to show inhibitory effects against the host cell line A549 with $CC_{50}$ values of 386.1, 8649, 4129, 190.0, 108.2, 6.14, 121.6, 35.2, 17.7, 6.68, 4.85, 61.6, 30.7, 1038, 1349 and 2.99 nM, respectively. Compounds 17a and 25a were further evaluated for its toxicity in mice with each having two doses at 25 and 50 mg/kg in comparison with a vehicle control group. At the end of the animal study, no toxic symptoms (weight loss, skin damage, food and water intake impairment and postual abnormality) and mortality were observed for the mice of all groups. The excised organs of all mice appeared as normal at the end of the experiment.

Materials and Methods

General Experimental Procedures 1D and 2D NMR spectra were recorded on a Bruker DRX-400 MHz spectrometer (Rheinstetten, Germany). Chemical shifts (δ) were expressed in ppm and coupling constants (J) are reported in Hz. All NMR experiments were obtained by using standard pulse sequences supplied by the vendor. Chemical shifts (δ) were expressed in ppm with reference to the solvent signals ($CD_3OD$: $^1H$: 3.31 ppm, $^{13}C$: 49.00 ppm; $CDCl_3$: $^1H$: 7.27 ppm, $^{13}C$: 77.23 ppm; DMSO-$d_6$: $^1H$: 2.50 ppm, $^{13}C$: 39.51 ppm; acetone-$d_6$: $^1H$: 2.05 ppm, $^{13}C$: 29.92, 206.68 ppm.), and coupling constants (J) are reported in Hz. Column chromatography was carried out on silica gel (230-400 mesh, Natland International Corporation, Research Triangle Park, N.C., USA). Thin-layer chromatography (TLC) was performed on EMD glass-backed plates coated with 0.25 mm layers of silica gel 60 F254 (Kassel, Germany). HRTOFMS spectra were recorded on a Micromass QTOF-2 (Milford, Mass., USA), an Agilent 6540 Q-TOF (Santa Clara, Calif., USA), an Agilent 6460 Triple Quadrupole, or a Bruker Q-TOF mass spectrometer (Bremen, Germany). All reagents were purchased from commercial sources and used without further purification.

Compound 5

To a suspension of the crude 2-bromo-4,5-dimethoxybenzaldehyde (30 g, 125 mmol) in toluene (1 L) was added ethylene glycol (14 mL, 250 mmol) and p-toluenesulfonic acid (TsOH) (5.2 g, 25 mmol). A Dean-Stark apparatus filled with toluene (PhMe) was fitted to the round bottom flask, and the reaction was refluxed overnight. After cooling to room temperature (r.t.), toluene was removed under reduced pressure. The crude mixture was then dissolved in ethyl acetate (EtOAc) and washed with sodium bicarbonate ($NaHCO_3$) aqueous, water, then brine, dried with anhydrous sodium sulfate ($Na_2SO_4$), and concentrated under reduced pressure. Separation of the mixture on silica gel flash chromatography (deactivated silica gel, 16%-25% EtOAc in n-hexane) afforded 2-(2-bromo-4,5-dimethoxyphenyl)-1,3-dioxolane (2) as an off-white solid (33.5 g, 95%). To a stirring solution of the acetal (2) (30 g, 104 mmol) in 1 L of tetrahydrofuran (THF), after cooled to −78° C., n-buyllithium (n-BuLi) (1.8 M, 69.3 mL, 124.8 mmol) was added drop-wise for an additional 30 min. Following the addition, the reaction mixture was stirred for 30 min at −50° C., and then piperonal (114.4 mmol) was added. The mixture was stirred at −78° C. for 0.5 h, and then the reaction was allowed to warm to r.t. for an additional 2 h. The reaction was then quenched with water, and the aqueous layer was extracted with EtOAc. The combined organic layers were washed with water, then brine, dried with $Na_2SO_4$, and concentrated under reduced pressure to afford a pale-yellow syrup (3), which was immediately subjected to a Diels-Alder reaction. To a solution of the crude intermediate in dichloromethane ($CH_2Cl_2$) (100 mL) was added acetic acid (AcOH) (35 mL) and dimethyl acetylenedicarboxylate (DMADC) (16.7 mL, 104 mmol). The reaction was stirred at 140° C. for 12 h. Upon cooling to r.t., the reaction was diluted with water, and the aqueous layer was extracted with $CH_2Cl_2$. The combined organic layers were washed, dried and filtered through a plug of silica gel to remove the majority of impurities. The resulted red viscous oil was purified by recrystallization in ethanol (EtOH). The crude diester (4a, 5 mmol) was dissolved in THF (70 mL) with the drop-wise addition of sodium borohydride ($NaBH_4$) (0.945 g, 25 mmol), and the reaction was stirred at 80° C. for 12 h. The reaction was then cooled back to r.t. The resulting slurry was acidified to a pH value of approximately 2 with dilute HCl (2 M). Following acidification, the aqueous layer was extracted with EtOAc, and the combined organic layer was washed with water, then brine, dried with $Na_2SO_4$ and concentrated. The resulted red viscous oil was purified by silica gel column chromatography to give the target compound 5. HR-EIMS: m/z $[M+H]^+$ 381.0974 (calcd. 381.0912). $^1H$ NMR (400 MHz, acetone-$d_6$) δ 7.69 (1H, s, H-2), 7.09 (1H, s, H-5), 6.96 (1H, d, J=7.9 Hz, H-5'), 6.85 (1H, d, J=1.6 Hz, H-2'), 6.91 (1H, dd, J=7.9, 1.7 Hz, H-6'), 6.09 (1H, br s, $OCH_2O$), 6.07 (1H, br s, $OCH_2O$), 5.37 (2H, s, H-9), 3.99 (3H, s, 3-$OCH_3$), 3.73 (3H, s, 4-$OCH_3$).

Compound 12a

To a solution of diphyllin (5, 190 mg, 0.5 mmol) and t-BuOCOCH2Br (193 mg, 1 mmol) in DMF (5 mL) was added $Cs_2CO_3$ (326 mg, 1 mmol). The mixture was stirred at r.t. for 2 h. After quenched with water, the aqueous layer was then extracted with EtOAc and the combined organic layer were washed with water, then brine, dried with $Na_2SO_4$ and concentrated under reduced pressure. The mixture was purified by prep-TLC to afford a light-yellow solid (12a, 247 mg, 99%). HR-EIMS: m/z [M+H]+ 495.1638 (calcd. 495.1655). $^1$H NMR (400 MHz, CDCl$_3$) δ 7.73 (1H, s, H-2), 7.07 (1H, s, H-5), 6.96 (11H, d, J=7.9 Hz, H-5'), 6.82 (11H, d, J=1.3 Hz, H-2'), 6.79 (1H, dd, J=7.9, 1.7 Hz, H-6'), 6.09 (11H, br s, —OCH$_2$O—), 6.05 (1H, br s, —OCH$_2$O—), 5.48 (2H, s, H-9), 4.69 (2H, s, OCH$_2$C=O), 4.09 (3H, s, 3-OCH$_3$), 3.81 (3H, s, 4-OCH$_3$), 1.51 (9H, s, t-Bu). $^{13}$C NMR (100 MHz, CDCl$_3$) δ 169.5 (C-9'), 167.8 (O—C=O), 151.8 (C-3), 150.4 (C-4), 147.5 (C-4', C-7), 146.7 (C-3'), 135.5 (C-7'), 130.8 (C-6), 128.3 (C-1'), 126.4 (C-8'), 126.2 (C-1), 123.6 (C-6'), 119.1 (C-8), 110.7 (C-2'), 108.2 (C-5'), 106.2 (C-5), 101.3 (C-2), 100.9 (—OCH$_2$O—), 82.9 (t-Bu), 69.8 (OCH$_2$C=O), 66.4 (C-9), 56.2 (3-OCH$_3$), 55.9 (4-OCH$_3$), 28.1 (t-Bu).

Compound 12b

To a solution of diphyllin (5, 38 mg, 0.1 mmol) and EtOCOCH$_2$Br (33 mg, 0.2 mmol) in 1 mL DMF was added Cs$_2$CO$_3$ (65 mg, 0.2 mmol). The mixture was stirred at r.t. for 2 h. After quenched with water, the aqueous layer was then extracted with EtOAc and the combined organic layers were washed with water, then brine, dried with Na$_2$SO$_4$ and concentrated under reduced pressure. The mixture was purified by prep-TLC to afford 12b (46 mg, 99%). HR-EIMS: m/z 467.1316 [M+H]+(calcd. 467.1342). $^1$H NMR (400 MHz, DMSO-d$_6$) δ 7.73 (1H, s, H-2), 7.03 (1H, d, J=7.9 Hz, H-5'), 6.96 (1H, s, H-5), 6.87 (1H, d, J=1.5 Hz, H-2'), 6.75 (1H, dd, J=7.9, 1.7 Hz, H-6'), 6.12 (2H, br s, —OCH$_2$O—), 5.59 (2H, s, H-9), 5.02 (2H, s, OCH$_2$C=O), 4.23 (2H, q, J=7.1 Hz, Et), 3.95 (3H, s, 3-OCH$_3$), 3.66 (3H, s, 4-OCH$_3$), 1.24 (3H, t, J=7.1 Hz, Et). $^{13}$C NMR (100 MHz, DMSO-d$_6$) δ 169.0 (C-9'), 169.0 (O—C=O), 151.4 (C-3), 150.1 (C-4), 147.0 (C-3'), 146.9 (C-4'), 146.0 (C-7), 133.8 (C-7'), 129.6 (C-6), 128.2 (C-1'), 126.0 (C-8'), 125.6 (C-1), 123.6 (C-6'), 118.8 (C-8), 110.8 (C-2'), 108.0 (C-5'), 105.5 (C-5), 101.2 (C-2), 100.9 (—OCH$_2$O—), 68.7 (OCH$_2$C=O), 66.4 (C-9), 61.0 (Et), 55.7 (3-OCH$_3$), 55.3 (4-OCH$_3$), 14.1 (Et).

Compound 13

To a solution of 12a (247 mg, 0.5 mmol) in 10 mL CH$_2$Cl$_2$, 1 mL DMF and 2 mL TFA was added. The mixture was stirred for 12 h at r.t. TLC showed that the reaction had completed and a new spot with higher polarity appeared. After the reaction mixture was concentrated, EtOH was added to promote the precipitation. The solid was collected to afford 13 (210 mg, 95%). HR-EIMS: m/z [M+H]+ 439.100 (calcd. 439.1029). $^1$H NMR (400 MHz, DMSO-d$_6$) δ 7.78 (1H, s, H-2), 7.04 (1H, d, J=8.0 Hz, H-5'), 6.97 (1H, s, H-5), 6.89 (1H, d, J=1.5 Hz, H-2'), 6.77 (11H, dd, J=7.9, 1.7 Hz, H-6'), 6.13 (2H, s, —OCH$_2$O—), 5.76 (1H, s, OH), 5.60 (2H, s, H-9), 4.93 (2H, s, OCH$_2$C=O), 3.96 (3H, s, 3-OCH$_3$), 3.67 (3H, s, 4-OCH$_3$). $^{13}$C NMR (100 MHz, DMSO-d$_6$) δ 170.9 (C-9'), 169.4 (O—C=O), 151.7 (C-3), 150.5 (C-4), 147.4 (C-3'), 147.3 (C-4'), 146.7 (C-7), 134.1 (C-7'), 130.0 (C-6), 128.7 (C-1'), 126.3 (C-6'), 126.1 (C-8'), 124.0 (C-1), 119.3 (C-8), 111.3 (C-2'), 108.4 (C-5'), 105.9 (C-5), 101.6 (C-2), 101.5 (—OCH$_2$O—), 69.1 (OCH$_2$C=O), 66.8 (C-9), 56.1 (3-OCH$_3$), 55.7 (4-OCH$_3$).

Compound 14a

To a solution of 13 (44 mg, 0.1 mmol) in CH$_2$Cl$_2$ (10.00 mL) were added Et$_3$N (30 mg, 0.3 mmol) NH$_4$Cl (16 mg, 0.3 mmol) and HATU (114 mg, 0.3 mmol) at 25° C., the reaction was stirred at 25° C. for 16 h. After quenched with water, the aqueous layer was then extracted with EtOAc and the combined organic layer were washed with water, then brine, dried with Na$_2$SO$_4$ and concentrated under reduced pressure. The mixture was purified by prep-TLC to afford 14a (40 mg, 92%). HR-EIMS: m/z 438.1167 [M+H]+(calcd. 438.1189). $^1$H NMR (400 MHz, DMSO-d$_6$) δ 7.80 (11H, s, NH$_2$), 7.70 (11H, s, H-2), 7.55 (1H, s, NH$_2$), 7.04 (1H, d, J=7.9 Hz, H-5'), 6.97 (1H, s, H-5), 6.89 (1H, d, J=1.5 Hz, H-2'), 6.77 (1H, dd, J=7.9, 1.6 Hz, H-6'), 6.12 (2H, s, —OCH$_2$O—), 5.60 (2H, s, H-9), 4.70 (2H, s, OCH$_2$C=O), 3.97 (3H, s, 3-OCH$_3$), 3.66 (3H, s, 4-OCH$_3$). $^{13}$C NMR (100 MHz, DMSO-d$_6$) δ 170.1 (C-9'), 169.0 (O—C=O), 151.3 (C-3), 150.0 (C-4), 147.0 (C-3'), 146.9 (C-4'), 146.1 (C-7), 133.7 (C-7'), 129.6 (C-6), 128.3 (C-1'), 126.1 (C-8'), 125.7 (C-1), 123.6 (C-6'), 118.9 (C-8), 110.9 (C-2'), 108.0 (C-5'), 105.5 (C-5), 101.2 (C-2, —OCH$_2$O—), 70.6 (OCH$_2$C=O), 66.5 (C-9), 55.8 (3-OCH$_3$), 55.3 (4-OCH$_3$).

Compound 14b

To a solution of 13 (44 mg, 0.1 mmol in CH$_2$Cl$_2$ (10.00 mL) and DMF (1 mL) were added Et$_3$N (30 mg, 0.3 mmol) and MeNH$_2$ (0.3 mL, 0.3 mmol) and HATU (114 mg, 0.3 mmol) at 25° C., the resulting mixture was stirred at 25° C. for 16 h. After quenched with water, the aqueous layer was then extracted with EtOAc and the combined organic layer were washed with water, then brine, dried with Na$_2$SO$_4$ and concentrated under reduced pressure. The mixture was purified by prep-TLC to afford 14b (30 mg, 66%). HR-EIMS: m/z 452.1312 [M+H]+(calcd. 452.1345). $^1$H NMR (400 MHz, DMSO-d$_6$) δ 7.61 (1H, s, H-2), 6.96 (1H, d, J=7.9 Hz, H-5'), 6.90 (1H, s, H-5), 6.81 (1H, d, J=1.5 Hz, H-2'), 6.69 (1H, dd, J=7.9, 1.7 Hz, H-6'), 6.04 (2H, s, —OCH$_2$O—), 5.50 (2H, s, H-9), 4.65 (2H, s, OCH$_2$C=O), 3.90 (3H, s, 3-OCH$_3$), 3.58 (3H, s, 4-OCH$_3$), 2.60 (3H, s, NH-Me). $^{13}$C NMR (100 MHz, DMSO-d$_6$) δ 169.0 (C-9'), 168.2 (O—C=O), 151.4 (C-3), 150.1 (C-4), 147.0 (C-3'), 146.9 (C-4'), 146.1 (C-7), 133.9 (C-7'), 129.6 (C-6), 128.3 (C-1'), 126.5 (C-8'), 125.8 (C-1), 123.6 (C-6'), 118.9 (C-8), 110.9 (C-2'), 108.0 (C-5'), 105.5 (C-5), 101.2 (C-2), 101.1 (—OCH$_2$O—), 71.0 (OCH$_2$C=O), 66.4 (C-9), 55.8 (3-OCH$_3$), 55.3 (4-OCH$_3$), 25.6 (NH-Me).

Compound 15a

A mixture of TBAB (16 mg, 0.05 mmol), PdCl$_2$ (1.7 mg, 0.01 mmol) and K$_2$CO$_3$ (6.9 mg, 0.05 mmol) was dissolved in deionized H$_2$O (2.00 mL) and stirred at 60° C. for 15 mins. Then diphyllin (5, 38 mg, 0.1 mmol) and 0.3 mL ethylene oxide were added and stirred at 60° C. for 5 h. TLC showed the reaction completed and the one main spot with less polarity formed. The mixture was concentrated to give a yellow green solid which was washed by EtOH to give desired product 15a (40 mg, 95%). HR-EIMS: 425.1207 m/z [M+H]+ (calcd. 425.1236).

$^1$H NMR (400 MHz, DMSO-d$_6$) δ 7.76 (1H, s, H-2), 7.03 (1H, d, J=7.9 Hz, H-5'), 6.97 (1H, s, H-5), 6.89 (1H, d, J=1.5 Hz, H-2'), 6.77 (1H, dd, J=7.9, 1.6 Hz, H-6'), 6.12 (2H, s, —OCH$_2$O—), 5.75 (1H, s, OH), 5.58 (2H, s, H-9), 4.28-4.22 [2H, m, O(CH$_2$)$_2$OH], 3.95 (3H, s, 3-OCH$_3$), 3.81 [2H, m, O(CH$_2$)$_2$OH], 3.66 (3H, s, 4-OCH$_3$). $^{13}$C NMR (100 MHz, DMSO-d$_6$) δ 169.2 (C-9'), 151.2 (C-3), 150.0 (C-4), 146.9 (C-3'), 146.8 (C-4'), 146.6 (C-7), 133.3 (C-7'), 129.6 (C-6), 128.4 (C-1'), 126.6 (C-8'), 126.1 (C-1), 123.7 (C-6'), 118.9 (C-8), 110.9 (C-2'), 108.0 (C-5'), 105.5 (C-5), 101.1 (C-2, —OCH$_2$O—), 74.4 [O(CH$_2$)$_2$OH], 66.6 (C-9), 60.4 [O(CH$_2$)$_2$OH], 55.7 (3-OCH$_3$), 55.2 (4-OCH$_3$).

Compound 15b

Cs$_2$CO$_3$ (100 mg, 0.3 mmol) was added to a mixture of 5 (38 mg, 0.1 mmol) and isobutylene oxide (71 mg, 1 mmol) in 2 mL DMF and stirred at 120° C. for 12 h. TLC showed that the reaction had completed with one main spot with less polarity formed. The mixture was concentrated to give a yellow green solid, which was washed by EtOH to give desired product 15b (38 mg, 84%). HR-EIMS: m/z [M+H]+ 453.1524 (calcd. 453.1549). $^1$H NMR (400 MHz, DMSO-$d_6$) δ 7.71 (1H, s, H-2), 7.04 (1H, d, J=7.9 Hz, H-5'), 6.97 (1H, s, H-5), 6.89 (1H, d, J=1.6 Hz, H-2'), 6.77 (1H, dd, J=7.9, 1.7 Hz, H-6'), 6.13 (2H, s, —OCH$_2$O—), 5.63 (2H, s, H-9), 4.03 (2H, s, CH$_2$), 3.95 (3H, s, 3-OCH$_3$), 3.67 (3H, s, 4-OCH$_3$), 1.34 (6H, s, Me). $^{13}$C NMR (100 MHz, DMSO-$d_6$) δ 169.1 (C-9'), 151.1 (C-3), 149.9 (C-4), 146.9 (C-3'), 146.8 (C-4'), 146.7 (C-7), 132.8 (C-7'), 129.5 (C-6), 128.4 (C-1'), 125.5 (C-8'), 125.5 (C-1), 123.6 (C-6'), 118.9 (C-8), 110.8 (C-2'), 107.9 (C-5'), 105.5 (C-5), 101.1 (C-2), 101.0 (—OCH$_2$O—), 79.9 (CH$_2$), 69.1 (C), 66.6 (C-9), 55.5 (3-OCH$_3$), 55.2 (4-OCH$_3$), 26.4 (Me).

Compound 16

A solution of 5 (19 mg, 0.05 mmol) in dry pyridine (1 mL) was added Ac$_2$O (7.1 μL, 0.075 mmol). The resulting mixture was stirred under r.t. overnight. After the reaction was complete, it was diluted by CH$_2$Cl$_2$ and washed with 10% HCl solution. The combined organic phase was further extracted with a saturate aqueous solution of NaHCO$_3$ and dried over Na$_2$SO$_4$. After concentration, the crude product was purified prep-TLC (1:1 n-hexane:ethyl acetate) to give 16 (20 mg, 94.6%) as a colorless solid. HR-EIMS: 423.1077 m/z [M+H]+(calcd. 423.1080). $^1$H NMR (400 MHz, CDCl$_3$) δ 7.17 (1H, s, H-2), 7.12 (1H, s, H-5), 6.97 (1H, d, J=7.8 Hz, H-5'), 6.86 (1H, d, J=1.4 Hz, H-2'), 6.83 (1H, dd, J=7.9, 1.7 Hz, H-6'), 6.10 (1H, d, J=1.5 Hz, —OCH$_2$O—), 6.05 (1H, d, J=1.5 Hz, —OCH$_2$O—), 5.26 (2H, s, H-9), 4.06 (3H, s, 3-OCH$_3$), 3.81 (3H, s, 4-OCH$_3$), 2.53 (3H, s, OAc).

Compound 17a

To a solution of 5 (38 mg, 0.1 mmol) and bromoacetonitrile (24 mg, 0.2 mmol) in 1 mL acetone was added Cs$_2$CO$_3$ (65 mg, 0.2 mmol). The mixture was stirred at r.t. for 2 hours. TLC show one spot with less polarity. The mixture was purified by prep-TLC to give desired product 17a (40 mg, 95%). HR-EIMS: m/z [M+H]+ 420.1053 (calcd. 420.1083). $^1$H NMR (400 MHz, DMSO-$d_6$) δ 7.52 (1H, s, H-2), 7.05 (1H, d, J=7.9 Hz, H-5'), 7.01 (1H, s, H-5), 6.91 (1H, d, J=1.6 Hz, H-2'), 6.79 (1H, dd, J=1.7, 7.9 Hz, H-6'), 6.13 (2H, s, —OCH$_2$O—), 5.60 (2H, s, CH$_2$), 5.34 (2H, s, H-9), 3.99 (3H, s, 3-OCH$_3$), 3.68 (3H, s, 4-OCH$_3$). $^{13}$C NMR (100 MHz, DMSO-$d_6$) δ 168.8 (C-9'), 151.8 (C-3), 150.2 (C-4), 147.1 (C-3'), 147.0 (C-4'), 144.7 (C-7), 135.5 (C-7'), 129.8 (C-6), 128.4 (C-1'), 127.9 (C-8'), 126.0 (C-1), 123.6 (C-6'), 118.8 (C-8), 117.1 (C≡N), 110.8 (C-2'), 108.1 (C-5'), 105.8 (C-5), 101.2 (C-2), 100.3 (—OCH$_2$O—), 66.1 (C-9), 58.0 (CH$_2$), 55.9 (3-OCH$_3$), 55.3 (4-OCH$_3$).

Compound 17b

To a solution of 5 (19 mg, 0.05 mmmol) in acetone (0.6 mL) was added Cs$_2$CO$_3$ (32.5 mg, 0.1 mmol) and the solution was cooled to 0° C. Iodomethane (10.6 mg, 0.075 mmol) was added dropwise and the mixture was warmed to r.t. The reaction was complete after 12 h as shown by TLC. The mixture was quenched with saturated NH$_4$Cl solution, extracted with EtOAc, and washed with brine. After drying (Na$_2$SO$_4$) the solvent was removed under reduced pressure and the residue was purified by prep-TLC (n-hexane:ethyl acetate, 3:1) to afford the product 17b as white solid (17.7 mg, 90%). HR-EIMS: m/z [M+H]+ 395.1125 (calcd. 395.1131). $^1$H NMR (400 MHz, CDCl$_3$) (7.54 (1H, s, H-2), 7.05 (1H, s, H-5), 6.95 (1H, d, J=7.8 Hz, H-5'), 6.78 (2H, m, H-2', H-6'), 6.09 (1H, d, J=1.5 Hz, —OCH$_2$O—), 6.04 (1H, d, J=1.5 Hz, —OCH$_2$O—), 5.54 (2H, s, H-9), 4.13 (3H, s, OCH$_3$), 4.07 (3H, s, 3-OCH$_3$), 3.80 (3H, s, 4-OCH$_3$).

Compound 17c

To a solution of 5 (38 mg, 0.1 mmol) and propynyl bromide (30 mg, 0.2 mmol) in acetone was added Cs$_2$CO$_3$ (65 mg, 0.2 mmol). The mixture was stirred at r.t. for 2 h. TLC showed one spot with less polarity. The mixture was purified by a silica gel column to give desired product 17c (40 mg, 95%). HR-EIMS: m/z [M+H]+ 419.1112 (calcd. 419.1131). $^1$H NMR (400 MHz, DMSO-$d_6$) δ 7.57 (1H, s, H-2), 7.04 (1H, d, J=7.9 Hz, H-5'), 6.98 (1H, s, H-5), 6.91 (1H, d, J=1.5 Hz, H-2'), 6.78 (1H, dd, J=7.9, 1.6 Hz, H-6'), 6.12 (2H, s, —OCH$_2$O—), 5.62 (2H, s, H-9), 5.04 (2H, d, J=2.4 Hz, CH$_2$), 3.96 (3H, s, 3-OCH$_3$), 3.71 (1H, t, J=2.4 Hz, C≡CH), 3.66 (3H, s, 4-OCH$_3$). $^{13}$C NMR (100 MHz, DMSO-$d_6$) δ 169.0 (C-9'), 151.4 (C-3), 150.1 (C-4), 147.0 (C-3'), 147.0 (C-4'), 145.6 (C-7), 134.2 (C-7'), 129.7 (C-6), 128.2 (C-1'), 127.2 (C-1), 126.3 (C-8'), 123.7 (C-6'), 118.8 (C-8), 110.9 (C-2'), 108.1 (C-5'), 105.6 (C-5), 101.2 (C-2), 100.8 (—OCH$_2$O—), 79.7 (CH$_2$), 79.5 (C≡CH), 66.6 (C-9), 55.7 (3-OCH$_3$), 55.3 (4-OCH$_3$).

Compound 17d

To a solution of 5 (38 mg, 0.1 mmol) and 2-chloropyrimidine (23 mg, 0.2 mmol) in 1 mL DMF was added K$_2$CO$_3$ (40 mg, 0.3 mmol). The mixture was stirred for 12 h at 100° C. TLC showed one spot with less polarity. The mixture was purified by prep-TLC to give desired product 17d (35 mg, 76%). HR-EIMS: m/z [M+H]+ 459.1161 (calcd. 459.1192).1H NMR (400 MHz, DMSO-$d_6$) δ 8.71 (2H, d, J=4.8 Hz, pyrimidine), 7.37 (1H, t, J=4.8 Hz, pyrimidine), 7.19 (1H, s, 1H-2), 7.08 (1H, s, H-5), 7.08 (1H, d, J=7.9 Hz, H-5'), 7.01 (1H, d, J=1.5 Hz, H-2'), 6.87 (1H, dd, J=7.9, 1.7 Hz, H-6'), 6.15 (2H, br s, —OCH$_2$O—), 5.24 (2H, s, H-9), 3.81 (3H, s, 3-OCH$_3$), 3.69 (3H, s, 4-OCH$_3$). $^{13}$C NMR (100 MHz, CDCl$_3$) δ 169.8 (pyrimidine), 169.1 (C-9'), 160.1 (pyrimidine), 160.0 (pyrimidine), 151.6 (C-3), 150.2 (C-4), 147.1 (C-4'), 147.1 (C-3'), 146.8 (C-7), 134.9 (C-7'), 129.9 (C-6), 128.8 (C-1'), 127.7 (C-1), 127.0 (C-8'), 123.8 (pyrimidine), 123.8 (C-6'), 119.2 (C-8), 110.9 (C-2'), 108.4 (C-5'), 106.2 (C-5), 101.0 (C-2), 100.8 (—OCH$_2$O—), 66.7 (C-9), 56.03 (3-OCH$_3$), 55.4 (4-OCH$_3$).

Compound 17e 5 (38 mg, 0.1 mmol), Et$_3$N (30 mg, 0.3 mmol) and DMAP (catalyzed amount) were dissolved in 2 mL of dry CH$_2$Cl$_2$. Cyclopropanecarbonyl chloride (31 mg, 0.3 mmol) was added to the mixture at 0° C. The reaction mixture was allowed to warm up to 25° C. and kept stirred at 25° C. for 2 h. The mixture was purified by a silica gel column to give desired product 17e (43 mg, 98%). HR-EIMS: m/z [M+H]+ 449.1241 (calcd. 449.1236). $^1$H NMR (400 MHz, CDCl$_3$) δ 7.20 (1H, s, H-2), 7.10 (1H, s, H-5), 6.96 (1H, d, J=7.9 Hz, H-5'), 6.85 (1H, d, J=1.5 Hz, H-2'), 6.82 (1H, dd, J=7.9, 1.7 Hz, H-6'), 6.09 (1H, br s, —OCH$_2$O—), 6.04 (1H, br s, —OCH$_2$O—), 5.24 (2H, s, H-9), 4.05 (3H, s, 3-OCH$_3$), 3.80 (3H, s, 4-OCH$_3$), 2.12-2.04 (1H, m, cyclopropanecarbonyl), 1.34-1.27 (2H, m, cyclopropanecarbonyl), 1.20 (2H, dt, J=3.3, 8.0 Hz, cyclopropanecarbonyl). $^{13}$C NMR (100 MHz, CDCl$_3$) δ 172.2 (cyclopropanecarbonyl), 169.4 (C-9'), 152.3 (C-3), 150.4 (C-4), 147.7 (C-3'), 147.6 (C-4'), 138.2 (C-7), 137.5 (C-7'), 130.7 (C-6), 130.3 (C-1), 128.0 (C-1'), 126.3 (C-8'), 123.6 (C-6'), 119.1 (C-8), 110.7 (C-2'), 108.3 (C-5'), 106.4 (C-5), 101.3 (C-2), 99.2 (—OCH$_2$O—), 66.3 (C-9), 56.0 (3-OCH$_3$), 55.9 (4-OCH$_3$), 12.7 (cyclopropanecarbonyl), 9.9 (cyclopropanecarbonyl).

Compound 17f 5 (38 mg, 0.1 mmol), Et$_3$N (30 mg, 0.3 mmol) and DMAP (catalyzed amount) were dissolved in 2 mL of dry CH$_2$Cl$_2$. Cyclopentanecarbonyl chloride (40 mg, 0.3 mmol) was added to the mixture at 0° C. The reaction mixture was allowed to warm up to 25° C. and kept stirred at 25° C. for 2 h. The mixture was purified by a silica gel column to give desired product 17f (45 mg, 97%). HR-EIMS: m/z [M+H]$^+$ 477.1547 (calcd. 477.1549). $^1$H NMR (400 MHz, CDCl$_3$) δ 7.12 (1H, s, H-2), 7.04 (1H, s, H-5), 6.90 (1H, d, J=7.9 Hz, H-5'), 6.79 (1H, d, J=1.5 Hz, H-2'), 6.76 (1H, dd, J=7.9, 1.7 Hz, H-6'), 6.09 (1H, br s, —OCH$_2$O—), 6.04 (1H, br s, —OCH$_2$O—), 5.16 (2H, s, H-9), 3.96 (3H, s, 3-OCH$_3$), 3.74 (3H, s, 4-OCH$_3$), 3.16 (1H, p, J=8.0 Hz, cyclopentanecarbonyl), 2.19-2.08 (2H, m, cyclopentanecarbonyl), 2.07-1.96 (2H, m, cyclopentanecarbonyl), 1.80 (2H, dt, J=6.1, 17.0 Hz, cyclopentanecarbonyl), 1.70 (2H, tdd, J=2.2, 4.0, 11.4 Hz, cyclopentanecarbonyl). $^{13}$C NMR (100 MHz, CDCl$_3$) δ 173.8 (cyclopentanecarbonyl), 169.4 (C-9'), 152.2 (C-3), 150.4 (C-4), 147.7 (C-3'), 147.6 (C-4'), 138.2 (C-7), 137.5 (C-7'), 130.7 (C-6), 130.2 (C-1), 128.0 (C-1'), 126.3 (C-8'), 123.7 (C-6'), 119.1 (C-8), 110.7 (C-2'), 108.3 (C-5'), 106.4 (C-5), 101.3 (C-2), 99.2 (—OCH$_2$O—), 66.3 (C-9), 56.0 (3-OCH$_3$), 55.9 (4-OCH$_3$), 43.8 (cyclopentanecarbonyl), 30.5 (cyclopentanecarbonyl), 25.9 (cyclopentanecarbonyl).

Compound 17g 5 (38 mg, 0.1 mmol), Et$_3$N (30 mg, 0.3 mmol) and DMAP (catalyzed amount) were dissolved in 2 mL of dry CH$_2$Cl$_2$. 4-Fluorobenzoyl chloride (40 mg, 0.3 mmol) was added to the mixture at 0° C. The reaction mixture was allowed to warm up to 25° C. and kept stirred at 25° C. for 2 h. The mixture was purified by a silica gel column to give desired product 17g (45 mg, 90%). HR-EIMS: m/z [M+H]$^+$ 503.1133 (calcd. 503.1142). $^1$H NMR (400 MHz, CDCl$_3$) δ 8.37 (2H, dd, J=8.9, 5.3 Hz, 4-fluorobenzoyl), 7.29 (2H, t, J=8.6 Hz, 4-fluorobenzoyl), 7.21 (1H, s, H-2), 7.15 (1H, s, H-5), 6.98 (1H, d, J=7.9 Hz, H-5'), 6.88 (1H, d, J=1.3 Hz, H-2'), 6.85 (1H, dd, J=7.9, 1.7 Hz, H-6'), 6.09 (1H, br s, —OCH$_2$O—), 6.04 (1H, br s, —OCH$_2$O—), 5.29 (2H, s, H-9), 3.95 (3H, s, 3-OCH$_3$), 3.82 (3H, s, 4-OCH$_3$). $^{13}$C NMR (100 MHz, CDCl$_3$) δ 169.7 (C-9'), 168.4 (4-fluorobenzoyl), 165.8 (4-fluorobenzoyl), 163.1 (4-fluorobenzoyl), 152.8 (C-3), 150.9 (C-4), 148.1 (C-3'), 148.0 (C-4'), 138.5 (C-7), 138.3 (C-7'), 133.6 (4-fluorobenzoyl), 133.5 (4-fluorobenzoyl), 131.2 (C-1), 130.8 (C-6), 128.3 (C-1'), 126.7 (C-8'), 124.1 (C-6'), 119.6 (C-8), 116.9 (4-fluorobenzoyl), 116.7 (4-fluorobenzoyl), 111.1 (C-2'), 108.7 (C-5'), 106.9 (C-5), 101.7 (C-2), 99.5 (—OCH$_2$O—), 66.8 (C-9), 56.4 (3-OCH$_3$), 56.3 (4-OCH$_3$).

Compound 17h 5 (38 mg, 0.1 mmol), Et$_3$N (30 mg, 0.3 mmol) and DMAP (catalyzed amount) were dissolved in 2 mL of dry CH$_2$Cl$_2$. 4-Methoxybenzoyl chloride (51 mg, 0.3 mmol) was added to the mixture at 0° C. The reaction mixture was allowed to warm up to 25° C. and kept stirred at 25° C. for 2 h. The mixture was purified by a silica gel column to give desired product 17h (45 mg, 90%). HR-EIMS: m/z [M+H]$^+$ 515.1338 (calcd. 515.1342). $^1$H NMR (400 MHz, CDCl$_3$) δ 8.33-8.25 (2H, m, 4-methoxybenzoyl), 7.26 (1H, s, H-2), 7.14 (1H, s, H-5), 7.10-7.03 (2H, m, 4-methoxybenzoyl), 6.97 (1H, d, J=7.9 Hz, H-5'), 6.88 (1H, d, J=1.4 Hz, H-2'), 6.86 (1H, dd, J=7.9, 1.7 Hz, H-6'), 6.09 (1H, d, J=1.4 Hz, —OCH$_2$O—), 6.04 (1H, d, J=1.4 Hz, —OCH$_2$O—), 5.29 (2H, s, H-9), 3.94 (3H, s, 3-OCH$_3$), 3.93 (3H, s, 4-methoxybenzoyl), 3.81 (3H, s, 4-OCH$_3$). $^{13}$C NMR (100 MHz, CDCl$_3$) δ 169.4 (C-9'), 164.7 (4-methoxybenzoyl), 163.4 (4-methoxybenzoyl), 152.3 (C-3), 150.4 (C-4), 147.7 (C-3'), 147.6 (C-4'), 138.5 (C-7), 137.5 (C-7'), 132.7 (4-methoxybenzoyl), 130.7 (C-6), 130.6 (C-1), 128.0 (C-1'), 126.6 (C-8'), 123.7 (C-6'), 120.3 (4-methoxybenzoyl), 119.2 (C-8), 114.4 (4-methoxybenzoyl), 110.7 (C-2'), 108.3 (C-5'), 106.4 (C-5), 101.3 (C-2), 99.4 (—OCH$_2$O—), 66.6 (C-9), 56.0 (3-OCH$_3$), 55.9 (4-OCH$_3$), 55.7 (4-methoxybenzoyl).

Compound 18

Under nitrogen, diphyllin (5, 760 mg, 2 mmol) and DMAP (488 mg, 4 mmol) were dissolved in 10 mL dry CH$_2$Cl$_2$. The solution was cooled to 0° C. Then trifluoromethanesulfonic anhydride (Tf$_2$O) (0.5 mL, 2.4 mmol) was added slowly via syringe over 5 min. The reaction was allowed to warm up to r.t. and kept stirred at r.t. for 4 h. TLC showed that the reaction had completed, and a new spot formed. The mixture was concentrated in vacuo to give a yellow solid, which was washed with EtOH to give desired product 18 (0.97 g, 95%). HR-EIMS: m/z [M+H]$^+$ 513.0455 (calcd. 513.0467). $^1$H NMR (400 MHz, DMSO-d$_6$) δ 7.35 (1H, s, H-2), 7.11 (1H, s, H-5), 7.08 (1H, d, J=7.9 Hz, H-5'), 7.01 (1H, d, J=1.6 Hz, H-2'), 6.87 (1H, dd, J=7.9, 1.7 Hz, H-6'), 6.15 (2H, s, —OCH$_2$O—), 5.56 (2H, s, H-9), 3.99 (3H, s, 3-OCH$_3$), 3.72 (3H, s, 4-OCH$_3$). $^{13}$C NMR (100 MHz, DMSO-d$_6$) δ 167.7 (C-9'), 153.1 (C-3), 150.6 (C-4), 147.5 (C-3'), 147.1 (C-4'), 139.7 (C-7), 135.2 (C-7'), 131.6 (C-6), 130.2 (C-1), 126.8 (C-1'), 125.2 (C-8'), 123.6 (C-6'), 119.7 (OTf), 119.4 (C-8), 110.7 (C-2'), 108.1 (C-5'), 106.2 (C-5), 101.3 (C-2), 98.7 (—OCH$_2$O—), 65.4 (C-9), 55.9 (3-OCH$_3$), 55.5 (4-OCH$_3$).

Compound 19a

In an oven dried round bottom flask under an atmosphere of nitrogen was placed [Pd(dppf)Cl$_2$] CH$_2$Cl$_2$ complex (244 mg, 0.025 mmol), B$_2$Pin$_2$ (191 mg, 0.75 mmol), KOAc (147 mg, 1.5 mmol) and 18 (256 mg, 0.5 mmol). To the flask was added freshly distilled 1,4-dioxane (2 mL). The mixture was degassed with N$_2$. The flask was equipped with a reflux condenser and heated at 100° C. for 3 h under a nitrogen atmosphere. The mixture was concentrated in vacuo to give a yellow solid, which was washed with EtOH to give desired product 19a (229.5 mg, 85%). HR-EIMS: m/z [M+H]$^+$ 491.3626 (calcd. 491.1882). $^1$H NMR (400 MHz, DMSO-d$_6$) δ 7.51 (1H, s, H-2), 7.04 (1H, d, J=7.9 Hz, H-5'), 6.98 (1H, s, H-5), 6.92 (1H, d, J=1.6 Hz, H-2'), 6.79 (1H, dd, J=7.9, 1.7 Hz, H-6'), 6.13 (2H, br s, —OCH$_2$O—), 5.43 (2H, s, H-9), 3.94 (3H, s, 3-OCH$_3$), 3.66 (3H, s, 4-OCH$_3$), 1.06 (12H, s, Me). $^{13}$C NMR (100 MHz, DMSO-d$_6$) δ 169.5 (C-9'), 151.5 (C-3), 149.8 (C-4), 147.0 (C-3', C-4'), 139.9 (C-7), 138.4 (C-7'), 133.0 (C-6), 128.4 (C-1'), 127.8 (C-1), 123.5 (C-6'), 118.9 (C-8), 117.9 (C-8'), 110.7 (C-2'), 108.0 (C-5'), 106.7 (C-5), 105.0 (C-2), 101.2 (—OCH$_2$O—), 79.1 (C—O), 73.6 (C—O), 68.1 (C-9), 55.9 (3-OCH$_3$), 55.2 (4-OCH$_3$), 25.0 (CH$_3$).

Compound 19b

An oven-dried 10-mL flask was charged with Pd(dppf)Cl$_2$ (3.7 mg, 0.005 mmol) and 18 (51 mg, 0.1 mmol). The flask was capped and then backfilled with N2. Toluene (2.00 mL) was added via syringe, followed by the addition of AlMe$_3$ (0.15 mL, 0.3 mmol). The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19b (25 mg, 66%). HR-EIMS: m/z [M+H]+ 379.1156 (calcd. 379.1182). $^1$H NMR (400 MHz, DMSO-d$_6$) δ 7.40 (1H, s, H-2), 7.04 (1H, d, J=7.9 Hz, H-5'), 7.01 (1H, s, H-5), 6.88 (1H, d, J=1.6 Hz, H-2'), 6.77 (1H, dd, J=7.9, 1.7 Hz, H-6'), 6.12 (2H, s, —OCH$_2$O—), 5.44 (s, 2H, H-9), 3.99 (3H, s, 3-OCH$_3$), 3.65 (3H, s, 4-OCH$_3$), 2.57 (3H, s, Me). $^{13}$C NMR (100 MHz, DMSO-d$_6$) δ 169.9 (C-9'), 151.3 (C-3), 149.3 (C-4), 147.0 (C-3', C-4'), 138.2 (C-7), 136.5 (C-7'), 131.5 (C-6), 128.6 (C-1'), 128.1 (C-1), 125.6 (C-8'), 123.6 (C-6'), 117.4 (C-8), 110.8

(C-2'), 108.0 (C-5'), 105.9 (C-5), 102.8 (C-2), 101.2 (—OCH$_2$O—), 67.9 (C-9), 55.8 (3-OCH$_3$), 55.2 (4-OCH$_3$), 14.3 (CH$_3$).

Compound 19c

An oven-dried 10-mL flask was charged with Pd(dppf)$_2$Cl$_2$ (7.31 mg, 0.01 mmol), Na$_2$CO$_3$ (65 mg, 0.6 mmol), 18 (102 mg, 0.2 mmol) and pyridine-4-boronic acid (52 mg, 0.4 mmol). The flask was capped and then backfilled with N$_2$. Dioxane and H$_2$O (2/0.4 mL) was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19c (22 mg, 50%). HR-EIMS: m/z [M+H]$^+$ 442.1300 (calcd. 442.1291). $^1$H NMR (400 MHz, DMSO-d$_6$) δ 8.79 (2H, d, J=5.8 Hz, pyridine), 7.62 (2H, s, H-2, pyridine), 7.09 (1H, s, pyridine), 7.08 (1H, d, J=8.1 Hz, H-5'), 7.01 (1H, s, H-5), 6.97 (1H, d, J=1.5 Hz, H-2'), 6.85 (1H, dd, J=7.9, 1.7 Hz, H-6'), 6.14 (2H, s, —OCH$_2$O—), 5.27 (2H, s, H-9), 3.72 (3H, s, 3-OCH$_3$), 3.68 (3H, s, 4-OCH$_3$). $^{13}$C NMR (100 MHz, DMSO-d$_6$) δ 169.2 (C-9'), 151.8 (C-3), 150.4 (pyridine), 149.7 (C-4), 147.1 (C-3'), 147.0 (C-4'), 143.8 (pyridine), 138.9 (C-7), 138.2 (C-7'), 129.9 (C-6), 128.5 (C-1), 128.0 (C-1'), 124.5 (pyridine, C-8'), 123.5 (C-6'), 117.9 (C-8), 110.6 (C-2'), 108.1 (C-5'), 105.8 (C-5), 103.3 (C-2), 101.2 (—OCH$_2$O—), 67.5 (C-9), 55.4 (3-OCH$_3$), 55.3 (4-OCH$_3$).

Compound 19d

An oven-dried 10-mL flask was charged with Pd(OAc)$_2$ (1.1 mg, 0.01 mmol), PPh$_3$ (2.6 mg, 0.02 mmol) and 18 (0.1 mmol). The flask was capped and then backfilled with argon (this was repeated two additional times). DMF (1.00 mL) was added via syringe, followed by the addition of Et$_3$N (43 mL, 0.3 mmol) and HCO$_2$H (8 μL, 0.2 mmol) in a like manner. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19d (35 mg, 98%). HR-EIMS: m/z [M+H]$^+$ 365.1010 (calcd. 365.1025). $^1$H NMR (400 MHz, DMSO-d$_6$) δ 7.94 (1H, s, H-7), 7.51 (1H, s, H-2), 7.05 (1H, d, J=7.9 Hz, H-5'), 6.99 (1H, s, H-5), 6.92 (1H, d, J=1.6 Hz, H-2'), 6.80 (1H, dd, J=7.9, 1.7 Hz, H-6'), 6.13 (2H, s, —OCH$_2$O—), 5.43 (2H, s, H-9), 3.94 (3H, s, 3-OCH$_3$), 3.66 (3H, s, 4-OCH$_3$). $^{13}$C NMR (100 MHz, DMSO-d$_6$) δ 169.5 (C-9'), 151.5 (C-3), 149.8 (C-4), 147.0 (C-3', C-4'), 139.9 (C-7), 138.3 (C-7'), 132.9 (C-6), 128.4 (C-1'), 127.8 (C-1), 123.5 (C-6'), 118.8 (C-8), 117.9 (C-8'), 110.7 (C-2'), 108.0 (C-5'), 106.7 (C-5), 105.0 (C-2), 101.2 (—OCH$_2$O—), 68.1 (C-9), 56.0 (3-OCH$_3$), 55.8 (4-OCH$_3$).

Compound 19e

An oven-dried 10-mL flask was charged with Pd(OAc)$_2$ (1.12 mg, 0.005 mmol), BINAP (5 mg, 0.008 mmol), Cs$_2$CO$_3$ (49 mg, 0.15 mmol) and 18 (51 mg, 0.1 mmol). The flask was capped and then backfilled with N$_2$. A solution of 4-aminobenzotrifluoride (32 mg, 0.2 mmol) in PhMe was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19e (45 mg, 86%). HR-EIMS: m/z [M+H]$^+$ (calcd. 524.1321). $^1$H NMR (400 MHz, CDCl$_3$) δ 7.44 (2H, d, J=8.5 Hz, benzotrifluoride), 7.32 (1H, s, H-2), 7.15 (1H, s, H-5), 6.93 (1H, d, J=7.9 Hz, H-5'), 6.86 (1H, d, J=1.5 Hz, H-2'), 6.83 (1H, dd, J=7.9, 1.7 Hz, H-6'), 6.70 (2H, d, J=8.4 Hz, benzotrifluoride), 6.06 (1H, br s, —OCH$_2$O—), 5.96 (1H, br s, —OCH$_2$O—), 5.13 (2H, s, H-9), 3.88 (3H, s, 3-OCH$_3$), 3.81 (3H, s, 4-OCH$_3$). $^{13}$C NMR (100 MHz, CDCl$_3$) δ 170.6 (C-9'), 152.6 (C-3), 150.7 (C-4), 148.2 (benzotrifluoride), 148.1 (C-3'), 148.0 (C-4'), 138.3 (C-7), 136.0 (C-7'), 130.9 (benzotrifluoride), 130.8 (C-6), 128.6 (C-8'), 128.5 (C-1), 127.3 (C-1'), 124.0 (C-6'), 119.4 (C-8), 114.3 (benzotrifluoride), 111.0 (C-2'), 108.6 (C-5'), 107.1 (C-5), 101.9 (C-2), 101.8 (—OCH$_2$O—), 67.8 (C-9), 56.5 (3-OCH$_3$), 56.3 (4-OCH$_3$).

Compound 19f

An oven-dried 10-mL flask was charged with Pd(OAc)$_2$ (1.12 mg, 0.005 mmol), BINAP (5 mg, 0.008 mmol), Cs$_2$CO$_3$ (49 mg, 0.15 mmol) and 18 (51 mg, 0.1 mmol). The flask was capped and then backfilled with N$_2$. A solution of aminobenzene (19 mg, 0.2 mmol) in PhMe was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19g (38.7 mg, 85%). HR-EIMS: m/z [M+H]+(calcd. 456.1447). $^1$H NMR (400 MHz, CDCl$_3$) δ 7.40 (1H, s, H-2), 7.22 (2H, dd, J=8.5, 7.4 Hz, aminobenzene), 7.14 (1H, s, H-5), 6.93 (1H, d, J=7.9 Hz, H-5'), 6.89-6.87 (1H, m, aminobenzene), 6.86 (1H, d, J=1.5 Hz, H-2'), 6.83 (1H, dd, J=7.9, 1.7 Hz, H-6'), 6.72 (2H, dd, J=1.0, 8.5 Hz, aminobenzene), 6.06 (1H, br s, —OCH$_2$O—), 5.98 (1H, br s, —OCH$_2$O—), 5.07 (2H, s, H-9), 3.89 (3H, s, 3-OCH$_3$), 3.80 (3H, s, 4-OCH$_3$). $^{13}$C NMR (100 MHz, CDCl$_3$) δ 170.4 (C-9'), 151.9 (C-3), 150.1 (C-4), 147.6 (C-3'), 147.6 (C-4'), 144.6 (C-7), 136.4 (C-7'), 133.9 (aminobenzene), 130.4 (C-6), 129.8 (C-1), 129.7 (C-8'), 129.5 (aminobenzene), 128.6 (C-1'), 123.7 (C-6'), 120.2 (C-8), 119.2 (aminobenzene), 115.6 (aminobenzene), 110.8 (C-2'), 108.2 (C-5'), 106.7 (C-5), 101.7 (C-2), 101.3 (—OCH$_2$O—), 67.7 (C-9), 56.1 (3-OCH$_3$), 55.9 (4-OCH$_3$).

Compound 19g

An oven-dried 10-mL flask was charged with Pd(PPh$_3$)$_4$ (6.22 mg, 0.005 mmol) and 18 (51 mg, 0.1 mmol). The flask was capped and then backfilled with N$_2$. THF (2.00 mL) was added via syringe, followed by the addition of Et$_2$Zn. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19g (25 mg, 64%). HR-EIMS: m/z [M+H]$^+$ 393.1324 (calcd. 393.1338). $^1$H NMR (400 MHz, DMSO-d$_6$) δ 7.43 (1H, s, H-2), 7.04 (1H, d, J=8.1 Hz, H-5'), 7.02 (1H, s, H-5), 6.90 (1H, d, J=1.3 Hz, H-2'), 6.77 (1H, dd, J=7.7, 1.3 Hz, H-6'), 6.12 (2H, s, —OCH$_2$O—), 5.47 (2H, s, H-9), 3.99 (3H, s, 3-OCH$_3$), 3.65 (3H, s, 4-OCH$_3$), 3.03 (2H, q, J=7.3 Hz, Et), 1.28 (3H, t, J=7.5 Hz, Et). $^{13}$C NMR (100 MHz, DMSO-d$_6$) δ 169.9 (C-9'), 151.5 (C-3), 149.3 (C-4), 147.0 (C-3'), 146.9 (C-4'), 137.7 (C-7), 136.7 (C-7'), 131.7 (C-6), 130.6 (C-1), 128.7 (C-8'), 128.5 (C-1'), 123.6 (C-6'), 117.6 (C-8), 110.8 (C-2'), 108.1 (C-5'), 106.1 (C-5), 102.5 (C-2), 101.2 (—OCH$_2$O—), 67.6 (C-9), 55.8 (3-OCH$_3$), 55.2 (4-OCH$_3$), 21.5 (Et), 13.9 (Et).

Compound 19h

An oven-dried 10-mL flask was charged with Pd(PPh$_3$)$_4$ (6.22 mg, 0.005 mmol), K$_2$CO$_3$ (40 mg, 0.3 mmol), 18 (51 mg, 0.1 mmol) and thiophene-2-boronic acid (26 mg, 0.2 mmol). The flask was capped and then backfilled with N$_2$. DMF was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19h (38 mg, 92%). HR-EIMS: m/z [M+H]$^+$ 447.0889 (calcd. 447.0902). $^1$H NMR (400 MHz, DMSO-d$_6$) δ 7.87 (1H, dd, J=5.1, 1.2 Hz, thiophene), 7.42 (1H, dd, J=3.5, 1.2 Hz, thiophene), 7.41 (1H, s, H-2), 7.33 (1H, dd, J=5.1, 3.5 Hz, thiophene), 7.07 (1H, d, J=7.9 Hz, H-5'), 7.06 (1H, s, H-5), 6.95 (1H, d, J=1.5 Hz, H-2'), 6.83 (1H, dd, J=7.9, 1.7 Hz, H-6'), 6.13 (2H, br s, —OCH$_2$O—), 5.32 (2H, s, H-9), 3.77 (3H, s, 3-OCH$_3$), 3.67 (3H, s, 4-OCH$_3$). $^{13}$C NMR (100 MHz, DMSO-d$_6$) δ 169.2 (C-9'), 151.7 (C-3), 149.6 (C-4), 147.0 (C-3', C-4'), 139.6 (C-7), 138.7 (thiophene), 135.4 (C-7'), 131.4 (C-6), 129.0 (C-1), 128.6 (C-1'), 128.1 (thiophene), 128.1 (thiophene), 128.1 (thiophene), 123.6 (C-6'), 123.5 (C-8'), 118.0 (C-8), 110.6 (C-2'), 108.1 (C-5'), 105.7 (C-5), 103.7 (C-2), 101.2 (—OCH$_2$O—), 67.9 (C-9), 55.4 (3-OCH$_3$), 55.3 (4-OCH$_3$).

Compound 19i

An oven-dried 10-mL flask was charged with Pd(PPh$_3$)$_4$ (6.22 mg, 0.005 mmol), K$_2$CO$_3$ (42 mg, 0.3 mmol), 18 (51 mg, 0.1 mmol) and pyridine-3-boronic acid (25 mg, 0.2 mmol). The flask was capped and then backfilled with N$_2$. 2 mL DMF was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19i (30 mg, 75%). HR-EIMS: m/z [M+H]$^+$ 442.1293 (calcd. 442.1291). $^1$H NMR (400 MHz, DMSO-d$_6$) δ 8.80 (2H, s, pyridine), 8.09 (1H, s, pyridine), 7.71 (1H, s, H-2), 7.09 (1H, s, pyridine), 7.08 (2H, d, J=8.3 Hz, H-5'), 6.97 (1H, d, J=4.2 Hz, H-2'), 6.95 (1H, s, H-5), 6.85 (1H, dd, J=8.6, 4.2 Hz, H-6'), 6.14 (2H, br s, —OCH$_2$O—), 5.36-5.19 (2H, m, H-9), 3.71 (3H, s, 3-OCH$_3$), 3.68 (3H, s, 4-OCH$_3$). $^{13}$C NMR (100 MHz, DMSO-d$_6$) δ 169.3 (C-9'), 151.7 (C-3), 149.6 (C-4, pyridine), 147.1 (C-3', C-4'), 139.0 (C-7), 138.7 (pyridine), 138.0 (C-7'), 130.8 (C-6), 128.5 (C-1', C-1), 128.1 (pyridine), 127.1 (C-8'), 123.5 (C-6'), 117.8 (C-8), 110.6 (C-2'), 108.1 (C-5'), 105.7 (C-5), 103.4 (C-2), 101.2 (—OCH$_2$O—), 67.5 (C-9), 55.4 (3-OCH$_3$), 55.3 (4-OCH$_3$).

Compound 19j

An oven-dried 10-mL flask was charged with Pd(PPh$_3$)$_4$ (6.22 mg, 0.005 mmol), K$_2$CO$_3$ (42 mg, 0.3 mmol), 18 (51 mg, 0.1 mmol) and thiophene-3-boronic acid (26 mg, 0.2 mmol). The flask was capped and then backfilled with N$_2$. DMF 2 mL was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19j (22 mg, 50%). HR-EIMS: m/z [M+H]$^+$ 447.0867 (calcd. 447.0902). $^1$H NMR (400 MHz, DMSO-d$_6$) δ 7.91 (1H, d, J=1.4 Hz, thiophene), 7.84 (1H, d, J=4.7 Hz, thiophene), 7.44 (1H, d, J=4.9 Hz, thiophene), 7.27 (1H, s, H-2), 7.06 (1H, d, J=7.9 Hz, H-5'), 7.05 (1H, s, H-5), 6.95 (1H, d, J=1.0 Hz, H-2'), 6.83 (1H, dd, J=7.8, 1.3 Hz, H-6'), 6.13 (2H, s, —OCH$_2$O—), 5.32 (2H, s, H-9), 3.76 (3H, s, 3-OCH$_3$), 3.66 (3H, s, 4-OCH$_3$). $^{13}$C NMR (100 MHz, DMSO) δ 170.0 (C-9'), 151.9 (C-3), 150.0 (C-4), 147.5 (C-3', C-4'), 139.0 (C-7), 138.3 (C-7'), 136.0 (thiophene), 131.3 (C-6), 129.2 (C-1), 129.0 (thiophene), 128.8 (C-1'), 127.8 (C-8'), 126.6 (thiophene), 125.9 (thiophene), 123.9 (C-6'), 118.4 (C-8), 111.1 (C-2'), 108.5 (C-5'), 106.1 (C-5), 104.4 (C-2), 101.7 (—OCH$_2$O—), 68.4 (C-9), 55.8 (3-OCH$_3$), 55.7 (4-OCH$_3$).

Compound 19k

An oven-dried 10-mL flask was charged with Pd(PPh$_3$)$_4$ (6.22 mg, 0.005 mmol), Na$_2$CO$_3$ (32 mg, 0.3 mmol), 18 (51 mg, 0.1 mmol) and furan-2-boronic acid (26 mg, 0.2 mmol). The flask was capped and then backfilled with N$_2$. Dioxane and H$_2$O (2/0.4 mL) was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19k (30 mg, 70%). HR-EIMS: m/z [M+H]$^+$ 431.1098 (calcd. 431.1131). $^1$H NMR (400 MHz, DMSO-d$_6$) δ 7.99 (1H, dd, J=1.8, 0.7 Hz, furan), 7.73 (1H, s, H-2), 7.14 (1H, dd, J=3.4, 0.6 Hz, furan), 7.07 (1H, d, J=7.9 Hz, H-5'), 7.06 (1H, s, H-5), 6.95 (d, 1H, J=1.5 Hz, furan), 6.82 (1H, dd, J=7.9, 1.8 Hz, H-6'), 6.82 (1H, d, J=1.9 Hz, H-2'), 6.14 (2H, s, —OCH$_2$O—), 5.51 (2H, s, H-9), 3.92 (3H, s, 3-OCH$_3$), 3.68 (3H, s, 4-OCH$_3$). $^{13}$C NMR (100 MHz, DMSO-d$_6$) δ 169.2 (C-9'), 152.0 (C-3), 149.6 (C-4), 148.9 (furan), 147.1 (C-3'), 147.0 (C-4'), 143.9 (furan), 138.5 (C-7), 138.4 (C-7'), 129.1 (C-6), 128.9 (C-1), 128.2 (C-1'), 123.5 (C-6'), 119.8 (C-8), 118.3 (C-8'), 112.1 (furan), 111.8 (furan), 110.7 (C-2'), 108.1 (C-5'), 105.9 (C-5), 104.1 (C-2), 101.3 (—OCH$_2$O—), 68.6 (C-9), 55.5 (3-OCH$_3$), 55.2 (4-OCH$_3$).

Compound 19l

An oven-dried 10-mL flask was charged with Pd(PPh$_3$)$_4$ (24 mg, 0.02 mmol), Na$_2$CO$_3$ (120 mg, 1.2 mmol), 18 (204 mg, 0.4 mmol), 3,6-dihydro-2H-pyridine-1-N-Boc-4-boronic acid, and pinacol ester (186 mg, 0.6 mmol). The flask was capped and then backfilled with N2. Dioxane and water (4/0.8 mL) were added via syringe. The reaction mixture was heated to 80° C. for 10 h. After cooling to r.t., the reaction solution was quenched with water and extracted with CH$_2$Cl$_2$. The mixture was purified by a silica gel column to give desired product 19l (69 mg, 27%). HR-EIMS: m/z [M+H]$^+$ 546.2109 (calcd. 546.2128).1H NMR (400 MHz, CDCl$_3$) δ 7.12 (1H, s, H-2), 7.11 (1H, s, H-5), 6.96 (1H, d, J=7.9 Hz, H-5'), 6.84 (1H, br s, H-2'), 6.81 (1H, d, J=8.1 Hz, H-6'), 6.09 (1H, br s, —OCH$_2$O—), 6.04 (1H, br s, —OCH$_2$O—), 5.88 (1H, s, 3,6-dihydro-2H-pyridine), 5.29 (2H, s, H-9), 4.42-4.05 (2H, m, 3,6-dihydro-2H-pyridine) 3.99 (3H, s, 3-OCH$_3$), 3.80 (3H, s, 4-OCH$_3$), 3.69 (2H, s, 3,6-dihydro-2H-pyridine), 2.59-2.29 (2H, m, 3,6-dihydro-2H-pyridine), 1.53 (9H, s, Boc). $^{13}$C NMR (100 MHz, CDCl$_3$) δ 170.1 (C-9'), 155.1 (Boc), 151.7 (C-3), 149.8 (C-4), 147.6 (C-3'), 147.6 (C-4'), 138.9 (C-7), 136.9 (C-7'), 131.9 (3,6-dihydro-2H-pyridine), 130.7 (C-6), 129.4 (C-1), 128.4 (C-1'), 124.5 (3,6-dihydro-2H-pyridine), 123.6 (C-6'), 123.5 (C-8'), 118.3 (C-8), 108.3 (C-2', C-5'), 106.5 (C-5), 103.5 (C-2), 101.3 (—OCH$_2$O—), 80.2 (Boc), 67.7 (3,6-dihydro-2H-pyridine), 67.1 (C-9), 55.9 (3-OCH$_3$), 55.9 (4-OCH$_3$), 53.5 (3,6-dihydro-2H-pyridine), 29.4 (3,6-dihydro-2H-pyridine), 28.5 (Boc).

Compound 19m

An oven-dried 10-mL flask was charged with Pd$_2$(dba)$_3$ (4.58 mg, 0.005 mmol), XantPhos (2.89 mg, 0.005 mmol), Cs$_2$CO$_3$ (65 mg, 0.2 mmol) and 18 (51 mg, 0.1 mmol). The flask was capped and then backfilled with N$_2$. A solution of morpholine (17 mg, 0.2 mmol) in toluene was added via syringe. The reaction mixture was heated to 100° C. for 10 h. After cooling to r.t., the reaction solution was quenched with water and extracted with CH$_2$Cl$_2$. The obtained solution was concentrated and purified by prep-TLC to give desired product 19m (20 mg, 40%). HR-EIMS: m/z [M+H]$^+$ (calcd. 450.1553). $^1$H NMR (400 MHz, CDCl$_3$) δ 7.79 (1H, s, H-2), 7.07 (1H, s, H-5), 6.96 (1H, d, J=7.9 Hz, H-5'), 6.82 (1H, d, J=1.4 Hz, H-2'), 6.79 (1H, dd, J=7.9, 1.7 Hz, H-6'), 6.09 (1H, br s, —OCH$_2$O—), 6.05 (1H, br s, —OCH$_2$O—), 5.52 (2H, s, H-9), 4.07 (3H, s, 3-OCH$_3$), 4.05-4.01 (2H, m, morpholine), 3.93 (2H, td, J=10.9, 2.2 Hz, morpholine), 3.80 (3H, s, 4-OCH$_3$), 3.28 (2H, td, J=11.3, 2.9 Hz, morpholine), 3.13 (2H, d, J=11.8 Hz, morpholine). $^{13}$C NMR (100 MHz, CDCl$_3$) δ 169.6 (C-9'), 151.8 (C-3), 150.1 (C-4), 147.5

(C-3', C-4'), 142.2 (C-7), 139.4 (C-7'), 136.8 (C-6), 132.1 (C-1), 130.5 (C-8'), 129.9 (C-1'), 128.6 (C-8), 123.5 (C-6'), 110.6 (C-2'), 108.2 (C-5'), 106.5 (C-5), 102.6 (C-2), 101.2 (—OCH$_2$O—), 67.8 (morpholine), 67.3 (C-9), 55.9 (3-OCH$_3$), 55.9 (4-OCH$_3$), 51.5 (morpholine).

Compound 19n

A solution of 18 (256 mg, 0.5 mmol), tributyl (1-ethoxyvinyl) stannane (216 mg, 0.6 mmol) and 5 mL toluene was degassed for 30 min while stirring. PdCl$_2$(PPh$_3$)$_2$ (34 mg, 0.05 mmol) was then added, the solution was heated to 100° C. overnight with stirring. 10 mL of 50% HCl (aq.) was added to the reaction mixture and the solution was stirred for 6 h, followed by filtration through celite that effectively removed the palladium black. The mixture was purified by a silica gel column to give desired product 19n (180 mg, 88%). HR-EIMS: m/z [M+H]$^+$ 393.1324 (calcd. 393.1338). $^1$H NMR (400 MHz, DMSO-d$_6$) δ 7.64 (1H, s, H-2), 7.07 (1H, d, J=7.9 Hz, H-5'), 7.06 (1H, s, H-5), 6.96 (1H, d, J=1.6 Hz, H-2'), 6.82 (1H, dd, J=7.9, 1.7 Hz, H-6'), 6.14 (2H, s, —OCH$_2$O—), 5.55 (2H, s, H-9), 3.97 (31H, s, 3-OCH$_3$), 3.68 (3H, s, 4-OCH$_3$), 2.76 (3H, s, CH$_3$). $^{13}$C NMR (100 MHz, DMSO-d$_6$) δ 202.0 (Me-C=O), 168.9 (C-9'), 152.4 (C-3), 149.7 (C-4), 147.3 (C-3'), 147.1 (C-4'), 141.6 (C-7), 139.6 (C-7'), 129.4 (C-6), 129.1 (C-1), 129.0 (C-8'), 127.9 (C-1'), 123.5 (C-6'), 118.0 (C-8), 110.6 (C-2'), 108.2 (C-5'), 106.0 (C-5), 104.4 (C-2), 101.4 (—OCH$_2$O—), 68.6 (C-9), 55.9 (3-OCH$_3$), 55.3 (4-OCH$_3$), 31.8 (CH$_3$).

Compound 19o

An oven-dried 25-mL flask was charged with Pd(PPh$_3$)$_2$Cl$_2$ (17.5 mg, 0.025 mmol), CuI (14.3 mg, 0.075 mmol) and 18 (255 mg, 0.5 mmol). The flask was capped and then backfilled with N$_2$. A solution of trimethylsilylacetylene (100 mg, 1 mmol) and Et$_3$N (150 mg, 1.5 mmol) in 5 mL DMF was added via syringe. The reaction mixture was heated to 80° C. for 10 h. After cooling to r.t., the reaction solution was quenched with water and extracted with CH$_2$Cl$_2$. The obtained solution was concentrated and purified by a silica gel column to give desired product 19o (207 mg, 90%). HR-EIMS: m/z [M+H]$^+$ 461.1404 (calcd. 461.1420). $^1$H NMR (400 MHz, CDCl$_3$) 37.62 (1H, s, H-2), 7.06 (1H, s, H-5), 6.90 (1H, d, J=7.9 Hz, H-5'), 6.78 (1H, d, J=1.5 Hz, H-2'), 6.75 (1H, dd, J=7.9, 1.7 Hz, H-6'), 6.03 (1H, br s, —OCH$_2$O—), 5.99 (1H, br s, —OCH$_2$O—), 5.34 (2H, s, H-9), 4.02 (3H, s, 3-OCH$_3$), 3.75 (3H, s, 4-OCH$_3$), 0.29 (9H, s, TMS). $^{13}$C NMR (100 MHz, CDCl$_3$) δ 169.9 (C-9'), 152.6 (C-3), 150.3 (C-4), 147.9 (C-3'), 147.7 (C-4'), 143.2 (C-7), 140.1 (C-7'), 133.3 (C-6), 128.9 (C-1'), 128.1 (C-1), 123.7 (C-8', C-6'), 118.5 (C-8), 110.7 (C-2'), 108.4 (C-5'), 106.5 (C-5), 106.2 (C≡C), 104.5 (C≡C), 101.5 (C-2), 98.8 (—OCH$_2$O—), 68.3 (C-9), 56.1 (3-OCH$_3$), 56.0 (4-OCH$_3$), 0.23 (TMS).

Compound 19p

A 25 mL round-bottomed flask (equipped with thermocouple, overhead stirring and a nitrogen inlet) was charged with cesium carbonate (74.1 mg, 0.228 mmol), palladium(II) acetate (0.7 mg, 0.003 mmol), and 4,5-bis-diphenylphosphanyl-9,9-dimethyl-9H-xanthene (Xantphos, 2.82 mg, 0.005 mmol). The flask was evacuated and backfilled with nitrogen 3×.

Dioxane (2 mL) was added followed by another set of three cycles of evacuation and backfilling with nitrogen. The canary yellow slurry was stirred at r.t. for 10 min, and triethylamine (0.68 μL, 0.005 mmol) was added. Continued stirring for 10 min at r.t. gradually changed the color from yellow to red. 18 (83 mg, 0.162 mmol) and benzophenone imine (32.7 μL, 0.195 mmol) were added in 1 mL of dioxane via syringe (1 mL wash). The reaction mixture was warmed to an internal temperature of 100° C. for 12 h. Cooling the reaction mixture to ambient temperature was followed by pouring the slurry into 10 mL of ethyl acetate. The organics were washed with 2×50 mL of water, and the ethyl acetate solution was concentrated in vacuo. The mixture was purified by flash chromatography on silica gel, eluting with 1:1 n-hexane:ethyl acetate, to give 19p (50 mg, 57%) as a yellow solid. $^1$H NMR (400 MHz, CDCl$_3$) δ 7.88 (2H, dt, J=7.1, 1.4 Hz, phenyl), 7.64-7.55 (1H, m, H-2), 7.50 (2H, ddd, J=8.1, 6.5, 1.4 Hz, phenyl), 7.37-7.30 (2H, m, phenyl), 7.25-7.18 (2H, m, phenyl), 7.16-7.10 (2H, m, phenyl), 7.10 (1H, s, H-5), 6.94 (1H, dd, J=7.9, 0.5 Hz, H-5'), 6.82 (1H, dd, J=1.7, 0.5 Hz, H-2'), 6.79 (1H, dd, J=7.9, 1.7 Hz, H-6'), 6.08 (1H, d, J=1.5 Hz, —OCH$_2$O—), 6.03 (1H, d, J=1.5 Hz, —OCH$_2$O—), 5.29 (2H, s, H-9), 3.98 (3H, s, 3-OCH$_3$), 3.82 (3H, s, 4-OCH$_3$). $^{13}$C NMR (100 MHz, CDCl$_3$) δ 170.1 (C-9'), 151.3 (C-3), 149.8 (C-4), 147.2 (C-3'), 147.2 (C-4'), 135.7 (C-7), 134.6 (C-7'), 131.5 (C-6), 130.2 (C-1), 129.9 (C-1'), 129.8 (phenyl), 129.3 (phenyl), 128.4 (phenyl), 128.3 (phenyl), 128.2 (phenyl), 128.1 (phenyl), 126.0 (C-6'), 123.6 (C-8'), 118.3 (C-8), 110.8 (C-2'), 107.9 (C-5'), 106.3 (C-5), 101.7 (C-2), 101.0 (—OCH$_2$O—), 67.0 (C-9), 56.0 (3-OCH$_3$), 55.6 (4-OCH$_3$).

Compound 20

To a solution of 19n (41 mg, 0.1 mmol) in 1 mL MeOH was added NaBH$_4$ (6 mg, 0.15 mmol). The mixture was stirred at r.t. for 1 h. TLC showed that the reaction had finished with one spot and the mixture was purified by prep-TLC to give desired product 20 (40 mg, 99%). HR-EIMS: m/z [M+H]$^+$ 409.1272 (calcd. 409.1287). $^1$H NMR (400 MHz, DMSO-d$_6$) δ 7.48 (1H, d, J=2.1 Hz, H-2), 7.03 (1H, d, J=7.9 Hz, H-5'), 6.99 (1H, d, J=4.0 Hz, H-5), 6.89 (1H, dd, J=5.8, 1.5 Hz, H-2'), 6.76 (1H, ddd, J=7.8, 6.0, 1.7 Hz, H-6'), 6.12 (2H, s, —OCH$_2$O—), 5.70 (1H, m, CH—OH), 5.59 (2H, br s, H-9), 3.97 (3H, s, 3-OCH$_3$), 3.64 (3H, s, 4-OCH$_3$), 1.51 (3H, dd, J=6.3, 1.3 Hz, Me). $^{13}$C NMR (100 MHz, DMSO-d$_6$) δ 169.5 (C-9'), 151.2 (C-3), 149.2 (C-4), 147.0 (C-3'), 146.9 (C-4'), 137.2 (C-7), 136.2 (C-7'), 134.7 (C-6), 128.8 (C-1), 128.6 (C-1'), 123.5 (C-8'), 123.4 (C-6'), 118.2 (C-8), 110.9 (C-2'), 108.0 (C-5'), 105.8 (C-5), 102.9 (C-2), 101.2 (—OCH$_2$O—), 68.9 (CH—OH), 65.6 (C-9), 55.8 (3-OCH$_3$), 55.1 (4-OCH$_3$), 23.3 (CH$_3$).

Compound 21

To a solution of 19o (207 mg, 0.45 mmol) was added K$_2$CO$_3$. The mixture was stirred for 2 h. TLC showed one spot with less polarity. The mixture was purified by a silica gel column to give desired product 21 (122 mg, 70%). HR-EIMS: m/z [M+H]$^+$ 389.1000 (calcd. 389.1025). $^1$H NMR (400 MHz, CDCl$_3$) δ 7.68 (1H, s, H-2), 7.14 (1H, s, H-5), 6.97 (1H, d, J=7.9 Hz, H-5'), 6.85 (1H, d, J=1.3 Hz, H-2'), 6.82 (1H, dd, J=7.9, 1.7 Hz, H-6'), 6.03 (1H, br s, —OCH$_2$O—), 5.99 (1H, br s, —OCH$_2$O—), 5.43 (2H, s, H-9), 4.10 (3H, s, 3-OCH$_3$), 3.82 (3H, s, 4-OCH$_3$), 3.78 (1H, s, C≡CH). $^{13}$C NMR (100 MHz, CDCl$_3$) δ 169.6 (C-9'), 152.7 (C-3), 150.3 (C-4), 147.8 (C-3'), 147.6 (C-4'), 143.8 (C-7), 140.4 (C-7'), 133.3 (C-6), 128.8 (C-1'), 127.9 (C-1), 123.5 (C-6'), 121.4 (C-8'), 118.4 (C-8), 110.5 (C-2'), 108.3 (C-5'), 106.4 (C-5), 104.1 (C-2), 101.4 (—OCH$_2$O—), 87.7 (C≡CH), 77.7 (C≡CH), 68.2 (C-9), 56.2 (3-OCH$_3$), 55.9 (4-OCH$_3$).

Compound 22

The crude ketimine 19p (115.8 mg, 0.21 mmol) was suspended in 1:1 (v/v) ratio of 1N HCl:THF (4 mL) solution and stirred at r.t. for 3-5 h. Upon consumption of the ketimine as determined by TLC, THE was removed and the aqueous residue was basified using 1N KOH to a pH of 10-14. The aqueous layer was then extracted three times with ethyl acetate (30 mL). The organic layer was dried with anhydrous $NaSO_4$, filtered and concentrated in vacuo to give the crude amine. Upon purification via column chromatography the pure product 22 (70 mg, 84%) was obtained after solvent removal. HR-EIMS: m/z $[M+H]^+$ 380.0849 (calcd. 380.1134). $^1H$ NMR (400 MHz, DMSO-$d_6$) δ 7.62 (1H, s, H-2), 7.02 (1H d, J=7.9 Hz, H-5'), 6.95 (1H, s, H-5), 6.86 (1H, d, J=1.5 Hz, H-2'), 6.75 (1H, dd, J=7.9, 1.6 Hz, H-6'), 6.11 (2H, s, —$OCH_2O$—), 5.75 (1H, s, $NH_2$), 5.36 (2H, s, H-9), 3.94 (3H, s, 3-$OCH_3$), 3.65 (3H, s, 4-$OCH_3$). $^{13}C$ NMR (100 MHz, DMSO-$d_6$) δ 169.9 (C-9'), 150.6 (C-3), 149.8 (C-4), 147.0 (C-3'), 146.7 (C-4'), 145.1 (C-7), 134.8 (C-7'), 129.6 (C-6), 129.0 (C-1), 128.9 (C-1'), 123.9 (C-6'), 123.5 (C-8'), 121.9 (C-8), 111.2 (C-2'), 108.0 (C-5'), 105.5 (C-5), 101.2 (C-2), 101.0 (—$OCH_2O$—), 67.0 (C-9), 55.8 (3-$OCH_3$), 55.3 (4-$OCH_3$).

Compound 23

To solution of 22 (38 mg, 0.1 mmol) and propynyl bromide (30 mg, 0.2 mmol) in MeCN (2 mL) was added $Cs_2CO_3$. The mixture was stirred for 12 h at 60° C. After TLC show one spot with less polarity, the reaction solution was quenched with water and extracted with $CH_2Cl_2$. The obtained solution was concentrated and purified by prep-TLC to give desired product 23 (4.6 mg, 11%). HR-EIMS: m/z $[M+H]^+$ 418.1279 (calcd. 418.1291). $^1H$ NMR (400 MHz, $CDCl_3$) δ 7.19 (1H, d, J=4.2 Hz, H-2), 7.14 (1H, s, H-5), 6.97 (1H, d, J=6.1 Hz, H-5'), 6.83 (1H, d, J=1.6 Hz, H-2'), 6.80 (1H, dd, J=7.9, 1.7 Hz, H-6'), 6.10 (2H, m, —$OCH_2O$—), 6.06 (2H, m, —$OCH_2O$—), 5.75 (1H, s, NH), 5.30 (2H, s, H-9), 4.16 (2H, s, $CH_2C≡CH$), 4.06 (3H, s, 3-$OCH_3$), 3.83 (1H, s, $CH_2C≡CH$), 3.81 (3H, s, 4-$OCH_3$). $^{13}C$ NMR (100 MHz, DMSO-$d_6$) δ 169.7 (C-9'), 150.5 (C-3), 149.7 (C-4), 146.8 (C-3'), 146.6 (C-4'), 144.9 (C-7), 134.8 (C-7'), 129.5 (C-1), 129.5 (C-1'), 128.7 (C-6), 123.8 (C-6'), 123.3 (C-8'), 121.7 (C-8), 111.0 (C-2'), 107.9 (C-5'), 105.4 (C-5), 101.0 (C-2), 100.7 (—$OCH_2O$—), 79.7 ($CH_2C≡CH$), 74.1 ($CH_2C≡CH$), 66.6 (C-9), 55.6 (3-$OCH_3$), 55.1 (4-$OCH_3$), 33.2 ($CH_2C≡CH$).

Compound 24

A solution of 22 (38 mg, 0.1 mmol) in dry pyridine (2 mL) was added $Ac_2O$ (14.2 µL, 0.15 mmol). The resulting mixture was stirred under r.t. overnight. After the reaction was complete, it was diluted by $CH_2Cl_2$ and washed with 10% HCl solution. The combined organic phase was further extracted with a saturate aqueous solution of $NaHCO_3$ and dried over $Na_2SO_4$. After concentration, the crude product was purified prep-TLC (1:1 n-hexane:ethyl acetate), to give 24 (15 mg, 36%) as a white solid. HR-EIMS: m/z $[M+H]^+$ 433.1149 (calcd. 422.1240). $^1H$ NMR (400 MHz, $CDCl_3$) δ 7.18 (1H, s, H-2), 7.01 (1H, s, H-5), 6.82 (1H, d, J=7.9 Hz, H-5'), 6.77 (1H, d, J=1.6 Hz, H-2'), 6.72 (1H, dd, J=7.9, 1.7 Hz, H-6'), 6.01 (1H, d, J=1.4 Hz, —$OCH_2O$—), 5.93 (1H, d, J=1.5 Hz, —$OCH_2O$—), 5.17 (21-1, s, H-9), 3.90 (3H, s, 3-$OCH_3$), 3.75 (3H, s, 4-$OCH_3$), 2.30 (3H, d, J=0.9 Hz, OAc). $^{13}C$ NMR (100 MHz, $CDCl_3$) δ 170.6 (OAc), 169.7 (C-9'), 152.2 (C-3), 150.1 (C-4), 147.6 (C-3'), 147.6 (C-4'), 138.5 (C-7), 135.7 (C-7'), 130.0 (C-1), 128.9 (C-1'), 128.2 (C-6), 124.4 (C-8'), 123.6 (C-6'), 118.6 (C-8), 110.7 (C-2'), 108.2 (C-5'), 106.5 (C-5), 101.4 (C-2), 100.9 (—$OCH_2O$—), 68.3 (C-9), 56.1 (3-$OCH_3$), 55.9 (4-$OCH_3$), 23.40 (OAc).

General Procedure A: Glycosylated Modification

A solution of sugar (0.61 mmol) in dry pyridine (2 mL) was added acetic anhydride ($Ac_2O$) (0.4 mL, 4.21 mmol). The resulting mixture was stirred under r.t. overnight. After the reaction was complete, it was diluted by dichloromethane ($CH_2Cl_2$) and washed with 10% hydrogen chloride (HCl) solution. The combined organic phase was further extracted with a saturated aqueous solution of sodium bicarbonate ($NaHCO_3$) and dried over sodium sulfate ($Na_2SO_4$). After concentration, the crude product was directly used for next step without further purification.

The crude per-acetylated glycoside was dissolved in $CH_2Cl_2$ (5 mL) and cooled to 0° C. before the drop-wise addition of hydrogen bromide (33% in acetic acid, 1.5 mL). The reaction was warmed to r.t. and stirred for an additional 4 h. Following completion, the reaction was quenched with water, and the aqueous layer was extracted with $CH_2Cl_2$. The organic layers were combined and washed with water, sodium bicarbonate, and brine, dried with $Na_2SO_4$, and concentrated under reduced pressure to afford the glycosyl bromide. After concentration, the crude product was directly used for next step without further purification.

Diphyllin (5) (215 mg, 0.61 mmol) was dissolved in chloroform ($CHCl_3$) (15 mL) and aqueous sodium hydroxide (NaOH) (0.1 M, 20 mL) prior to adding tetra-n-butylammonium bromide (TBAB) (306 mg, 0.95 mmol). The reaction was then heated to 40° C. for 10 min before adding the glycosyl bromide (0.61 mmol), and the reaction was then stirred at 40° C. overnight. After cooling to r.t., the aqueous layer was extracted with $CHCl_3$ and the combined organic layers were washed with brine, dried with $Na_2SO_4$ and concentrated under reduced pressure. Flash chromatographic separation of the reaction mixture (silica gel, 45%-52% ethyl acetate in n-hexane) afford the target diphyllin per-acetylated glycoside (25a-25g). The reaction mixtures of compounds 25c-25g were not purified, but they were directly treated with basic reagents to produce their corresponding hydrolyzed compounds 26c-26g.

Potassium carbonate ($K_2CO_3$) (168.4 mg, 1.2 mmol) was added to a solution of a diphyllin per-acetylated glycoside (25a-25g) in MeOH (10 mL) and stirred at r.t. for 30 min. When no starting material was observed by TLC, the reaction was quenched by the addition of dilute HCl (2 M), filtered through filter paper, and concentrated under reduced pressure. Flash chromatographic separation of the reaction mixture (silica gel, 2%-10% MeOH in $CHCl_3$) afforded the target glycoside (26a-26g).

Peracetylated 7β-D-xylosyloxydiphyllin (25a, total yield 80%)

HR-EIMS: m/z $[M+H]^+$ 639.5780 (calcd. 639.1714). $^1H$ NMR (400 MHz, $CDCl_3$) δ 7.51 (1H, d, J=1.0 Hz, H-2), 7.07 (1H, s, H-5), 6.95 (1H, d, J=7.8 Hz, H-5'), 6.84-6.80 (1H, m, H-2'), 6.80-6.76 (1H, m, H-6'), 6.11-6.03 (2H, m, —$OCH_2O$—), 5.50-5.44 (1H, m, H-1''), 5.44-5.40 (2H, m, H-9), 5.31 (1H, br t, J=8.9 Hz, H-3''), 5.13 (1H, dd, J=8.8, 5.2 Hz, H-2''), 5.12 (1H, dd, J=8.3, 6.2 Hz, H-4''), 4.26 (1H, dd, J=11.8, 5.2 Hz, H-5''a), 4.16-4.10 (1H, m, H-5''b), 4.07 (3H, s, 3-$OCH_3$), 3.80 (3H, s, 4-$OCH_3$), 2.12 (3H, s, —OAc), 2.10 (3H, s, —OAc), 2.04 (3H, s, —OAc).

Peracetylated Patentiflorin A (25b, total yield 71%)

HR-EIMS: m/z $[M+H]^+$ 653.1744 (calcd. 653.1870). $^1H$ NMR (400 MHz, $CDCl_3$) δ 7.53 (1H, d, J=1.9 Hz, H-2), 7.07 (1H, s, H-5), 6.96 (1H, d, J=7.8 Hz, H-5'), 6.85-6.81 (1H, m, H-2'), 6.81-6.77 (1H, m, H-6'), 6.12-6.04 (2H, m, —$OCH_2O$—), 5.50-5.43 (2H, m, H-9), 5.39 (1H, dd, J=14.7, 2.4 Hz, H-2''), 5.27 (1H, t, J=9.6 Hz, H-3''), 5.12 (1H, d, J=7.9 Hz, H-1''), 5.00 (1H, t, J=9.6 Hz, H-4''), 4.07 (3H, s, 3-$OCH_3$), 3.81 (3H, s, 4-$OCH_3$), 3.61 (1H, ddd, J=9.7, 6.1, 1.2 Hz, H-5''), 2.12 (3H, s, —OAc), 2.06 (3H, s, —OAc), 2.06 (3H, s, —OAc), 1.28 (3H, dd, J=6.1, 1.4 Hz, H-6'').

7β-D-xylosyloxydiphyllin (26a, total yield 66%)

HR-EIMS: m/z $[M+H]^+$ 513.1389 (calcd. 513.1397). $^1H$ NMR (400 MHz, methanol-$d_6$) δ 8.13 (1H, s, H-2), 7.09 (1H, d, J=1.8 Hz, H-5), 6.97 (1H, d, J=7.9 Hz, H-5'), 6.82

(1H, dd, J=3.1, 1.3 Hz, H-2'), 6.79 (1H, dt, J=7.9, 1.8 Hz, H-6'), 6.08-6.04 (2H, m, —OCH$_2$O—), 5.58 (11H, dd, J=15.2, 1.6 Hz, H-9), 5.46 (1H, dd, J=15.2, 2.0 Hz, H-9), 4.03 (3H, s, 3-OCH$_3$), 3.98 (1H, d, J=6.5 Hz, H-1"), 3.98-3.92 (1H, m, H-5"), 3.74 (3H, s, 4-OCH$_3$), 3.64 (1H, m, H-2"), 3.51-3.44 (1H, m, H-4"), 3.16-3.11 (2H, m, H-3", H-5").

Patentiflorin A (26b, total yield 68%)

HR-EIMS: m/z [M+H]$^+$ 527.1526 (calcd. 527.1553). $^1$H NMR (400 MHz, CD$_3$OD) δ 7.99-7.92 (1H, m, H-2), 6.86 (1H, m, H-5), 6.82-6.77 (1H, m, H-5'), 6.63 (1H, m, H-2'), 6.59 (1H, m, H-6'), 5.94 (1H, d, J=1.2 Hz, —OCH$_2$O—), 5.93 (1H, dd, J=2.2, 1.3 Hz, —OCH$_2$O—), 5.50-5.27 (2H, m, H-9), 4.67 (1H, d, J=7.9 Hz, H-1"), 3.88 (3H, s, 3-OCH$_3$), 3.57 (3H, s, 4-OCH$_3$), 3.54 (1H, m, H-2"), 3.33 (1H, t, J=9.1 Hz, H-3"), 3.05 (1H, t, J=9.2 Hz, H-4"), 3.170 (1H, m, H-5"), 1.21 (3H, m, H-6").

7-O-α-L-arabinosyldiphyllin (26c, total yield 45%)

HR-EIMS: m/z [M+H]$^+$ 513.1305 (calcd. 513.1397). $^1$H NMR (400 MHz, acetone-d$_6$) δ 8.21 (1H, s, H-2), 7.07 (1H, d, J=2.2, H-5), 6.95 (1H, d, J=7.9 Hz, H-5'), 6.85 (1H, dd, J=5.8, 1.7 Hz, H-2'), 6.79 (1H, dt, J=7.9, 2.0 Hz, H-6'), 6.10-6.04 (2H, m, —OCH$_2$O—), 5.62-5.34 (3H, m, H-9, H-1"), 4.98 (1H, dt, J=4.2, 1.9 Hz, OH-3"), 4.87 (1H, dd, J=7.1, 2.0 Hz, H-1"), 4.24 (1H, t, J=5.9 Hz, OH-2"), 4.03 (1H, ddd, J=8.7, 7.0, 4.3 Hz, H-2"), 3.96 (3H, s, 3-OCH$_3$), 3.98-3.94 (1H, m, H-5"), 3.91-3.84 (1H, m, H-4"), 3.70 (3H, s, 4-OCH$_3$), 3.68-3.72 (1H, m, H-3"), 3.57 (1H, d, J=12.4 Hz, H-5").

7-O-β-L-fucopyranosyldiphyllin (26d, total yield 49%)

HR-EIMS: m/z [M+H]$^+$ 527.1433 (calcd. 527.1553). $^1$H NMR (400 MHz, DMSO-d$_6$) δ 8.20 d (1.9 Hz, H-2), 7.05 (1H, dd, J=7.9, 1.4 Hz, H-5'), 6.99 (1H, d, J=2.1 Hz, H-5), 6.94 (1H, dd, J=11.1, 1.5 Hz, H-2'), 6.81 (1H, ddd, J=7.8, 6.0, 1.6 Hz, H-6'), 6.13 (2H, s, —OCH$_2$O—), 5.59-5.44 (3H, m, H-9, OH-2"), 4.89 (1H, dd, J=14.7, 3.1 Hz, OH-3"), 4.70 (1H, dd, J=7.7, 4.9 Hz, H-1"), 4.20 (1H, d, J=7.3 Hz, OH-4"), 3.95 (3H, s, 3-OCH$_3$), 3.75 (dd, J=9.4, 7.7 Hz, 1H), 3.67 (3H, s, 4-OCH$_3$), 3.62 (1H, d, J=6.4 Hz, H-2"), 3.50-3.42 (3H, m, H-3", H-4", H-5"), 1.19 (3H, d, J=6.2 Hz, H-6").

7-O-β-D-fucopyranosyldiphyllin (26e, total yield 67%)

HR-EIMS: m/z [M+H]$^+$ 527.1550 (calcd. 527.1553). $^1$H NMR (400 MHz, acetone-d$_6$) S 8.29-8.08 (1H, m, H-2), 7.12-7.01 (1H, m, H-5), 6.96 (1H, q, J=7.8 Hz, H-5'), 6.81 (2H, m, H-2', H-6'), 6.08 (2H, t, J=7.5 Hz, —OCH$_2$O—), 5.62-5.48 (1H, m, H-9), 5.50-5.35 (1H, m, H-9), 5.30-5.15 (1H, m, OH-2"), 4.87 (1H, dt, J=11.7, 6.2 Hz, H-1"), 4.69 (1H, s, OH-4"), 4.02-3.95 (2H, m, H-3", H-4"), 3.79 (3H, d, J=7.4 Hz, 3-OCH$_3$), 3.76-3.72 (1H, m, H-2"), 3.70 (4H, m, 4-OCH$_3$, H-5"), 1.29 (q, J=8.2, 7.7 Hz, 3H).

7-O-β-D-glucopyranosyldiphyllin (26f, total yield 48%)

HR-EIMS: m/z [M+H]$^+$ 543.1500 (calcd. 543.1503). $^1$H NMR (400 MHz, acetone-d$_6$) S 8.22 (1H, dq, J=9.0, 4.9 Hz, H-2), 7.05 (1H, m, H-5), 6.95 (1H, tq, J=8.2, 4.0 Hz, H-5'), 6.89-6.74 (2H, m, H-2', H-6'), 6.07 (2H, m, —OCH$_2$O—), 5.73 (1H, m, H-9), 5.48-5.36 (1H, m, H-9), 5.22 (1H, q, J=4.3 Hz, OH-3"), 4.91 (1H, tt, J=7.6, 3.9 Hz, OH-4"), 4.65 (1H, d, J=4.6 Hz, H-1"), 4.43 (1H, d, J=4.8 Hz, OH-6"), 3.97 (4H, m, 3-OCH$_3$, H-6"), 3.70 (5H, m, 4-OCH$_3$, H-6", H-2"), 3.61-3.43 (2H, m, H-5", H-3"), 3.39 (1H, m, H-4").

7-O-β-D-galactopyranosyldiphyllin (26g, total yield 64%)

HR-EIMS: m/z [M+H]$^+$ 543.1370 (calcd. 543.1503). $^1$H NMR (400 MHz, acetone-d$_6$) δ 8.22 (1H, d, J=1.0 Hz, H-2), 7.10 (1H, s, H-5), 6.98 (1H, dt, J=7.9, 0.6 Hz, H-5'), 6.91-6.85 (1H, m, H-2'), 6.85-6.79 (1H, m, H-6'), 6.13-6.06 (2H, m, —OCH$_2$O—), 5.84-5.35 (2H, m, H-9), 4.96-4.83 (1H, m, H-1"), 4.34-4.19 (1H, m, OH), 4.08-4.01 (2H, m, H-2", H-4"), 4.00 (3H, s, 3-OCH$_3$), 3.97-3.82 (3H, m, H-5", H-6"), 3.73 (3H, s, 4-OCH$_3$), 3.54-3.69 (1H, m, H-3").

General Procedure B: Selective Modification of 3"-Hydroxy Group

The glycoside 26a or 26b (0.3 mmol) was allowed to react with acetic anhydride (32 μL, 0.32 mmol) in dry acetonitrile (MeCN) (1.5 mL) at 40° C. for 12 h in the presence of tetrabutylammonium acetate (TBOAc) (27 mg, 0.09 mmol). The solution was concentrated in vacuo to yield a mixture containing 27aa-27af (the total mixture yield from 26a: 52%) or a mixture containing 27ba-27bf (the total mixture yield from 26b: 50%) as a pale-yellow solid.

The compound mixture containing 27aa-27af was purified by flash column chromatography (petroleum ether/EtOAc=1.5/1) to afford the six single compounds 27aa-27af (27aa, 27ab, 27ac, 27ad, 27ae and 27af). The compound mixture containing 27ba-27bf was purified by flash column chromatography (petroleum ether/EtOAc=1.5/1) to afford the six single compounds 27ba-27bf (27ba, 27bb, 27bc, 27bd, 27be and 27bf).

To the suspension of the 27ab or 27bb (0.036 mmol) in CH$_2$Cl$_2$ (3 mL) was added triethylamine (Et$_3$N) (50 L, 0.36 mmol) and allyl chloroformate (AllocOCl) (10.7 μL, 0.1 mmol) at 0° C., and the reaction was slowly warmed to r.t. After 12 h, the reaction mixture was poured into H$_2$O and was extracted with CH$_2$Cl$_2$. The organic layer was washed with brine, dried over Na$_2$SO$_4$, and evaporated under reduced pressure to give a compound mixture containing 28ab1-28ab3 (the total mixture yield from 27ab: 45%) or a compound mixture containing 28bb1-28bb3 (the total mixture yield from 27bb: 52%) as white solids. The compound mixture containing 28ab1-28ab3 was purified by flash column chromatography (petroleum ether/EtOAc=1/1) to afford the three single compounds 28ab1-28ab3 (28ab1, 28ab2 and 28ab3). The compound mixture containing 28bb1-28bb3 was purified by flash column chromatography (petroleum ether/EtOAc=1/1) to afford the three single compounds 28bb1-28bb3 (28bb1, 28bb2 and 28bb3).

To a solution of 28ab3 or 28bb3 (0.004 mmol) in 6 mL of MeOH/CH$_2$Cl$_2$ (v/v=1/2) was added acetyl chloride (AcCl) (15 μL) dropwise at 0° C. The reaction mixture was stirred for 72 h, and then quenched with Et$_3$N. The volatile was removed in vacuo. The resulting residue was purified by silica gel column chromatography (petroleum ether/EtOAc 1/1) to afford 29a or 29b (18.4 mg, 67%) as white solids.

29a or 29b (0.05 mmol), Et$_3$N (20.8 μL, 0.15 mmol) and 4-dimethylaminopyridine (DMAP) (catalyzed amount) were dissolved in 2 mL of dry CH$_2$Cl$_2$. Selected acyl chloride (0.15 mmol) was added to the mixture at 0° C. The reaction mixture was allowed to warm up to 25° C. and kept stirred at 25° C. for 2 h. The mixture was purified by prep-TLC (petroleum ether/EtOAc=1/1) to give desired products 30a-30k.

To a solution of 29a (20 mg, 0.036 mmol) in dry THF (2 mL) were added successively, freshly powdered KOH (3.6 mg, 0.0648 mmol), 18-crown-6 (0.4 mg, 0.0014 mmol) and benzyl bromide (11 μL, 0.09 mmol). The mixture was stirred at r.t. and the reaction is monitored by TLC; at the end of the reaction, the mixture was diluted with CH$_2$Cl$_2$ and washed several times with water. The combined organic phase dried over Na$_2$SO$_4$ and concentrated. The obtained residue was purified by s prep-TLC (petroleum ether/EtOAc=1/1) to give desired products 30l.

To a solution of 30a-30l (0.045 mmol) in dry THF (4 ml) were added triphenylphosphine (PPh$_3$) (5.9 mg, 0.023 mmol), Et₃N (31.2 μL, 0.225), HCOOH (17 μL, 0.45 mmol) and tetrakis(triphenylphosphine)palladium(0)[Pd(PPh₃)₄] (5 mg, 0.0025 mmol) in sequence. The solution was stirred for 4 h at 55° C. under nitrogen, and concentrated in vacuo to give a mixture, which was chromatographed on prep-TLC (petroleum ether/EtOAc=1/1) to give desired products 31a-31l.

4″-Acetyl-7-O-β-D-xylosyldiphyllin (27aa)

HR-EIMS: m/z [M+H]⁺ 555.1406 (calcd. 555.1503). ¹H NMR (400 MHz, Acetone-d₆) δ 7.63 (1H, d, J=1.0 Hz, H-2), 7.07 (1H, d, J=2.3 Hz, H-5), 7.01-6.94 (1H, m, H-5′), 6.85 (1H, d, J=1.6 Hz, H-2′), 6.80 (1H, ddd, J=7.9, 1.6, 0.4 Hz, H-6′), 6.10 (2H, dt, J=4.9, 1.0 Hz, —OCH₂O—), 5.60-5.45 (2H, m, H-9), 5.33 (1H, d, J=7.8 Hz, H-1″), 5.22 (1H, dd, J=9.1, 7.8 Hz, H-2″), 4.08 (1H, dd, J=11.4, 5.2 Hz, H-5″a), 4.03 (3H, s, 3-OCH₃), 3.70-3.80 (1H, m H-3″), 3.70-3.80 (1H, m H-4″), 3.73 (3H, s, 4-OCH₃), 3.46 (1H, dd, J=11.3, 10.1 Hz, H-5″b), 2.09 (3H, s, OAc).

3″-Acetyl-7-O-β-D-xylosyldiphyllin (27ab)

HR-EIMS: m/z [M+H]⁺ 555.1439 (calcd. 555.1503). ¹H NMR (400 MHz, acetone-d₆) δ 8.08 (1H, d, J=3.3 Hz, H-2), 7.05 (1H, br s, H-5), 6.99-6.93 (1H, m, H-5′), 6.89 (1H, m, H-2′), 6.79 (1H dd, J=1.8, 6.0 Hz, H-6′), 6.13-6.07 (2H, m, —OCH₂O—), 5.53 (1H, d, J=15.0 Hz, H-1″), 5.41 (1H d, J=15.1 Hz, H-3″), 5.11-5.01 (2H, m, br s, H-9), 4.04 (1H, m, H-5″), 3.94 (3H, s, 3-OCH₃), 3.91-3.82 (1H, m, H-2″), 3.69 (3H, d, J=6.5 Hz, 4-OCH₃), 3.47-3.35 (1H, m, H-5″), 2.10 (3H, s, OAc). ¹³C NMR (100 MHz, acetone-d₆) δ 171.0 (OAc), 169.8 (C-9′), 153.0 (C-3), 151.5 (C-4), 148.4 (C-3′), 148.3 (C-4′), 145.8 (C-7), 136.7 (C-7′), 131.4 (C-1), 129.7 (C-6), 128.1 (C-1′), 124.6 (C-6′), 120.0 (C-8), 111.8 (C-8′), 111.7 (C-2′), 108.7 (C-5′), 106.7 (C-5), 106.6 (C-1″), 102.4 (C-2), 102.2 (—OCH₂O—), 78.8 (C-3″), 73.2 (C-2″), 69.1 (C-4″), 67.8 (C-9), 66.8 (C-5″), 56.4 (3-OCH₃), 55.8 (4-OCH₃), 21.2 (—OAc).

3″,4″-Diacetyl-7-O-β-D-xylosyldiphyllin (27ad)

HR-EIMS: m/z [M+H]⁺ 597.1533 (calcd. 597.1608). ¹H NMR (400 MHz, Acetone-d₆) δ 7.53 (1H, d, J=0.8 Hz, H-2), 7.02 (1H, d, J=2.1 Hz, H-5), 6.91 (1H, d, J=7.9 Hz, H-5′), 6.79 (1H, dd, J=3.3, 1.4 Hz, H-2′), 6.74 (1H, ddd, J=7.9, 2.7, 1.7 Hz, H-6′), 6.03 (2H, dt, J=4.8, 0.9 Hz, —OCH₂O—), 5.59-5.45 (2H, m, H-9), 5.42 (1H, d, J=7.6 Hz, H-1″), 5.23 (1H, dd, J=9.8, 7.6 Hz, H-2″), 5.14 (1H, br t, J=9.3 Hz, H-3″), 4.06 (1H, dd, J=11.5, 5.6 Hz, H-5″a), 3.95 (3H, s, 3-O-CH₃), 3.94 (1H, br td, J=10.3, 5.3 Hz, H-4″), 3.66 (3H, s, 4-OCH₃), 3.51 (1H, br t, J=10.8 Hz, H-5″b), 2.03 (3H, s, —OAc), 1.98 (3H, s, —OAc).

2″,4″-Diacetyl-7-O-β-D-xylosyldiphyllin (27ae)

HR-EIMS: m/z [M+H]⁺ 597.1509 (calcd. 597.1608). ¹H NMR (400 MHz, Acetone-d₆) δ 7.62 (1H, d, J=1.8 Hz, H-2), 7.03 (1H, d, J=2.1 Hz, H-5), 6.92 (1H, dd, J=7.9, 1.1 Hz, H-5′), 6.80 (1H, d, J=1.6 Hz, H-2′), 6.77-6.71 (1H, m, H-6′), 6.07-6.00 (2H, m, —OCH₂O—), 5.54-5.40 (2H, m, H-9), 5.43 (1H, d, J=7.1 Hz, H-1″), 5.27 (1H, dd, J=8.8, 7.2 Hz, H-2″), 4.90 (1H, br td, J=9.0, 5.2 Hz, H-4″), 4.15 (1H, dd, J=11.6, 5.1 Hz, H-5″a), 4.04-3.99 (1H, br t, J=8.7 Hz, H-3″), 3.98 (3H, s, 3-OCH₃), 3.67 (3H, s, 4-OCH₃), 3.50 (1H, dd, J=11.6, 9.5 Hz, H-5″b), 2.10 (3H, s, —OAc), 2.03 (3H, s, —OAc).

2″,3″-Diacetyl-7-O-β-D-xylosyldiphyllin (27af)

HR-EIMS: m/z [M+H]) 597.1505 (calcd. 597.1608). ¹H NMR (400 MHz, Acetone-d₆) δ 8.10 (1H, d, J=1.5 Hz, H-2), 7.10 (1H, d, J=4.5 Hz, H-5), 6.98 (1H, dd, J=7.9, 1.2 Hz, H-5′), 6.88 (1H, br d, J=1.3 Hz, H-2′), 6.81 (1H, dd, J=7.9, 1.7 Hz, H-6′), 6.10 (2H, ddd, J=4.8, 1.6, 1.1 Hz, —OCH₂O—), 5.58-5.41 (2H, m, H-9), 5.25 (1H, br t, J=9.5 Hz, H-3″), 5.13 (1H, d, J=7.6 Hz, H-1″), 5.00 (1H, br td, J=9.6, 5.5 Hz, H-4″), 4.16 (1H, dd, J=11.5, 5.5 Hz, H-5″a), 4.02 (1H, d, J=9.6, 7.7 Hz, H-2″), 3.97 (3H, s, 3-OCH₃), 3.72 (3H, s, 4-OCH₃), 3.54 (1H, dd, J=11.5, 9.9 Hz, H-5″b), 2.06 (3H, s, —OAc), 1.98 (3H, s, —OAc).

4″-Acetyl-7-O-β-D-patentiflorin A (27ba)

HR-EIMS: m/z [M+H]⁺ 569.1612 (calcd. 569.1659). ¹H NMR (400 MHz, CDCl₃) δ 7.58 (1H, d, J=1.5 Hz, H-2), 7.07 (1H, s, H-5), 6.96 (1H, d, J=7.8 Hz, H-5′), 6.86-6.81 (1H, m, H-2′), 6.81-6.77 (1H, m, H-6′), 6.12-6.01 (2H, n, —OCH₂O—), 5.51-5.37 (2H, m, H-9), 5.272 (1H, dd, J=9.8, 7.9 Hz, H-2″), 5.06 (1H, d, J=7.8 Hz, H-1″), 4.07 (3H, s, 3-OCH₃), 3.81 (3H, s, 4-OCH₃), 3.67 (1H, t, J=9.2 Hz, H-3″), 3.44 (1H, m, H-4″), 3.43 (1H, m, H-5″), 2.20 (3H, s, OAc), 1.39 (3H, d, J=4.0 Hz, H-6″).

3″-Acetyl-7-O-β-D-patentiflorin A (27bb)

HR-EIMS: m/z [M+H]⁺ 569.1602 (calcd. 569.1659). ¹H NMR (400 MHz, CDCl₃) δ 7.93 (1H, s, H-2), 7.02 (1H, d, J=3.6 Hz, H-5), 6.91 (1H, dd, J=9.2, 8.0 Hz, H-5′), 6.82-6.67 (2H, m, H-2′,6′), 6.11-5.99 (2H, m, —OCH₂O—), 5.55-5.34 (2H, m, H-9), 4.86 (1H, t, J=9.2 Hz, H-3″), 4.82 (1H, d, J=7.8 Hz, H-1″), 3.99 (3H, s, 3-OCH₃), 3.93 (1H, dd, J=9.5, 7.8 Hz, H-2″), 3.77 (3H, d, J=2.3 Hz, 4-OCH₃), 3.42 (1H, t, J=9.2 Hz, H-4″), 3.37-3.28 (1H, m, H-5″), 2.20 (3H, s, —OAc), 1.34 (3H, dd, J=6.0, 1.2 Hz, H-6″). ¹³C NMR (100 MHz, CDCl₃) δ 173.5 (OAc), 170.3 (C-9′), 152.1 (C-3), 150.3 (C-4), 147.6 (C-3′), 147.6 (C-4′), 144.5 (C-7), 136.8 (C-7′), 131.2 (C-8), 130.8 (C-6), 128.3 (C-1′), 127.4 (C-1), 123.7 (C-6′), 119.1 (C-8′), 110.8 (C-2′), 108.3 (C-5′), 106.2 (C-1″), 104.7 (C-5), 101.4 (C-2), 101.1 (—OCH₂O—), 79.4 (C-3″), 73.9 (C-4″), 73.0 (C-2″), 72.4 (C-5″), 67.7 (C-9), 56.4 (3-OCH₃), 55.9 (4-OCH₃), 21.20 (C-6″), 17.7 (OAc).

2″-Acetyl-7-O-β-D-patentiflorin A (27bc)

HR-EIMS: m/z [M+H]⁺ 569.1596 (calcd. 569.1659). ¹H NMR (400 MHz, CDCl₃) δ 7.96 (1H, s, H-2), 7.09 (1H, s, H-5), 6.96 (1H, d, J=7.9 Hz, H-5′), 6.84 (1H, dd, J=3.1, 1.4 Hz, H-2′), 6.83-6.78 (1H, m, H-6′), 6.12-6.03 (2H, m, —OCH₂O—), 5.54-5.39 (2H, m, H-9), 4.83 (1H, dt, J=8.7, 1.4 Hz, H-4″), 4.74 (1H, t, J=9.5 Hz, H-1″), 4.04 (3H, s, 3-OCH₃), 3.92 (1H, dd, J=9.3, 7.9 Hz, H-2″), 3.81 (3H, s, 4-OCH₃), 3.67 (1H, t, J=9.3 Hz, H-3″), 3.51-3.44 (1H, m, H-5″), 2.15 (3H, s, OAc), 1.27 (3H, d, J=1.5 Hz, H-6″).

3″,4″-Diacetyl-7-O-β-D-patentiflorin A (27bd)

HR-EIMS: m/z [M+H]⁺ 611.1705 (calcd. 609.1972). ¹H NMR (400 MHz, CDCl₃) δ 7.53 (1H, d, J=1.5 Hz, H-2), 7.07 (1H, s, H-5), 6.98-6.94 (1H, m, H-5′), 6.84-6.80 (1H, m, H-2′), 6.81-6.76 (1H, m, H-6′), 6.11-6.02 (2H, m, —OCH₂O—), 5.50-5.43 (2H, m, H-9), 5.42-5.36 (1H, m, H-2″), 5.12 (1H, d, J=7.9 Hz, H-1″), 5.06 (1H, t, J=9.8 Hz, H-3″), 4.06 (3H, s, 3-OCH₃), 3.80 (3H, s, 4-OCH₃), 3.54 (1H, t, J=9.1 Hz, H-4″), 3.48 (1H, ddd, J=8.8, 5.6, 1.1 Hz, H-5″), 2.14 (3H, s, —OAc), 2.11 (3H, s, —OAc), 1.40 (3H, dd, J=5.8, 1.2 Hz, H-6″).

2″,4″-Diacetyl-7-O-β-D-patentiflorin A (27be)

HR-EIMS: m/z [M+H]⁺ 611.1721 (calcd. 609.1972). ¹H NMR (400 MHz, CDCl₃) δ 7.58 (1H, d, J=1.7 Hz, H-2), 7.07 (1H, s, H-5), 6.96 (1H, d, J=7.9 Hz, H-5′), 6.83 (1H, dd, J=3.0, 1.5 Hz, H-2′), 6.80 (1H, ddd, J=7.9, 3.0, 1.7 Hz, H-6′), 6.12-6.03 (2H, m, —OCH₂O—), 5.50-5.38 (2H, m, H-9), 5.38-5.29 (1H, m, H-2″), 5.05 (1H, d, J=7.9 Hz, H-1″), 4.84 (1H, t, J=9.5 Hz, H-4″), 4.07 (3H, s, 3-OCH₃), 3.81 (3H, s, 4-OCH₃), 3.77 (1H, t, J=9.6 Hz, H-3″), 3.60-3.50 (1H, m, H-5″), 2.20 (3H, s, —OAc), 2.15 (3H, s, —OAc), 1.29 (3H, dd, J=6.2, 1.4 Hz, H-6″).

2″,3″-Diacetyl-7-O-β-D-patentiflorin A (27bf)

HR-EIMS: m/z [M+H]⁺ 611.1699 (calcd. 609.1972). ¹H NMR (400 MHz, Chloroform-d) δ 7.93 (1H, s, H-2), 7.08 (1H, s, H-5), 6.97-6.93 (1H, m, H-5′), 6.86-6.81 (1H, m, H-2'), 6.80-6.76 (1H, m, H-6'), 6.11-6.02 (2H, m, —OCH$_2$O—), 5.53-5.37 (2H, m, H-9), 5.08 (1H, t, J=9.5 Hz, H-3'), 4.92 (1H, t, J=9.6 Hz, H-4"), 4.88 (1H, d, J=7.8 Hz, H-1"), 4.04 (1H, dd, J=9.3, 7.9 Hz, H-2"), 4.02 (3H, s, 3-OCH$_3$), 3.80 (3H, s, 4-OCH$_3$), 3.55-3.46 (1H, m, H-5"), 2.15 (3H, s, —OAc), 2.06 (3H, s, —OAc), 1.24 (3H, d, J=5.6 Hz, H-6").

4"-O-allyl oxycarbonyl-3"-acetyl-7-O-β-D-xylosyldiphyllin (28ab1)

HR-EIMS: m/z [M+H]$^+$ 639.1514 (calcd. 639.1714). $^1$H NMR (400 MHz, Acetone-d$_6$) δ 7.66 (1H, s, H-2), 7.10 (1H, d, J=3.3 Hz, H-5), 6.98 (1H, dd, J=7.9, 1.8 Hz, H-5'), 6.92-6.77 (2H, m, H-2', H-6'), 6.10 (2H, dt, J=4.8, 1.3 Hz, —OCH$_2$O—), 5.96 (1H, ddt, J=16.2, 10.9, 5.6 Hz, O-Alloc), 5.63-5.46 (2H, m, H-9), 5.44 (1H, d, J=7.6 Hz, H-1"), 5.34 (1H, dq, J=17.2, 1.6 Hz, O-Alloc), 5.24 (1H, bt t, J=9.4 Hz, H-3") 5.29-5.20 (1H, m, O-Alloc), 5.08 (1H, dd, J=9.8, 7.8 Hz, H-2"), 4.85 (1H, dd, J=5.1, 2.1 Hz, O-Alloc), 4.71 (1H, m, O-Alloc), 4.10 (1H, dd, J=11.2, 5.5 Hz, H-5"a), 4.02 (3H, s, 3-OCH$_3$), 3.99 (1H, br td, J=10.2, 5.5 Hz, H-4"), 3.72 (3H, s, 4-OCH$_3$), 3.51 (1H, br t, J=10.9 Hz, H-5"b), 2.08 (3H, s, OAc).

2"-O-allyl oxycarbonyl-3"-acetyl-7-O-β-D-xylosyldiphyllin (28ab2)

HR-EIMS: m/z [M+H]$^+$ 639.1514 (calcd. 639.1714). $^1$H NMR (400 MHz, Acetone-d$_6$) δ 8.09 (1H, s, H-2), 7.10 (1H, dd, J=4.1, 1.6 Hz, H-5), 6.98 (1H, dd, J=7.9, 1.6 Hz, H-5'), 6.91-6.85 (1H, m, H-2'), 6.85-6.78 (1H, m, H-6'), 6.10 (2H, dt, J=5.2, 1.3 Hz, —OCH$_2$O—), 5.93 (1H, ddt, J=16.2, 10.8, 5.6 Hz, O-Alloc), 5.76 (1H, dt, J=5.0, 2.4 Hz, O-Alloc), 5.60-5.41 (2H, m, H-9), 5.29 (1H, bt t, J=9.5 Hz, H-3"), 5.25-5.20 (1H, m, O-Alloc), 5.14 (1H, d, J=7.6 Hz, H-1"), 4.88 (1H, br td, J=9.5, 5.5 Hz, H-4"), 4.68-4.54 (2H, m, O-Alloc), 4.26 (1H, dd, J=11.6, 5.5 Hz, H-5"a), 4.03 (1H, dd, J=9.5, 7.6 Hz, H-2"), 3.96 (3H, s, 3-OCH$_3$), 3.72 (3H, s, 4-OCH$_3$), 3.61 (1H, br t, J=11.2 Hz, H-5"b), 2.06 (3H, s, OAc).

2",4"-O-diallyl oxycarbonyl-3"-acetyl-7-O-β-D-xylosyldiphyllin (28ab3)

HR-EIMS: m/z [M+H]$^+$ 723.1703 (calcd. 723.1925). $^1$H NMR (400 MHz, CDCl$_3$) δ 7.55 (1H, s, H-2), 7.09 (1H, s, H-5), 6.96 (1H, dd, J=8.2, 1.0 Hz, H-2'), 6.87-6.77 (2H, m, H-5',6'), 6.12-6.04 (2H, m, —OCH$_2$O—), 5.90 (2H, m, H-9), 5.52-5.20 (8H, m, O-alloc), 5.05 (1H, d, J=7.7 Hz, H-1"), 5.04-4.95 (1H, m, H-3"), 4.75-4.59 (4H, m, O-alloc), 4.24 (1H, dd, J=11.8, 5.5 Hz, H-5"), 4.06 (3H, s, 3-OCH$_3$), 3.81 (3H, s, 4-OCH$_3$), 3.36 (1H, dd, J=11.7, 10.1 Hz, H-5"), 2.11 (3H, s, OAc). $^{13}$C NMR (100 MHz, acetone-d$_6$) δ 170.2 (OAc), 169.6 (C-9'), 155.3 (O-alloc), 155.1 (O-alloc), 153.2 (C-3), 151.5 (C-4), 148.4 (C-3'), 148.3 (C-4'), 144.7 (C-7), 132.9 (O-alloc), 132.8 (O-alloc), 136.7 (C-7'), 131.4 (C-1), 129.6 (C-6), 127.2 (C-1'), 124.6 (C-6'), 120.1 (C-8), 119.2 (O-alloc), 118.9 (O-alloc), 111.7 (C-2'), 111.7 (C-8'), 108.7 (C-1", C-5'), 106.9 (C-5), 102.5 (C-2), 102.2 (—OCH$_2$O—), 79.1 (C-3"), 75.7 (C-2"), 72.1 (C-4"), 69.6 (O-alloc), 69.3 (Alloc), 67.5 (C-9), 63.4 (C-5"), 56.5 (3-OCH$_3$), 55.8 (4-OCH$_3$), 21.2 (O-alloc).

2",4"-O-diallyl oxycarbonyl-3"-acetyl-7-O-β-D-patentiflorin A (28bb3)

HR-EIMS: m/z [M+H]$^+$ 737.1950 (calcd. 737.2082). $^1$H NMR (400 MHz, CDCl$_3$) δ 7.56 (1H, s, H-2), 7.08 (1H, s, H-5), 7.00-6.91 (1H, m, H-5'), 6.86-6.73 (2H, m, H-2',6'), 6.08 (1H, br s, OCH$_2$O) 6.04 (I H, br s, —OCH$_2$O—), 5.90 (2H, m, H-9), 5.53-5.20 (9H, m, O-alloc, 2",4"), 5.08 (1H, dd, J=8.5, 4.4 Hz, H-1"), 4.78 (1H, td, J=9.4, 4.5 Hz, H-3"), 4.65 (4H, dt, J=22.0, 5.1 Hz, O-alloc), 4.04 (3H, s, 3-OCH$_3$), 3.79 (3H, s, 4-OCH$_3$), 3.58 (1H, dq, J=10.5, 5.0 Hz, H-5"), 2.06 (3H, s, OAc), 1.27 (3H, d, J=25.1 Hz, H-6"). $^{13}$C NMR (100 MHz, CDCl$_3$) δ 170.1 (OAc), 169.6 (C-9'), 154.1 (O-alloc), 152.2 (C-3), 150.3 (C-4), 147.6 (C-3'), 147.5 (C-4'), 143.3 (C-7), 137.0 (C-7'), 131.5 (C-6), 131.2 (C-8), 131.0 (C-1), 130.8 (O-alloc), 128.1 (C-1'), 123.6 (C-6'), 119.9 (O-alloc), 119.4 (O-alloc), 118.9 (C-8'), 110.6 (C-2'), 108.2 (C-5'), 106.3 (C-1"), 101.5 (C-5), 101.3 (C-2), 100.0 (—OCH$_2$O—), 75.9 (C-3"), 72.3 (C-2"), 70.4 (C-4"), 69.4 (O-alloc), 69.1 (O-alloc), 68.5 (C-5"), 67.2 (C-9), 56.6 (3-OCH$_3$), 55.9 (4-OCH$_3$), 20.7 (C-6"), 17.4 (OAc).

2",4"-O-diallyl oxycarbonyl-7-O-β-D-xylosyldiphyllin (29a, yield 92%)

HR-EIMS: m/z [M+H]$^+$ 681.1696 (calcd. 681.1819). H NMR (400 MHz, acetone-d$_6$) δ 7.58 (1H, s, H-2), 6.99 (1H, s, H-5), 6.86 (1H, m, H-5'), 6.72 (2H, m, H-2',6'), 5.98 (2H, m, H-9), 5.85 (9H, m, O-alloc, —OCH$_2$O—, H-1", H-2", H-4"), 4.73 (1H, d, J=7.7 Hz, H-5"), 4.56 (4H, m, O-alloc), 4.12 (1H, m, H-3"), 3.92 (3H, s, 3-OCH$_3$), 3.61 (3H, s, 4-OCH$_3$), 3.42 (1H, m, H-5"). $^{13}$C NMR (100 MHz, acetone-d$_6$) δ 169.6 (C-9'), 155.4 (O-alloc), 155.2 (O-alloc), 153.2 (C-3), 151.6 (C-4), 148.4 (C-3'), 148.3 (C-4'), 144.7 (C-7), 138.1 (C-7'), 132.9 (O-alloc), 132.8 (O-alloc), 131.4 (C-1), 129.1 (C-6), 127.2 (C-1'), 124.6 (C-8), 124.5 (C-6'), 120.1 (O-alloc), 119.2 (O-alloc), 118.9 (C-8'), 111.7 (C-2'), 108.7 (C-1", C-5'), 106.9 (C-5), 102.6 (C-2), 102.2 (—OCH$_2$O—), 78.7 (C-3"), 75.7 (C-2"), 72.1 (C-4"), 69.6 (O-alloc), 69.3 (O-alloc), 67.5 (C-9), 63.4 (C-5"), 56.5 (3-OCH$_3$), 55.8 (4-OCH$_3$).

2",4"-O-diallyl oxycarbonyl-7-O-β-D-patentiflorin A (29b, yield 83%)

HR-EIMS: m/z [M+H]$^+$ 695.1911 (calcd. 695.1976). $^1$H NMR (400 MHz, CDCl$_3$) δ 7.62 (11H, s, H-2), 7.09 (1H, s, H-5), 6.95 (1H, dd, J=8.2, 1.4 Hz, H-5'), 6.84-6.77 (2H, m, H-2',6'), 6.12-6.01 (2H, m, —OCH$_2$O—), 5.93 (2H, m, O-alloc), 5.50-5.25 (6H, m, H-9, O-alloc), 5.15 (1H, dd, J=9.7, 8.1 Hz, H-1"), 4.99 (1H, d, J=8.1 Hz, H-2"), 4.74-4.63 (5H, m, H-4", O-alloc), 4.06 (3H, s, 3-OCH$_3$), 3.88 (1H, t, J=9.5 Hz, H-3"), 3.80 (31H, s, 4-OCH$_3$), 3.49 (1H, ddt, J=12.7, 6.6, 4.9 Hz, H-5"), 1.31 (3H, dd, J=6.1, 1.7 Hz, H-6"). $^{13}$C NMR (100 MHz, CDCl$_3$) δ 169.8 (C-9'), 155.0 (O-alloc), 154.9 (O-alloc), 152.3 (C-3), 150.4 (C-4), 147.7 (C-3'), 147.7 (C-4'), 143.7 (C-7), 137.0 (C-7'), 131.1 (C-8), 130.9 (C-1), 128.3 (C-6), 126.9 (C-1'), 123.7 (C-6'), 120.2 (O-alloc), 119.7 (O-alloc), 119.3 (C-8'), 110.8 (C-2'), 108.3 (C-5'), 106.4 (C-1"), 101.6 (C-5), 101.4 (C-2), 100.2 (—OCH$_2$O—), 79.3 (C-3"), 78.2 (C-1"), 73.5 (C-4"), 70.5 (C-5"), 69.7 (O-alloc), 69.4 (O-alloc), 67.3 (C-9), 56.7 (3-OCH$_3$), 56.0 (4-OCH$_3$), 17.5 (C-6").

2",4"-O-diallyl oxycarbonyl-3"-O-dimethylcarbamyl-7-O-β-D-xylosyldiphyllin (30a, yield 99%)

HR-EIMS: m/z [M+H]$^+$ 752.2133 (calcd. 752.2191). $^1$H NMR (400 MHz, CDCl$_3$) δ 7.56 (1H, s, H-2), 7.07 (1H, d, J=1.8 Hz, H-5), 6.93 (1H, dd, J=8.1, 1.1 Hz, H-5'), 6.83-6.74 (2H, m, H-2', H-6'), 6.05 (2H, dt, J=17.9, 1.5 Hz, —OCH$_2$O—), 5.89 (2H, ddtd, J=17.6, 10.4, 5.8, 1.5 Hz, O-Alloc), 5.52-5.39 (2H, m, H-9), 5.35 (1H, m, H-1"), 5.31 (1H, br t, J=1.6 Hz, H-3"), 5.27-5.23 (4H, m, O-Alloc), 5.10-5.06 (1H, m, H-2"), 5.02 (1H, tdd, J=9.7, 4.8, 2.1 Hz, H-4"), 4.73-4.59 (4H, m, O-Alloc), 4.20 (1H, ddd, J=11.8, 5.4, 1.1 Hz, H-5"a), 4.04 (3H, s, 3-OCH$_3$), 3.78 (3H, s, 4-OCH$_3$), 3.40 (1H, ddd, J=11.9, 9.9, 0.9 Hz, H-5"b), 2.91 [6H, s, OC(O)N(CH$_3$)$_2$].

2",4"-O-diallyl oxycarbonyl-3"-O-(3,5-dinitrobenzoyl)-7-O-β-D-xylosyldiphyllin (30b, yield 90%)

HR-EIMS: m/z [M+H]$^+$ 889.1763 (calcd. 889.1940). $^1$H NMR (400 MHz, CDCl$_3$) δ 9.26 (1H, t, J=2.1 Hz, 3,5-dinitrobenzoyl), 9.15 (2H, d, J=2.1 Hz, 3,5-dinitrobenzoyl), 7.59 (1H, s, H-2), 7.09 (1H, d, J=1.2 Hz, H-5), 6.94 (1H, dd, J=7.9, 3.8 Hz, H-5'), 6.81 (1H, dd, J=9.7, 1.6 Hz, H-2'), 6.78-6.72 (1H, m, H-6'), 6.10-6.01 (2H, m, —OCH$_2$O—), 5.76 (2H, ddt, J=17.2, 16.1, 5.7 Hz, O-Alloc), 5.61 (1H, t, J=9.4 Hz, O-Alloc), 5.54-5.48 (1H, m, O-Alloc), 5.48-5.43 (2H, m, H-9), 5.24 (1H, d, J=8.2 Hz, H-1"), 5.20 (2H, ddd, J=8.0, 2.8, 1.4 Hz, O-Alloc), 5.14 (1H, dd, J=6.4, 1.2 Hz, H-2"), 5.11 (1H, dd, J=6.5, 1.2 Hz, H-3"), 5.02 (1H, t, J=9.5 Hz, H-4"), 4.55 (4H, ddt, J=20.0, 5.7, 1.4 Hz, O-Alloc), 4.06 (3H, s, 3-OCH$_3$), 3.79 (3H, s, 4-OCH$_3$), 3.73-3.67 (1H, m, H-5"), 1.37 (3H, dd, J=6.1, 1.7 Hz, H-6").

3"-O-dimethylcarbamyl-7-O-β-D-xylosyldiphyllin (31a, yield 69% of two steps)

HR-EIMS: m/z [M+H]$^+$ 584.1723 (calcd. 584.1768). $^1$H NMR (400 MHz, acetone-d$_6$) δ 8.15 (1H, d, J=1.6 Hz, H-2), 7.10 (1H, d, J=4.4 Hz, H-5), 6.98 (1H, dd, J=7.9, 1.5 Hz, H-5'), 6.88 (1H, dd, J=15.7, 1.6 Hz, H-2'), 6.83 (1H, td, J=7.9, 1.7 Hz, H-6'), 6.10 (2H, dt, J=4.8, 1.3 Hz, —OCH$_2$O—), 5.56-5.38 (3H, m, H-9, H-1"), 5.02 (1H, d, J=7.6 Hz, H-3"), 4.79-4.67 (2H, m, OH-2", OH-4"), 4.05 (1H, ddd, J=11.5, 5.5, 1.9 Hz, H-2"), 3.97 (3H, s, 3-OCH$_3$), 3.89 (2H, m, H-4", H-5"), 3.73 (3H, d, J=1.4 Hz, 4-OCH$_3$), 3.39 (1H, ddd, J=11.4, 10.0, 1.1 Hz, H-5"), 3.02 (3H, s, OCON(CH$_3$)$_2$), 2.93 (3H, s, OCON(CH$_3$)$_2$). $^{13}$C NMR (100 MHz, acetone-d$_6$) δ 169.8 (C-9'), 158.3 (OCON(CH$_3$)$_2$), 153.0 (C-3), 151.5 (C-4), 148.4 (C-3'), 148.3 (C-4'), 145.9 (C-7), 136.7 (C-7'), 131.5 (C-1), 131.4 (C-6), 129.7 (C-1'), 128.1 (C-8), 124.6 (C-6'), 120.0 (C-8'), 111.8 (C-2'), 111.7 (C-5'), 108.7 (C-1"), 106.8 (C-2), 102.4 (C-5), 102.2 (—OCH$_2$O—), 81.5 (C-3"), 73.5 (C-2"), 69.3 (C-4"), 67.8 (C-9), 66.7 (C-5"), 56.3 (3-OCH$_3$), 55.8 (4-OCH$_3$), 36.7 (OCON(CH$_3$)$_2$), 36.2 (OCON(CH$_3$)$_2$).

3"-O-(3,5-dinitrobenzoyl)-7-O-β-D-patentiflorin A (31b, yield 77% of two steps)

HR-EIMS: m/z [M+H]$^+$ 721.1337 (calcd. 721.1517). $^1$H NMR (400 MHz, acetone-d$_6$) δ 9.17 (3H, m, 3,5-Dinitrobenzoyl), 8.11 (1H, dt, J=6.9, 3.1 Hz, H-2), 7.13-7.05 (1H, m, H-5), 6.99 (1H, dd, J=7.7, 1.7 Hz, H-5'), 6.89 (1H, dd, J=11.2, 1.5 Hz, H-2'), 6.83 (1H, ddd, J=9.4, 5.5, 1.6 Hz, H-6'), 6.16-6.08 (2H, m, —OCH$_2$O—), 5.75-5.41 (4H, m, H-9, OH-2", OH-4"), 5.18 (1H, d, J=7.8 Hz, H-1"), 4.95 (1H, d, J=4.9 Hz, H-2"), 4.21 (1H, ddd, J=9.7, 7.8, 5.3 Hz, H-4"), 3.95 (3H, s, 3-OCH$_3$), 3.71 (5H, m, 4-OCH$_3$, H-3", H-5"), 1.41 (3H, d, J=5.1 Hz, H-6"). $^{13}$C NMR (100 MHz, acetone-d$_6$) δ 169.8 (C-9'), 163.4 (3,5-dinitrobenzoyl), 152.9 (C-3), 151.4 (3,5-dinitrobenzoyl), 151.3 (3,5-dinitrobenzoyl), 149.7 (C-4), 148.3 (C-3'), 148.3 (C-4'), 145.8 (C-7), 136.7 (C-7'), 134.8 (3,5-dinitrobenzoyl), 131.4 (C-1), 130.1 (3,5-dinitrobenzoyl), 129.6 (C-8), 128.1 (C-6), 124.6 (C-1'), 123.3 (C-6'), 120.0 (3,5-dinitrobenzoyl), 111.7 (C-8'), 111.7 (C-2'), 108.7 (C-5'), 106.7 (C-2), 105.5 (C-1"), 102.3 (C-5), 102.2 (—OCH$_2$O—), 81.4 (C-3"), 74.1 (C-2"), 73.4 (C-4"), 73.0 (C-5"), 67.8 (C-9), 56.3 (3-OCH$_3$), 55.8 (4-OCH$_3$), 18.1 (C-6").

3"-O-butyryl-7-O-β-D-patentiflorin A (31c, yield 77% of two steps)

HR-EIMS: m/z [M+H]$^+$ 597.1968 (calcd. 597.1972). $^1$H NMR (400 MHz, acetone-d$_6$) δ 8.12 (1H, s, H-2), 7.08 (1H, t, J=4.7 Hz, H-5), 6.98 (1H, ddd, J=8.0, 3.6, 1.3 Hz, H-5'), 6.93-6.75 (2H, m, H-2', H-6'), 6.14-6.05 (2H, n, H-9), 5.64-5.39 (2H, m, —OCH$_2$O—), 5.31 (1H, ddt, J=6.2, 4.6, 1.8 Hz, H-1"), 5.13-5.02 (2H, m, OH), 4.52 (1H, d, J=6.0 Hz, H-3"), 3.96 (3H, d, J=2.9 Hz, 3-OCH$_3$), 3.91-3.82 (1H, m, H-2"), 3.71 (3H, dd, J=5.5, 3.1 Hz, 4-OCH$_3$), 3.55 (1H, dd, J=9.7, 5.9 Hz, H-4"), 3.37 (1H, ddd, J=9.6, 5.6, 3.8 Hz, H-5"), 2.38 (2H, td, J=7.4, 1.6 Hz, O-butyryl), 1.66 (2H, dd, J=7.5, 1.6 Hz, O-butyryl), 1.35 (3H, dd, J=5.9, 1.8 Hz, O-butyryl), 0.97 (3H, td, J=7.4, 1.7 Hz, H-6"). $^{13}$C NMR (100 MHz, acetone-d$_6$) δ 173.6 (O-butyryl), 169.8 (C-9'), 152.9 (C-3), 151.4 (C-4), 148.3 (C-3'), 148.3 (C-4'), 145.9 (C-7), 136.6 (C-7'), 131.3 (C-6), 129.7 (C-1'), 128.2 (C-8), 124.6 (C-6'), 111.8 (C-8'), 111.7 (C-2'), 108.6 (C-5'), 106.6 (C-2), 105.8 (C-1"), 102.4 (C-5), 102.2 (—OCH$_2$O—), 78.3 (C-3"), 74.5 (C-2"), 73.7 (C-4"), 73.1 (C-5"), 67.9 (C-9), 56.3 (3-OCH$_3$), 55.7 (4-OCH$_3$), 36.7 (O-butyryl), 19.0 (C-6"), 18.1 (O-butyryl), 13.9 (O-butyryl).

3"-O-benzoyl-7-O-β-D-patentiflorin A (31d, yield 72% of two steps)

HR-EIMS: m/z [M+H]$^+$ 631.1810 (calcd. 631.1816). $^1$H NMR (400 MHz, acetone-d$_6$) δ 8.13 (1H, dt, J=6.2, 3.0 Hz, H-2), 8.11-8.04 (2H, m, O-Benzoyl), 8.01 (1H, dd, J=8.3, 2.7 Hz, O-Benzoyl), 7.51 (2H, d, J=6.1 Hz, O-Benzoyl), 7.05 (1H, dq, J=10.2, 3.4 Hz, H-5), 6.95 (1H, dq, J=6.9, 3.8 Hz, H-5'), 6.90-6.73 (2H, m, H-2', H-6'), 6.07 (2H, q, J=2.9, 2.2 Hz, —OCH$_2$O—), 5.62-5.28 (4H, m, H-9, OH), 5.12 (1H, dd, J=7.8, 2.1 Hz, H-1"), 4.07 (1H, q, J=9.1, 6.1 Hz, H-3"), 3.91 (3H, q, J=2.9, 2.5 Hz, 3-OCH$_3$), 3.67 (3H, dt, J=7.1, 3.5 Hz, 4-OCH$_3$), 3.64-3.53 (3H, m, H-2",4" and 5"), 1.42-1.32 (3H, m, H-6"). $^{13}$C NMR (100 MHz, acetone-d$_6$) δ 169.9 (C-9'), 166.6 (O-benzoyl), 152.9 (C-3), 151.4 (C-4), 148.3 (C-3'), 148.3 (C-4'), 146.0 (C-7), 136.6 (C-7'), 133.8 (O-benzoyl), 133.7 (O-benzoyl), 131.6 (C-1), 131.5 (C-6), 131.3 (C-8), 130.5 (O-benzoyl), 130.4 (O-benzoyl), 129.3 (O-benzoyl), 129.3 (O-benzoyl), 128.2 (C-1'), 124.6 (C-6'), 111.8 (C-8'), 111.7 (C-2'), 108.7 (C-5'), 106.6 (C-2), 105.8 (C-1"), 102.4 (C-5), 102.2 (—OCH$_2$O—), 79.5 (C-3"), 74.5 (C-2"), 73.8 (C-4"), 73.1 (C-5"), 67.9 (C-9), 56.3 (3-OCH$_3$), 55.7 (4-OCH$_3$), 18.2 (C-6").

3"-O-p-dimethylaminobenzoyl-7-O-β-D-patentiflorin A (31e, yield 51% of two steps)

HR-EIMS: m/z [M+H]$^+$ 674.2099 (calcd. 674.2238). $^1$H NMR (400 MHz, acetone-d$_6$) δ 8.21 (1H, d, J=1.7 Hz, H-2), 7.95-7.90 (2H, m, O-p-dimethylaminobenzoyl), 7.11 (1H, d, J=2.9 Hz, H-5), 7.01-6.96 (1H, m, H-5'), 6.93-6.81 (2H, m, H-2', 6'), 6.79-6.75 (m, 2H, O-p-dimethylaminobenzoyl), 6.10 (2H, ddd, J=4.4, 1.7, 1.1 Hz, —OCH$_2$O—), 5.60 (1H, d, J=15.0 Hz, H-1"), 5.50-5.42 (2H, m, H-9), 5.24 (1H, t, J=9.3 Hz, OH), 5.11 (1H, d, J=7.8 Hz, OH), 4.67 (1H, dd, J=5.7, 1.0 Hz, H-3"), 4.07-3.99 (1H, m, H-2"), 3.96 (3H, s, 3-OCH$_3$), 3.73 (3H, d, J=1.2 Hz, 4-OCH$_3$), 3.65-3.57 (1H, m, H-5"), 3.52 (1H, td, J=9.2, 5.5 Hz, H-4"), 3.07 (6H, s, O-p-dimethylaminobenzoyl), 1.39 (3H, dd, J=6.0, 1.5 Hz, H-6"). $^{13}$C NMR (100 MHz, acetone-d$_6$) δ 169.9 (C-9'), 167.4 (O-p-dimethylaminobenzoyl), 154.6 (O-p-dimethylaminobenzoyl), 153.0 (C-3), 151.5 (C-4), 148.4 (C-3'), 148.3 (C-4'), 146.1 (C-7), 136.6 (C-7'), 132.3 (O-p-dimethylaminobenzoyl), 132.1 (O-p-dimethylaminobenzoyl), 131.4 (C-1), 131.4 (C-6), 129.7 (C-8), 128.2 (C-1'), 124.6 (C-6'), 120.0 (O-p-dimethylaminobenzoyl), 117.8 (O-p-dimethylaminobenzoyl), 111.8 (C-8'), 111.5 (C-2'), 108.7 (C-5'), 106.7 (C-2), 105.9 (C-1"), 102.5 (C-5), 102.2 (—OCH$_2$O—), 78.9 (C-3"), 74.7 (C-2"), 74.0 (C-4"), 73.2 (C-5"), 67.9 (C-9), 56.3 (3-OCH$_3$), 55.8 (4-OCH$_3$), 40.1 (O-p-dimethylaminobenzoyl), 40.1 (O-p-dimethylaminobenzoyl), 18.2 (C-6").

3"-O-dimethylcarbamyl-7-O-β-D-patentiflorin A (31f, yield 66% of two steps)

HR-EIMS: m/z [M+H]$^+$ 674.2099 (calcd. 598.1925). $^1$H NMR (400 MHz, acetone-d$_6$) δ 8.16 (1H, d, J=2.7 Hz, H-2), 7.07 (1H, d, J=4.9 Hz, H-5), 6.97 (1H, dd, J=7.9, 2.7 Hz, H-5'), 6.92-6.78 (2H, m, H-2', 6'), 6.13-6.07 (2H, m, —OCH$_2$O—), 5.59-5.47 (2H, m, H-9), 5.42 (1H, dd, J=15.0, 0.8 Hz, H-1"), 5.02 (1H, d, J=7.8 Hz, H-3"), 4.80-4.72 (2H, m, OH), 3.95 (3H, s, 3-OCH$_3$), 3.90 (1H, ddd, J=9.4, 7.8, 4.5

Hz, H-2"), 3.70 (3H, d, J=2.6 Hz, 4-OCH₃), 3.56-3.45 (1H, m, H-4"), 3.39 (1H, td, J=9.2, 4.4 Hz, H-5"), 3.02 (3H, s, O-dimethylcarbamyl), 2.92 (3H, s, O-dimethylcarbamyl), 1.35 (3H, dd, J=6.0, 1.5 Hz, H-6"). ¹³C NMR (100 MHz, acetone-d₆) δ 169.9 (C-9'), 158.4 (O-dimethylcarbamyl), 152.9 (C-3), 151.4 (C-4), 148.3 (C-3'), 148.2 (C-4'), 146.0 (C-7), 136.6 (C-7'), 131.6 (C-1), 131.5 (C-6), 129.7 (C-8), 128.2 (C-1'), 124.6 (C-6'), 111.8 (C-8'), 111.7 (C-2'), 108.6 (C-5'), 106.6 (C-2), 105.9 (C-1"), 102.5 (C-5), 102.2 (—OCH₂O—), 81.4 (C-3"), 74.7 (C-2"), 74.0 (C-4"), 73.0 (C-5"), 67.9 (C-9), 56.3 (3-OCH₃), 55.7 (4-OCH₃), 36.7 (O-dimethylcarbamyl), 36.2 (O-dimethylcarbamyl), 18.1 (C-6").

3"-O-cyclopropanecarbonyl-7-O-4i-D-patentiflorin A (31g, yield 62% of two steps)

HR-EIMS: m/z [M+H]⁺ 595.1808 (calcd. 595.1816). ¹H NMR (400 MHz, acetone-d₆) δ 8.15 (1H, d, J=2.1 Hz, H-2), 7.09 (1H, d, J=4.2 Hz, H-5), 6.98 (1H, dd, J=7.9, 2.8 Hz, H-5'), 6.91-6.79 (2H, m, H-2', 6'), 6.12-6.07 (2H, m, —OCH₂O—), 5.61-5.40 (3H, m, H-9, 1"), 5.10-5.01 (2H, m, OH), 4.69-4.61 (1H, m, H-3"), 3.95 (3H, s, 3-OCH₃), 3.89 (1H, ddd, J=12.2, 8.3, 4.1 Hz, H-2"), 3.71 (3H, d, J=2.3 Hz, 4-OCH₃), 3.59-3.49 (1H, m, H-4"), 3.38 (1H, dd, J=10.7, 7.7 Hz, H-5"), 1.69 (1H, tt, J=7.9, 4.7 Hz, O-cyclopropanecarbonyl), 1.35 (3H, dd, J=6.1, 1.5 Hz, H-6"), 0.90-0.83 (4H, m, O-cyclopropanecarbonyl). ¹³C NMR (100 MHz, acetone-d₆) δ 175.1 (O-cyclopropanecarbonyl), 169.8 (C-9'), 152.9 (C-3), 151.4 (C-4), 148.3 (C-3'), 148.3 (C-4'), 146.0 (C-7), 136.6 (C-7'), 131.4 (C-1), 131.3 (C-6), 129.7 (C-8), 128.2 (C-1'), 124.6 (C-6'), 111.7 (C-8'), 111.7 (C-2'), 108.6 (C-5'), 106.6 (C-2), 105.8 (C-1"), 102.5 (C-5), 102.2 (—OCH₂O—), 78.7 (C-3"), 74.5 (C-2"), 73.7 (C-4"), 73.1 (C-5"), 67.9 (C-9), 56.3 (3-OCH₃), 55.7 (4-OCH₃), 18.1 (c-6"), 13.6 (O-cyclopropanecarbonyl), 8.7 (O-cyclopropanecarbonyl), 8.2 (O-cyclopropanecarbonyl).

3"-O-p-chlorobenzoyl-7-O-β-D-patentiflorin A (31h, yield 80% of two steps)

HR-EIMS: m/z [M+H]⁺ 665.1413 (calcd. 665.1426). ¹H NMR (400 MHz, acetone-d₆) δ 8.15 (1H, d, J=2.4 Hz, H-2), 8.14-8.08 (2H, m, O-p-chlorobenzoyl), 7.61-7.55 (2H, m, O-p-chlorobenzoyl), 7.08 (1H, d, J=6.3 Hz, H-5), 7.00-6.95 (1H, m, H-5'), 6.93-6.78 (2H, m, H-2', 6'), 6.13-6.08 (2H, m, —OCH₂O—), 5.61-5.42 (3H, m, H-5, 1"), 5.35 (1H, t, J=9.2 Hz, OH), 5.15 (1H, dd, J=7.8, 1.2 Hz, OH), 4.80 (1H, dd, J=5.7, 1.1 Hz, H-3"), 4.09 (1H, ddd, J=9.5, 7.8, 5.4 Hz, H-2"), 3.94 (3H, s, 3-OCH₃), 3.70 (3H, d, J=3.7 Hz, 4-OCH₃), 3.68-3.54 (2H, m, H-4", 5"), 1.40 (3H, dd, J=5.9, 1.2 Hz, H-6"). ¹³C NMR (100 MHz, acetone-d₆) δ 169.9 (C-9'), 165.8 (O-p-chlorobenzoyl), 152.9 (C-3), 151.4 (C-4), 148.3 (C-3'), 148.3 (C-4'), 145.9 (C-7), 139.5 (O-p-chlorobenzoyl), 136.7 (C-7'), 132.2 (O-p-chlorobenzoyl), 131.4 (C-1), 131.3 (C-6), 130.4 (C-8), 129.5 (O-p-chlorobenzoyl), 128.2 (C-1'), 124.6 (C-6'), 111.8 (C-8'), 111.7 (C-2'), 108.7 (C-5'), 106.6 (C-2), 105.7 (C-1"), 102.4 (C-5), 102.2 (—OCH₂O—), 79.8 (C-3"), 74.4 (C-2"), 73.7 (C-4"), 73.1 (C-5"), 67.9 (C-9), 56.3 (3-OCH₃), 55.7 (4-OCH₃), 18.2 (C-6").

3"-O-pyrazinecarbonyl-7-O-β-D-patentiflorin A (31i, yield 52% of two steps)

HR-EIMS: m/z [M+H]⁺ 633.1709 (calcd. 633.1720). ¹H NMR (400 MHz, acetone-d₆) δ 8.89 (1H, d, J=1.5 Hz, O-pyrazinecarbonyl), 8.49 (1H, d, J=2.4 Hz, O-pyrazinecarbonyl), 8.43 (1H, dd, J=2.5, 1.5 Hz, O-pyrazinecarbonyl), 7.62 (I H, d, J=2.1 Hz, H-2), 6.60 (1H, dd, J=7.9, 2.4 Hz, H-5'), 6.55 (1H, d, J=2.7 Hz, H-5), 6.49 (1H, dd, J=12.2, 1.7 Hz, H-6'), 6.36 (1H, ddd, J=8.6, 7.9, 1.7 Hz, H-2'), 5.89 (1H, dd, J=5.6, 3.3 Hz, H-3"), 5.68 (2H, q, J=1.2 Hz, —OCH₂O—), 5.16-5.01 (3H, m, H-9, 1"), 4.76 (1H, t, J=9.3 Hz, OH), 4.60 (1H, dd, J=7.8, 4.9 Hz, OH), 3.47 (3H, s, 3-OCH₃), 3.45-3.39 (1H, m, H-2"), 3.22 (3H, s, 4-OCH₃), 3.16-3.07 (2H, m, H-4", 5"), 0.86-0.80 (3H, m, H-6"). ¹³C NMR (100 MHz, acetone-d₆) δ 169.9 (C-9'), 168.6 (O-pyrazinecarbonyl), 153.0 (C-3), 151.5 (C-4), 149.7 (C-3'), 148.3 (C-4'), 146.2 (O-pyrazinecarbonyl), 145.9 (O-pyrazinecarbonyl), 145.5 (C-7), 144.8 (O-pyrazinecarbonyl), 144.2 (O-pyrazinecarbonyl), 136.8 (C-7'), 131.5 (C-1), 131.4 (C-6), 130.1 (C-8), 128.2 (C-1'), 124.6 (C-6'), 111.8 (C-8'), 111.7 (C-2'), 108.7 (C-5'), 105.6 (C-1"), 102.4 (C-5), 102.2 (—OCH₂O—), 81.5 (C-3"), 74.2 (C-2"), 73.5 (C-4"), 73.0 (C-5"), 67.9 (C-9), 56.3 (3-OCH₃), 55.8 (4-OCH₃), 18.2 (C-6").

3"-O-cyanoacetyl-7-O-β-D-patentiflorin A (31j, yield 49% of two steps)

HR-EIMS: m/z [M+H]) 594.1609 (calcd. 594.1612). ¹H NMR (400 MHz, acetone-d₆) δ 7.85 (1H, s, H-2), 7.09 (1H, m, H-5), 6.98 (1H, dd, J=7.9, 2.5 Hz, H-5'), 6.89 (1H, dd, J=12.2, 1.6 Hz, H-2'), 6.85-6.79 (1H, m, H-6'), 6.15-6.02 (2H, m, —OCH₂O—), 5.70-5.37 (2H, m, H-9), 5.12-4.98 (2H, m, H-1", H-3"), 3.96 (3H, d, J=1.6 Hz, 3-OCH₃), 3.91 (1H, dd, J=9.5, 7.8 Hz, H-2"), 3.78-3.66 (3H, m, 4-OCH₃), 3.55 (1H, dd, J=9.5, 6.1, 1.2 Hz, H-4"), 3.35 (3H, m, O-cyanoacetyl, H-5"), 1.36 (3H, dd, J=6.0, 1.3 Hz, H-6"). ¹³C NMR (100 MHz, acetone-d₆) δ 169.9 (C-9'), 167.8 (O-cyanoacetyl), 153.0 (C-3), 151.5 (C-4), 148.4 (C-3'), 148.3 (C-4'), 146.0 (C-7), 136.6 (C-7'), 131.4 (C-1), 131.3 (C-6) 129.7 (C-8), 128.2 (C-1'), 124.6 (C-6'), 113.8 (O-cyanoacetyl), 111.8 (C-2'), 111.8 (C-8'), 108.7 (C-5'), 106.7 (C-2), 105.8 (C-1"), 102.5 (C-5), 102.2 (—OCH₂O—), 79.2 (C-3"), 74.6 (C-2"), 73.9 (C-4"), 73.1 (C-5"), 67.9 (C-9), 56.4 (3-OCH₃), 55.8 (4-OCH₃), 25.1 (O-cyanoacetyl), 18.2 (C-6").

3"-O-trichloroacetyl-7-O-β-D-patentiflorin A (31k, yield 53% of two steps)

HR-EIMS: m/z [M+H]⁺ 671.0325 (calcd. 671.0490). ¹H NMR (400 MHz, acetone-d₆) δ 8.15 (1H, d, J=1.5 Hz, H-2), 7.11 (1H, t, J=2.4 Hz, H-5), 6.98 (1H, dd, J=7.9, 2.5 Hz, H-5'), 6.90 (1H, d, J=1.6 Hz, H-2'), 6.88-6.80 (1H, m, H-6'), 6.10 (2H, dt, J=4.7, 1.2 Hz, —OCH₂O—), 5.74-5.66 (1H, m, 4"-OH), 5.61-5.41 (2H, m, H-9), 5.12-5.02 (1H, m, 2"-OH), 4.92 (1H, t, J=9.3 Hz, H-1"), 4.84 (1H, d, J=8.7 Hz, H-3"), 3.97 (3H, d, J=1.3 Hz, 3-OCH₃), 3.91 (1H, ddd, J=9.5, 7.8, 5.4 Hz, H-2"), 3.73 (3H, d, J=1.6 Hz, 4-OCH₃), 3.56 (1H, dq, J=12.2, 6.2 Hz, H-4"), 3.42 (1H, td, J=9.3, 5.9 Hz, H-5"), 1.36 (3H, dd, J=6.1, 1.5 Hz, H-6"). ¹³C NMR (100 MHz, acetone-d₆) δ 169.8 (C-9'), 162.5 (O-trichloroacetyl), 153.0 (C-3), 151.5 (C-4), 148.4 (C-3'), 148.3 (C-4'), 145.9 (C-7), 136.7 (C-7'), 131.5 (C-1), 131.4 (C-6), 129.7 (C-8), 128.2 (C-1'), 124.6 (C-6'), 111.8 (C-8'), 111.7 (C-2'), 108.7 (C-5'), 106.7 (C-2), 105.7 (C-1"), 102.5 (C-5), 102.2 (—OCH₂O—), 91.4 (O-trichloroacetyl), 79.6 (C-3"), 74.1 (C-2"), 73.3 (C-4"), 73.1 (C-5"), 67.9 (C-9), 56.4 (3-OCH₃), 55.8 (4-OCH₃), 18.1 (C-6").

3"-O-benzyl-7-O-β-D-xylosyldiphyllin (31l, yield 59% of two steps)

HR-EIMS: m/z [M+H]⁺ 603.1676 (calcd. 603.1866). ¹H NMR (400 MHz, CDCl₃) δ 7.85 (1H, s, H-2), 7.30 (5H, m, O-Bn), 7.01 (1H, m, H-5), 6.89 (1H, m, H-5'), 6.74 (1H, m, H-2'), 6.74 (1H, m, H-6'), 5.99 (2H, m, —OCH₂O—), 5.38 (2H, m, H-9), 4.96 (1H, m, H-1"), 4.69 (2H, m, O-Bn), 3.96 (3H, s, 3-OCH₃), 3.81 (1H, dd J=8.6, 7.2 Hz, H-3"), 3.73 (3H, s, 4-OCH₃), 3.60 (3H, m, H-2",4",5"), 3.12 (1H, m, H-5"). ¹³C NMR (100 MHz, CDCl₁) δ 169.9 (C-9'), 152.0 (C-3), 150.2 (C-4), 147.6 (C-3'), 147.5 (C-4'), 144.3 (C-7), 137.6 (C-7'), 136.6 (O-Bn), 130.8 (C-1), 130.7 (C-6), 128.8

(C-8), 128.8 (O-Bn), 128.5 (O-Bn), 128.3 (O-Bn), 128.3 (C-1'), 127.9 (O-Bn), 127.0 (O-Bn), 123.6 (C-6'), 119.2 (C-8'), 110.7 (C-2'), 108.2 (C-5'), 106.4 (C-2), 104.8 (C-1"), 101.3 (C-5), 100.9 (—OCH$_2$O—), 81.1 (C-3"), 75.6 (C-2"), 75.3 (C-4"), 73.4 (C-5"), 73.04 (O-Bn), 67.4 (C-9), 56.3 (3-OCH$_3$), 55.9 (4-OCH$_3$).

3", 4"-Acetonide-4-O-β-D-glucopyranosyldiphyllin (32a)

To the solution of compound 26f (54.2 mg, 0.1 mmol) in 3 mL of 2,2-dimethoxypropane (DMP) was added catalytic amount of TsOH (0.19 mg, 0.001 mmol) (As illustrated in FIG. 6). After the reaction was stirred for 12 h at r.t., the excess DMP was removed under evaporation in reduced pressure. The residue was purified by a silica gel column separation (n-hexane:ethyl acetate=1:1) to afford 32a as a white solid (11.4 mg, 20%): HR-EIMS: m/z [M+H]$^+$ 583.1656 (calcd. 583.1816). $^1$H NMR (400 MHz, Acetone-d$_6$) δ 8.22 (1H, s, H-2), 7.09 (1H, s, H-5), 6.97 (1H, dd, J=7.8, 2.2 Hz, H-5'), 6.87 (1H, dd, J=6.8, 2.2 Hz, H-2'), 6.81 (1H, q, J=7.4 Hz, H-6'), 6.10 (2H, d, J=3.6 Hz, —OCH$_2$O—), 5.52-5.34 (2H, m, H-9), 5.32 (1H, s, —OH), 5.03 (1H, dd, J=7.7, 2.8 Hz, H-1"), 4.66 (1H, s, —OH), 3.98 (3H, s, 3-OCH$_3$), 3.96-3.82 (2H, m, H-2", H-3"), 3.79 (1H, td, J=7.9, 3.3 Hz, H-6"), 3.72 (3H, s, 4-OCH$_3$), 3.68-3.64 (2H, m, H-5", H-6"), 3.34 (i H, q, J=7.9, 6.8 Hz, H-4"), 1.52 (3H, s, O-isopropylidene), 1.32 (3H, s, O-isopropylidene).

To the solution of compound 26g (50 mg, 0.09 mmol) in 3 mL of DMP was added catalytic amount of TsOH (0.19 mg, 0.001 mmol) (As illustrated in FIG. 6). After the reaction was stirred for 12 h at r.t., the excess DMP was removed under evaporation in reduced pressure. The residue was purified by a silica gel column separation (45-52% ethyl acetate in n-hexane) to afford 32b (18 mg, 34%), 32c (20 mg, 38%) and 32d (2 mg, 4%) with each as a white solid, respectively.

3", 4"-Acetonide-4-O-β-D-galactopyranosyldiphyllin (32b)

HR-EIMS: m/z [M+H]$^+$ 583.1666 (calcd. 583.1816). $^1$H NMR (400 MHz, Acetone-d$_6$) δ 8.21 (1H, s, H-2), 7.09 (1H, s, H-5), 6.97 (1H, d, J=7.4 Hz, H-5'), 6.90-6.75 (2H, m, H-2', H-6'), 6.10 (2H, d, J=4.5 Hz, —OCH$_2$O—), 5.78 (1H, d, J=15.6 Hz, —OH), 5.48-5.39 (2H, m, H-9), 4.88 (1H, d, J=9.5 Hz, H-1"), 4.28 (1H, d, J=5.9 Hz, H-3"), 4.23 (1H, t, J=6.0 Hz, H-4"), 4.07 (1H, q, J=5.7, 5.2 Hz, H-2"), 4.00 (3H, s, 3-OCH$_3$), 3.96-3.83 (3H, m, H-5", H-6"), 3.73 (3H, s, 4-OCH$_3$), 1.53 (3H, s, O-isopropylidene), 1.33 (3H, s, O-isopropylidene).

4",6"-Acetonide-4-O-β-D-galactopyranosyldiphyllin (32c)

HR-EIMS: m/z [M+H]$^+$ 583.1688 (calcd. 583.1816). $^1$H NMR (400 MHz, Acetone-d$_6$) δ 8.28-8.19 (1H, m, H-2), 7.09 (1H, s, H-5), 6.98 (1H, dt, J=8.0, 1.1 Hz, H-5'), 6.90-6.78 (2H, m, H-2', H-6'), 6.10 (2H, dt, J=5.0, 1.1 Hz, —OCH$_2$O—), 5.84-5.32 (2H, m, H-9), 4.94-4.83 (1H, m, H-1"), 4.32-4.20 (1H, m, H-6"), 4.04 (1H, dt, J=9.6, 7.6 Hz, H-2"), 4.00 (3H, s, 3-OCH$_3$), 3.97-3.81 (3H, m, H-3", H-4", H-6"), 3.73 (3H, s, 4-OCH$_3$), 3.66 (1H, tt, J=6.7, 4.3 Hz, H-5"), 1.53 (3H, s, O-isopropylidene), 1.33 (3H, s, O-isopropylidene).

2",3"-Acetonide-4-O-β-D-galactopyranosyldiphyllin (32d)

HR-EIMS: m/z [M+H]$^+$ 583.1648 (calcd. 583.1816). $^1$H NMR (400 MHz, Acetone-d$_6$) δ 8.25 (1H, s, H-5), 7.11 (1H, s, H-5), 6.98 (1H, dd, J=7.8, 1.0 Hz, H-5'), 6.90-6.86 (1H, m, H-2'), 6.83 (1H, dd, J=7.9, 1.7 Hz, H-6'), 6.10 (2H, dd, J=4.3, 1.0 Hz, —OCH$_2$O—), 5.65-5.45 (2H, m, H-9), 4.96-4.90 (1H, m, H-1"), 4.26 (1H, d, J=3.5 Hz, H-3"), 4.15 (1H, dt, J=12.8, 2.1 Hz, H-2"), 4.01 (3H, s, 3-OCH$_3$), 3.93-3.83 (2H, m, H-6"), 3.73 (3H, s, 4-OCH$_3$), 3.68 (1H, ddd, J=9.5, 7.9, 3.6 Hz, H-4"), 3.57-3.50 (1H, m, H-5"), 1.47 (3H, s, O-isopropylidene), 1.41 (3H, s, O-isopropylidene).

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds are disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter is claimed, it should be understood that compounds known and available in the art prior to applicants' invention, including compounds for which an enabling disclosure is provided in the references cited herein, are not intended to be included in the composition of matter claims herein.

What is claimed:

1. A compound of Formula (I):

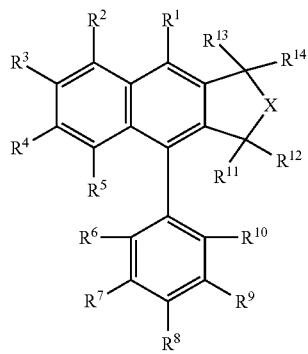

or a pharmaceutically acceptable salt or pro-drug thereof wherein,

X is oxygen;

$R^1$ is $R^{15}$, $R^{16}$; or —NH(CH$_2$R$^{16}$);

$R^2$, $R^5$, $R^6$, $R^{10}$, $R^{13}$, and $R^{14}$ are each hydrogen;

$R^3$ and $R^4$ are each independently —O-alkyl;

$R^7$, $R^8$, and $R^9$ are each independently selected from the group consisting of hydrogen and —O-alkyl; or $R^7$ and $R^8$ taken together with the carbon atoms to which they are attached to form a 5-6 membered heterocyclyl optionally substituted with 1, 2, 3, 4 or 5 group(s) independently selected from $C_{1-6}$ alkyl; or $R^8$ and $R^9$ taken together with the carbon atoms to which they are attached to form a 5-6 membered heterocyclyl optionally substituted with 1, 2, 3, 4 or 5 group(s) independently selected from $C_{1-6}$ alkyl;

$R^{11}$ and $R^{12}$ taken together form oxo;

$R^{15}$ is a glycosidic group represented by the Formula (V):

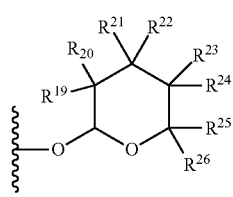

wherein, each of $R^{19}$, $R^{21}$, $R^{23}$ and $R^{25}$ is hydrogen;

$R^{20}$ is selected from the group consisting of —OR$^{27}$, —OC(O)R$^{27}$, —OC(O)N(R$^{27}$)R$^{27}$, and —OC(O)OR$^{27}$;

$R^{22}$ is selected from the group consisting of —OR$^{27}$, —OC(O)R$^{27}$, —OC(O)N(R$^{27}$)R$^{27}$, and —OC(O)OR$^{27}$;

$R^{24}$ is selected from the group consisting of —OR$^{27}$, —OC(O)R$^{27}$, —OC(O)N(R$^{27}$)R$^{27}$, and —OC(O)OR$^{27}$;

at least one of $R^{20}$, $R^{22}$ and $R^{24}$ is selected from the group consisting of —OC(O)R$^{27}$, —OC(O)N(R$^{27}$)R$^{27}$, and —OC(O)OR$^{27}$;

at least one of $R^{20}$, $R^{22}$ and $R^{24}$ is hydroxyl;

$R^{26}$ is hydrogen or methyl; $R^{27}$ for each occurrence is independently selected from the group consisting of hydrogen, halogen, trichloromethyl, trifluoromethyl, cyano, nitro, —OR$^{29}$, —C(O)R$^{30}$, —C(O)N(R$^{29}$)R$^{30}$, —C(O)OR$^{29}$, —OC(O)R$^{29}$, —S(O)$_2$R$^{29}$, —S(O)$_2$N(R$^{29}$)R$^{30}$, —N(R$^{29}$)R$^{30}$, —N(R$^{29}$)N(R$^{29}$)R$^{30}$, —N(R$^{29}$)C(O)R$^{30}$, —N(R$^{29}$)S(O)$_2$R$^{30}$, hydrocarbyl optionally substituted with 1, 2, 3, 4 or 5 group(s) independently selected from $R^{28}$, heterocyclcyl optionally substituted with 1, 2, 3, 4 or 5 group(s) independently selected from $R^{28}$, and —(CH$_2$)$_k$-heterocyclyl optionally substituted with 1, 2, 3, 4 or 5 group(s) independently selected from $R^{28}$, wherein k is an integer between 1-6;

$R^{28}$ for each occurrence is independently selected from halogen, trichloromethyl, trifluoromethyl, cyano, nitro, oxo, =NR$^{29}$, —OR$^{29}$, —C(O)R$^{30}$, —C(O)N(R$^{29}$)R$^{30}$, —C(O)OR$^{29}$, —OC(O)R$^{29}$, —S(O)$_2$R$^{29}$, —S(O)$_2$N(R$^{29}$)R$^{30}$, —N(R$^{29}$)R$^{30}$, —N(R$^{29}$)N(R$^{29}$)R$^{30}$, —N(R$^{29}$)C(O)R$^{30}$ and —N(R$^{29}$)S(O)$_2$R$^{30}$; and $R^{29}$ and $R^{30}$ for each occurrence are each independently hydrogen or selected from hydrocarbyl and heterocyclyl, either of which is optionally substituted with 1, 2, 3, 4 or 5 group(s) independently selected from halogen, cyano, amino, hydroxy, $C_{1-6}$ alkyl and $C_{1-6}$ alkoxy; and $R^{16}$ is selected from the group consisting of cyano, alkynyl, and alkynyl optionally substituted with a trialkylsilane.

2. The compound of claim 1, wherein $R^8$ and $R^9$ taken together with the carbon atoms to which they are attached form a methylenedioxy ring.

3. The compound of claim 1, wherein $R^1$ is —C≡CH, —C≡C—Si(CH$_3$)$_3$, or —NH(CH$_2$—C≡CH).

4. The compound of claim 3, wherein each of $R^3$ and $R^4$ is —OCH$_3$; and $R^8$ and $R^9$ taken together with the carbon atoms to which they are attached form a methylenedioxy ring.

5. The compound of claim 1, wherein the compound is selected from the group consisting of 19o, 21, and 23:

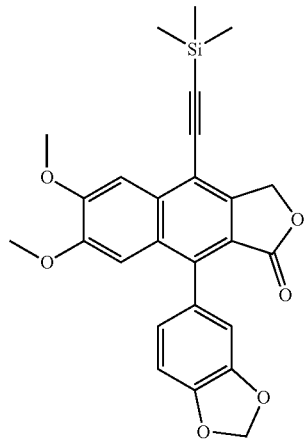

19o

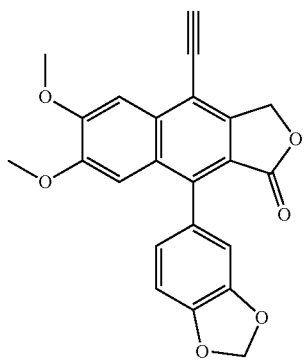

21

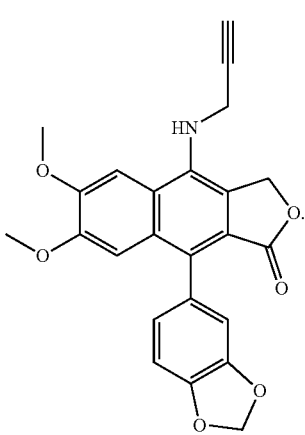

23

6. The compound of claim 1, wherein the glycosidic group is an isomer selected from the group consisting of α-D, α-L, β-D, and β-L.

7. The compound of claim 1, wherein the glycosidic group is a monosaccharide selected from the group consisting of an α-L isomer and an β-L isomer.

8. The compound of claim 1, wherein the compound is selected from the group consisting of 27aa, 27ab, 27ac, 27ad, 27ae, 27af, 27ba, 27bb, 27bc, 27bd, 27be, 27bf, 28ab1, 28ab2, 28bb1, 28bb2, 29a, 29b, 31a, 31b, 31c, 31d, 31e, 31f, 31g, 31h, 31i, 31j, and 31k:

27aa

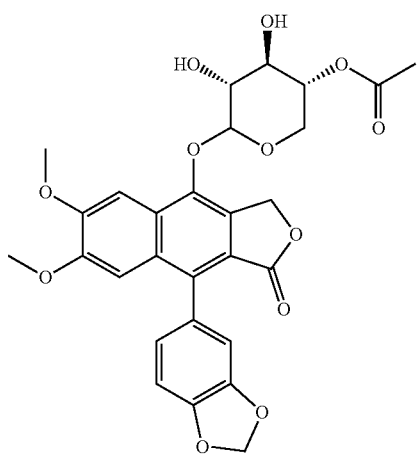

27ab

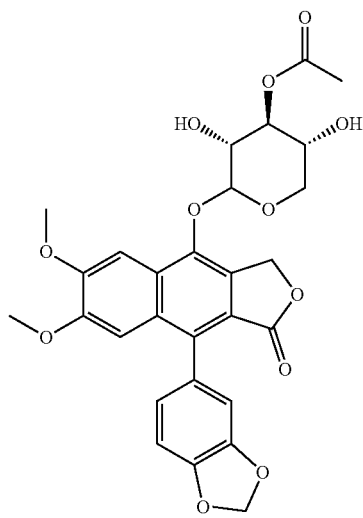

27ac

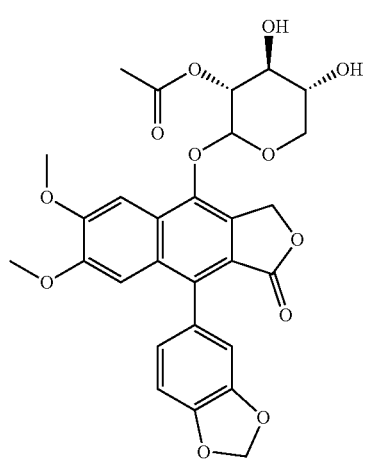

27ad

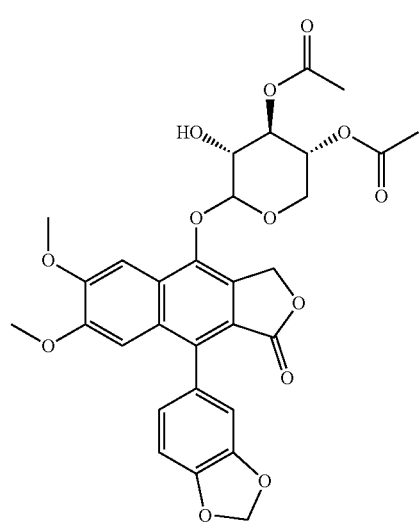

27ae
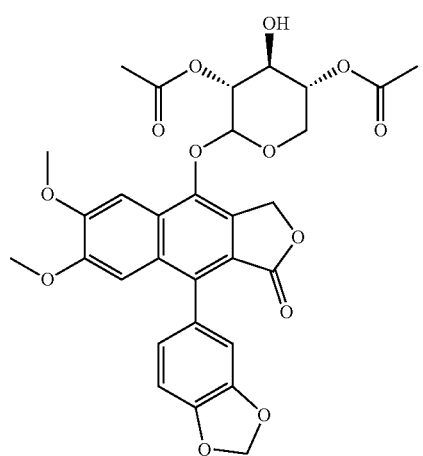
27af
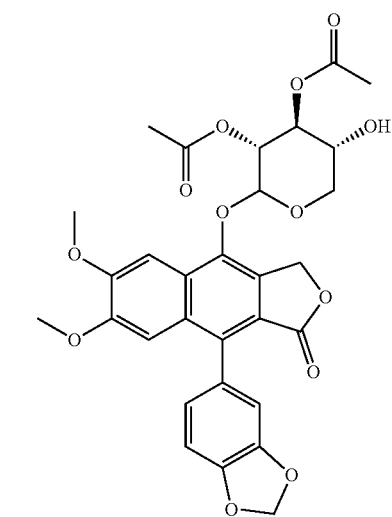
27ba
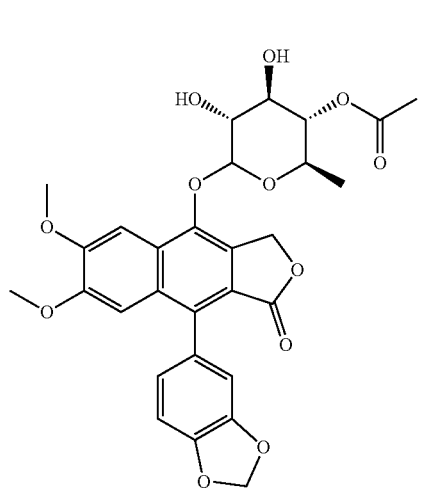
27bb
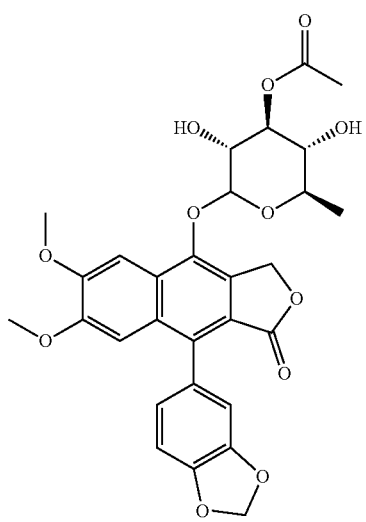
27bc
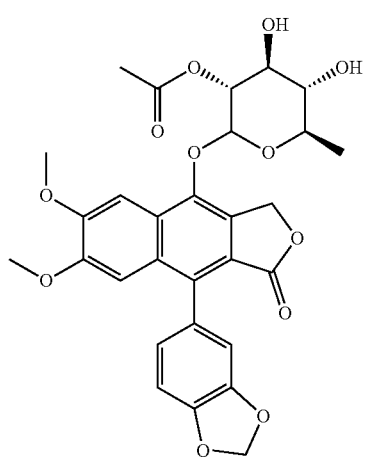
27bd
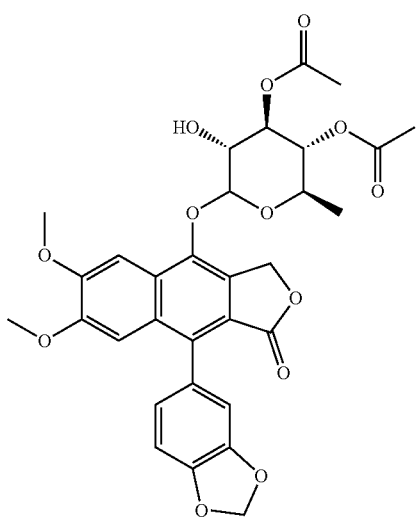

207
27be
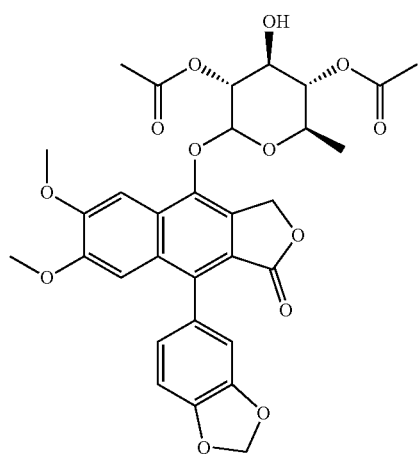
27bf
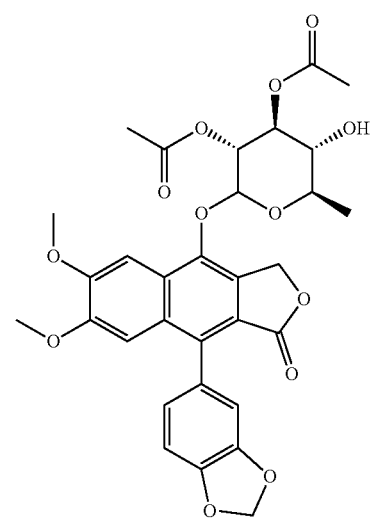
28ab1
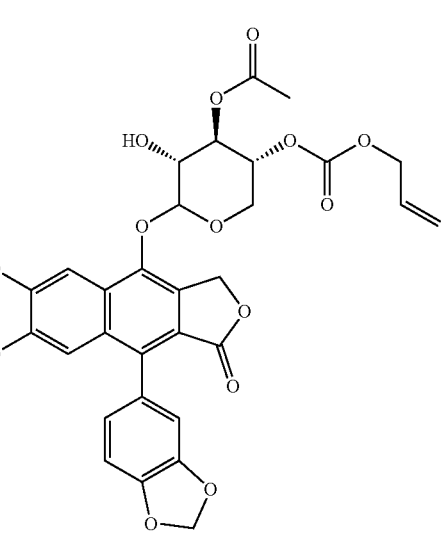
208
28ab2
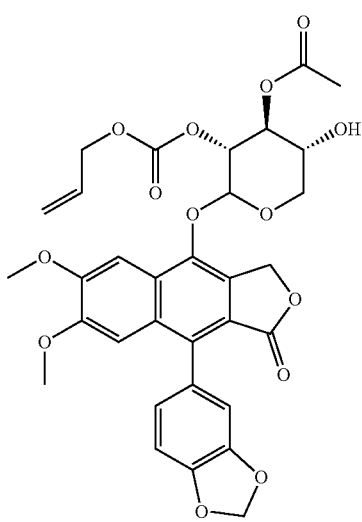
28bb1
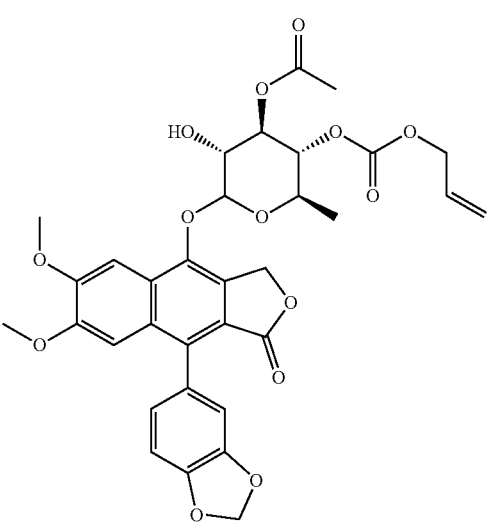
28bb2
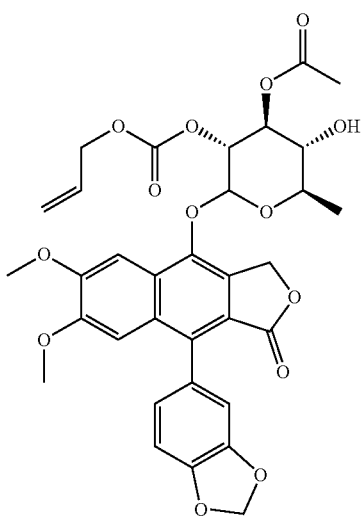

-continued
29a
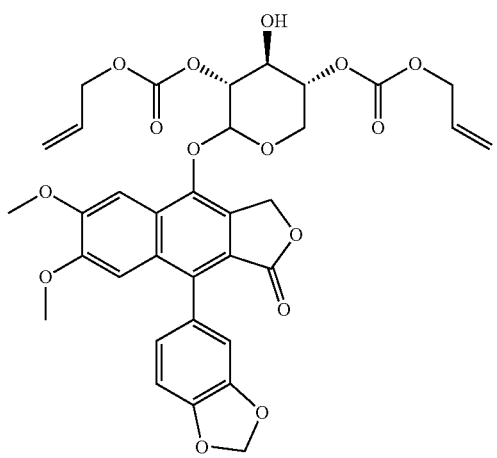
29b
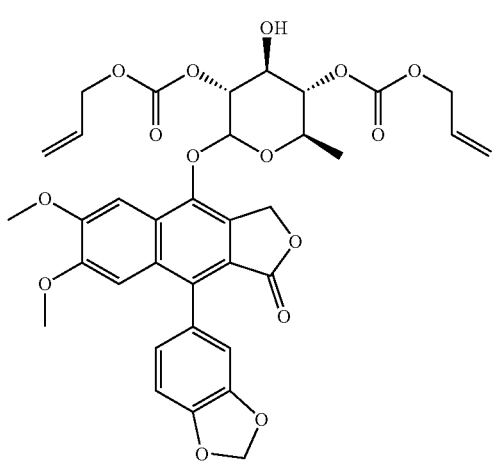
31a
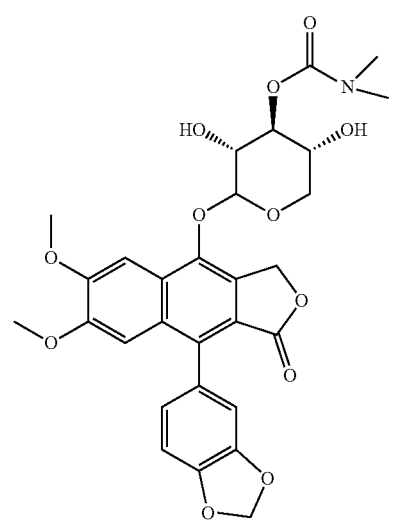
-continued
31b
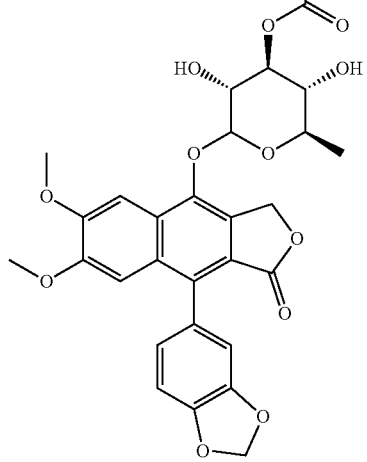
31c
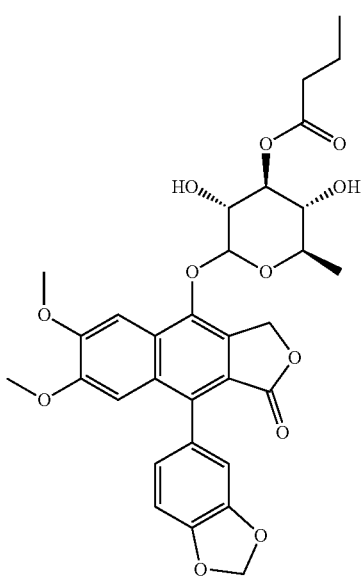

-continued
31d
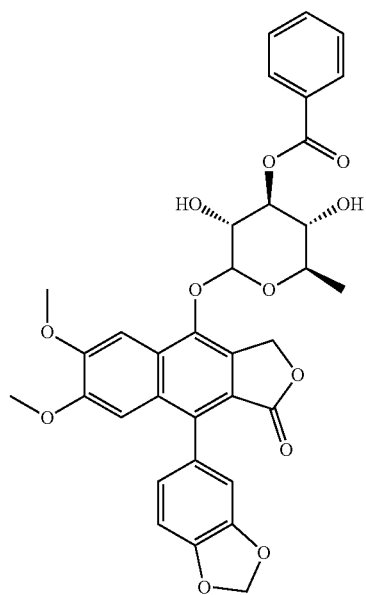
31e
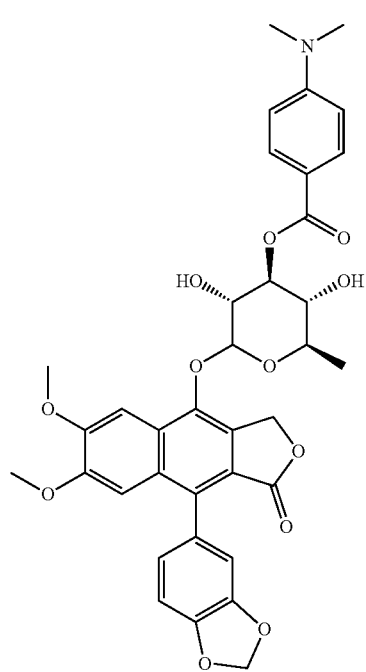
-continued
31f
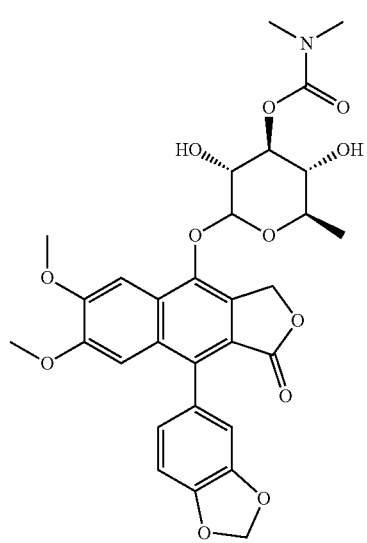
31g

213
-continued

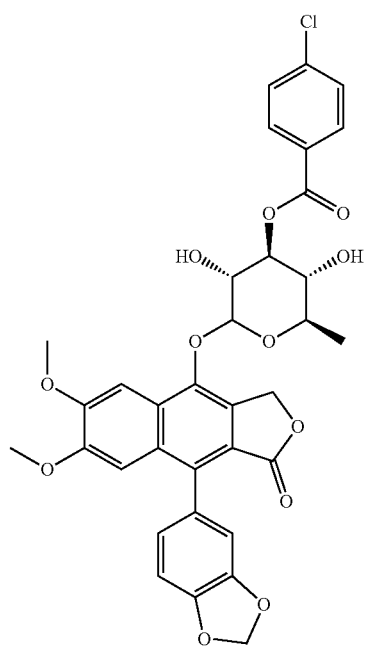

31h

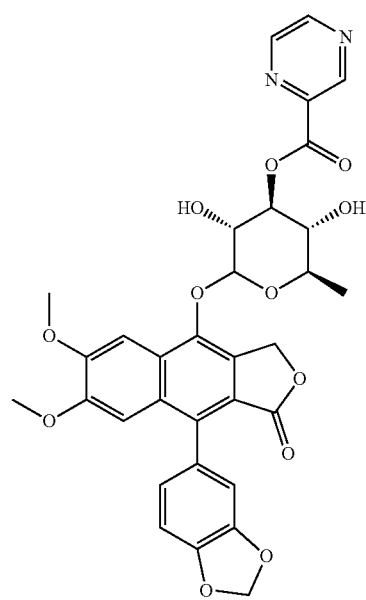

31i

214
-continued

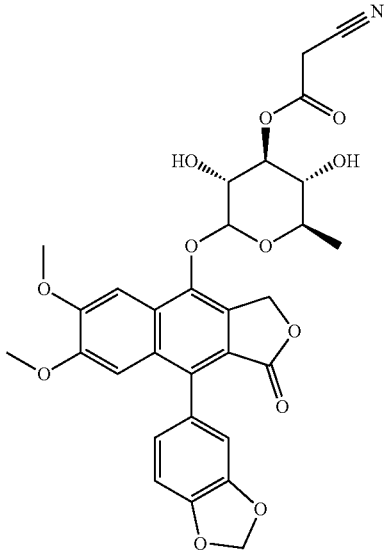

31j

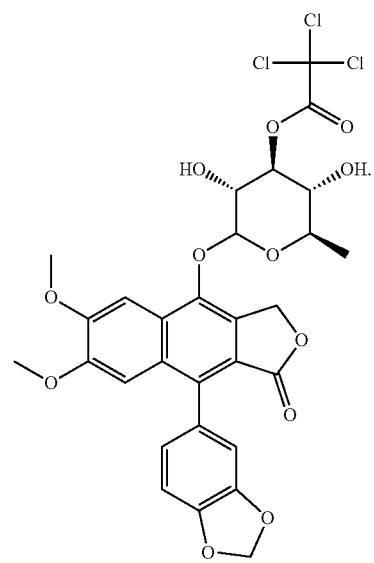

31k

9. A pharmaceutical composition comprising a compound of claim 1 at least one pharmaceutically acceptable excipient.

10. The compound of claim 8, wherein the compound is selected from the group consisting of 27ba, 27bb, 27bc, 27bd, 27be, 27bf, 28ab2, 29b, 31b, 31c, 31d, 31e, 31i, and 31j.

11. A method of treating an HIV infection in a subject in need thereof, the method comprising administering a therapeutically effective amount of a compound of claim 1 to the subject.

* * * * *